US012674175B2

(12) United States Patent
Gentile et al.

(10) Patent No.: US 12,674,175 B2
(45) Date of Patent: Jul. 7, 2026

(54) POLYNUCLEOTIDES, PRIMERS, AND METHODS FOR DETECTION OF TRANSGENIC EVENT, GENETIC CONSTRUCT, KIT FOR DETECTION MATERIAL FROM A PLANT SAMPLE, EVENT CTC91087-6, INSECT-RESISTANT SUGARCANE PLANT, AND METHOD FOR PRODUCING AN INSECT-RESISTANT SUGARCANE PLANT, PLANT CELL, PLANT PART OR SEED

(71) Applicant: CTC—CENTRO DE TECNOLOGIA CANAVIEIRA S.A., Piracicaba SP (BR)

(72) Inventors: Agustina Gentile, Piracicaba SP (BR); Karina Yanagui de Almeida, Piracicaba SP (BR); Maria Lorena Sereno, Piracicaba SP (BR); Wladecir Salles de Oliveira, Piracicaba SP (BR); Adriana Cheavegatti Gianotto, Piracicaba SP (BR); Camila Fornezari Rabello, Piracicaba SP (BR)

(73) Assignee: CTC—CENTRO DE TECNOLOGIA CANAVIEIRA S.A., Piracicaba SP (BR)

( * ) Notice: Subject to any disclaimer, the term of this patent is extended or adjusted under 35 U.S.C. 154(b) by 255 days.

(21) Appl. No.: 17/616,623

(22) PCT Filed: Jun. 4, 2020

(86) PCT No.: PCT/BR2020/050201
§ 371 (c)(1),
(2) Date: Dec. 3, 2021

(87) PCT Pub. No.: WO2020/243806
PCT Pub. Date: Dec. 10, 2020

(65) Prior Publication Data
US 2022/0235370 A1     Jul. 28, 2022

(30) Foreign Application Priority Data
Jun. 4, 2019     (BR) ............... BR 10 2019 011600 5

(51) Int. Cl.
*C12N 15/82*     (2006.01)
*C12Q 1/6895*     (2018.01)

(52) U.S. Cl.
CPC ....... *C12N 15/8286* (2013.01); *C12Q 1/6895* (2013.01); *C12N 2310/20* (2017.05); *C12Q 2600/13* (2013.01); *C12Q 2600/156* (2013.01); *C12Q 2600/16* (2013.01)

(58) Field of Classification Search
None
See application file for complete search history.

(56) References Cited

FOREIGN PATENT DOCUMENTS

| | | |
|---|---|---|
| CN | 103805620 A | 5/2014 |
| WO | 2017218969 A1 | 12/2017 |

OTHER PUBLICATIONS

Accession No. AQ683700.1, 2010, Human Male BAC Library Clone, ncbi.nlm.nih.gov/nuccore/AQ683700.1 (Year: 2010).*
NCBI GenBank Accession No. AQ683700.1 (2010) (Year: 2010).*
NCBI Genbank Accession No. HG968795.1 (2014) (Year: 2014).*
Gao et al (2016, PLoS ONE 11(4):e0153929) (Year: 2016).*
Database Genbank [Online] May 2010, "HS_5454_B2_E06_SP6E RPCI-11 Human Male BAC Library *Homo sapiens* genomic clone Plate=1030 Col=12 Row=J, genomic survey sequence", Database Accession No. (AQ683700.1).
Gianotto et al., "The insect-protected CTC91087-6 sugarcane event expresses Cry1Ac protein preferentially in leaves and presents compositional equivalence to conventional sugarcane", GM Crops & Food—Biotechnology in Agriculture and the Food Chain, Aug. 20, 2019, vol. 1, pp. 1-12.
International Search Report and Written Opinion for PCT/BR2020/050201 dated Sep. 5, 2020, 17 pages.
Weng et al., "Transgenic sugarcane plants expressing high levels of modified cry1Ac provide effective control against stem borers in field trials", Transgenic Res., 2011, vol. 20, No. 4, pp. 759-772, doi: 10.1007/s11248-010-9456-8.
Zhou et al., "Cry1Ac transgenic sugarcane does not affect the diversity of microbial communities and has no significant effect on enzyme activities in rhizosphere soil within on crop season", Front Plant Sci., 2016, vol. 7, Article 265, doi: 10.3389/fpls.2016.00265.

* cited by examiner

*Primary Examiner* — Brent T Page
*Assistant Examiner* — Aleksandar Radosavljevic
(74) *Attorney, Agent, or Firm* — Sheppard Mullin Richter & Hampton LLP

(57) ABSTRACT

The present invention relates to the field of biotechnology. More precisely, a genetic construct and method for producing a transgenic plant event, especially a sugarcane event {*Saccharum* spp.), which is resistant to infestation by the *Diatraea saccharalis* pest, popularly known as a pest, ordinary borer, reed borer or just borer is described. The invention describes the event, the methods for event identification as well as the insertion detection method based on the unique region of intersection between the insert and the host genome and the flanking regions that characterize it.

6 Claims, 14 Drawing Sheets

Specification includes a Sequence Listing.

POLYNUCLEOTIDES, PRIMERS, AND METHODS FOR DETECTION OF TRANSGENIC EVENT, GENETIC CONSTRUCT, KIT FOR DETECTION MATERIAL FROM A PLANT SAMPLE, EVENT CTC91087-6, INSECT-RESISTANT SUGARCANE PLANT, AND METHOD FOR PRODUCING AN INSECT-RESISTANT SUGARCANE PLANT, PLANT CELL, PLANT PART OR SEED

CROSS REFERENCE TO RELATED APPLICATIONS

The present application is a U.S. National Stage Application under 35 U.S.C. 371 of International Application No. PCT/BR2020/050201, filed Jun. 4, 2020, which claims priority to BR 10 2019 01 1600 5, filed Jun. 4, 2019, the content of each of which is incorporated herein by reference in its entirety in the present disclosure.

REFERENCE TO AN ELECTRONIC SEQUENCE LISTING

The contents of the electronic sequence listing (345733_ST25.txt; Size: 210,648 bytes; and Date of Creation: Jul. 30, 2024) is herein incorporated by reference in its entirety.

TECHNICAL FIELD

The present invention relates to the field of biotechnology. More specifically, there is described a genetic construct and a method for producing a transgenic plant event, especially a sugarcane (*Saccharum* spp.) event, which expresses the Cry1Ac toxin conferring resistance to infestation by the pest *Diatraea saccharalis*, popularly known as common borer, cane borer or just borer. The invention describes a method for detecting the event and material derived from the event resistant to cane borer infestation, as well as polynucleotides, primers, probes and the flanking regions identifying such an event.

BACKGROUND

Sugarcane (*Saccharum* spp.) is a grass belonging to the botanical family Poaceae, originating from Southeast Asia, more precisely from the large central region of New Guinea and Indonesia. It is one of the most important plant species grown in the tropical and subtropical regions, with an area of over 23 million hectares spread over 121 countries (FAO Statistical Yearbook 2012 p. 233).

Sugarcane is a source of raw material for the production of sugar, wine, molasses, rum, cachaça (Brazil's national distillate) and ethanol for fuel. The bagasse that is produced after the sugarcane milling can be used for baling, supplying heat energy, processing at mills, producing electricity (that is typically sold to the consumer's electric grid), or as raw material for the production of sugarcane second-generation ethanol (BR 11 2014 02385-1). Thus, the sugarcane agro-industry has great economic and social importance by generating millions of jobs in the area and fostering foreign exchange through the commercialization of sugar and ethanol and sustainable and optimal use of plant biomass.

More recently, with the advent of global warming and the subsequent desire for alternatives to fossil fuels (biofuels), worldwide interest in sugarcane has increased significantly.

The use of sugarcane-based ethanol as a renewable energy source has been considered extremely important for reducing greenhouse gases and dependence on fossil fuels, thus making it a key element in efforts to control global climate change (Savage, 2011).

Due to the economic and social importance of sugarcane, an increasing amount of research has been directed toward defining best agricultural practices for its cultivation and improving the quality of cultivated varieties. Efforts to improve sugarcane agronomic characteristics have focused on increasing sugar production and accumulation, increasing tolerance to biotic and abiotic stresses, resistance and tolerance to pests and pathogens, and developing alternative technologies for the production of sugarcane ethanol from lignocellulosic biomass (PI 0802153-8; PI 0904538-4; PI 1101295-1).

The complexity of the polyploid and aneuploid genome of modern sugarcane varieties, coupled with their relatively restricted genetic base and low fertility, impose great difficulties and numerous limitations on the selection of plants with desirable agronomic characteristics using conventional breeding (Souza et al, 2011; D'Hont & Glaszmann, 2005, Basel, v. 109, no. 1-3, p. 27-33; Cheavegatti-Gianotto et al., 2011). Therefore, high production costs, the necessity of manual labor, and long product-to-market timelines may prevent the sugarcane industry from meeting the growing demands of the global market.

Due to the limitations of conventional breeding methods and the increasing need to rapidly and efficiently incorporate desirable traits, the use of genetic engineering (biotechnology) in sugarcane breeding programs has gained prominence, in particular due to the commercial success of incorporating desirable agronomic traits through genetic engineering into other plant species (soybean, corn, canola, beet and cotton, for example).

Plant genetic engineering involves the transfer of genes-of-interest into plant cells (genetic transformation) in such a way that a fertile and agronomically superior progeny maintain and stably express the gene responsible for the desired trait.

Despite the potential of sugarcane genetic alteration (incorporation of desirable characteristics) by genetic engineering [virus resistance (Guo et al., 2015; Zhu et al., 2011), insects (Kalunke, Kolge, Babu, & Prasad, 2009; Weng et al., 2011), herbicides (Enríquez-Obregon, Vazquez-Padron, Prieto-Samsonov, De la Riva, & Selman-Housein, 1998; van der Vyver, Conradie, Kossmann, & Lloyd, 2013), drought tolerance (Molinari et al., 2007; Reis et al., 2014), salinity (Kumar, Uzma, Khan, Abbas, & Ali, 2014) and aluminum toxicity (Ribeiro, 2016), increased production and accumulation of sugar (Bewg, Poovaiah, Lan, Ralph, & Coleman, 2016; Mudge et al., 2013)], this approach is limited by intrinsic characteristics of sugarcane. Unlike maize, rice, wheat and other commercial cereals, sugarcane exhibits difficulties in tissue culture propagation, low rates of induction and regeneration of embryogenic calluses, and the impossibility of using the zygotic embryo as a target tissue in genetic transformation [(Anderson & Birch, 2012; Basnayake, Moyle, & Birch, 2011; Molinari et al., 2007)]. Low rates of transformation efficiency and high variability between sugarcane genotypes are frequently observed, and there are still numerous challenges to overcome in order to successfully incorporate desirable agronomic traits into sugarcane using genetic engineering.

Sugarcane is considered a recalcitrant species for genetic transformation, and although several genetic engineering approaches have been evaluated for this species, there are still no standard protocols that guarantee the production of transgenic events (Smith et al. 1992; Rathius & Birch 1992.; Chen et al. 1987; Arencibia 1998; Manickavasagam et al. 2004; Elliott et al. 1998).

In addition to the inherent limitations of the species that prevent the application of existing genetic engineering techniques, the complexity of the sugarcane genome (high ploidy level and aneuploidy), prevents trait introgression into specific cultivars through backcrossing (reconstitution of a specific genotype), as is commonly performed in other crops of commercial interest.

The genotypic complexity of the species also significantly impacts the characterization of the events generated in order to ensure the necessary characteristics for their commercialization. The unambiguous identification of transgenic events is fundamental to ensure their traceability and monitoring, which is a regulatory requirement for their commercialization. The high polyploidy of the sugarcane genome and the high number of repeated regions, coupled with the lack of information on their organization and structure, make the characterization of the transgenic events generated even more difficult.

There are several technical challenges to be overcome in the field of sugarcane breeding to increase the predictability of results, even when applying widely known conventional and/or molecular/genetic techniques. Despite all the technical challenges for obtaining more productive varieties of sugarcane, there is no doubt about the urgency of obtaining improved varieties that have characteristics that significantly impact crop productivity and therefore its market.

Historically, agricultural pests are one of the main factors that cause losses in agriculture. In Brazil, the main sugarcane pest is the species *Diatraea saccharalis* (first described by Fabricius in 1794), popularly known as the common borer, cane borer or just borer. It is a member of the Crambidae family and *Lepidoptera* order. The borer is found practically everywhere the crop is cultivated, an area of approximately 10 million hectares for the 2019/20 crop season (CONAB, 2019).

After mating, the female sugarcane borer lays 200 to 400 eggs distributed on either side of the leaves as well as the leaf sheaths. After hatching, neonate larvae feed on the leaf parenchyma, migrating to the sheath region for shelter. They remain in this region for 7 to 10 days, feeding by scraping the leaf sheath or bark of the young internodes. After an ecdysis, the caterpillars pierce the stem, penetrating inside. The insect creates tunnels inside the stem, usually upwards as it feeds. Inside the culm, the caterpillar goes through approximately six ecdyses before becoming a winged adult (DINARDO-MIRANDA, 2014). This is the developmental stage of the insect that causes economic damage to the crop (FIG. 1).

The attack of the sugarcane borer also causes serious secondary damage to the quality of the raw material used for sugar and alcohol production, because the drilling of the sugarcane stem by the borer creates favorable conditions for fungal entry and opportunistic bacteria, especially *Fusarium moniiform* and *Colletotrichum falcatum*, causing red rot (FIG. 2). Bacteria associated with the red rot raw material produce undesirable fermentations, resulting in products foreign to industrial alcoholic fermentation. Moreover, these bacteria also produce organic acids and gums (dextrans) from the sugars contained in the wort, which negatively affect the viability of yeast cells, requiring their replacement in fermentation reactors (Prececti and Terán 1983; Prececti et al., 1988; BOTELHO and MACEDO, 2002). Another problem arising from the presence of bacteria in fermentation reactors is the possibility of yeast flocculation occurring. In this case, the contaminating bacteria form mucilage that aggregates the yeast cells, causing them to flocculate. Finally, plants attacked by the borer/red rot complex also have high levels of phenolic compounds (METCALF and LUCKMANN, 1994; PRICE, 1997).

Assuming a 4% borer Infestation Infection Index (typical for Brazilian sugarcane fields), average agricultural losses, and pest control costs, it is estimated that the borer causes economic losses of more than R$5 billion annually to the sugar and ethanol production industries.

The sugarcane borer is difficult to control with chemical insecticides due to the feeding behavior of the larva in the stem, which prevents the insecticide from effectively contacting the insect. As an alternative to chemical insecticides, insecticidal proteins, mainly identified from the bacterium *Bacillus thuringiensis* (Bt), have been used to control agricultural pests, including *Diatraea* sp. Among the insecticidal proteins derived from Bt strains, Cry crystalline proteins stand out for their specific toxicity to larvae of common lepidopteran, dipteran and coleopteran species. These proteins, produced as protoxins (65-149 KDa), are solubilized and activated in the intestines of susceptible insects by proteolysis and bind to the intestinal cell membrane, inducing osmotic lysis of the epithelium, which causes the insect to die.

Cry proteins are classified into several groups according to sequence homology, among them, the protein group classified as Cry1 presents high specificity against lepidopteran insects, making it an excellent candidate for introduction into sugarcane germplasm to produce sugarcane borer resistant varieties. The heterologous expression of Cry1 proteins in sugarcane varieties, although challenging, has great potential for sugarcane borer control, reducing economic losses to the sugarcane industry, as well as the release of chemical insecticides in the environment.

Therefore, there remains a need to develop strategies to mitigate the damage caused to sugarcane crops by pest infestation, especially by infestation by the sugarcane borer pest. By offering sugarcane growers varieties with both high yield potential and borer resistance traits, agricultural biotechnology makes an important contribution to the sugarcane industry and Brazilian sugarcane growers.

EMBODIMENTS

In a first embodiment the invention provides polynucleotides that unambiguously identify the event CTC91087-6.

The invention also identifies primers pairs and probes able to identify polynucleotides that characterize the event CTC91087-6.

In a third embodiment the invention provides methods for detecting plant material derived from the CTC91087-6 event.

Other embodiment of the invention defines a kit for detecting the presence of event CTC91087-6 in a sample of plant material.

The fifth embodiment of the present invention is a genetic construct capable of imparting to a sugarcane (*Saccharum* spp.) plant, resistance to insect infestation, particularly by *Diatraea saccharalis* pest.

Also, the invention provides a genetically modified sugarcane, a plant part, plant cell, plant tissue, or seed comprising the genetic construct of interest located at a site defined in the genome of the transformed sugarcane plant, characterized by specific flanking sequences.

The seventh embodiment of the present invention is to provide a commodity product.

The eighth embodiment of the present invention is a method of producing an insect resistant plant.

Finally, the ninth and tenth embodiments of the invention are to provide a method of making and cultivating an insect resistant sugarcane plant and/or plant cell, plant part, or seed.

SUMMARY OF THE INVENTION

The first embodiment is achieved by providing polynucleotides comprising at least 14 to 26 contiguous nucleotides of sequences selected from the group consisting of SEQ ID NO: 5, SEQ ID NO: 12, SEQ ID NO: 13, SEQ ID NO: 18, SEQ ID NO: 19, and SEQ ID NO: 22.

The second embodiment of the invention is achieved by providing primers pairs wherein the forward primer consists of SEQ ID NO: 6 and the reverse primer consists of SEQ ID NO: 7 and/or the forward primer consists of SEQ ID NO: 8 and the reverse primer is SEQ ID NO: 9.

The third embodiment is achieved by a method of detecting plant material derived from event CTC91087-6 comprising the steps of:

a) obtaining a sample for analysis;

b) extracting DNA from the sample;

c) providing primer pairs comprising at least a forward and a reverse primer;

d) amplifying a region between the primer pair; and detecting the presence of a product from amplification.

Also to achieve the third embodiment the primer pairs in step c) are designed to bind to a polynucleotide comprising contiguous nucleotides of sequences selected from the group consisting of SEQ ID NO: 22 and SEQ ID NO: 29, wherein at least one pair of primers comprises contiguous nucleotides of sequences selected from the group consisting of SEQ ID NO: 23, SEQ ID NO: 24, SEQ ID NO: 30 and SEQ ID NO: 31.

Still to achieve the third embodiment, the present invention describes a method of detecting plant material derived from event CTC91087-6 comprising the steps of:

a) obtaining a plant material sample for analysis;

b) extracting DNA or RNA from the sample;

c) providing a probe designed to bind to the complement of a polynucleotide comprising at least 14 contiguous nucleotides of sequences selected from the group consisting of SEQ ID NO: 18, SEQ ID NO: 19, SEQ ID NO: 32 and SEQ ID NO: 33;

d) hybridizing said probe with the sample; and e) detecting the actual hybridization of the probe.

The fourth embodiment of the invention is evidenced by a kit for detecting the presence of event CTC91087-6 in a plant sample, the kit comprising a means to detect the presence of a polynucleotide comprising, at least, 14 contiguous nucleotides of SEQ ID NO: 18 and/or of SEQ ID NO: 19 and/or a pesticidal crystal protein (Cry).

The fifth embodiment is achieved through providing a genetic construct comprising SEQ ID NO: 1.

The sixth embodiment is achieved through a genetically modified sugarcane (*Saccharum* spp.) plant, a plant part, plant cell, plant tissue, or seed comprising SEQ ID NO: 18 or SEQ ID NO: 19.

The seventh embodiment is achieved by providing a commodity product produced from the genetic modified sugarcane from the present invention.

The eighth embodiment is achieved by a method of producing an insect resistant plant comprising SEQ ID NO: 20 and SEQ ID NO: 21

The ninth embodiment of the present invention provides a method of making an insect resistant sugarcane plant comprising introducing a genetic modification to a sugarcane (*Saccharum* spp.) plant comprising SEQ ID NO: 5 or SEQ ID NO: 22 to produce a genetically modified sugarcane (*Saccharum* spp.) plant of event CTC91087-6.

Finally, the tenth embodiment of the invention describes a method of cultivating a genetically modified sugarcane (*Saccharum* spp.) plant of event CTC91087-6, comprising growing a genetically modified sugarcane (*Saccharum* spp.) plant of event CTC91087-6 comprising SEQ ID NO: 5 or SEQ ID NO: 22 under conditions comprising insect infestation.

DETAILED DESCRIPTION OF THE INVENTION

Figure 1:
FIG. 1 exemplifies the damage to sugarcane stalks caused by *D. saccharalis* (sugarcane borer).
Figure 2:
FIG. 2 exemplifies the red rot-borer complex due to *D. saccharalis* (cane borer) attack.

First, the term "event" refers to the transgenic plant produced through genetic transformation that stably expresses the desired trait conferred by the introduced transgene. More particularly, in the present case, the term "event" is considered to be the transgenic plant, preferably a sugarcane transgenic plant (*Saccharum* spp.) which, after genetic modification, expresses the characteristic of pest resistance, particularly resistance to the pest *Diatraea saccharalis* (sugarcane borer). In a preferred embodiment, the transgenic sugarcane produced through the genetic transformation is designated 'CTC91087-6' and may alternately be referred to as "CTC91087-6 event".

Also, for reference purposes, unless expressly mentioned otherwise, "LB region" means the left border (edge) of T-DNA transfer (5'), and "RB region" means the right border (edge) of T-DNA transfer (3').

Additionally, all biological sequences describe herein, except otherwise explicitly stated, encompass sequences having at least 80%, preferably 85%, 90%, 95%, 98%, 99% or 100% of identity with the described sequences.

Finally, "plant material" means any and all plant tissue or derivatives thereof, such as, but not limited to, seeds, stems, stalks, leaves, straws, bark, roots, cells, molecules of plant origin, among others. In addition, "plant material" may include any product of a plant or derivative thereof, for example, but not limited to, sap, sugar, ethanol, among others.

Recombinant DNA technology has enabled the isolation of genes and their stable insertion into a host genome. This technique, also called genetic transformation, can be defined as the controlled introduction of nucleic acids ("DNA" or DNA) into a recipient genome, excluding introduction by fertilization. It is a controlled process where a defined DNA fragment is introduced into the host (or recipient) genome and must be integrated into it. The stable insertion of these molecules into a host genome gives rise to an individual with the genome equal or substantially equal to the recipient (host) of the recombinant molecule, but with a new and particular feature. "Substantially equal" means a genome with more than 80%, preferably 85%, 90%, 95%, 98%, 99% or 100% of identity in relation to the recipient.

There are several plant genetic transformation techniques grouped into two main categories: indirect and direct gene transfer. Indirect transfer is when exogenous DNA is inserted into the genome by the action of a biological vector, while direct transfer is based on physical-biochemical processes.

Different tissues and/or cells could be used according to the genetic transformation technique and according to the species or genotypes to be transformed. Generally, these tissues or cells include, without limitation, embryogenic callus, callus, protoplasts, embryos, somatic embryos, meristematic tissues, an any other part, tissue or cell of plant with regenerative capacity.

Indirect transformation is based on the bacterium-mediated system of the genus *Agrobacterium* and has been the most widely used method for obtaining transgenic plants. Advantages to this method include the ability to transfer relatively long DNA segments without rearrangement while maintaining low copy number integration of the transgenes, thus ensuring greater genotypic stability for the generated events. Several *Agrobacterium* species and strains, plasmids and protocols have been developed and adapted for genetic transformation of several plant species. The advantages of these methods include higher probabilities to single copy events, stable integration, and genetic heritage of the introduced genetic traits, as well as, consistent genic expression through generations and lower rates of gene silencing.

*Agrobacterium tumefaciens* and *A. rhizogenes* are gram negative soil phytopathogenic bacteria belonging to the Rhizobiaceae family that cause diseases in dicotyledons, known as crown and hairy root galls, respectively. In this plant-pathogen interaction there is a process of natural gene transfer between the *agrobacterium* and the plant cell wherein fragments of bacterial DNA are transferred into the plant cell (T-DNA), integrating with the nuclear genome. In its natural form, the bacterium transfers T-DNA ("transferred DNA"), which is part of the bacterial plasmid called Ti ("tumor-inducing") and integrates into the genome of infected plant cells. The T-DNA fragment that is transferred to the plant cell is comprised of genes involved in the constitutive biosynthesis of phytohormones (auxins and cytokinins), which alter the normal developmental program of infected tissue and cause tumor formation. In addition, it also contains oncogenes for the synthesis of sugars and amino acids called opines, which serve as carbon and nitrogen sources for bacteria (Oger et al. 1997). Repeated ends of 25 base pairs (bp) at the right and left borders delimit the T-DNA and are essential for its transfer. Phenolic compounds released by injured plant tissues activate specific regions (vir regions), initiating the process of transfer of T-DNA to the plant cell. *Agrobacterium* also has chromosomal (chv) genes that promote binding between bacterial and host cells, allowing the formation of the pore passage of the T-DNA-containing complex (Sheng & Citovsky. 1996).

Since the segment to be transferred is defined by its borders, any sequence flanked by the borders can be transferred to a plant by means of agrobacteria, making it possible to manipulate these sequences in order to transfer coding sequences of interest. The replacement or deletion of the coding regions of wild-type T-DNA (oncogenes) allows for the generation of non-oncogenic (disarmed) *Agrobacterium* strains, which can carry the sequences of interest. The modified T-DNA is able to transfer the sequences of interest to plants because the virulence genes (vir region) remain intact.

Additionally, the *Agrobacterium* indirect transformation system allows for the transfer of artificial plasmid constructs to plants as long as the constructs contain such T-DNA borders, which enables the flexibility to use molecular tools and materials developed for other bacterial strains.

These artificial plasmid constructs have promoters from different origins, as for example, plant promoters, viral promoters, bacterial and or chimeric promoters, besides genes that confer antibiotic resistance, herbicide resistance or tolerance, or enzymatic activity (phosphomannose isomerase (PMI)/mannose (Man)), so these markers can be used for the selection of transformed cells or plants.

These constructions also can contain auxiliaries genes which interfere with relevant morphogenesis signaling pathways, enhancing the efficiency of the genetic transformation process and regeneration of vegetal tissues. Included, without limitations, LEAFY COTYLEDON1 (Lotan et al., 1998), Lec (Lowe et al., 2002), LEAFY COTYLEDON2 (Stone et al., 2001), WUSCHEL (WUS; Zuo et al., 2002), e BABY BOOM (BBM; Boutilier et al., 2002), among others.

In a first aspect of the present invention, foreign or exogenous DNA to be introduced into the plant is cloned into a binary plasmid between the left and right border consensus sequences (T-DNA). The binary plasmid is transferred to an *Agrobacterium* cell, which is subsequently used to infect plant tissue. The T-DNA region of the vector comprising the exogenous DNA is inserted into the plant genome. The marker gene expression cassette and the characteristic gene expression cassette may be present in the same region of T-DNA, in different regions of T-DNA on the same plasmid, or in different regions of T-DNA on different plasmids. In one embodiment of the present invention, the cassettes are present in the same region as the T-DNA. One of skill in the art is familiar with the methods of indirect transformation by *Agrobacterium*.

Alternatively, direct DNA transfer can be used to directly introduce DNA into a plant cell. One method of direct DNA transfer is to bombard plant cells with a vector comprising DNA for insertion using a particle gun (particle-mediated biolistic transformation). Other methods for transformation of plant cells include protoplast transformation (optionally in the presence of polyethylene glycols); ultrasound treatment of plant tissues, cells, or protoplasts in a medium comprising the polynucleotide or the vector; microinjection of the polynucleotide or vector into plant material; microinjection, vacuum infiltration, sonication, use of silicon carbide, chemical transformation with PEG, electroporation of plant cells and the like. Between the disadvantages of direct transformation are challenges related to regeneration of plant tissue and the low transgene expression.

In addition, genetic transformation could be performed by site direct insertion through homologous recombination mediated by nucleases (genome editing). In recent years, genome editing technology based on use of engineered or chimeric nucleases has enabling the generation of genetically modified organisms in a more precise and specific way. The introduction of exogenous or foreign genes occur by homologous recombination through introduction of a Homologous recombination template (HR) having the exogeneous DNA linked to a DNA fragment homologous to the genome of the receptor organism. Between the tools available are the chimeric enzymatic system CRISPR(clustered, regularly interspaced, short palindromic repeats)—Cas, the Zinc finger (ZFN)nucleases and TAL effector nucleases (TALENs). Crispr-Cas systems are enzymatic systems comprising two main components: a endonuclease (Cas) and a guide-RNA (single-guide RNA—sgRNA; a guide to the specific cleavage site of Cas endonuclease). The guide RNA may also comprise of two components: a Crispr RNA (crRNA)—a sequence of 17-20 mer complementary to specific DNA genomic sequences and, optionally, of a tracr RNA. The specific cleavage performed by endonuclease and guide by the sgRNA would be repair by homologous recombination, specifically inserting the exogenous DNA flanked by the homologous sequences to the cleavage site. The introduction of this enzymatic system to the cell could occur by several manners, using plasmids, through direct or indirect transformation, or using carriers like proteins and other chemical agents. The expression of the system components would occur in a transient or stable manner, using the cellular machinery of the receptor organism or being realized in a exogeneous way, in vitro, delivering to the target cell or tissue all the components ready to use (endonucleases+sgRNA, in vitro transcribed and combined before cell delivery). The description presented herein is not exhaustive and should not limit the use of different variations, systems and methods of genome editing on scope of the present invention, known in the State of the Art and even the ones not yet discovered.

Following transformation, transgenic plants are regenerated from the transformed plant tissue and the progeny that have exogenous DNA can be selected using an appropriate marker such as kanamycin or ammonium glufosinate resistance. One skilled in the art is familiar with the composition of suitable regeneration media.

Alternatively, other selection methods could be applied, without the insertion of any gene marker in the host genome (receptor organism) as described before.

In a preferred embodiment, genetic transformation is mediated through a bacterium of the genus *Agrobacterium*.

In an even more preferred embodiment, genetic transformation is mediated by *Agrobacterium tumefaciens*.

CTC91087-6 event exhibits a new genotype comprising two expression cassettes. The first expression cassette comprises a promoter suitable for plant expression operably linked to a gene encoding a Cry1Ac insecticide toxin useful in controlling lepidopteran insect pests and a suitable polyadenylation signal. The second expression cassette comprises a promoter suitable for plant expression operably linked to a gene encoding a protein used as a selective marker in obtaining the event of the present invention.

Promoters suitable for plant expression may be isolated from plants or from other organisms. Several promoters have been isolated or developed including constitutive promoters, "on and off" promoters, and promoters that are responsive to tissue-specific abiotic stresses, among others. Many of these promoters have intronic sequences described as relevant for proper gene expression. In a preferred aspect of the invention, promoters are constitutive promoters and may be selected from the non-limiting group consisting of CaMV 35S, CoYMV (*Commelina* yellow mottle virus), FMV 35S, Ubiquitin, Actin Rice Promoter (Act-1), Act-2, nopaline synthase promoter (NOS), octopine synthase promoter (OCS), corn alcohol dehydrogenase promoter (Adh-1), PvUbi1, among others.

In one embodiment of the invention, the promoter is the maize Ubiquitin (pUBI) gene promoter. In an even more preferred embodiment, the maize Ubiquitin promoter contains an intron in the 5' sequence of the leader RNA.

The promoter region of the present invention (UBI-1) has 1992 base pairs which are subdivided into: promoter fragment (899 bases), first exon of the polyubiquitin-1 gene (83 bases) and first intron (1,010 bases).

Additional elements such as enhancer sequences and transporters (transporters) may also be incorporated into the expression cassette for the purpose of enhancing gene expression levels, for example, transcriptional or translation enhancers such as CaMV 35S enhancers, FMV 35S, Nos, supP, among others.

Terminator sequences are also contemplated on the expression cassette. Examples of suitable and functional plant polyadenylation signals include those from the *Agrobacterium tumefaciens* nopaline synthase gene (nos), proteinase inhibitor II gene rbcS (pea ribulose-1,5-bisphosphate carboxylase small subunit), Lhcb1 (tobacco chlorophyll a/b-binding proteins), CaMV 35S, octopine synthase, alpha-tubulin gene, among others.

In one embodiment of the present invention, the polyadenylation signal is that derived from the *Agrobacterium tumefaciens* nopaline synthase (nos) gene.

Preferably, the expression of cry1Ac and bar genes is regulated by the maize ubiquitin gene promoter—UBI-1 (which has an endogenous intron). Both expression cassettes use the *Agrobacterium tumefaciens* nopaline synthase terminator—NOS.

The cry1Ac gene encodes a 615 amino acid toxin with an estimated molecular weight of 68 kDa, originating from *Bacillus thuringiensis* serovar kustaki (strain HD73), which confers resistance to *Diatraea saccharalis* (cane borer). The present invention contemplates gene modifications for expression of the active tryptic nucleus of native Cry1Ac protein only. Thus, in a preferred embodiment of the present invention, the polynucleotide encoding the Cry1Ac protein is truncated, encoding the 52 kDa tryptic insecticide nucleus. In a more preferred embodiment, the Cry1Ac protein is SEQ ID NO 34. The present invention also contemplates sequences having at least 80%, preferably 85%, 90%, 95%, 98%, 99% or 100% of identity with SEQ ID NO: 34. The tryptic nucleus is responsible for the insecticidal activity of the protein, binding to specific proteins of the insect's gut leading to disruption of the functional and anatomical integrity of this organ. Ingestion of the Cry1Ac protein by the target insect causes altered nutrient absorption, which leads to rapid toxicity and subsequent death of the insect.

According to the invention, the polynucleotide encoding the Cry1Ac protein may have optimized (or otherwise altered) codons to improve expression in plant material. Such codon optimization may be used to alter the predicted secondary structure of the RNA transcription product produced in any transformed cell or to destroy the cryptic RNA instability elements present in the unchanged transcription product, thereby enhancing the stability and/or availability of the transcription product in the transformed cell.

Preferably, the cry1Ac gene present at the event of the invention corresponds to a truncated synthetic DNA sequence optimized with preferred sugarcane codons. In an even more preferred aspect of the present invention, the cry1Ac gene has the sequence SEQ ID NO: 20. The invention also contemplates sequences having at least 80%, preferably 85%, 90%, 95%, 98%, 99% or 100% of identity with SEQ ID NO: 20.

Several marker genes for plant event selection have already been characterized, including some that confer tolerance to antibiotics and others that confer resistance to herbicides. Examples of marker genes that may be selected for use in the present invention include those that confer resistance or tolerance to hygromycin, kanamycin, gentamicin, glyphosate, ammonium glufosinate or resistance to toxins such as eutypine. Other forms of selection are also available such as hormone-based selection systems, visual selection through expression of fluorescent proteins, mannose isomerase, xylose isomerase, among others. In one embodiment of the present invention, the event selection marker gene is one which confers tolerance to ammonium glufosinate.

In a preferred embodiment of the invention, the marker gene used in the second expression cassette is the bialaphos resistance (bar) gene, which encodes the 183 amino acid phosphinothricin acetyltransferase (Pat) enzyme having an estimated molecular weight of 22 kDa. In an even more preferred aspect of the present invention, the bar gene has the sequence SEQ ID NO: 21. Phosphinothricin acetyltransferase confers resistance to the ammonium glufosinate herbicide, which was used in the initial selection process of transformants. The bar gene used as a selective marker to obtain the event of the present invention is derived from *Streptomyces hygroscopicus*. The PAT protein can also be expressed from the pat gene of *Streptomyces viridochromogenes*.

The use of selection marker genes, such as the bar gene, is essential for selecting transformed cells during the process of transformation (HORSCH et al., 1985). The purpose of insertion of the bar gene in the event of the present invention was therefore the selection of cells transformed with the cry1Ac gene. In particular, this gene was chosen because the ammonium glufosinate herbicide is not used for weed control in sugarcane cultivation and cannot be used in the handling of the event of the invention under field conditions.

In addition to the expression cassettes described, additional expression cassettes may also be used in event CTC91087-6.

The first and second expression cassettes comprised in event CTC91087-6 may be introduced into the plant on the same or on different plasmids. If the first and second expression cassettes are located on the same plasmid and are introduced into the plant by an *Agrobacterium*-mediated transformation method, they may be present within the same or different regions of T-DNA. In one embodiment of the present invention, the first and second expression cassettes are present in the same region as the T-DNA.

More particularly, the event of the present invention was obtained by *Agrobacterium tumefasciens*-mediated transformation with a genetic construct comprising a DNA fragment (T-DNA) containing the cry1Ac and bar gene expression cassettes. Preferably, the genetic construct of the present invention comprises the nucleotide of sequence SEQ ID NO:1.

The event of the present invention was obtained by *Agrobacterium tumefasciens*-mediated transformation containing the T-DNA fragment as defined above (SEQ ID NO:1).

Figure 4:
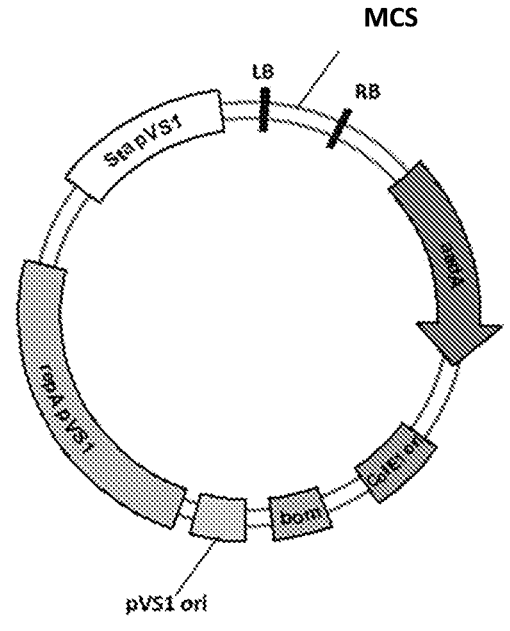
FIG. 4 represents the plasmid used as a base for constructing the plasmid used in the present invention.
Figure 5:
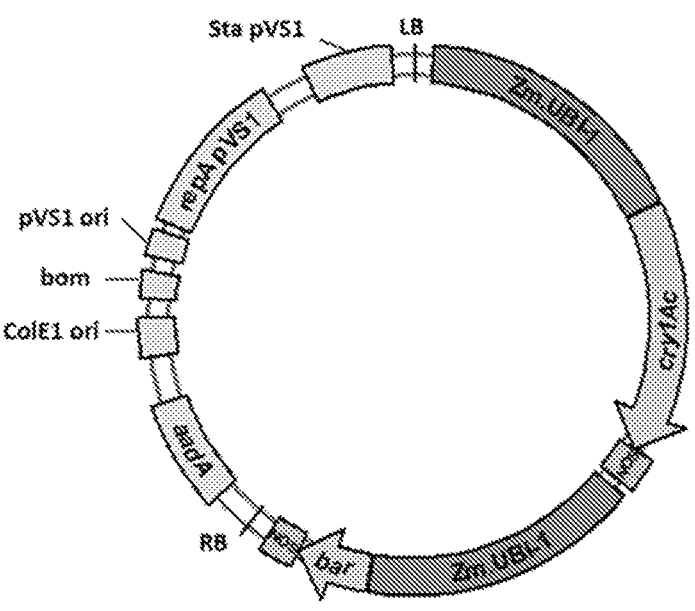
FIG. 5 represents the resulting plasmid used to obtain the event of interest.

This T-DNA fragment was inserted into a binary plasmid that contains in its host spectrum the bacteria *Escherichia coli* and *Agrobacterium tumefaciens*. Specific genetic elements and the origins of the components of the original binary plasmid of the present invention are shown in FIG. 4. The binary plasmid comprising the construct of the present invention is depicted in FIG. 5.

In a preferred embodiment, the genetic construct of the present invention comprises the sequence of SEQ ID NO:14.

Said construct is transferred to an *Agrobacterium tumefaciens* (vector) strain by techniques known to one of ordinary skill in the art, such as electroporation or thermal shock, among others.

In an even more preferred embodiment, the vector is an *Agrobacterium tumefaciens* strain EHA105.

A method for producing the event of interest is further described. In a preferred embodiment, the said method comprising the steps of:

a) introducing a genetic construct into an *Agrobacterium* strain;
   b) obtaining embryogenic callus from immature leaf rolls or top stalks of sugarcane (*Saccharum* spp.);
   c) co-cultivating embryogenic callus with a culture of *Agrobacterium;*
   d) selecting transformed cells containing the functional fragment in culture medium containing ammonium glufosinate; and
   e) regenerating transformed sugarcane plants.

In one embodiment, the step a) of the method of producing a genetically modified sugarcane (*Saccharum* spp.) plant of event CTC91087-6 comprises introducing a genetic construct comprising SEQ ID NO: 20 and SEQ ID NO: 21 into an *Agrobacterium* strain. Additionally, step e) of said method comprises regenerating transformed sugarcane plants, wherein the genetically modified sugarcane plants comprise SEQ ID NO: 20 and SEQ ID NO: 21. The invention also contemplates, a plant part, plant cell, plant tissue, or seed of the genetically modified sugarcane plants produced by the method described herein.

Those skilled in the art are familiar with the composition of suitable culture media for the generation of embryogenic callus (stage b), as well as the means of the co-cultivation stages (stage c: co-cultivation+rest), selection (stage d), and regeneration (stage e; regeneration+elongation). Preferably, the culture media used are based on compositions comprising ingredients such as MS salts (Murashige and Skoog, 1962), sucrose, and vitamins B5. Optionally, the following can also be added: amino acids selected from the group comprising proline and asparagine; casein hydrolysate; citric acid; mannitol; copper sulfate; glycine; gelling agent; auxins; antibiotics; acetosyringone; and selection agents. The use of auxins is especially important in embryogenic callus generation, co-cultivation and selection, as well as ammonium glufosinate in the selection medium.

The "co-cultivation" step refers to the incubation of plant tissue that has been infected or contacted with *Agrobacterium* to allow the transfer of *Agrobacterium* T-DNA to plant cells. This stage corresponds to the period from the moment immediately after inoculation (contact of *Agrobacterium* with plant tissue) until the moment the bacterium is removed or inactivated.

Inoculated tissue may be co-cultured for about 1 to 30 days, preferably from 1 to 20 days, or more preferably from 1 to 10 days.

During the co-cultivation step, the temperature may be any suitable temperature known in the art for the target plant. Illustratively, for sugarcane, the temperature may range from about 15° C. to about 30° C. and from about 16° C. to about 29° C. In some embodiments, the co-cultivation step occurs in the absence of light.

Following co-cultivation with *Agrobacterium*, the medium is removed and the cells are transferred to a culture medium lacking *Agrobacterium*. The cells are then incubated in the dark at a temperature between about 20° C. and about 26° C. for a period of 1 to 20 days.

The method provided herein further includes selecting cells comprising at least one copy of the genetic sequence of interest. "Select" as used herein means the situation in which a selective agent is used for transformants, wherein said selective agent will allow preferential growth of plant cells containing at least one copy of the marker gene positioned within the T-DNA. Whereas, those cells that were not transformed will not contain the marker gene that permits survival in the selective agent. As indicated above, any suitable selection marker may be used. Preferably, the selection marker gene used is the bar gene, which encodes an enzyme that confers resistance to ammonium glufosinate.

In some embodiments, an agent that inhibits *Agrobacterium* growth is also added.

Selection may occur under light or dark conditions, depending on the plant species being transformed and on the genotype, for example. In some cases, embryogenic callus or other tissues undergoing transformation may be subcultured at regular or irregular intervals in the same medium. In the case of callus transformation, individual calluses can be kept separate to ensure that only one plant is regenerated by each callus (thus ensuring that all regenerated plants are derived from independent transformation events). In a preferred embodiment, the selection step occurs in the dark using ammonium glufosinate as a selection agent for about 1 to 10 weeks. More preferably the selection step occurs for about 2 to 5 weeks.

After the selection period, plant tissue that has continued to grow in the presence of the selection agent, and has therefore been genetically modified, can be manipulated and regenerated by placing it in suitable culture media and growth conditions. The transgenic plants thus obtained can be tested for the presence of the DNA of interest. For the purpose of this invention, the term "regenerate" refers to the formation of a plant comprising both an aerial part and roots. Regenerated plants can be planted on suitable substrate (such as soil) and transferred to the greenhouse. As used herein, "genetically modified" or "transgenic" or "stably transformed" means a plant cell, plant part, plant tissue, or plant that comprises a DNA sequence of interest that is introduced into its genome by transformation.

In one embodiment, the bacterium is of the genus *Agrobacterium*.

In a more preferred embodiment, the bacterium is *Agrobacterium tumefaciens*.

In an even more preferred embodiment, the bacterium is an *Agrobacterium tumefaciens* strain EHA105.

The present invention also relates to the characterization of the selected event (CTC91087-6) and methods of detecting plant material derived therefrom. Analytical methods for detection and characterization of transgenic plants include indirect methods (protein-based detection methods) or direct methods (DNA-based detection methods).

The definition of the T-DNA stable integration site in the host cell genome and the characterization of its flanking sequences is necessary for the development and validation of methodologies for the unambiguous identification and characterization of the event.

Figure 3:
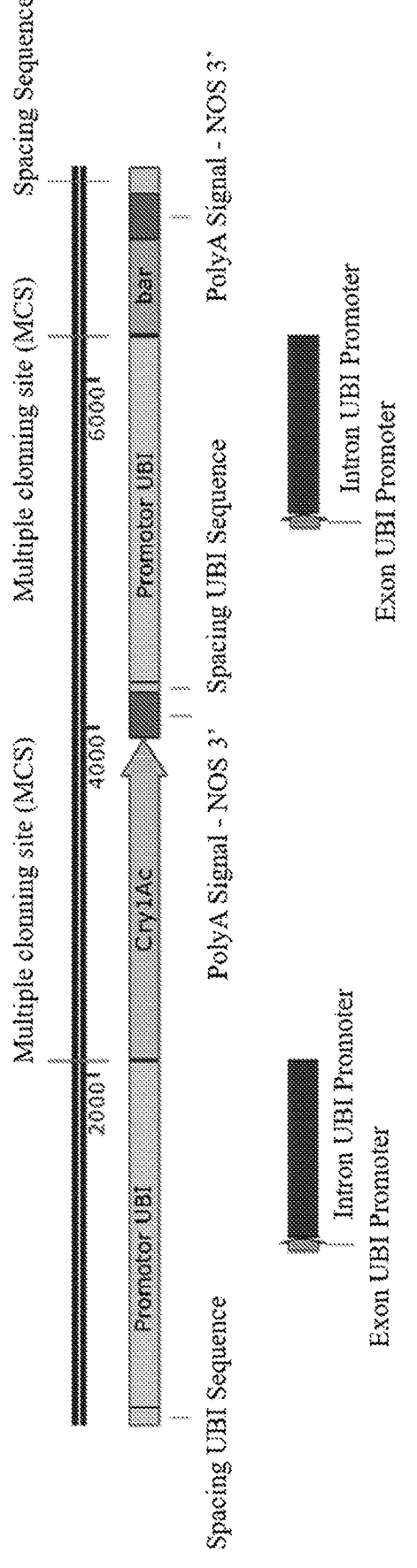
FIG. 3 represents the map of the T-DNA introduced in the event of the present invention.

To identify the flanking regions at the ends of the T-DNA insert in event CTC91087-6, several DNA amplification and sequencing experiments were performed. Inverse PCR (iPCR) assays were performed at both ends of the T-DNA to isolate and clone the flanking regions of the insert. Subsequently, the fragments obtained and isolated were sequenced using the Sanger method to validate the results obtained by iPCR. The genetic insertion map present in event CTC91087-6 resulting from the data generated by these experiments is shown in FIG. 3 and SEQ ID NO: 2. The flanking sequences of event CTC91087-6 are shown in SEQ ID NO: 23 and SEQ ID NO: 24.

According to one aspect of the invention, a polynucleotide comprising at least 14 contiguous nucleotides of the 26 nucleotide sequence of SEQ ID NO: 18 is provided. In one embodiment, a polynucleotide comprising at least 15 contiguous nucleotides of the 26 nucleotide sequence of SEQ ID NO: 18 is provided. In one embodiment, a polynucleotide comprising at least 16 contiguous nucleotides of the 26 nucleotides of SEQ ID NO: 18 is provided. In one embodiment, said polynucleotide comprises at least 17 contiguous nucleotides of the 26 nucleotides of SEQ ID NO: 18. In one embodiment, said polynucleotide comprises at least 18 contiguous nucleotides of the 26 nucleotide sequence of SEQ ID NO: 18. In one embodiment, said polynucleotide comprises at least 19 contiguous nucleotides of the 26 nucleotide sequence of SEQ ID NO: 18. In one embodiment, said polynucleotide comprises at least 20 contiguous nucleotides of the 26 nucleotide sequence of SEQ ID NO: 18. In one embodiment, said polynucleotide comprises at least 21 contiguous nucleotides of the 26 nucleotide sequence of SEQ ID NO: 18. In one embodiment, said polynucleotide comprises at least 22 contiguous nucleotides of the 26 nucleotide sequence of SEQ ID NO: 18. In one embodiment, said polynucleotide comprises at least 23 contiguous nucleotides of the 26 nucleotide sequence of SEQ ID NO: 18. In one embodiment, said polynucleotide comprises at least 24 contiguous nucleotides of the 26 nucleotide sequence of SEQ ID NO: 18. In one embodiment, said polynucleotide comprises at least 25 contiguous nucleotides of the 26 nucleotide sequence of SEQ ID NO: 18. In one embodiment, said polynucleotide comprises SEQ ID NO: 18. In one further aspect of the invention, said polynucleotide comprises SEQ ID NO: 13.

According to one aspect of the invention, a polynucleotide comprising at least 14 contiguous nucleotides of the 26 nucleotide sequence of SEQ ID NO 19 is provided. In one embodiment, a polynucleotide comprising at least 15 contiguous nucleotides of the 26 nucleotide sequence of SEQ ID NO 19 is provided. According to one aspect of the invention, a polynucleotide comprising at least 16 contiguous nucleotides of the 26 nucleotide sequence of SEQ ID NO 19 is provided. In one embodiment, a polynucleotide comprising at least 17 contiguous nucleotides of the 26 nucleotide sequence of SEQ ID NO: 19 is provided. In one embodiment, a polynucleotide comprising at least 18 contiguous nucleotides of the 26 nucleotide sequence of SEQ ID NO: 19 is provided. In one embodiment, a polynucleotide comprising at least 19 contiguous nucleotides of the 26 nucleotide sequence of SEQ ID NO: 19 is provided. In one embodiment, a polynucleotide comprising at least 20 contiguous nucleotides of the 26 nucleotide sequence of SEQ ID NO: 19 is provided. In one embodiment, a polynucleotide comprising at least 21 contiguous nucleotides of the 26 nucleotide sequence of SEQ ID NO: 19 is provided. In one embodiment, a polynucleotide comprising at least 22 contiguous nucleotides of the 26 nucleotide sequence of SEQ ID NO: 19 is provided. In one embodiment, a polynucleotide comprising at least 23 contiguous nucleotides of the 26 nucleotide sequence of SEQ ID NO: 19 is provided. In one embodiment, a polynucleotide comprising at least 24 contiguous nucleotides of the 26 nucleotide sequence of SEQ ID NO: 19 is provided. According to one aspect of the invention, a polynucleotide comprising at least 25 contiguous nucleotides of the 26 nucleotides of SEQ ID NO: 19 is provided. In one embodiment, a polynucleotide comprising SEQ ID NO: 19 is provided. In one aspect of the invention, a polynucleotide comprising SEQ ID NO: 12 is provided.

In a further aspect of the present invention a polynucleotide comprising the sequence of SEQ ID NO: 5 is provided. In still another aspect of the invention, a polynucleotide comprising the sequence SEQ ID NO: 22 is provided.

According to one aspect of the invention, there is provided a plant comprising at least 14 contiguous nucleotides of the 26 nucleotide sequence of SEQ ID NO: 18. In one embodiment, a plant comprising at least 15 contiguous nucleotides of the 26 nucleotide sequence of SEQ ID NO: 18 is provided. According to one aspect of the invention, there is provided a plant comprising at least 16 contiguous nucleotides of the 26 nucleotide sequence of SEQ ID NO: 18. In one embodiment, a plant comprising at least 17 contiguous nucleotides of the 26 nucleotide sequence of SEQ ID NO: 18 is provided. In one embodiment, a plant comprising at least 18 contiguous nucleotides of the 26 nucleotide sequence of SEQ ID NO: 18 is provided. In one embodiment, a plant comprising at least 19 contiguous nucleotides of the 26 nucleotide sequence of SEQ ID NO: 18 is provided. In one embodiment, a plant comprising at least 20 contiguous nucleotides of the 26 nucleotide sequence of SEQ ID NO: 18 is provided. In one embodiment, a plant comprising at least 21 contiguous nucleotides of the 26 nucleotide sequence of SEQ ID NO: 18 is provided. In one embodiment, a plant comprising at least 22 contiguous nucleotides of the 26 nucleotide sequence of SEQ ID NO: 18 is provided. In one embodiment, a plant comprising at least 23 contiguous nucleotides of the 26 nucleotide sequence of SEQ ID NO: 18 is provided. In one embodiment, a plant comprising at least 24 contiguous nucleotides of the 26 nucleotide sequence of SEQ ID NO: 18 is provided. In one embodiment, a plant comprising at least 25 contiguous nucleotides of the 26 nucleotide sequence of SEQ ID NO: 18 is provided. In one embodiment, a plant comprising SEQ ID NO: 18 is provided. In an additional embodiment, a plant comprising SEQ ID NO: 13 is provided.

According to one aspect of the invention, there is provided a plant comprising at least 14 contiguous nucleotides of the 26 nucleotide sequence of SEQ ID NO: 19. In one embodiment, a plant comprising at least 15 contiguous nucleotides of the 26 nucleotide sequence of SEQ ID NO: 19 is provided. In one embodiment, a plant comprising at least 16 contiguous nucleotides of the 26 nucleotide sequence of SEQ ID NO: 19 is provided. In one embodiment, a plant comprising at least 17 contiguous nucleotides of the 26 nucleotide sequence of SEQ ID NO: 19 is provided. In one embodiment, a plant comprising at least 18 contiguous nucleotides of the 26 nucleotide sequence of SEQ ID NO: 19. In one embodiment, a plant comprising at least 19 contiguous nucleotides of the 26 nucleotide sequence of SEQ ID NO: 19 is provided. In one embodiment, a plant comprising at least 20 contiguous nucleotides of the 26 nucleotide sequence of SEQ ID NO: 19 is provided. In one embodiment, a plant comprising at least 21 contiguous nucleotides of the 26 nucleotide sequence of SEQ ID NO: 19 is provided. In one embodiment, a plant comprising at least 22 contiguous nucleotides of the 26 nucleotide sequence of SEQ ID NO: 19 is provided. In one embodiment, a plant comprising at least 23 contiguous nucleotides of the 26 nucleotide sequence of SEQ ID NO: 19 is provided. In one embodiment, a plant comprising at least 24 contiguous nucleotides of the 26 nucleotides of sequence SEQ ID NO: 19 is provided. In one embodiment, a plant comprising at least 24 contiguous nucleotides of the 26 nucleotide sequence of SEQ ID NO: 19 is provided. In one embodiment, a plant comprising at least 25 contiguous nucleotides of the 26 nucleotide sequence of SEQ ID NO: 19 is provided. In one embodiment, a plant comprising SEQ ID NO: 19 is provided. In an additional embodiment, a plant comprising SEQ ID NO: 12 is provided.

In one embodiment of the present invention, said plant is a genetically modified sugarcane (*Saccharum* spp.) plant. Additionally, said plant is insect resistant and comprises the sequence SEQ ID NO: 5. Still in a further aspect, the insect resistant plant of the present invention comprises SEQ ID NO: 22. In a further embodiment, said plant is an insect-resistant sugarcane plant of event CTC91087-6 or a plant derived therefrom.

In one aspect of the invention, event CTC91087-6 is a sugarcane (*Saccharum* spp.) plant comprising SEQ ID NO: 5. In a further aspect, event CTC91087-6 comprises SEQ ID NO: 22.

In other embodiment a specific method for detection and identification of CTC91087-6 event is provided.

According to the present invention, there is provided a method of detecting plant material derived from genetically modified sugarcane of event CTC91087-6 comprising the steps of:
  a) obtaining a plant material sample for analysis;
  b) extracting DNA from the sample;
  c) providing primer pairs comprising at least a forward and a reverse primer;
  d) amplifying a region between the primer pairs; and
  e) detecting the presence of a product from amplification.
In one embodiment, the primer pairs in step c) are designed to bind to a polynucleotide comprising contiguous nucleotides of sequences selected from the group consisting of SEQ ID NO: 22 and SEQ ID NO: 29, wherein at least one pair of primers comprises contiguous nucleotides sequences selected from the group consisting of SEQ ID NO: 23, SEQ ID NO: 24, SEQ ID NO: 30 and SEQ ID NO: 31. In one embodiment, the primer pairs above (step c) are designed to bind to a polynucleotide comprising at least 14 contiguous nucleotides of sequences selected from the group consisting of SEQ ID NO: 22 and SEQ ID NO: 29, wherein at least one primer pair comprises at least 3 contiguous nucleotides of sequences selected from the group consisting of SEQ ID NO: 23, SEQ ID NO: 24, SEQ ID NO: 30 and SEQ ID NO: 31. In one embodiment, the primer pairs are designed to bind to a polynucleotide comprising at least 14 contiguous nucleotides of sequences selected from the group consisting of SEQ ID NO: 22 and SEQ ID NO: 29, wherein at least one primer pair comprises at least 7 contiguous nucleotides of sequences selected from the group consisting of SEQ ID NO: 23, SEQ ID NO: 24, SEQ ID NO: 30 and SEQ ID NO: 31. In addition, the primer pairs are designed to bind to a polynucleotide comprising at least 14 contiguous nucleotides of sequences selected from the group consisting of SEQ ID NO: 22 and SEQ ID NO: 29, wherein at least one primer pair comprises at least 14 contiguous nucleotides of sequences selected from the group consisting of SEQ ID NO: 23, SEQ ID NO: 24, SEQ ID NO: 30 and SEQ ID NO: 31.

Additionally, primer pairs according to the detection method described are designed to bind to a polynucleotide comprising contiguous nucleotides of sequences selected from the group consisting of SEQ ID NO: 22 and SEQ ID NO: 29, where at least one primer pair consists of a first primer comprising contiguous nucleotides of sequences selected from the group consisting of SEQ ID NO: 23, SEQ ID NO: 24, SEQ ID NO: 30 and SEQ ID NO: 31 and a second primer comprising contiguous nucleotides of sequences selected from the group consisting of SEQ ID NO: 2 and SEQ ID NO: 36.

In one embodiment, the primer pairs according to the detection method described are designed to bind to a polynucleotide comprising at least 14 contiguous nucleotides of sequences selected from the group consisting of SEQ ID NO: 22 and SEQ ID NO: 29, wherein at least one primer pair consists of a first primer comprising at least 3 contiguous nucleotides of sequences selected from the group consisting of SEQ ID NO: 23, SEQ ID NO: 24, SEQ ID NO: 30 and SEQ ID NO: 31 and a second primer comprising at least 3 contiguous nucleotides of sequences selected from the group consisting of SEQ ID NO: 2 and SEQ ID NO: 36. In an additional embodiment, primer pairs are designed to bind to a polynucleotide comprising at least 14 contiguous nucleotides of sequences selected from the group consisting of SEQ ID NO: 22 and SEQ ID NO: 29, wherein at least one primer pair consists of a first primer comprising at least 7 contiguous nucleotides of sequences selected from the group consisting of SEQ ID NO: 23, SEQ ID NO: 24, SEQ ID NO: 30 and SEQ ID NO: 31 and a second primer comprising at least 7 contiguous nucleotides of sequences selected from the group consisting of SEQ ID NO: 2 and SEQ ID NO: 36. In addition, primer pairs are designed to bind to a polynucleotide comprising at least 14 contiguous nucleotides of sequences selected from the group consisting of SEQ ID NO: 22 and SEQ ID NO: 29, wherein at least one primer pair consists of a first primer comprising at least 14 contiguous nucleotides of sequences selected from the group consisting of SEQ ID NO: 23, SEQ ID NO: 24, SEQ ID NO: 30 and SEQ ID NO: 31 and a second primer comprising at least 14 contiguous nucleotides of sequences selected from the group consisting of SEQ ID NO: 2 and SEQ ID NO: 36.

In one embodiment, primer pairs according to the detection method described are designed to bind to a polynucleotide comprising contiguous nucleotides of sequences selected from the group consisting of SEQ ID NO: 5 and SEQ ID NO: 37, wherein at least one pair of primers comprises contiguous nucleotides of sequences selected from the group consisting of SEQ ID NO: 3, SEQ ID NO: 4, SEQ ID NO: 38 and SEQ ID NO: 39. In one embodiment, primer pairs according to the detection method described are designed to bind to a polynucleotide comprising at least 14 contiguous nucleotides of sequences selected from the group consisting of SEQ ID NO: 5 and SEQ ID NO: 37, wherein at least one primer pair comprises at least 3 contiguous nucleotides of sequences selected from the group consisting of SEQ ID NO: 3, SEQ ID NO: 4, SEQ ID NO: 38 and SEQ ID NO: 39. In one embodiment, primer pairs are designed to bind to a polynucleotide comprising at least 14 contiguous nucleotides of sequences selected from the group consisting of SEQ ID NO: 5 and SEQ ID NO: 37, wherein at least one primer pair comprises at least 7 contiguous nucleotides of sequences selected from the group consisting of SEQ ID NO: 3, SEQ ID NO: 4, SEQ ID NO: 38 and SEQ ID NO: 39. In addition, primer pairs are designed to bind to a polynucleotide comprising at least 14 contiguous nucleotides of sequences selected from the group consisting of SEQ ID NO: 5 and SEQ ID NO: 37, wherein at least one primer pair comprises at least 14 contiguous nucleotides of sequences selected from the group consisting of SEQ ID NO: 3, SEQ ID NO: 4, SEQ ID NO: 38 and SEQ ID NO: 39.

In one embodiment, primer pairs according to the detection method described are designed to bind to a polynucleotide comprising contiguous nucleotides of sequences selected from the group consisting of SEQ ID NO: 5 and SEQ ID NO: 37, wherein at least one primer pair consists of a first primer comprising contiguous nucleotides of sequences selected from the group consisting of SEQ ID NO: 3, SEQ ID NO: 4, SEQ ID NO: 38 and SEQ ID NO: 39 and a second primer comprising contiguous nucleotides of sequences selected from the group consisting of SEQ ID NO: 2 and SEQ ID NO: 36. In one embodiment, primer pairs, according to the detection method described, are designed to bind to a polynucleotide comprising at least 14 contiguous nucleotides of sequences selected from the group consisting of SEQ ID NO: 5 and SEQ ID NO: 37, wherein at least one primer pair consists of a first primer comprising at least 3 contiguous nucleotides of sequences selected from the group consisting of SEQ ID NO: 3, SEQ ID NO: 4, SEQ ID NO: 38 and SEQ ID NO: 39 and a second primer comprising at least 3 contiguous nucleotides of sequences selected from the group consisting of SEQ ID NO: 2 and SEQ ID NO: 36. In one embodiment, primer pairs are designed to bind to a polynucleotide comprising at least 14 contiguous nucleotides of sequences selected from the group consisting of SEQ ID NO: 2, SEQ ID NO: 5, SEQ ID NO: 36 and SEQ ID NO: 37, wherein at least one primer pair consists of a first primer comprising at least 7 contiguous nucleotides of sequences selected from the group consisting of SEQ ID NO: 3, SEQ ID NO: 4 SEQ ID NO: 38 and SEQ ID NO: 39 and a second primer comprising at least 7 contiguous nucleotides of sequences selected from the group consisting of SEQ ID NO: 2 and SEQ ID NO 36. Additionally, primer pairs are designed to bind to a polynucleotide comprising at least 14 contiguous nucleotides of sequences selected from the group consisting of SEQ ID NO: 5 and SEQ ID NO: 37, wherein at least one primer pair consists of a first primer comprising at least 14 contiguous nucleotides of sequences selected from the group consisting of SEQ ID NO: 3, SEQ ID NO: 4, SEQ ID NO: 38 and SEQ ID NO: 39 and a second primer comprising at least 14 contiguous nucleotides of sequences selected from the group consisting of SEQ ID NO: 2 and SEQ ID NO: 36.

It is well known, especially to those skilled in the art, that the DNA molecule (or DNA) is made up of two strands (of nucleotides) that are held together by hydrogen bridges between the nucleotide bases. Pairing occurs according to the complementarity of the bases, following the general rule of: Adenine with Thymine and Cytosine with Guanine. Thus, although representation of nucleotide sequences is performed for only one of the strands, their complementary strand or complementary sequence is included within the scope of this invention and is considered for the definition of primers and probes described herein.

Methods for obtaining samples for DNA extraction are widely known to one of ordinary skill in the art and include the collection of any plant material derived from the CTC91087-6 transgenic event such as stems, roots, and leaves. Preferably, the samples are obtained from intact leaves. Plant DNA extraction methods include, without limitation, those based on the use of CTAB detergent (Alianabi et al., 1999), (optionally) followed by further sample purification with cesium chloride or ammonium acetate, as well as other commercially available methods.

Primer pairs suitable for use in this detection method may be designed using parameters well known to those skilled in the art of molecular biology now that SEQs ID Nos: 2, 3, 4, 5, 22, 23, 24, 29, 30, 31, 36, 37, 38 and 39 have become available. For example, one or both primers of the pair may be designed to be construct-specific, trait gene-specific, promoter-specific, sequence-specific to the junction between inserted DNA and genomic DNA, and/or flanking sequence-specific.

There are many amplification methods that can be used in accordance with this aspect of the invention. One of the most common amplification techniques known to those skilled in the art, is the polymerase chain reaction (PCR). The amplification product of a PCR reaction can be visualized by staining the nucleotide chain with a fluorescent tag such as ethidium bromide and then exciting it with UV light (typically after size separation using agarose gel electrophoresis).

One embodiment of the present invention employs variations of the PCR principle such as quantitative real-time PCR, nested PCR, inverse PCR (iPCR), digital PCR, Long PCR, Touchdown PCR, Hot Start PCR, Multiplex PCR, among others. The amplification product can also be detected by different methodologies which are contemplated in the present invention, such as the SYBR Green™ system which emits fluorescence when this reagent binds to double stranded DNA and the TAQMAN® system where detection is based on the interaction of fluorescent probes. The TAQMAN® methodology uses a probe that is complementary to the intended PCR product segment located between the reaction primers. During the hybridization stage of the PCR cycle the probe is bound to the target DNA, and during Taq polymerase extension, through its 5'-exonuclease activity, it removes the probe, releasing the fluorochrome and emitting fluorescence. Additional embodiments of this aspect of the present invention include, but are not limited to: loop-mediated isothermal amplification (LAMP), capillary gel electrophoresis (CGE), microarray technology Luminex, "DNA walking" and Next Generation Sequencing (NGS), Sanger method, Illumina, among others.

The present invention describes a specific detection methodology based on the quantitative real-time PCR (qPCR) technique known as "Plus-Minus" or "Presence—Absence," presenting two variations of the methodology: SYBR GREEN™ and TAQMAN® technology.

In one embodiment of the present invention, primer pairs are provided wherein the forward primer consists of SEQ ID NO: 6 and the reverse primer consists of SEQ ID NO: 7 and/or the forward primer is SEQ ID. NO: 8 and the reverse primer is SEQ ID NO: 9.

In an additional embodiment, the primer pairs used in step c) of the method of detecting plant material from genetically modified sugarcane of event CTC91087-6 comprise forward primer consists of SEQ ID NO: 6 and the reverse primer consists of SEQ ID NO: 7 and/or the forward primer is SEQ ID NO: 8 and the reverse primer is SEQ ID NO: 9. In addition, the amplicon (product from amplification) produced by the primers of SEQ ID NO: 6 and SEQ ID NO: 7 is viewed through a labeled probe of SEQ ID NO: 10. Alternatively, the amplicon produced by the primers of SEQ ID NO: 8 and SEQ ID NO: 9 is visualized through a labeled probe of SEQ ID NO 11. Thus, it is an aspect of the present invention that detection of the of the product from amplication obtained by the use of primers SEQ ID NO: 6 and SEQ ID NO: 7 and/or SEQ ID NO: 8 and SEQ ID NO: 9 is performed through hybridization of a probe comprising SEQ ID NO: 10 or SEQ ID NO: 11.

In one embodiment of the present invention, the region amplified by said method (the amplicon or product from amplification) is between 80 and 1000 base pairs in length. In an additional embodiment, the amplicon is between 100 and 300 base pairs in length. In one preferred embodiment, the amplicon obtained using the primers SEQ ID NO: 6 and SEQ ID NO: 7 is 117 base pairs in length, as defined by SEQ ID NO: 12. In another preferred embodiment, the amplicon obtained through the use of primers SEQ ID NO: 8 and SEQ ID NO: 9 is 149 base pairs in length, as defined by SEQ ID NO: 13.

Figure 6:
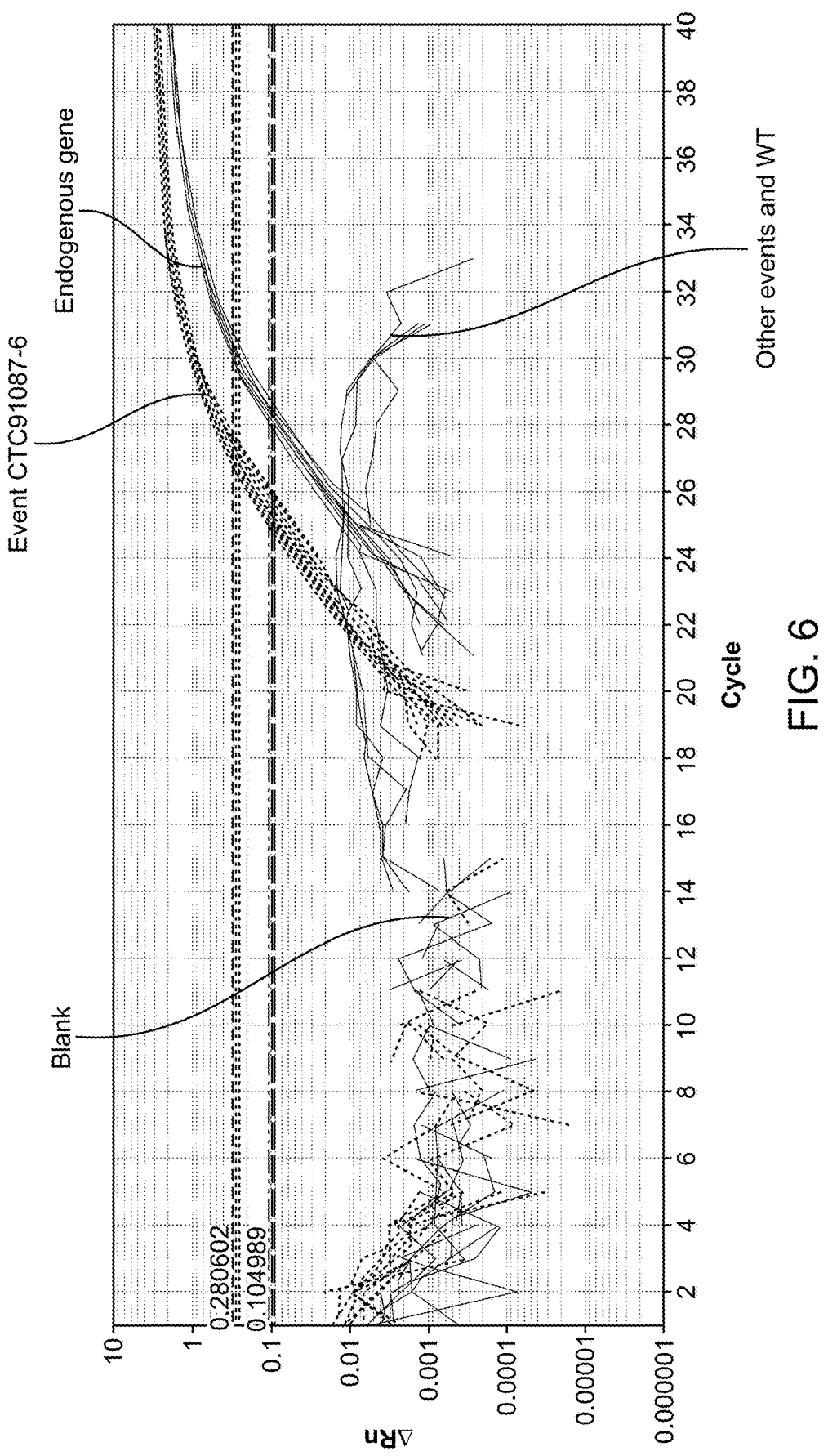
FIG. 6 is the graph of qPCR amplification via TAQMAN® (relative fluorescence x cycle) for the event of interest.

FIGS. 6 (event-specific detection reaction of the invention via TAQMAN®) and 7 (SYBR GREEN™ assay) represent the validation of both Methods.

Primers and probes described in the present invention may be used in combination to detect the CTC91087-6 event. Thus, a further embodiment of the present invention involves the use of multiplex PCR to identify plant material from the CTC91087-6 event.

Alternative primers and probes for the detection and characterization of the CTC91087-6 event are included in the invention. These and other variations may be used with but are not limited to any of the direct detection methods described above.

Additionally, the CTC91087-6 event can be detected from plant material by hybridizing DNA samples to the probes. Specifically, the present invention describes a method of detecting material from the genetically modified sugarcane event CTC91087-6 which comprises the steps of:

a) obtaining a plant material sample for analysis;
b) DNA or RNA extraction from the sample;
c) providing a probe designed to bind to a polynucleotide comprising 14 or more contiguous nucleotides of sequences selected from the group consisting of SEQ ID NO: 18, SEQ ID NO: 19, SEQ ID NO: 32 and SEQ ID NO: 33, when the polynucleotide is single stranded;
d) hybridizing said probe with the sample, and
e) detecting the actual hybridization of the probe.

According to one aspect of the invention, a probe designed to bind to a polynucleotide comprising at least 15 contiguous nucleotides of sequences selected from the group consisting of SEQ ID NO: 18, SEQ ID NO: 19, SEQ ID NO: 32 and SEQ ID NO: 33 is provided. In one embodiment, a probe designed to bind to a polynucleotide comprising at least 16 contiguous nucleotides of sequences selected from the group consisting of SEQ ID NO: 18, SEQ ID NO: 19, SEQ ID NO: 32 and SEQ ID NO: 33 is provided. According to one aspect of the invention, a probe designed to bind to a polynucleotide comprising at least 17 contiguous nucleotides of sequences selected from the group consisting of SEQ ID NO: 18, SEQ ID NO: 19, SEQ ID NO: 32 and SEQ ID NO: 33 is provided. In one embodiment, said polynucleotide comprises at least 18 contiguous nucleotides of sequences selected from the group consisting of SEQ ID NO: 18, SEQ ID NO: 19, SEQ ID NO: 32 and SEQ ID NO: 33. In one embodiment, said polynucleotide comprises at least 19 contiguous nucleotides of sequences selected from the group consisting of SEQ ID NO: 18, SEQ ID NO: 19, SEQ ID NO: 32 and SEQ ID NO: 33. In one embodiment, said polynucleotide comprises at least 19 contiguous nucleotides of sequences selected from the group consisting of SEQ ID NO: 18, SEQ ID NO: 19, SEQ ID NO: 32 and SEQ ID NO: 33. In one embodiment, said polynucleotide comprises at least 20 contiguous nucleotides of sequences selected from the group consisting of SEQ ID NO: 18, SEQ ID NO: 19, SEQ ID NO: 32 and SEQ ID NO: 33. In one embodiment, said polynucleotide comprises at least 21 contiguous nucleotides of sequences selected from the group consisting of SEQ ID NO: 18, SEQ ID NO: 19, SEQ ID NO: 32 and SEQ ID NO: 33. In one embodiment, said polynucleotide comprises at least 22 contiguous nucleotides of sequences selected from the group consisting of SEQ ID NO: 18, SEQ ID NO: 19, SEQ ID NO: 32 and SEQ ID NO: 33. In one embodiment, said polynucleotide comprises at least 23 contiguous nucleotides of sequences selected from the group consisting of SEQ ID NO: 18, SEQ ID NO: 19, SEQ ID NO: 32 and SEQ ID NO: 33. In one embodiment, said polynucleotide comprises at least 24 contiguous nucleotides of sequences selected from the group consisting of SEQ ID NO: 18, SEQ ID NO: 19, SEQ ID NO: 32 and SEQ ID NO: 33. According to one aspect of the invention, a polynucleotide comprising at least 25 contiguous nucleotides of sequences selected from the group consisting of SEQ ID NO: 18, SEQ ID NO: 19, SEQ ID NO: 32 and SEQ ID NO: 33 is provided. According to one aspect of the invention, a polynucleotide comprising at least 26 contiguous nucleotides of sequences selected from the group consisting of SEQ ID NO: 18, SEQ ID NO: 19, SEQ ID NO: 32 and SEQ ID NO: 33 is provided.

The probe may be, for example, a PCR product or a restriction digest fragment. In a further embodiment, the probe as described herein may be labeled with a fluorescent, radioactive, enzymatic, or other label suitable to enable hybridization to be detected. The person skilled in the art will now know how to design suitable probes given the advantage of the present disclosure.

In an additional embodiment, a probe hybridization method is provided to the sample under stringent conditions (high specificity). Stringent hybridization conditions are well known to those skilled in the art. Examples of stringent conditions include: hybridization at a temperature of approximately 65° C. in a solution containing 6×SSC, 0.01% SDS and 0.25% skimmed milk powder followed by washing at the same temperature in a solution containing 0.2×SSC and 0.1% SDS.

Suitable techniques for detecting plant material derived from event CTC91087-6 based on the hybridization principle include, but are not limited to, Southern Blots and in situ hybridization. One of skill in the art is familiar with such techniques.

Typically, these techniques involve incubating a probe with a sample, washing to remove the unbound probe, and detecting whether the probe has hybridized. Said detection method is dependent upon the type of label attached to the probe. For example, a radio-labelled probe can be detected by exposure to and development of X-ray film. Alternatively, an enzymatically labeled probe may be detected by converting a substrate to effect a color change.

Additionally, another aspect of the invention contemplates a method for detecting plant material derived from event CTC91087-6, which comprises: obtaining a sample for analysis; providing an antibody designed to bind to a Cry or Pat protein contained within a plant comprising at least 14 contiguous nucleotides of SEQ ID NO: 18 and/or SEQ ID NO: 19; incubating said antibody with the sample; and detecting whether the antibody bound. In one embodiment of the present invention, said Cry protein is encoded by nucleotide sequence SEQ ID NO: 20 and said Pat protein is encoded by nucleotide sequence SEQ ID NO: 21. In an additional embodiment, said Cry protein comprises SEQ ID NO: 34 and said Pat protein comprises SEQ ID NO: 35.

Suitable methods for detecting plant material derived from the CTC91087-6 event based on said antibody binding include (but are not limited to): western blots, ELISA (Enzyme-Linked ImmunoSorbent Assays), and mass spectrometry (e.g. surface-enhanced laser desorption/ionization (SELDI)). One of skill in the art is familiar with these immunological techniques. Typical steps include incubating a sample with an antibody that binds to the Cry or Pat protein, washing for removal of unbound antibody, and detecting whether the antibody has bound. Many such detection methods are based on enzymatic reactions: for example, the antibody may be linked with an enzyme such as peroxidase and upon application of a suitable substrate, a color change is detected. Such antibodies may be monoclonal or polyclonal.

Another aspect the invention contemplates a method for detecting plant material derived from event CTC91087-6, which comprises: obtaining a sample for analysis; providing a protein extract from the sample; providing test strips designed to detect the presence of a Cry or Pat protein in a plant comprising at least 14 contiguous nucleotides of SEQ ID NO: 18 and/or SEQ ID NO: 19; incubating the test strips with the sample; and detecting. In one embodiment of the present invention, said Cry protein is encoded by nucleotide sequence SEQ ID NO: 20 and the Pat protein is encoded by nucleotide sequence SEQ ID NO: 21. In an additional embodiment, said Cry protein comprises SEQ ID NO: 34 and said Pat protein comprises SEQ ID NO: 35.

In one embodiment of the invention there is provided a method for detecting plant material derived from the CTC91087-6 event, said method comprising: obtaining a sample derived from the CTC91087-6 event and a sample from a non-transgenic sugarcane variety for analysis (control); subjecting one or more insects of the species *Diatraea saccharallis* (susceptible to Cry1Ac) to the samples; detecting an insecticidal effect on the insects. In this aspect of the invention, "insecticide" refers to any inhibitory effect on the insect (including but not limited to): reduced feeding, retarded growth, reduced fecundity, paralysis, and death.

The method of detecting plant material from event CTC91087-6 includes, but is not limited to, biological leaf feeding assays where a leaf or other suitable part of the plant of event CTC91087-6, or any plant material derived from event CTC91087-6, is infested with one or more insect pests. Measurement of said detection can include: assessing leaf or plant damage after adjusted time periods, assessing mortality or assessing other insecticidal effects. Such biological assays may be performed in the field or greenhouses and may entail either natural or artificial insect infestation.

In another aspect of the invention, a kit for detecting in a plant sample the presence of event CTC91087-6 is provided, said kit comprising: a means for detecting the presence of a polynucleotide comprising at least 14 contiguous nucleotides of the sequence of SEQ ID NO: 18 and/or SEQ ID NO: 19 and/or a pesticidal crystal protein (Cry). In one embodiment of the present invention, said kit may comprise DNA amplification detection technology such as PCR, qPCR, or TAQMAN®. In a further embodiment of the present invention, said kit may comprise probe hybridization detection technology such as Southern Blots or in situ hybridization. In one aspect, the means to detect material from transgenic sugarcane comprising a Cry1Ac protein (event CTC91087-6) comprises primer pairs designed to bind to a polynucleotide comprising contiguous nucleotides of sequences selected from the group consisting of SEQ ID NO: 22 and SEQ ID NO: 29, wherein at least one pair of primers comprises contiguous nucleotides sequences selected from the group consisting of SEQ ID NO: 23, SEQ ID NO: 24, SEQ ID NO: 30 and SEQ ID NO: 31. Additionally, the means comprise primer pairs, wherein the forward primer comprises SEQ ID NO: 6 and the reverse primer comprises SEQ ID NO: 7, or the forward primer comprises SEQ ID NO: 8 and the reverse primer comprises SEQ ID NO: 9. In a further embodiment, the means to detect material from transgenic sugarcane comprising a Cry1Ac protein (event CTC91087-6) comprises a probe comprising SEQ ID NO: 10 or SEQ ID NO: 11. In another embodiment of the present invention, said kit may comprise antibody binding detection technology such as western blots, ELISAs, mass spectrometry (SELDI) or test strips. In a further embodiment of the present invention, said kit may comprise detection technology by biological insect testing such as leaf feeding biological assays or biological mortality assays. In a further embodiment of the present invention, said kit may comprise any combination of the detection technologies mentioned above.

The transgenic event as described in the present invention affect insects of one or more species of the group comprising insects of the order *Lepidoptera*. As a result, a reduced number of insecticidal sprays is required during cultivation of said plant compared with a non-transgenic sugarcane plant of the same variety.

The present invention is not itself bound to event CTC91087-6; rather, it is further extended to include any plant material derived therefrom, including seed, provided they contain at least one of the polynucleotides sequences of the present invention. In one embodiment, the present invention comprises a plant part, plant cell, plant tissue, or seed from the genetically modified sugarcane (*Saccharum* spp.) plant, wherein said plant part, plant cell, plant tissue, or seed comprises SEQ ID NO: 18 or SEQ ID NO: 19. In other embodiment, the invention contemplates plant part, plant cell, plant tissue, or seed comprising SEQ ID NO: 12 or SEQ ID NO: 13. Additionally, the invention includes a plant part, plant cell, plant tissue, or seed comprising SEQ ID NO: 5 or SEQ ID NO: 22. The present invention also includes, but is not limited to, plants that are derived from crossbred lineages with the CTC91087-6 event or a derivative thereof by conventional or other crossbreeding methods; thus, one embodiment of the present invention relates to the use of a plant, plant cell, plant part, or seed from the genetically modified sugarcane (*Saccharum* spp.) plant as described herein, which is used for regenerating a plant, planting, cultivating a field of plants, or producing a plant product. The present invention also contemplates a tissue culture of a genetically modified sugarcane (*Saccharum* spp.) plant comprising SEQ ID NO: 18 or SEQ ID NO: 19. In other embodiment, the invention includes a tissue culture of a genetically modified sugarcane (*Saccharum* spp.) plant comprising SEQ ID NO: 12 or SEQ ID NO: 13. Also contemplate in the present invention is a tissue culture of a genetically modified sugarcane (*Saccharum* spp.) plant comprising SEQ ID NO: 5 or SEQ ID NO: 22. Additionally, a genetic modified sugarcane (*Saccharum* spp.) plant regenerated from the tissue culture describe above is also included in the present invention, wherein the regenerate plant comprises SEQ ID NO: 18 or SEQ ID NO: 19. Examples of plant cells and plant parts include but are not limited to: suspension cells, callus, somatic embryos, meristematic tissue, top stalks, stalks, leaf, leaf discs, tiller, shoots. Another aspect contemplates a method for producing an insect-resistant sugarcane (*Saccharum* spp.) plant, comprising crossing a first sugarcane plant with a second sugar cane plant, wherein the second sugar cane plant is a plant comprising event CTC91087-6, and producing offspring sugarcane plants therefrom. The plant comprising event CTC91087-6 is a genetically modified sugarcane (*Saccharum* spp.) plant comprising SEQ ID NO: 18 or SEQ ID NO: 19. The present invention also contemplates a sugarcane (*Saccharum* spp.) plant and plant parts, plant cells, plant tissues, or seeds therefrom produced by the method for producing an insect-resistant sugarcane described above.

In a further embodiment, the present invention provides a commodity product, produced from a sugarcane plant comprising event CTC91087-6. Thus, the invention includes a commodity product, produced from a genetically modified sugarcane (*Saccharum* spp.) plant comprising SEQ ID NO: 18 or SEQ ID NO: 19. In one embodiment, the invention contemplates a commodity product, produced from a genetically modified sugarcane (*Saccharum* spp.) plant comprising SEQ ID NO: 12 or SEQ ID NO: 13. Additionally, the invention includes a commodity product, produced from a genetically modified sugarcane (*Saccharum* spp.) plant comprising SEQ ID NO: 5 or SEQ ID NO: 22. Examples of commodity products include but are not limited to: bagasse, sugarcane juice, syrup, first generation ethanol (produced from sugarcane juice), second generation ethanol (cellulosic ethanol; produced from biomass), biomass, sugar, raw sugar, refined sugar, molasses, vinasse, and fiber.

The present invention further provides a plant material from CTC91087-6 event comprising additional polynucleotide sequences, modified or smaller than CTC91087-6, or exhibit other phenotypic characteristics. For example, the plant material CTC91087-6 event could be transformed to produce a new event comprising additional characteristics, such as, a second insect resistance gene. This process is known as gene stacking. Such second insect resistance gene codes, for example, insecticidal lectins, insecticidal protease inhibitors and other insecticidal proteins derived from *Bacillus thuringiensis*.

The present invention further provides an insect control method comprising providing plant material derived from the CTC91087-6 event at a location where said insects feed. The invention further provides an insect control method comprising providing the CTC91087-6 derived plant material at the site where said insects feed and applying other agrochemical reagents to said plant material (e.g. herbicides, fungicides, and the like).

In other embodiment, the invention describes, a method of making a genetically modified sugarcane (*Saccharum* spp.) plant of event CTC91087-6, comprising introducing a genetic modification to a sugarcane (*Saccharum* spp.) plant comprising SEQ ID NO: 5 or SEQ ID NO: 22 to produce a genetically modified sugarcane (*Saccharum* spp.) plant of event CTC91087-6, wherein the genetically modified sugarcane (*Saccharum* spp.) plant has improved insect resistance as compared to a sugarcane (*Saccharum* spp.) plant without the genetic modification. In one additional embodiment, the invention provides a method of cultivating a genetically modified sugarcane (*Saccharum* spp.) plant of event CTC91087-6, comprising growing a genetically modified sugarcane (*Saccharum* spp.) plant of event CTC91087-6 comprising SEQ ID NO: 5 or SEQ ID NO: 22 under conditions comprising insect infestation, wherein the genetically modified sugarcane (*Saccharum* spp.) plant has an increase in insect resistance as compared to a sugarcane (*Saccharum* spp.) plant without the genetic modification grown under the same conditions. The invention also provides, a genetically modified sugarcane (*Saccharum* spp.) plant of event CTC91087-6 comprising SEQ ID NO: 5 or SEQ ID NO: 22.

Description of Transgenic Sugarcane 'CTC91087-6'

Transgenic hybrid sugarcane 'CTC91087-6' plants are genetically and phenotypically substantially equal to the recipient (host) of the recombinant molecule, the parental plant variety 'CTC9001', a commercial Brazilian sugarcane variety (Plant variety protection registry number (SNPC): 20130226), but with a new and particular feature (Cry1Ac expression), which guarantees the insect resistance to sugarcane borer *D. saccharalis* (*Lepidoptera*). As its parental variety 'CTC9001', 'CTC91087-6' is a modern sugarcane hybrid that holds several desirable agronomic characteristics such as adaptability to mechanical harvest system adopted by the majority of the Brazilian sugarcane growers, genetic potential for high ratoon cane sprouting vigor, high cane yield, excellent ratooning, low fiber and high sucrose content. 'CTC91087-6' demonstrates early maturity and, besides insect resistance, the event is also resistant to leaf scald, smut, brown and orange rust diseases.

Briefly, 'CTC91087-6' plants are characterized by purple stalks with greenish hues when exposed to sunlight and by yellowish green stalks under the straws. 'CTC91087-6' plants exhibit medium size curved-shaped internodes and narrow width greenish yellow growth rings. Internodes were smooth with few, if any, corky patches or cracks, without furrows and with a high wax layer. 'CTC91087-6' plants exhibit a round bud shape with an apical pore. Leaf architecture is erect with wide leaves. The average auricle shape is lanceolate with asymmetric distribution, presenting crescent-shaped ligule.

The average mature stalk height (330 Harvest Day after Planting—DAP; measured from the crown until the insertion of leaf+1), stalk diameter (5° stalk; average from 10 cane), number of tillers (at 120 DAP and 330 DAP), weight (330 DAP; 10 tillers), sugar content (BRIX %; 330 DAP; from extracted juice), flowering (330 DAP) and phenological status (measured by the number of tillers per ratoon) were evaluate in five different locations in comparison with the parental variety 'CTC9001'.

For each data set, data across all sites were combined for statistical analysis. Combined site analysis was done using the following statistical model:

$$y_{ijk} = \mu + S_i + B(S)_{ij} + G_k + (SG)_{ik} + \varepsilon_{ijk},$$

wherein $y_{ijk}$ is the measurement of replicate j on site i for treatment k; p is the overall mean; Si is the effect of site i (i=1 to 5); $B_j$ is the effect of replicate j (j=1 to 4); $B(S)_{ij}$ is the effect of replicate j on site i (j=1 to 4); $G_k$ is the effect of the treatment k (k=1 to 7 or 8); $(SG)_{ik}$ is the interaction between site i and treatment k; $\varepsilon_{ijk}$ is the experimental residual error.

The main effects analysis and model interaction were performed as described by Kuznetsova et al. (2017). All data were analyzed using mixed linear model by package lme4 (Bates et al., 2015).

The results of the agronomic and phenotypic characteristics analysis are shown in the table below and corroborate the conclusion that 'CTC91087-6' is substantially equivalent to its parental non-transgenic variety ('CTC9001').

TABLE 01

Average of agronomic and phenotypic characteristics for 'CTC91087-6' and 'CTC9001' parental (non-transgenic) variety. Combined analysis of five locations: Barrinha-SP, Camamu-BA, Piracicaba-SP, Quirinópolis-GO e Valparaiso-SP.

| | | Mean | | | Range* | |
| --- | --- | --- | --- | --- | --- | --- |
| | Parameter | CTC91087-6 | CTC9001 | SE | Min | Max |
| Com-bined analysis | Height (m) | 2.2 | 2.1 | 0.16 | 1.9 | 2.1 |
| | Diameter (cm) | 2.9 | 3.0 | 0.32 | 2.7 | 3.4 |
| | Tillers (120 DAP) | 81.4 | 72.8 | 17.9 | 57.2 | 95.5 |
| | Tillers (330 DAP) | 75.8 | 66.8 | 20.2 | 66.8 | 88.4 |
| | Weight (Kg) | 11.2 | 12.4 | 1.31 | 9.3 | 12.9 |
| | BRIX (%) | 17.3 | 17.2 | 0.70 | 14.8 | 18.1 |
| | Phenological status*** | 13.3** | 11.1 | 3.33 | 11.5 | 14.6 |
| | Flowering | 0 | 0 | — | 0 | 0 |

*Estimated based on the minimal and maximum observed values for 4 different commercial reference varieties cultivated in the same experimental conditions.
**Statistical difference (T-test; $p \leq 0.05$).
***Phenological status: the average number of tillers per ratoon was measured each 30 days (11 evaluations over the cycle). The average number of tillers/ratoon was higher for CTC91087-6 event in comparison to CTC9001 (13.30 vs. 11.0 un.), but it is still within the range of the commercial references.

Other compositional studies have been made and also demonstrated that 'CTC91087-6' is substantially equivalent to its conventional (non transgenic) counterpart 'CTC9001' [compositional parameters related to nutrition and the use of sugarcane in the diet, as defined by the OECD Guidance Document (OECD, 2011)]. Based on the results of combined data analysis (five representative locations in the Brazilian sugarcane growing regions), there were no statistically significant differences ($p \leq 0.05$) in any comparison of nutritional components between 'CTC91087-6' and the conventional counterpart 'CTC9001' (Table 02). The results also indicate that 'CTC91087-6' expresses Cry1Ac preferentially in leaves at levels required to control borer throughout sugarcane cultivation cycle and that no unintended effects of the genetic modification influencing plant metabolism have occurred.

TABLE 02

Mean values of compositional parameters measured in genetically-modified event 'CTC91087-6' and conventional counterpart 'CTC9001'.

| | | Mean | | Range* | |
| --- | --- | --- | --- | --- | --- |
| | Analyte | CTC91087-6 | CTC9001 | Min | Max |
| Com-bined analysis | Dry matter | 23.48 ± 1.06 | 22.73 ± 1.06 | 20.20 | 22.77 |
| | Moisture | 76.29 ± 0.81 | 76.33 ± 0.81 | 76.05 | 78.96 |
| | Crude protein[1] | 3.38 ± 0.23 | 3.56 ± 0.23 | 2.79 | 4.65 |
| | Crude fat[1] | 1.19 ± 0.11 | 1.10 ± 0.11 | 0.63 | 1.27 |
| | Ash[1] | 3.05 ± 0.41 | 3.26 ± 0.41 | 3.02 | 4.34 |
| | Crude fiber[1] | 25.82 ± 0.79 | 27.33 ± 0.79 | 23.91 | 31.32 |
| | NDF[1] | 47.79 ± 1.27 | 50.91 ± 1.27 | 46.07 | 56.89 |

28

TABLE 02-continued

Mean values of compositional parameters measured in genetically-modified event 'CTC91087-6' and conventional counterpart 'CTC9001'.

| | Mean | | Range* | |
| --- | --- | --- | --- | --- |
| Analyte | CTC91087-6 | CTC9001 | Min | Max |
| ADF[1] | 31.10 ± 0.77 | 32.95 ± 0.77 | 29.30 | 37.29 |
| Sucrose[2] | 11.63 ± 0.84 | 12.17 ± 0.84 | 9.20 | 12.28 |
| Glucose[2] | 0.91 ± 0.12 | 0.91 ± 0.12 | 0.62 | 1.11 |
| Fructose[2] | 0.75 ± 0.09 | 0.76 ± 0.09 | 0.55 | 0.84 |

[1]Results are expressed on dry weight basis;
[2]Values expressed sugarcane stalk basis;
[3]Minimum and maximum mean values of four commercial reference cultivars;
SEM: Standard Error of the Mean.
No significant difference between 'CTC91087-6' and conventional counterpart 'CTC9001' according to t-test at $p \leq 0.05$.

EXAMPLES

Example 1. CTC91087-6 Event Generation—*Agrobacterium* Transformation

Event CTC91087-6 was obtained by *Agrobacterium tumefasciens*-mediated genetic transformation of the CTC9001 cultivar.

The CTC9001 cultivar is a commercial hybrid developed by CTC and is the donor genotype of the CTC91087-6 event genetic background; that is, it represents the untransformed counterpart of the CTC91087-6 event. This cultivar has early maturation and is recommended for planting in the Brazilian states of Sao Paulo, Mato Grosso, Mato Grosso do Sul, Minas Gerais, Goiás and Northeast Brazil (BRASIL, 2012). As with other commercial sugarcane hybrids, it is high-ploidy material with numerous chromosomes derived from its two parental varieties: *S. officinarum* and *S. spontaneum* (DANIELS and ROACH, 1987; SREENIVASAN et al., 1987).

CTC91087-6 event has the cry1Ac gene, which expresses a toxin to control *D. saccharalis*, and the bar gene, used as a selection marker during the process of genetic modification. The expression of the cry1Ac and bar genes is regulated by the maize ubiquitin gene promoter UBI-1, which has an endogenous intron. Both expression cassettes use the *Agrobacterium tumefaciens* nopaline synthase (nos) terminator.

1.1 Construct Development Using Cry1Ac and Bar Genes (FIG. 5: SEQ ID NO 14).

Conventional gene cloning techniques using commercial bacterial plasmids, restriction enzyme digestion, and fragment ligation (with ligases) were used to develop the construct of the present invention (FIG. 5).

The construct of the present invention was developed by joining the UBI-cry1Ac-NOS and UBI-bar-NOS cassettes. T-DNA containing both cassettes was transferred from a cloning plasmid to the base plasmid (FIG. 4: binary plasmid vector, which contains in its host spectrum the bacteria *Escherichia coli* and *Agrobacterium tumefaciens*) using restriction enzymes, generating the construct of the present invention (FIG. 5; SEQ ID NO: 14).

After the final cloning step, the construct (SEQ ID NO: 14) was inserted into *Escherichia coli* strain DH5α using electroporation. An isolated colony containing the construct was inoculated into liquid LB medium supplemented with 150 µg/ml spectinomycin and incubated at 37° C. while shaking at 250 rpm for a period of 16 hours. Stocks were then prepared containing bacterial suspension and 10% (v/v) glycerol, which were stored in an ultrafreezer at −80° C.

The construct of the present invention was then transferred from *E. coli* to *Agrobacterium tumefaciens* strain EHA105 by isolation and purification of plasmid DNA and transformation of *Agrobacterium* by electroporation. As with the *E. coli* strain, stocks containing the bacterial suspension of *Agrobacterium* and 10% (v/v) glycerol were stored in an ultrafreezer at −80° C.

1.2 *Agrobacterium*-Mediated Plant Transformation

To obtain embryogenic callus, young CTC9001 sugarcane palm leaves, grown in the field or greenhouse for up to 12 months, were collected for isolation of the initial explants.

After surface disinfection, transverse sections about 0.05-5 mm thick were cut from above the meristem under aseptic conditions. The sections were placed on the surface of the callus induction culture medium [Sais MS—Murashige and Skoog, 1962; sucrose, vitamins B5, amino acids selected from the group comprising proline, casein hydrolyzate, citric acid, mannitol, copper sulfate, glycine, gelling agent, 2,4D]. The cultures were kept in the dark at 26±2° C. and sub-cultured every 15 days for three to five cycles of 7-28 days each. One week before transformation, calli were again selected for embryogenic characteristics (nodular, compact, opaque and slightly yellowish).

*Agrobacterium* culture, comprising strain EHA105 transformed with the construct of the present invention, was started from a glycerol stock and kept in the dark at 28° C. for two to three days. The *Agrobacterium* suspension to infect plant material was prepared by resuspending the culture in MS liquid medium plus acetosyringone, adjusting to a final OD600 of 0.1-1.0 (MS salts, sucrose, and vitamins B5).

The calli with embryogenic characteristics were visually selected and directly transferred to the *Agrobacterium* suspension, where they remained for 30 minutes in the dark with constant agitation at 50 rpm.

After this period, calli were separated from the *Agrobacterium* suspension and excess suspension was removed. Next, calli were cultured for 1-5 days in semi-solid (MS salts, sucrose, vitamins B5, citric acid, gelling agent, 2,4D and acetosyringone) at 22° C. in the dark.

After co-cultivation, callus was transferred to DT rest medium (MS salts; sucrose, B5 vitamins, amino acids selected from the group comprising proline and asparagine, casein hydrolyzate, citric acid, copper sulfate, glycine, gelling agent, 2,4D, timentin) and kept for 5-14 days at 26° C. in the dark.

Transformed cells were selected by successive sub-cultures in selection culture medium containing phytoregulators and the selective agent ammonium glufosinate. (Selection medium with ammonium glufosinate: MS salts, sucrose, vitamins B5, amino acids selected from the group comprising proline and asparagine, casein hydrolyzate, copper sulfate, glycine, gelling agent, 2,4D, timentin) The calli remained in this condition for 21 days at 26° C. in the dark, then the calli were transferred to the regeneration medium (equivalent to selection medium without 2,4D) and then to elongation medium (MS salts, sucrose, B5 vitamins, casein hydrolyzate, gelling agent, timentin). The calli were exposed to a 16-hour photoperiod at 4,000 lux in the presence of the herbicide used as a selective agent, then they were multiplied, rooted, and acclimatized before transfer to the greenhouse. This process was used to generate the clone that eventually created the event CTC91087-6.

Example 2. Molecular Characterization of Event CTC91087-6

2.1 DNA Extraction.

Approximately 10 mg of leaf tissue from event CTC91087-6 was used. Genomic DNA extraction was performed on the BioSprint 96 Nucleic Acid Extractor (Quiagen, GER) with the BioSprint 96 DNA Plant Kit Extraction Kit (Quiagen, GER) according to the manufacturer's instructions. The DNA was normalized to a concentration of 10 ng/μL in a Multiskan GO spectrometer (Thermo Scientific, USA).

2.2 Determination of the Number of Transgene Copies Inserted into the Host Plant Germplasm.

The copy number of cry1Ac and bar genes inserted into CTC91087-6 event was initially evaluated by quantitative TAQMAN® PCR (qPCR/TAQMAN®), and the results were confirmed via Southern blot and/or sequencing.

The TAQMAN® real time PCR reactions were realized with 7500 Real-Time PCR System (Applied Biosystems, EUA) in the Fast mode. The primer pairs and probes used are shown at Table 03. As endogenous control of the cry1Ac and bar reactions to confirm the presence and quality of the used DNA, as well as, effectiveness of the reaction, it was used the sugarcane polyubiquitin gene (forward primer: 5 'ACCATTACCCTGGAGGTTGAGA 3' (SEQ ID NO: 68); antisense initiator: 5 'GTCCTGGATCTTCGCCTTCA 3' (SEQ ID NO: 69); probe: VIC-5 'CTCTGACACCATCGAC 3'-MGB (SEQ ID NO: 70)) in multiplex mode.

Table 03: Primers and probes (TAQMAN®) used to determine copy number via qPCR.

TABLE 03

| Primers and probes (Taqman ®) used to determine copy number via qPCR. | | | | |
| --- | --- | --- | --- | --- |
| Assay | Primers/probe | Sequence | Target | Amplicon |
| UBI-cry | Ubi.BAR.CN.Fw | GCTCACCCTGTTGTTTGGTGTT (SEQ ID NO: 40) | cry1Ac | 69 bp |
| | CRY.4-ubi.CN.Rv | TCGTTGATGTTTGGGTTGTTGT (SEQ ID NO: 41) | | |
| | Ubi.BAR_probe | FAM-CTTCTGCAGGTCGACTC-MGB (SEQ ID NO: 42) | | |
| cry-cry | CRY.571.CN.Fw | AGCCGCTACAACGACCTGA (SEQ ID NO: 43) | cry1Ac | 79 bp |
| | CRY.649.CN.Rv | GCTCCAGGCCGGTGTTG (SEQ ID NO: 44) | | |
| | CRY.probe | FAM-GGCAACTACACCGACCACGC-MGB (SEQ ID NO: 45) | | |

TABLE 03-continued

| Primers and probes (Taqman ®) used to determine copy number via qPCR. | | | | |
|---|---|---|---|---|
| Assay | Primers/probe | Sequence | Target | Amplicon |
| UBI-bar | Ubi.BAR.CN.Fw | GCTCACCCTGTTGTTTGGTGTT (SEQ ID NO: 46) | bar | 62 bp |
| | Ubi.BAR.CN.Rv | CGTCGTTCTGGGCTCATTCT (SEQ ID NO: 47) | | |
| | Ubi.BAR_probe | FAM-CTTCTGCAGGTCGACTC-MGB (SEQ ID NO: 48) | | |

The qPCR reactions used 1× TAQMAN® Fast PCR Master Mix II (Applied Biosystems, USA), 300 nM from each primer and 200 nM from the corresponding probes. The cycling used was: a 50° C. cycle for 2 minutes for uracil N-glycosylase activation, a 95° C. cycle for 20 seconds for DNA polymerase activation, 40 cycles of 95° C. for 3 seconds (denaturation), and 60° C. for 30 seconds (annealing and extension).

Data analysis was performed by manually entering the threshold at the exponential phase of the amplification curve. For cry1Ac and bar genes, the copy number was inferred from DeltaCt (dCt) analysis, in which the Ct (cycle at which the fluorescence signal emitted by the amplification product reaches the threshold) of the endogenous gene is subtracted from the Ct of the target gene. In this type of analysis, the number of copies is assumed to double every Ct and the reference number of control copies of the same variety whose value is known is taken as a reference.

As a result, both assays pointed to the presence of 1 copy for the cry1Ac gene in the CTC91087-6 event genome. The same copy number (i.e., 1 copy) was detected for the bar gene, the assay of which is based on detection of the gene promoter.

2.3 Definition of Flanking Sequences.

To isolate the flanking regions at the ends of the T-DNA insert present in event CTC91087-6, several DNA sequencing experiments were performed. The map of the genetic insertion of event CTC91087-6 generated from the data of these experiments is shown in FIG. 3.

Inverse PCR (iPCR) assays were performed for both ends of the T-DNA to isolate and clone the flanking regions of the insert. The iPCR methodology is based on genomic DNA digestion using enzymes that cleave the T-DNA sequence and a random event genome sequence. The cleavage products are circularized and subjected to multiple nested PCR cycles using primers for known T-DNA regions (Table 04). The isolated fragments were then isolated, cloned and sequenced by Sanger methodology. Finally, a consensus sequence of the flanking regions was assembled (SEQ ID NO: 23 and SEQ ID NO: 24).

TABLE 04

| Restriction enzymes and primer sequences used for carrying out iPCR reactions and amplification reaction conditions. | | | |
|---|---|---|---|
| T-DNA Edge | Restriction Enzyme | Oligonucleotide | Sequence |
| Left | BsrGI | Nested PCR1 | 5'-TGCAATGCTCATTATCTCTAG-3' (SEQ ID NO: 49) |
| | | | 5'-AGCATCACCATCTACACCGAC-3' (SEQ ID NO: 50) |
| | | Nested PCR2 | 5'-TGCACTGCAGGCATCGATC-3' (SEQ ID NO: 51) |
| | | | 5'-AGCATCACCATCTACACCGAC-3' (SEQ ID NO: 50) |
| | | Nested PCR3 | 5'-GATATCAGTACTAATTCAGTAC-3' (SEQ ID NO: 52) |
| | | | 5'-AGCATCACCATCTACACCGAC-3' (SEQ ID NO: 50) |
| Left | NdeI | Nested PCR1 | 5'-TGCACTGCAGGCATCGATC-3' (SEQ ID NO: 53) |
| | | | 5'-ACGGATGCGACCTGTACG-3' (SEQ ID NO: 54) |
| | | Nested PCR2 | 5'-TGCACTGCAGGCATCGATC-3' (SEQ ID NO: 55) |
| | | | 5'-ACGGATGCGACCTGTACG-3' (SEQ ID NO: 54) |
| | | Nested PCR3 | 5'-GATATCAGTACTAATTCAGTAC-3' (SEQ ID NO: 56) |
| | | | 5'-ACGGATGCGACCTGTACG-3' (SEQ ID NO: 54) |
| Right | KpnI | Nested PCR1 | 5'-AATTATACATTTAATACGCG-3' (SEQ ID NO: 57) |
| | | | 5'-AATAACGTCATGCATTACATG-3' (SEQ ID NO: 58) |

TABLE 04-continued

Restriction enzymes and primer sequences used for carrying out iPCR reactions
and amplification reaction conditions.

| | | |
|---|---|---|
| Nested PCR2 | 5'-CGCGGTGTCATCTATGTTAC-3'<br>(SEQ ID NO: 59)<br>5'-GATAATCATCGCAAGACCGG-3'<br>(SEQ ID NO: 60) | |
| Nested PCR3 | 5'-TCGTCGACTCTAGACTCGAG-3'<br>(SEQ ID NO: 61)<br>5'-CGATCTCAGATCTCGGTGAC-3'<br>(SEQ ID NO: 62) | |

| Cycle Number | Denaturation | Ringing | Extension |
|---|---|---|---|
| 1st | 94° C., 5 min | — | — |
| 2-36th | 94° C., 30 sec | 50° C. 45 sec | 72° C., 3 min |
| 37th | — | — | 72° C., 7 min |

In parallel, as there is currently no fully sequenced genome that could be used as a reference for CTC9001 germplasm, a capture sequencing methodology was adopted as an additional effort to isolate the T-DNA inserted into the event CTC91087-6 and its flanking regions. In this strategy, small overlapping polynucleotide fragments (probes) were developed to cover the entire T-DNA sequence. These probes were hybridized to the fractionated genomic DNA of both CTC9001 and CTC91087-6 cultivars, and hybrid sequences were isolated. Isolated fragments were then sequenced using Illumina® technology according to standard protocol. The data obtained were aligned with the T-DNA sequence present in the transformation vector and, together with the iPCR data mentioned above, the complete T-DNA consensus sequence (SEQ ID NO: 2) of the CTC91087-6 event and its flanking sequences (SEQ ID NO: 22, SEQ ID NO: 5, SEQ ID NO: 23, SEQ ID NO: 24) were obtained.

2.4 Method for the Detection and Characterization of Event CTC91087-6 (Event-Specific Assay)

For the validation of the methodology, we used samples of event leaves from four different locations (Piracicaba, Barrinha, and Valparaiso (Sao Paulo); and Quirinópolis (Goiás). Both untreated control (WT) plants and other genetically-modified events having the same construct were used as experimental controls. DNA extraction occurred as described above.

Real-time PCR assays for identification of the CTC91087-6 event were designed and validated based upon the molecular characterization of the T-DNA insertion genomic flanking sequences. For the development of specific detection methodology, the real-time PCR (qPCR) technique known as "Plus-Minus" or "Presence—Absence" was chosen, validating the two variations of the methodology: via SYBR GREEN™ and via TAQMAN® technology. Specific primer pairs have been designed to generate information about the insertion of T-DNA in both methodologies, such that one primer binds in the construct and the second primer binds in the host genome. For the use of TAQMAN® technology, specific probes were designed between the primers.

In a preferred embodiment, the probe employed in TAQMAN® PCR technology consists of SEQ ID NO: 10 in the RB region and/or SEQ ID NO: 11 in the LB region.

TAQMAN® real-time PCR reactions were performed using the 7500 Real-Time PCR System (Applied Biosystems, USA) in its Fast mode.

The sugarcane poly-ubiquitin gene (endogenous gene) was used as an internal reaction control to confirm the presence and quality of the DNA used. The following reagents were multiplexed with the assay developed for the event: forward primer (SEQ ID NO: 15); reverse primer (SEQ ID NO: 16); probe (SEQ ID NO: 17).

qPCR reactions used 1× TAQMAN® Fast PCR Master Mix II (Applied Biosystems, USA), 150 nM from each event-specific primer and 100 nM from the corresponding probe, 300 nM from the primers for the endogenous poly-ubiquitin gene and 300 nM of its probe, 100-200 ng of DNA and enough water to complete the 20 μL volume. The following PCR program was used: a 50° C. cycle for 2 minutes for uracil N-glycosylase activation, a 95° C. cycle for 20 seconds for DNA polymerase activation, 40 cycles of 95° C. for 3 seconds (denaturation) and 87° C. for 30 seconds (annealing and extension).

qPCR reactions using SYBR GREEN™ were also performed using the 7500 Real-Time PCR System (Applied Biosystems, USA) in its standard mode for this type of assay. Reactions were performed using 1× QuantiFast SYBR Green™ PCR Kit (QIAGEN™), 40 nM RB forward primer and 28 nM RB reverse primer, 100-200 ng DNA and sufficient water for a final volume of 25 μL. The reactions were performed using the event of the invention, the other events transformed with the same construct as the event of the invention (negative controls), wild sugarcane (WT) samples, and experimental controls (extraction and reaction blank).

The following PCR program was used: a DNA denaturation cycle at 95° C. for 5 minutes, 35 primer annealing cycles and amplification at 95° C. for 15 seconds and 60° C. for 1 minute and a dissociation cycle for generation melting peak (95° C. for 15 sec, 60° C. for 1 min, 95° C. for 15 sec and 60° C. for 15 sec). The reaction with SYBR safe does not allow for the use of multiplex; therefore it is necessary to prepare a separate endogenous gene amplification reaction, using the same DNA, to eliminate false negatives.

As a result, it was possible to validate the event-specific detection reaction of the invention via high-accuracy TAQMAN®, as illustrated in FIG. 6.

Samples corresponding to the event of the invention showed specific amplification: having well-defined amplification curve formation and characteristic sigmoidal shape; whereas samples from other events, WT, and extraction and reaction blanks did not show event-specific amplification. As expected, the endogenous control presented amplification for all samples except extraction and reaction blanks, demonstrating both the quality of the DNA used in the reaction, as well as the quality of the reaction and cycling.

Figure 7:
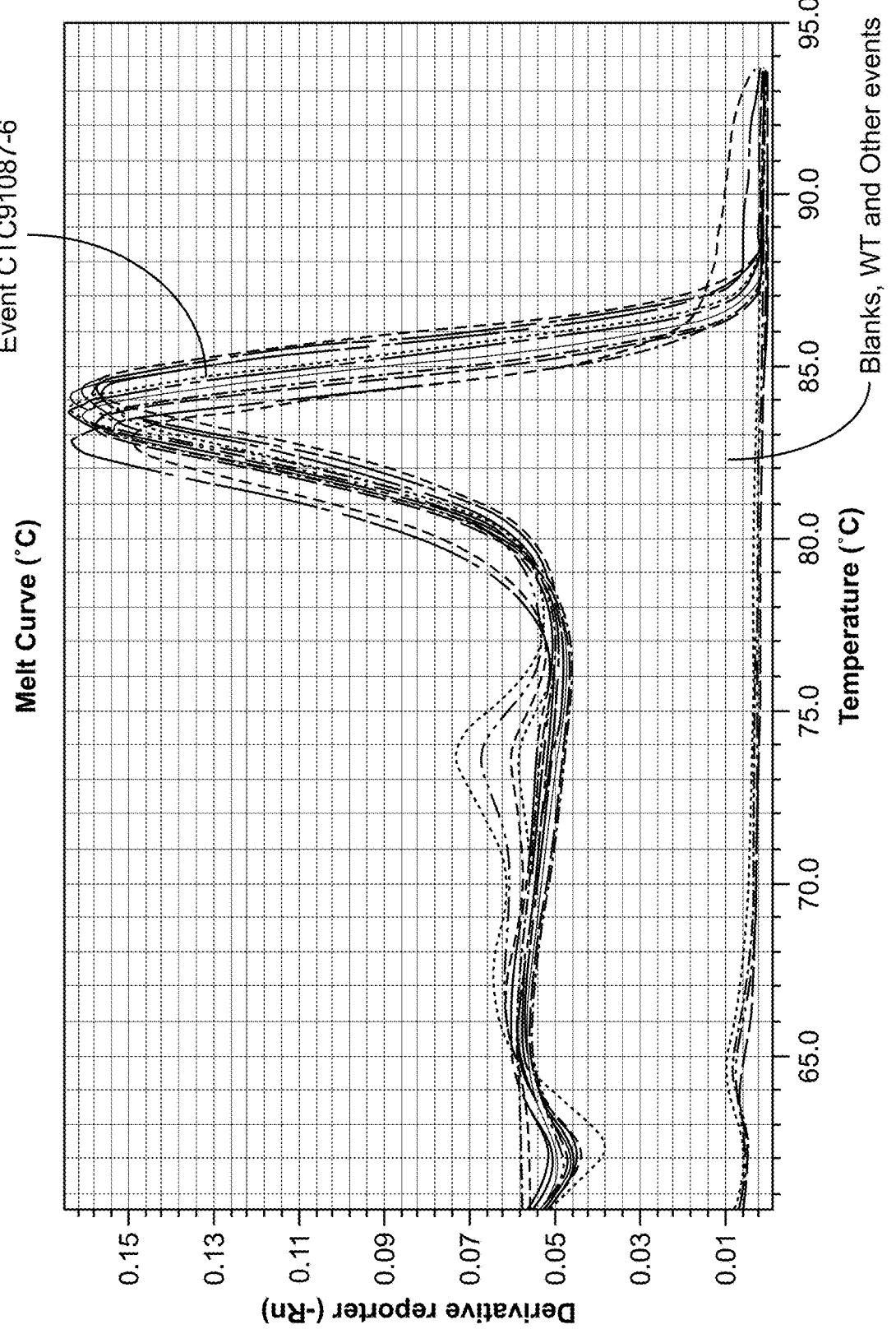
FIG. 7 is the qPCR melting curve via SYBR GREEN™ (relative fluorescence x temperature) for the event of interest. The arrows indicate the specific amplification peak of the event of interest at a temperature of 83.5° C. and the non-specific peak presented by some samples, as well as the baseline indications of no amplification for the other negative events and controls.

The SYBR GREEN™ assay showed specific amplification of the event samples at the expected melting temperature (83.5° C.). Samples of the other events, as well as WT and blanks did not peak at this temperature, although some samples of the event of interest showed a lower intensity curve before the specific peak (FIG. 7). Such a curve is characteristic of primer dimer formation during the PCR reaction, which would be expected because the technology is based on the binding of an intercalating agent to any double stranded DNA molecules—whether derived from specific amplification or binding between the primers. In contrast, TAQMAN® technology probes specifically bind to DNA and are released during DNA amplification, thus generating the fluorescence signal captured by the equipment during this process.

Example 3. Event CTC91087-6 Generation—Genome Editing (GE)

The event of the invention, CTC91087-6, is generated using a genome editing (GE) approach, thus recreating the event generated using the preferred *Agrobacterium*-mediated transformation methods described herein.

In this way, the event CTC91087-6 is recreated with the insertion of the cry1Ac gene into the same location of the genome as the CTC91087-6 event. Cry1Ac gene expression is regulated by a promoter or a promoter region and a terminator capable to drive the Cry1Ac protein expression at levels sufficient to control infestation of the target pest. Additionally, a marker gene or selection system is also inserted (transiently or stably) to enable event selection. Preferably, the T-DNA of the claimed invention (SEQ ID NO: 2) is inserted into the same location of the genome as the CTC91087-6 event. Thus, the event CTC91087-6 is recreated with the insertion of the cry1Ac gene, which expresses a toxin to control *D. saccharalis*, and the bar gene. The expression of the cry1Ac and bar genes is regulated by the maize ubiquitin gene promoter UBI-1, which has an endogenous intron. Both expression cassettes use the *Agrobacterium tumefaciens* nopaline synthase (nos) terminator.

In the case that the aforementioned genome editing approaches to generating event CTC91087-6 result in low-efficiency integration of the T-DNA at the target site, developmental genes or other regulatory elements could be delivered in conjunction with the GE reagents in order to improve the integration efficiency.

3.1 Constructs Development.

Conventional gene cloning techniques using commercial plasmids, restriction enzyme digestion, fragment ligation (with ligases) and other known methodologies are used to develop the constructs (plasmids) of the present invention.

Figure 21:
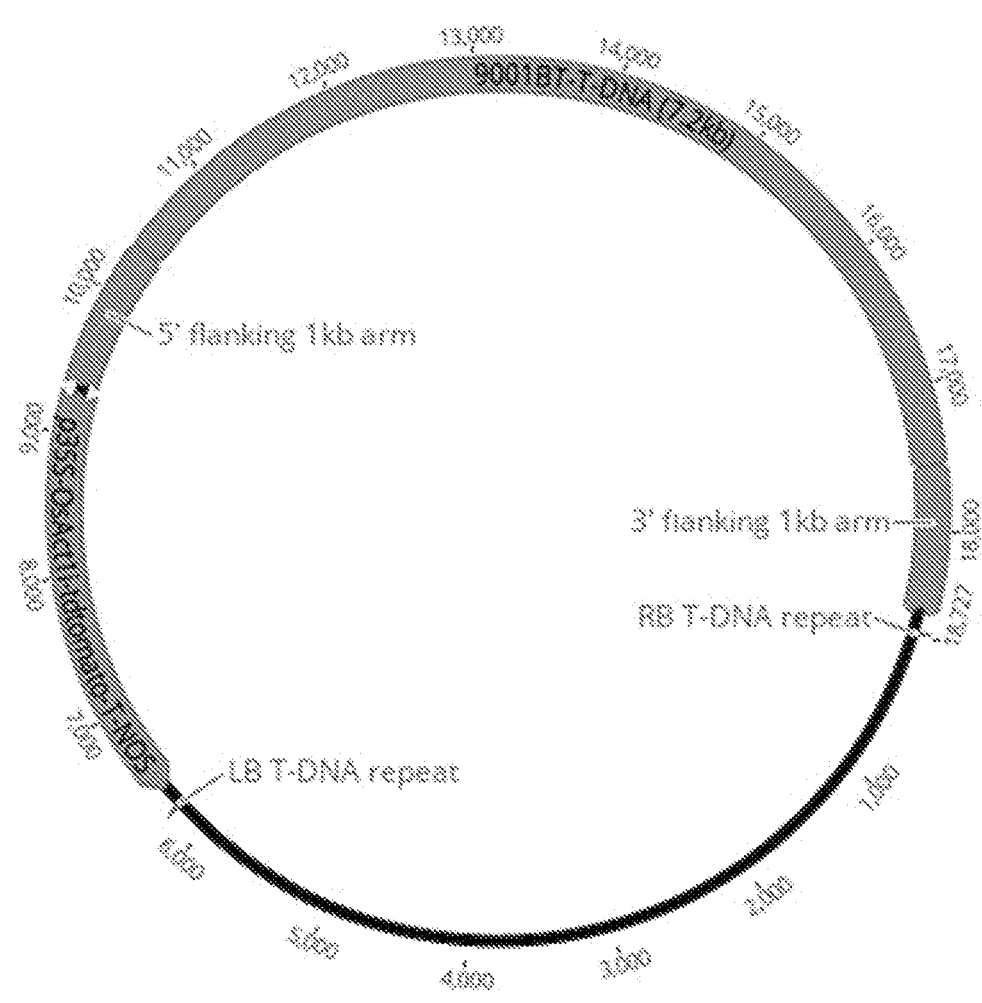
FIG. 21 shows an example of a gene editing construction comprising the HR template comprising 9001BT-T-DNA region with 1 kb homologous arms for site directed integration.

The GE reagents can be delivered on multiple plasmids, each one comprised of an element of the enzymatic complex (endonuclease, crRNA or guide RNA, and the homologous recombination (HR) template; FIG. 21).

Figure 20:
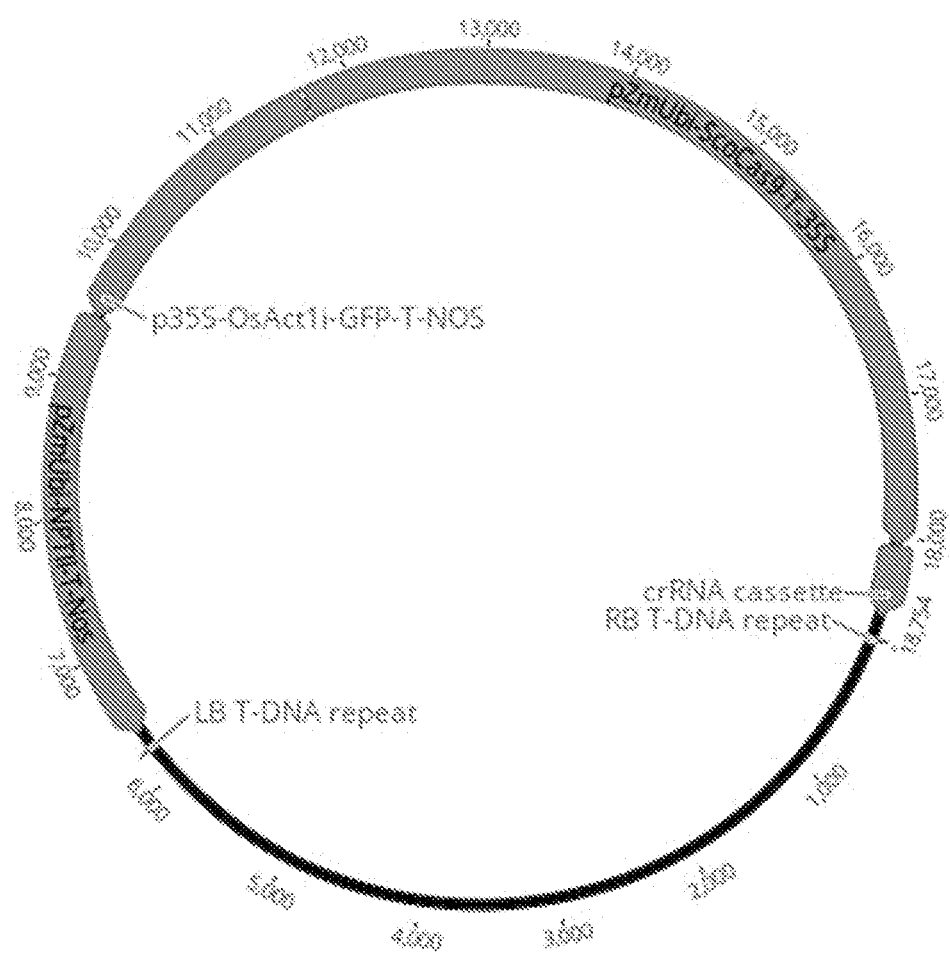
FIG. 20 represents an example of a gene editing construction comprising Cas 9 and crRNA Cassettes.

In one embodiment, the HR template constructs comprises the T-DNA (SEQ ID NO: 2) of the claimed invention flanked by approximately 1 kb of DNA homologous to the flanking sequences described for CTC91087-6 (SEQ ID Nos: 23 and 24) located on either side of the T-DNA. In a preferred embodiment, the HR template constructs comprises the SEQ ID NO: 26 (FIG. 21). The invention also comprises a second construct comprising an endonuclease expression cassette. In a preferred embodiment, the endonuclease expression cassette comprises a Cas9 endonuclease sequence. In more preferred embodiment the Cas9 sequence is codon optimized for sugarcane expression. In one embodiment, the Cas 9 construct comprises additionally the guide/crRNA sequence. Preferably, the Cas 9 construct comprises the crRNA sequence SEQ ID NO: 28. In a more specific embodiment, the Cas 9 construct comprises the SEQ ID NO: 27 (FIG. 20). A third construct comprising the guide RNA expression cassette alone is also contemplated in the present invention and comprises SEQ ID NO: 28.

Figure 22:
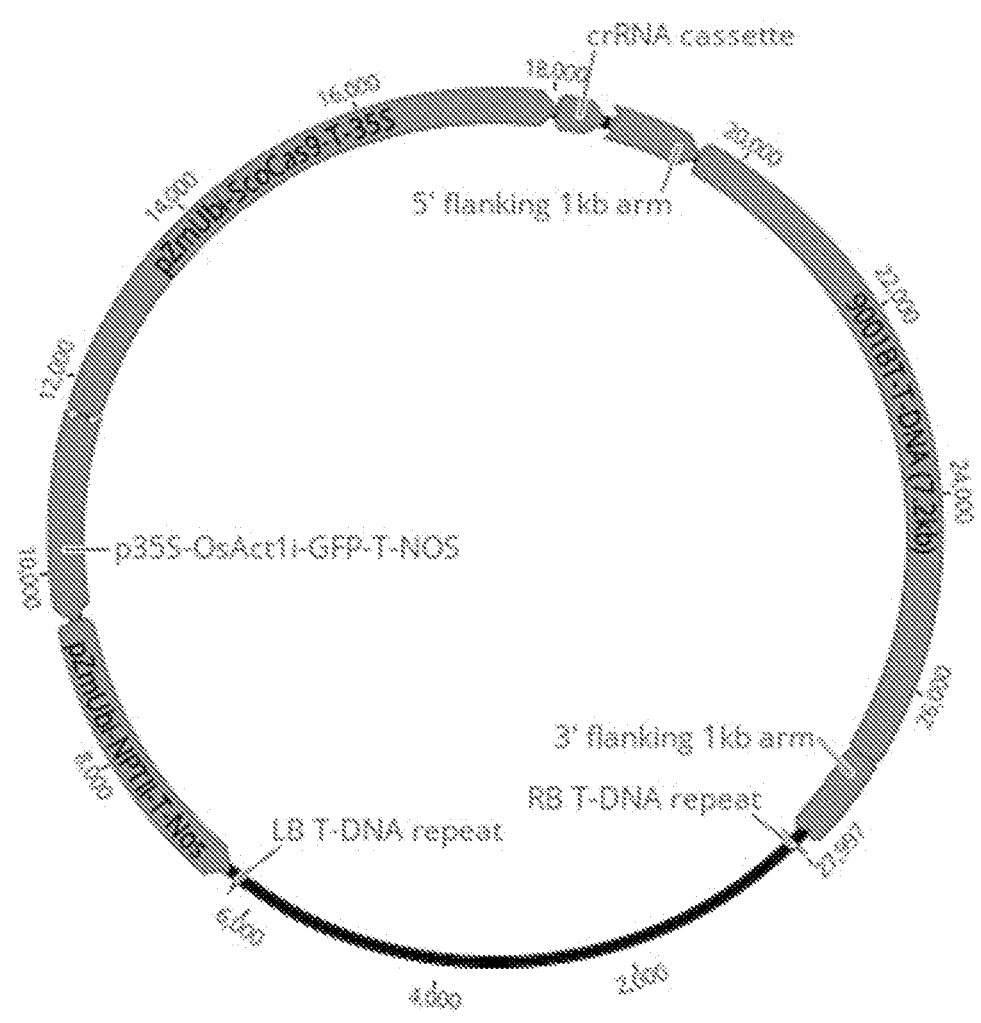
FIG. 22 represents a gene editing construction comprising the all the cassettes for generation of event CTC91087-6: a codon optimized Cas9 driven by pZmUbi promoter and T-35s terminator; a crRNA for Cas9 driven by wheat U3 promoter and the HR template comprising 9001BT-T-DNA region with 1 kb homologous arms for site directed integration.

In one additional embodiment the genome editing construct comprises HR template, the nuclease and the guide RNA expression cassettes, delivering all the GE reagents in a single construct. In one embodiment, the single construct comprises the T-DNA (SEQ ID NO: 2) of the claimed invention flanked by approximately 1 kb of DNA homologous to the flanking sequences described for CTC91087-6 (SEQ ID Nos: 23 and 24) located on either side of the T-DNA. In a preferred embodiment, the construct comprises the SEQ ID NO: 25 (FIG. 22).

Optionally, the constructs also comprise fluorescent/selection markers and/or other genetic engineering systems to remove marker genes and/or nucleases cassettes, such as a Cre/loxP recombination system from the bacteriophage P1. In this case, the marker/nuclease gene cassette, which should be deleted, is flanked by the loxP regions, while Cre recombinase removes this fragment during a transient expression.

3.2 Direct Delivery

In one embodiment, the event of the invention is generated using methodologies for direct delivery of proteins, RNA or plasmids. The methodologies for direct delivery are selected from the group consisting of particle bombardment, electroporation, lipofection and protoplast transfection; however, other delivery methodologies known to those of skill in the art could also be utilized.

3.2.1 Direct Delivery—RNP Approach

In one embodiment, the event of the invention is generated using ribonucleoprotein (RNP) delivery. The preferred methodologies for RNP delivery are selected of the group consisting of particle bombardment of sugarcane calli and protoplast transfection. Moreover, other sugarcane cell types can also be used for transformation including (but not limited to): leaf disc, meristem, and calli-derived suspension cells.

Using the RNP approach to genome editing, the endonuclease and crRNA or guide RNA are delivered in RNP form, separate from the HR template, which is delivered via plasmid.

The guide RNA may be preliminarily produced by in vitro transcription or be chemically synthesized as ribooligonucleotide, while the corresponding nuclease may be produced in vivo with further purification (bacterial expression) or purchased from any manufacturer of such products. In a preferred embodiment, the guide RNA comprises SEQ ID NO: 28. In another embodiment the nuclease is Cas9 nuclease.

A ready ribonucleoprotein (RNP) complex consisting of the corresponding nuclease and guide RNA, and the HR template plasmid are sorbed on golden particles and direct delivery to the cells or tissue.

3.2.2 Direct Delivery—Plasmid

In another embodiment of the invention, the event of the invention is generated using plasmid delivery, wherein the GE reagents will be expressed in a transient manner, thus achieving the site-directed integration of CTC91087-6 without the integration of additional transgenes associated with the GE approach.

Methodologies for plasmid delivery is selected from the group consisting of particle bombardment (biolistic) of sugarcane calli or polyethylene glycol transformation of protoplasts; however, other methodologies known to those of skill in the art could also be utilized. Moreover, other sugarcane cell types can also be used for transformation including (but not limited to): protoplast, leaf disc, meristem, and calli-derived suspension cells.

In yet another embodiment of the invention, the event of the invention is generated using plasmid delivery, where the GE reagents are stably expressed, thus requiring the excision of the integrated GE reagents and selectable marker using, for example, a Cre/Lox system. Using this approach, LoxP sites will remain in the genome of the event CTC91087-6 plant. Other DNA excision approaches known to those skilled in the art may also be used to remove the GE reagent DNA from the genome of the event CTC91087-6 plant.

3.3 Indirect Delivery

In one embodiment, the event of the invention is generated using methodologies for indirect delivery of plasmids, as *Agrobacterium* transformation. *Agrobacterium tumefaciens* and *Agrobacterium rhizogenes* can be used. Plant viruses also can be used for indirect delivery of plasmids to plant cells and tissues. For example, genetically modified plant geminiviruses make it possible to achieve higher transformation efficiency, specially without stable insertion into a genome. Moreover, different tissue and cell types can also be used for transformation including (but not limited to): calli, protoplast, leaf disc, meristem, and calli-derived suspension cells.

ment, the constructs is SEQ ID NO: 25 and comprises a selectable marker, a nuclease, crRNA or guide RNA, and homologous recombination (HR) template (FIG. 22). The HR template comprises T-DNA (SEQ ID NO: 2) of the claimed invention flanked by approximately 1 kb of DNA homologous to the flanking sequences described for CTC91087-6 (SEQ ID Nos: 23 and 24) located on either side of the expression cassettes.

In a preferred embodiment, the event of the invention is generated using plasmid delivery, where the GE reagents are stably expressed, thus requiring the excision of the integrated GE reagents and selectable marker using, for example, a Cre/Lox system. Using this approach, LoxP sites will remain in the genome of the event CTC91087-6 plant. Other DNA excision approaches known to those skilled in the art may also be used to remove the GE reagent DNA from the genome of the event CTC91087-6 plant.

With all the transformation processes described above, the resulting transformed cells will be regenerated to form a plant containing the event of the invention.

3.4 Molecular Characterization.

The event CTC91087-6, generated using genome editing, is evaluated for accurate insertion of the T-DNA into the target site of the genome using the primers of the invention (SEQ ID NO: 6-9) as is described in the specification herein.

Additionally, pair of primers designed to amplify sequences next to 1 Kb region of event CTC91087-6 flanking sequences are validated to evaluated the integrity of the recombination site (Table 05).

TABLE 05

Pair of primers designed for Flanking sequences of CTC91087-6 (1 Kb region).

| | Name | Oligonucleotides Sequence | Expected amplicon sizes flanking region |
|---|---|---|---|
| FS RB | FS_C91-087_RB_1,4k.a | 5'-CAACAACCCAAACATCAACG-3' (SEQ ID NO: 63) 5'-TAACATTTAGGGTGCGCTTG-3' (SEQ ID NO: 64) | 1394 |
| FS LB | FS_C91-087_LB_2k.a | 5'-GTTCTTGGGTGGCGGTAGTA-3' (SEQ ID NO: 65) 5'-CGTCGGTGTAGATGGTGATG-3' (SEQ ID NO: 66) | 2054 |
| | FS_C91-087_LB_2k.b | 5'-TTGGGTGGCGGTAGTAGTTG-3' (SEQ ID NO: 67) 5'-CGTCGGTGTAGATGGTGATG-3' (SEQ ID NO: 66) | 2050 |

| Cycle Number | Denaturation | Ringing | Extension |
|---|---|---|---|
| 1st | 94° C., 1 min | — | — |
| 2-30th | 98° C., 10 sec | 68° C. 9 min | — |
| 31th | — | — | 72° .C, 10 min |

In a preferred embodiment the *Agrobacterium* transformation is performed as describe at Example 1.

In another preferred embodiment, the event of the invention is generated using plasmid delivery by *Agrobacterium* transformation, wherein the GE reagents will be expressed in a transient manner, thus achieving the site-directed integration of CTC91087-6 without the integration of additional transgenes associated with the GE approach.

The GE reagents can be delivered on multiple plasmids, but preferably on a single plasmid. In a preferred embodi- Example 4. Evaluation of the Gene Expression Product Inserted in the Event of the Invention The gene expression product in the event of the present invention has been characterized in detail using ELISA to determine the concentration of Cry1Ac and Pat proteins and Western blot to confirm the identities of these heterologous proteins.

(ELISA) Enzyme-Linked Immunosorbent Assay

To evaluate cry1Ac and bar gene expression via ELISA, different sugarcane tissues were studied at different stages of crop development. To produce tissue samples of the event of the invention and the parental control, three types of experimental tests were conducted: PACE, EB and AGRO-PHENO.

Together, the PACE and AGROPHENO trials were conducted at five representative sites of the parental control cultivation area, three in the state of Sao Paulo (Barrinha, Piracicaba and Valparaiso), one in the state of Goiás (Quirinópolis), and one in the state of Bahia (Camamu). The experiments were conducted in a randomized complete block design with 4 replications. The plots were composed of four 12 meters rows (Barrinha, Piracicaba, Valparaiso and Quirinópolis) or of four 7 meters rows (Camamu). In all cases, the spacing between rows was 1.5 meter.

EB assays were performed at four sites, three in the state of Sao Paulo (Barrinha, Piracicaba and Valparaiso) and one in the state of Goiás (Quirinópolis). The experiments were conducted in a randomized block design with 4 replications. The plots consisted of 4 rows of 4 meters each. In all cases, the spacing between rows was 1.5 meter. Table 06 presents details of the tests performed at the respective locations.

TABLE 06

Assay information used for sample collection for analysis of cry1Ac and bar gene expression produced by the event of the invention. (Number of Days After Planting (DAP) represents time of sample collection for analysis.)

| Assay Type | Assay | Location | Tissue | DAP |
|---|---|---|---|---|
| PACE/ AGROPHENO | PACE CTC91-BA | Barrinha-SP | leaf stalk root | 100, 200, 300 330 330 |
| | PACE CTC91-PI | Piracicaba-SP | leaf stalk root | 100, 200, 300 330 330 |
| | PACE CTC91-VP | Valparaiso-SP | leaf stalk root | 100, 200, 300 330 330 |
| | PACE CTC91-QS | Quirinópolis-GO | leaf stalk root | 100, 200, 300 330 330 |
| | AGROPHENO CTC91-CA | Camamu-BA | leaf stalk root | 100, 200, 300 330 330 |
| EB | EB-BIO-BA | Barrinha-SP | leaf | 60, 120, 240, 300 |
| | EB-BIO-PI | Piracicaba-SP | leaf | 60, 120, 240, 300 |
| | EB-BIO-VP | Valparaíso-SP | leaf | 60, 120, 240, 300 |
| | EB-BIO-QS | Quirinópolis-GO | leaf | 60, 120, 240, 300 |

The expression analysis of Cry1Ac and Pat proteins produced by the event of the invention was investigated at different periods of sugarcane plant development. The conditions evaluated were:

Expression of heterologous proteins in leaves over a cultivation cycle of the event of the invention (100, 200 and 300 DAP);

Expression of heterologous proteins in leaves along a sugarcane cycle at 60 and 120 DAP, then at 240 and 300 DAP;

Expression of heterologous proteins in stems and roots at 330 DAP of the sugarcane cycle.

Leaf samples were collected on experimental treatment plots (invention and parental control) in the PACE/AGRO- PHENO assays at 100, 200 and 300 DAP. In EB assays, samples were collected at 60, 120, 240, and 300 DAP. Thatched and root samples were collected only at 330 DAP in the PACE/AGROPHENO assays. After collection, the samples were sent for ELISA analysis to determine Cry1Ac and Pat protein expression levels.

Leaf Samples: 30 cm of tissue were collected from the tip of 5 to 10 "diagnostic" leaves on zigzag lines 2 and 3 avoiding diseased leaves. After removal of the central rib, the leaves were chopped into pieces, homogenized and packed in previously identified ziplock bags.

Stalk Samples: 10 whole sugarcanes were collected. After removing the dried leaves and pointers, the canes were cut into small tails, homogenized, and packed into labelled packages.

Root Samples: A representative clump from rows 2 and 3 of the experimental plot was collected. The soil was crushed, and the roots were washed with clean water to remove excess soil. The clean roots were then minced into pieces, homogenized, and packaged into labelled plastic bags.

All samples (from leaf, stem, and root tissues) were transferred to dry ice in a Styrofoam box within 15 min of collection. The genetic identity of all clumps sampled was confirmed by event-specific assay as described above.

30 mg of leaf, 60 mg of stem, and 200 mg of root tissue (frozen in dry ice or liquid nitrogen) were macerated using TissueLyser equipment. To the macerated leaf tissue was added 750 µl saline phosphate extraction buffer (PBS) supplemented with Tween 20 (0.138 M NaCl; 0.027 mM KCl; 0.05% Tween 20, pH 7.4) diluted according to manufacturer's instructions (Envirologix™, USA). For stalk and root, 375 µL of the same buffer was used. After buffer addition, vortex homogenization was performed and then centrifugation for 20 minutes at maximum speed. The resulting supernatant was collected and total protein was quantified using the Bradford assay.

Quantitation of Cry1Ac and Pat proteins was performed according to the recommendations of the ThermoScientific™ Coomassie Plus (Bradford) Protein Assay Kit (23236)—Microplate Procedure. Thus, the standards used for obtaining the calibration curve were the already-diluted commercial BSA (Bovine Serum Albumin) standards supplied with the kit described above. The 2000, 1000, 500, 250, 125, and 0 µg/mL calibrators (prepared in PBST buffer) were used. 10 µL of each standard calibrator was added in triplicate to plate wells. In total, 6 curves were generated from independent dilutions. For the samples, 10 µL of the 3 individual protein extractions were used in each well. Then 200 µL of Coomassie Plus Reagent Solution was added to each well containing the calibrators and samples. The plates were covered and incubated for 5 minutes at room temperature. Absorbance was read at 595 nanometers (nm) using SoftmaxPro 7.0 software (Molecular Device).

Total proteins were obtained in triplicate for each sample studied. After the total protein quantification of each replicate, the sample with the smallest variation of the median quantification value was chosen for ELISA analysis. These samples were normalized following the standard Qiagility Automatic Pipettor (QIAGEN) operating procedure. Normalization was done to a final concentration of 150 µg/mL total protein. Subsequently, the samples were diluted to ensure that the protein concentrations to be identified were within the reliable quantitation range. For analysis of the presence of Cry1Ac protein, the dilution was made to have 1.000 ng/mL. For the analysis of the presence of Pat protein, the dilution was to 30,000 ng/mL. Standard samples were used as previously described for ELISA analysis.

Results were obtained by 96-well plate spectrometry reading at two different wavelengths: 450 nm and 630 nm for Cry1Ac and 450 nm for Bar on a SpectraMax Plate reader (Molecular Devices). For Cry1Ac the Envirologix AP003 CRBS kit is used for protein detection and quantification. For Pat (bar) the Envirologix AP013 BAR kit was used. In all cases, the manufacturers recommendations were followed.

The analysis was based on the association of the absorbance values of the test samples with the predicted values in an equation estimated by measuring the absorbance of a standard curve. Synthetic proteins were diluted to desired concentrations in PBST buffer. Analyzes were performed in experimental duplicate for each sample. Cry1Ac and Pat protein concentrations were presented based on Total Protein (μg/mg), Fresh Tissue (μg/g) and Dry Tissue (μg/g).

Cry1Ac protein expression data from leaves of the event of the invention over one year of cultivation (110, 200, and 300 DAP) at each of the five sites evaluated are shown in Table 07 below.

TABLE 07

Average Cry1Ac expression in leaves of the event of the invention over a year of sugarcane cultivation. Individual and combined statistical analysis for the 5 sites tested at 100, 200, and 300 DAP (SE: standard error).

| Location | Time DAP/Comparison | Event of the Invention μg Cry1Ac/mg Total Protein | SE | μg Cry1Ac/g Fresh Tissue | SE | μg Cry1Ac/g Dry Tissue | SE |
|---|---|---|---|---|---|---|---|
| Barrinha-SP | 100 | 3.3 | 0.19 | 24.6 | 3,32 | 83.5 | 10.80 |
| | 200 | 3.1 | 0.19 | 32.8 | 3.32 | 99.0 | 10.80 |
| | 300 | 3.5 | 0.19 | 44.1 | 3.32 | 143.8 | 10.80 |
| Camamu-BA | 100 | 3.2 | 0.12 | 30.3 | 1.96 | 127.2 | 6.62 |
| | 200 | 3.1 | 0.12 | 32.9 | 1.96 | 99.3 | 6.62 |
| | 300 | 2.4 | 0.12 | 27.5 | 1.96 | 89.5 | 6.62 |
| Piracicaba-SP | 100 | 3.5 | 0.17 | 31.1 | 2.84 | 119.6 | 10.40 |
| | 200 | 3.0 | 0.17 | 35.8 | 2.84 | 119.0 | 10.40 |
| | 300 | 3.7 | 0.17 | 39.1 | 2.84 | 123.0 | 10.40 |
| | 100 | 4.3 | 0.19 | 24.2 | 1.57 | 91.8 | 5.24 |
| Quirinópolis-GO | 200 | 2.8 | 0.19 | 22.1 | 1.57 | 65.9 | 5.24 |
| | 300 | 2.8 | 0.19 | 28.1 | 1.57 | 89.8 | 5.24 |
| | 100 | 3.6 | 0.24 | 24.3 | 2.52 | 91.7 | 8.49 |
| Valparaíso-SP | 200 | 3.3 | 0.24 | 25.5 | 2.52 | 85.2 | 8.49 |
| | 300 | 3.7 | 0.24 | 27.7 | 2.52 | 91.9 | 8.49 |
| | 100 | 3.6 | 0.11 | 26.9 | 1.76 | 102.8 | 5.91 |
| Combined Analysis | 200 | 3.0 | 0.11 | 29.8 | 1.76 | 93.7 | 5.91 |
| | 300 | 3.2 | 0.11 | 33.3 | 1.76 | 107.6 | 5.91 |

Figure 8:
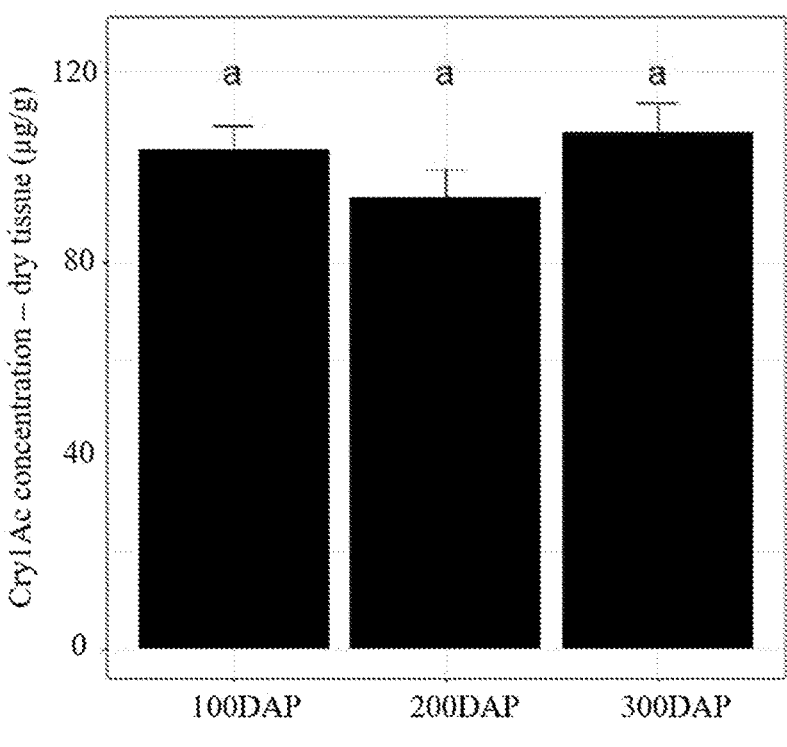
FIG. 8 is the result of comparing means of Cry1Ac protein expression in leaves of the event of the invention during the sugarcane cultivation cycle. Combined analysis for Barrinha, Piracicaba and Valparaiso (SP), Camamu-BA and Quirinópolis-GO. Bars followed by the same letter do not differ by Tukey's test at the 5% probability level.

Cry1Ac expression data (leaves) from the combined analysis of the 5 locations of the event of the invention over a year of cane cultivation (Table 07) are shown in FIG. 8 (in μg protein/g dry tissue).

Cry1Ac protein expression data in leaves of the event of the invention over a cycle of cane 60 and 120 DAP and cane 240 and 300 DAP are presented in Table 08.

TABLE 08

Comparison of means of Crt1Ac expression in leaves of the event of the invention over a cycle of cane 60 and 120 DAP and cane 240 and 300 DAP.

| Location | Time DAP/Comparison | Event of the Invention μg Cry1Ac/mg Total Proteing | SE | μg Cry1Ac/g Fresh Tissue | SE | μg Cry1Ac/g Dry Tissue | SE |
|---|---|---|---|---|---|---|---|
| | 60 | 3.2 | 0.14 | 37.4 | 1.41 | 142.7 | 4.96 |
| Barrinha-SP | 120 | 3.3 | 0.14 | 46.7 | 1.41 | 148.6 | 4.96 |
| | 240 | 2.3 | 0.14 | 20.9 | 1.41 | 72.8 | 4.96 |
| | 300 | 2.8 | 0.14 | 30.6 | 1.41 | 104.0 | 4.96 |
| | 60 | 3.8 | 0.29 | 40.8 | 5.05 | 179.9 | 15.40 |
| Piracicaba-SP | 120 | 3.3 | 0.29 | 68.4 | 5.05 | 118.3 | 15.40 |
| | 240 | 3.4 | 0.29 | 34.4 | 5.05 | 107.1 | 15.40 |
| | 300 | 3.0 | 0.29 | 27.4 | 5.05 | 95.0 | 15.40 |
| | 60 | 3.3 | 0.15 | 34.0 | 2.39 | 129.8 | 7.89 |
| Quirinópolis-GO | 120 | 3.0 | 0.15 | 51.2 | 2.39 | 163.7 | 7.89 |
| | 240 | 2.0 | 0.15 | 20.2 | 2.39 | 75.7 | 7.89 |
| | 300 | 2.4 | 0.15 | 28.0 | 2.39 | 87.9 | 7.89 |
| | 60 | 3.0 | 0.18 | 32.8 | 2.91 | 143.7 | 10.2 |
| Valparaíso-SP | 120 | 2.3 | 0.18 | 38.1 | 2.91 | 122.1 | 10.2 |
| | 240 | 2.0 | 0.18 | 16.7 | 2.91 | 62.0 | 10.2 |
| | 300 | 2.7 | 0.18 | 30.6 | 2.91 | 97.3 | 10.2 |
| | 60 | 3.3 | 0.16 | 36.3 | 2.14 | 147.0 | 5.17 |

TABLE 08-continued

| | Time | Event of the Invention | | | | | |
|---|---|---|---|---|---|---|---|
| Location | DAP/ Comparison | µg Cry1Ac/ mg Total Proteing | SE | µg Cry1Ac/ g Fresh Tissue | SE | µg Cry1Ac/ g Dry Tissue | SE |

Comparison of means of Crt1Ac expression in leaves of the event of the
invention over a cycle of cane 60 and 120 DAP and cane 240 and 300 DAP.

| | Time | Event of the Invention | | | | | |
|---|---|---|---|---|---|---|---|
| Location | DAP/ Comparison | µg Cry1Ac/ mg Total Proteing | SE | µg Cry1Ac/ g Fresh Tissue | SE | µg Cry1Ac/ g Dry Tissue | SE |
| Combined Analysis | 120 | 3.0 | 0.16 | 50.3 | 2.14 | 139.5 | 5.17 |
| | 240 | 2.4 | 0.16 | 22.7 | 2.14 | 77.5 | 5.17 |
| | 300 | 2.8 | 0.16 | 29.7 | 2.14 | 96.1 | 5.17 |

Figure 9:
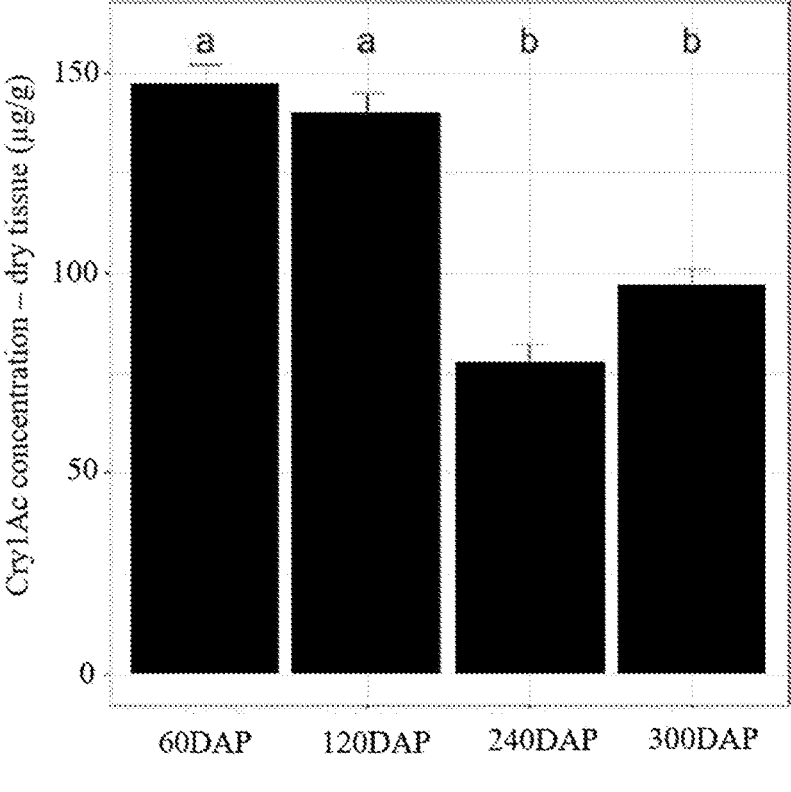
FIG. 9 is the result of comparing means of Cry1Ac expression in leaves of the event of the invention in sugarcane at 60 and 120 DAP and then 240 and 300 DAP. Combined analysis for Barrinha-SP, Piracicaba-SP, Quirinópolis-GO and Valparaiso-SP. Bars followed by the same letter do not differ by Tukey's test at the 5% probability level.

Cry1Ac expression data (leaves) from the combined analysis of 4 locations of the event of the invention in a crop cycle of cane 60 and 120 DAP and cane 240 and 300 DAP (Table 4) are shown in FIG. 9 (in µg protein/g dry tissue).

Cry1Ac protein expression data in mature stems from the event of the invention harvested at 330 DAP are shown in Table 09.

TABLE 09

Comparison of average Cry1Ac expression in mature stems
of the event of the invention harvested at 330 DAP.

| | Event of the Invention | | |
|---|---|---|---|
| Location/ Comparison | µg Cry1Ac/ mg Total Protein | µg Cry1Ac/ g Fresh Tissue | µg Cry1Ac/ g Dry Tissue |
| Barrinha-SP | 10.0 | 3.9 | 16.2 |
| Camamu-BA | 7.4 | 3.6 | 17.1 |
| Piracicaba-SP | 7.1 | 2.5 | 10.0 |

TABLE 09-continued

Comparison of average Cry1Ac expression in mature stems
of the event of the invention harvested at 330 DAP.

| | Event of the Invention | | |
|---|---|---|---|
| Location/ Comparison | µg Cry1Ac/ mg Total Protein | µg Cry1Ac/ g Fresh Tissue | µg Cry1Ac/ g Dry Tissue |
| Quirinópolis-GO | 9.7 | 3.9 | 16.0 |
| Valparaíso-SP | 10.0 | 4.3 | 17.6 |
| Standard Error | 1.1 | 0.5 | 2.3 |

Figure 10:
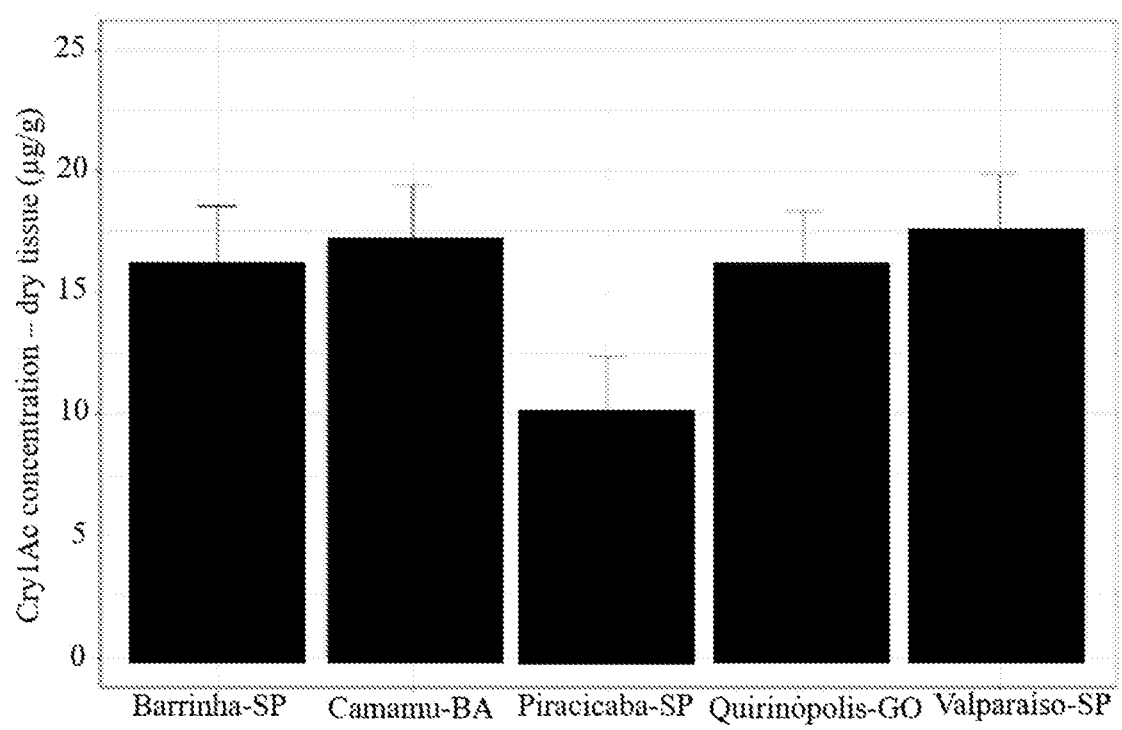
FIG. 10 is the result of comparing averages of Cry1Ac expression in stems of the event of the invention at 330 DAP.

Cry1Ac expression data in mature stems from the event of the invention at 330 DAP (Table 09) are shown in FIG. 10 (in µg protein/g dry tissue).

Pat protein expression data in leaves from the event of the invention over one year of cultivation (110, 200 and 300 DAP) for the five evaluated locations are presented in Table 10.

TABLE 10

Comparison of average Pat expression from leaves of the event of the
invention over a cane crop cycle (100, 200 and 300 DAP).

| | Time | Event of the Invention | | | | | |
|---|---|---|---|---|---|---|---|
| Location | DAP/ Comparison | µg Pat/ mg Total Protein | SE | µg Pat/ g Fresh Tissue | SE | µg Pat/ g Dry Tissue | SE |
| Barrinha-SP | 100 | 0.03 | 0.001 | 0.20 | 0.009 | 0.69 | 0.030 |
| | 200 | 0.01 | 0.001 | 0.12 | 0.009 | 0.37 | 0.030 |
| | 300 | 0.01 | 0.001 | 0.16 | 0.009 | 0.53 | 0.030 |
| Camamu-BA | 100 | 0.01 | 0.001 | 0.11 | 0.006 | 0.45 | 0.022 |
| | 200 | 0.01 | 0.001 | 0.10 | 0.006 | 0.29 | 0.022 |
| | 300 | 0.01 | 0.001 | 0.06 | 0.006 | 0.20 | 0.022 |
| Piracicaba-SP | 100 | 0.03 | 0.001 | 0.26 | 0.013 | 0.98 | 0.048 |
| | 200 | 0.01 | 0.001 | 0.16 | 0.013 | 0.52 | 0.048 |
| | 300 | 0.01 | 0.001 | 0.14 | 0.013 | 0.44 | 0.048 |
| Quirinópolis-GO | 100 | 0.03 | 0.001 | 0.15 | 0.009 | 0.59 | 0.034 |
| | 200 | 0.01 | 0.001 | 0.10 | 0.009 | 0.30 | 0.034 |
| | 300 | 0.01 | 0.001 | 0.11 | 0.009 | 0.35 | 0.034 |
| Valparaíso-SP | 100 | 0.08 | 0.002 | 0.12 | 0.011 | 0.47 | 0.039 |
| | 200 | 0.01 | 0.002 | 0.10 | 0.011 | 0.35 | 0.039 |
| | 300 | 0.01 | 0.002 | 0.10 | 0.011 | 0.33 | 0.039 |
| Combined Analysis | 100 | 0.03 | 0.003 | 0.17 | 0.012 | 0.64 | 0.045 |
| | 200 | 0.01 | 0.003 | 0.12 | 0.012 | 0.37 | 0.045 |
| | 300 | 0.01 | 0.003 | 0.11 | 0.012 | 0.37 | 0.045 |

Figure 11:
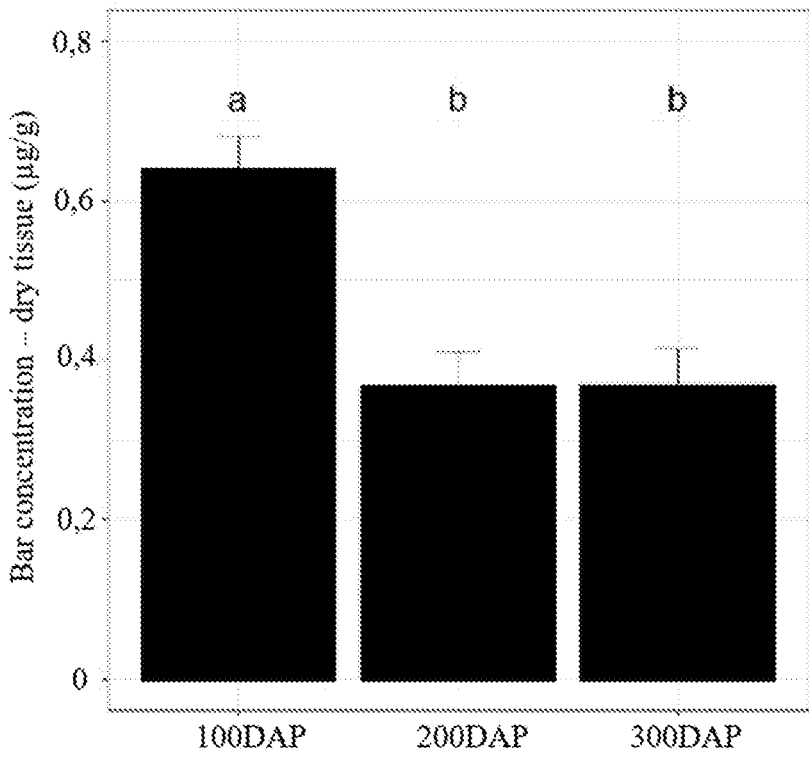
FIG. 11 is the result of comparing means of Pat protein expression in leaves of the event of the invention during the sugarcane cultivation cycle. Combined analysis for Barrinha, Piracicaba and Valparaiso (SP), Camamu (BA) and Quirinópoli (GO) locations. Bars followed by the same letter do not differ by Tukey's test at the 5% probability level.

Pat expression data (leaves) from the event of the invention from the combined analysis of the 5 locations over a year of cane plant cultivation (Table 10) are shown in FIG. 11 (in µg protein/g dry tissue).

Pat protein expression data from leaves of the event of the invention over a cycle of cane 60 and 120 DAP and cane 240 and 300 DAP at the four evaluated locations are presented in Table 11.

TABLE 11

Comparison of average leaf Pat expression from the event of the invention over
a cane cycle (60 and 120 DAP and 240 and 300 DAP).

| Location | Time DAP/ Comparison | Event of the Invention | | | | | |
|---|---|---|---|---|---|---|---|
| | | μg Pat/ mg Total Protein | SE | μg Pat/ g Fresh Tissue | SE | μg Pat/ g Dry Tissue | SE |
| Barrinha-SP | 60 | 0.011 | 0.001 | 0.13 | 0.010 | 0.45 | 0.033 |
| | 120 | 0.016 | 0.001 | 0.24 | 0.010 | 0.76 | 0.033 |
| | 240 | 0.017 | 0.001 | 0.15 | 0.010 | 0.53 | 0.033 |
| | 300 | 0.018 | 0.001 | 0.19 | 0.010 | 0.64 | 0.033 |
| Piracicaba-SP | 60 | 0.013 | 0.002 | 0.14 | 0.014 | 0.52 | 0.041 |
| | 120 | 0.016 | 0.002 | 0.21 | 0.014 | 0.68 | 0.041 |
| | 240 | 0.023 | 0.002 | 0.23 | 0.014 | 0.70 | 0.041 |
| | 300 | 0.021 | 0.002 | 0.19 | 0.014 | 0.67 | 0.041 |
| Quirinópolis-GO | 60 | 0.011 | 0.001 | 0.12 | 0.010 | 0.39 | 0.034 |
| | 120 | 0.009 | 0.001 | 0.16 | 0.010 | 0.52 | 0.034 |
| | 240 | 0.015 | 0.001 | 0.14 | 0.010 | 0.52 | 0.034 |
| | 300 | 0.017 | 0.001 | 0.19 | 0.010 | 0.60 | 0.034 |
| Valparaíso-SP | 60 | 0.013 | 0.001 | 0.14 | 0.013 | 0.46 | 0.045 |
| | 120 | 0.008 | 0.001 | 0.12 | 0.013 | 0.40 | 0.045 |
| | 240 | 0.015 | 0.001 | 0.12 | 0.013 | 0.45 | 0.045 |
| | 300 | 0.018 | 0.001 | 0.20 | 0.013 | 0.64 | 0.045 |
| Combined Analysis | 60 | 0.012 | 0.001 | 0.13 | 0.009 | 0.46 | 0.031 |
| | 120 | 0.012 | 0.001 | 0.18 | 0.009 | 0.59 | 0.031 |
| | 240 | 0.017 | 0.001 | 0.16 | 0.009 | 0.54 | 0.031 |
| | 300 | 0.018 | 0.001 | 0.19 | 0.009 | 0.64 | 0.031 |

Figure 12:
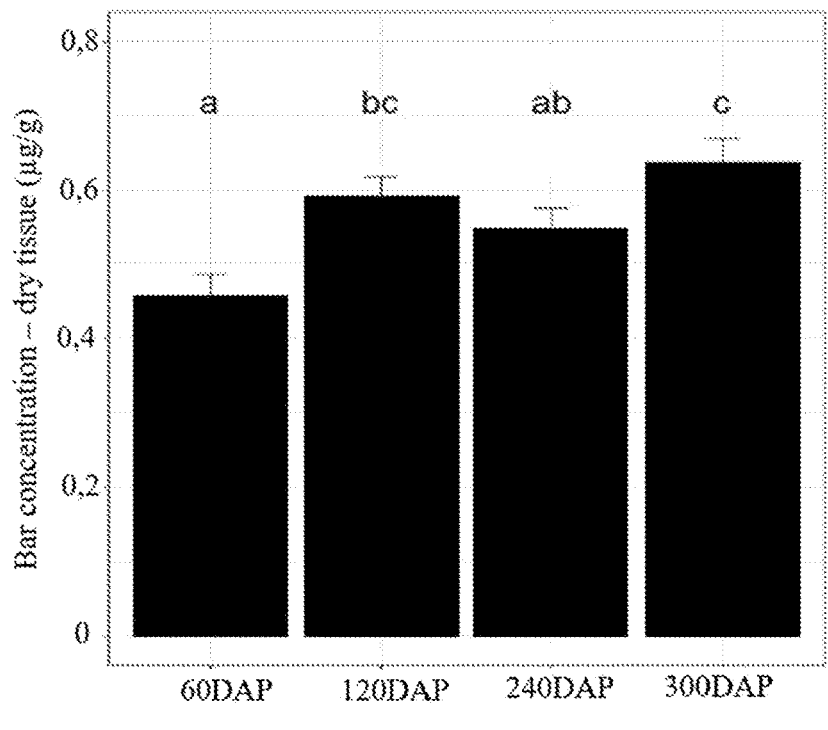
FIG. 12 is the result of comparing means of Pat protein expression in leaves of the event of the invention in sugarcane at 60 and 120 DAP and then 240 and 300 DAP. Combined analysis for Barrinha-SP, Piracicaba-SP, Quirinópolis-GO and Valparaiso-SP. Bars followed by the same letter do not differ by Tukey's test at the 5% probability level.

The data from the combined analysis of the 4 evaluated leaf expression locations from the event of the invention over a crop cycle of cane 60 and 120 DAP and cane 240 and 300 DAP (Table 11) are shown in FIG. 12 (in μg protein/g dry tissue).

Pat protein expression data from mature stems of the event of the invention collected at 330 DAP are shown in Table 12.

TABLE 12

Comparison of average Pat expression from mature stems of
the event of the invention harvested at 330 DAP.

| Location/ Comparison | Event of the Invention | | |
|---|---|---|---|
| | μg Pat/ mg Total Protein | μg Pat/ g Fresh Tissue | μg Pat/ g Dry Tissue |
| Barrinha-SP | 0.035 | 0.014 | 0.058 |
| Camamu-BA | 0.028 | 0.013 | 0.061 |
| Piracicaba-SP | 0.059 | 0.022 | 0.087 |
| Quirinópolis-GO | 0.021 | 0.009 | 0.035 |
| Valparaíso-SP | 0.034 | 0.015 | 0.062 |
| Standard Error | 0.005 | 0.002 | 0.006 |

Figure 13:
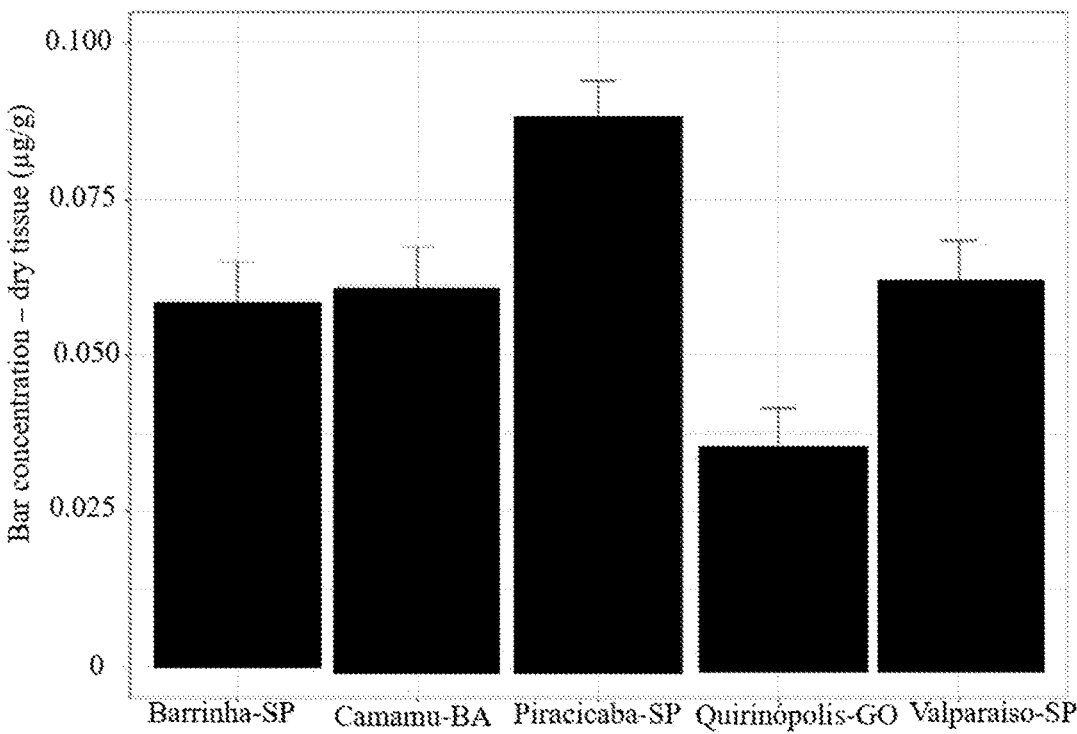
FIG. 13 is the result of comparing averages of Pat protein expression in stems of the event of the invention at 330 DAP in the PACE assays.

Bar expression on mature stem of the event of the invention at 330 DAP (Table 12) are shown in FIG. 13 (in μg protein/g dry tissue).

All root samples, from all plots and from all locations, had Cry1Ac protein expression values below the limit of quantification (<LOQ) for the previously validated analysis protocol, except for the Quirinópolis site where an experimental repetition contained 0.053 μg Cry1Ac per gram of fresh tissue. For Pat protein, the results showed that all samples from all plots and locations, without exception, were below the detection limit (<LOD) of the previously validated method (Table 13).

TABLE 13

Cry1Ac and Pat protein expression values in root tissues
of the event of the invention (μ/g fresh tissue).

| Tissue | Location | Cry1Ac | Pat |
|---|---|---|---|
| Root | Barrinha-SP | <LOQ | <LOD |
| | Piracicaba-SP | <LOQ | <LOD |
| | Valparaiso-SP | <LOQ | <LOD |
| | Quirinópolis-GO | 0.053[1] | <LOD |
| | Camamu-BA | <LOQ | <LOD |

[1]one repetition above LOQ.

The results obtained for leaf, stem, and roots indicate that the event of the invention has Cry1Ac protein expression levels much higher than Pat expression. For example, in leaves, the average Cry1Ac expression over sampled times/ sites ranged from 26.9 to 33.3 μg/g fresh tissue while mean Pat expression ranged from 0.11 to 0.18 μg/g fresh tissue. The average concentration of Cry1Ac from leaves of the event of the invention throughout the sugarcane cycle remained constant (or slightly decreased) across collection times of 100, 200, and 300 DAP, with concentrations of 26.9, 29.8, and 33.3 μg/g fresh tissue, respectively. Pat expression levels were higher at 100 DAP (0.17 μg/g fresh tissue) and decreased statistically at 200 and 300 DAP with means of 0.12 and 0.11 μg/g fresh tissue, respectively.

Leaf expression analysis revealed no relevant protein differences in relation to planting sites. For example, the average expression of Cry1Ac in event leaves of the invention at the five locations ranged from 24.2 to 31.1 μg/g fresh tissue (100 DAP), 22.1 to 35.8 μg/g fresh tissue (200 DAP), and 27.5 to 44.1 μg/g fresh tissue (300 DAP). Corresponding values for Pat expression were: 0.11 to 0.25 μg/g fresh tissue (100 DAP), 0.10 to 0.16 μg/g fresh tissue (200 DAP) and 0.06 to 0.16 μg/g fresh tissue (300 DAP).

Stem expression data collected at 330 DAP showed that Cry1Ac and Pat expression levels were 3.65 μg/g fresh tissue and 0.01 μg/g fresh tissue, respectively. The average expression of Cry1Ac at 330 DAP at the five locations ranged from 2.53 to 4.27 μg/g fresh tissue.

Expression data of Cry1Ac and Pat proteins in roots of the event of the invention indicate that these proteins are very poorly expressed in this tissue and cannot be accurately identified/quantified. Only the concentration of one repeat Cry1Ac in Quirinópolis was estimated (0.053 μg Cry1Ac per gram of fresh root). All other samples were below the LOD and/or LOQ according to the ELISA methodology employed.

The effect of clipping on expression levels was also evaluated. Leaf samples were collected at 60 and 120 DAP, the stems were cut to mimic a crop at 180 DAP, and they were resampled at 60 and 120 days after cutting (or 240 and 300 DAP). The mean combined concentrations of Cry1Ac across sites during these collection periods were 36.2 and 51.1 μg/g (60 and 120 DAP) and 23.1 and 29.2 μg/g fresh tissue (240 and 300 DAP). Pat expression levels were 0.11 and 0.18 (60 and 120 DAP) and 0.16 and 0.19 (240 and 300 DAP). Taken together, the ranges of the Cry1Ac and Pat (bar) protein expression are consistent with the expression data from the previously discussed experiment (100, 200 and 300 DAP) and suggest that the expression levels after shearing are similar to that of expression levels before cutting.

The apparent drop in Cry1Ac expression levels after shear, compared to Cry1Ac concentrations before shear, is probably due to sample variability. It is important to note that Cry1Ac expression levels in the previously-described experiment (100, 200 and 300 DAP), which was conducted in parallel with this experiment (in the field and in the laboratory), ranged from 26.9 to 29.8 μg/g fresh tissue. However, Cry1Ac expression levels in this experiment were numerically higher, 36.2 and 51.1 μg/g fresh tissue (60 and 120 DAP), giving the impression of expression drop after cutting. It is known that expression values in various cultures may vary at different sampling times due to experimental variability. The overall conclusion of expression data at 100, 200, and 300 DAP (26.9 to 33.3 μg/g fresh tissue) was replicated at collection points after cutting, 240 to 300 DAP (22.7 to 29.7 μg/g fresh tissue). Higher expression values at 60 and 120 DAP of the sugarcane/cane evaluation experiment can be attributed to the experimental variability and probably do not indicate a significant reduction of Cry1Ac expression levels after cutting the event of the invention.

It is therefore concluded that the expression levels of Cry1Ac and Pat proteins from the event of the invention was characterized at different times, tissues and planting sites representative of its cultivation in Brazil. Cry1Ac protein expression levels in the leaves of the event of the invention remain high throughout the cultivation cycle, ensuring the intended effect of resistance to *Diatraea saccharalis*. Expression levels of Cry1Ac and Pat proteins in stems from the event of the invention are very low and, therefore, food exposure via consumption of broth or derived products to heterologous proteins will be minimal.

Western Blot

For identification of the heterologous proteins expressed by the event of the invention, 50 mg of leaf frozen in liquid nitrogen was used. Maceration was performed in the TissueLyser equipment for 10 minutes at 25 Hz, with the addition of three steel beads (3 mm—Qiagen). To the macerated tissue, 750 μl of Tween 20-supplemented saline phosphate extraction buffer (PBS) was added (0.138 M NaCl; 0.027 mM KCl; 0.05% Tween 20, pH 7.4) diluted according to manufacturer's instructions (Envirologix™, USA). After buffer addition, vortex homogenization was performed, and the mixture was centrifuged for 10 minutes at 9,500 RPM at 4° C. The resulting supernatant was collected and total protein was quantified.

Quantitation adopted for analysis of Cry1Ac and Pat proteins was performed according to the recommendations of ThermoScientific™ Coomassie Plus (Bradford) Protein Assay Kit (23236)—Microplate Procedure. Thus, the standards used for obtaining the calibration curve were the already-diluted commercial BSA (Bovine Serum Albumin) standards supplied with the kit described above. The 2000, 1000, 500, 250, 125, and 0 μg/ml calibrators prepared in PBST buffer were used. 10 μL of each standard calibrator was added to the plate wells in triplicate. The plates were covered and incubated for 5 minutes at room temperature. Absorbance was read at 595 nanometers (nm) using SoftmaxPro 7.0 software (Molecular Device). After total protein extraction, 2.5 μg of protein extract was mixed with 2× Laemmli Sample Buffer (Bio-Rad, USA) and subjected to denaturation via heating at 100° C. for 5 minutes.

As a negative control of the presence of heterologous proteins, 2.5 μg of protein extract from the conventional parental variety (WT) was used. In addition, positive controls were prepared to detect Cry1Ac and Pat proteins. The first positive control was prepared using either 50 ng CTC internally-purified synthesized Cry1Ac protein or 1 ng commercially-available purified bar protein (Novoprotein, USA), diluted in total protein solution extracted from conventional parental variety (WT) leaves. The second positive control was made by diluting 5 ng of purified Cry1Ac protein (GenScript, USA) or 1 ng of bar protein (Novoprotein, USA) in PBST extraction buffer. Alternatively, other positive controls were added to the assay, such as commercial Bt11 maize and another genetically-modified sugarcane event containing the same proteins upon analysis.

Samples were denatured and applied on 4-20% polyacrylamide gel (Mini-PROTEAN® TGX™ Precast Gel) submerged in Tris/glycine/SDS running buffer (Bio-Rad, USA) and separated by electrophoresis at 50V for 5 minutes and then at 120V for approximately 90 minutes. Next, the polyacrylamide gels were equilibrated in Tris/Glycine Transfer Buffer (Bio-Rad, USA), which was added with 20% methanol for 10-15 minutes. The PVDF membrane was treated with absolute methanol. The transfer system was mounted in a container filled with the cold Transfer Buffer for immersion transfer ("wet transfer") at a constant voltage of 50V for 3 hours. Upon completion of the transfer, the membrane was blocked for 16 hours at 4° C., under constant agitation, in blocking solution [5% skimmed milk powder (Bio-Rad, USA) and TBS/T (20 mM Tris, 150 mM NaCl, 1% Tween20)] to prevent possible nonspecific membrane binding.

In the next step, the membrane was incubated with the primary antibody for 90 minutes to detect and confirm the presence and integrity of the Cry1Ac and Pat proteins. The polyclonal antibodies used in this assay were rabbit Anti-Cry1Ab (Fitzgerald, USA), which bind both Cry1Ac and Cry1Ab proteins; and rabbit Anti-Bar (Abcam, USA), which reacts with PAT/Bar protein, diluted 1: 100 in TBS/T (v/v).

The membrane was washed in 3 5-minute (3×5) cycles in TBS/T and incubated with goat-produced HRP-conjugated secondary Anti-Rabbit antibody (Sigma) at a concentration of 1: 20,000 or at a concentration of 1:5,000—v/v (Fitzgerald) for 60 minutes. After incubations, the membrane was again washed with TBS/T (3×5 minutes), and the enzyme-linked immunoassay was verified on Amersham Hyperfilm ECL X-ray films (GE Healthcare, USA) by Clarit Western ECL Substrate Kit substrate reaction (Biorad, USA) according to the manufacturer's instructions. X-ray film exposure to membrane ranged from 15 seconds to 3 minutes.

Figure 14:
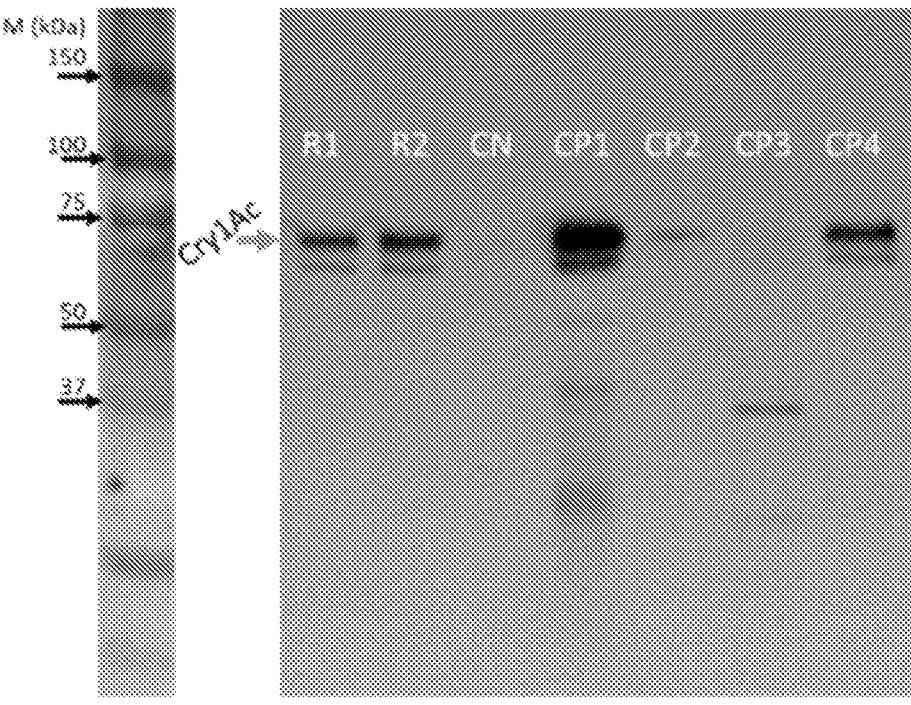
FIG. 14 is the result of the Western blot methodology for identifying the Cry1Ac protein. M: molecular weight marker (kDa). R1 and R2: Event of the invention. CN: parental cultivar. CP1: 50 ng of purified Cry1Ac protein, diluted in total proteins of the parental cultivar. CP2: 5 ng commercial Cry1Ac protein diluted in PBST buffer. CP3: Bt11 corn. CP4: GM sugarcane event expressing Cry1Ac protein.

The results revealed that the expression profile of Cry1Ac protein appears as two nearly-identical molecular weight immunoreactive bands of ~69 and ~66 kDa, commonly called doublets, in samples R1 and R2 (FIG. 14). Both samples are biological replicates of the event of the invention, obtained from two experimental plots at the Piracicaba Polo. Protein doublets usually come from the removal of terminal amino acid residues by proteases. As expected, the negative control (NC) in turn showed no immunoreactivity. The negative control consisted of total protein samples extracted from the parental variety. The approximately 69 and 66 kDa bands are also present in positive control 1 (CP1) where the internally purified CT1-purified Cry1Ac protein (50 ng) was added to the total protein extracted from the parental cultivar. Some extra bands of lower molecular weight (between 50 and 30 kDa) are observed in positive control 1 (CP1). These bands are visible, possibly, because the Cry1Ac protein used as a control has been partially purified (34% pure) with other bacterial proteins. Positive control 2 (CP2) consisted of commercial Cry1Ac (5 ng) protein (GeneScript) diluted in PBST extraction buffer. This protein has been isolated with >95% purity and has a single band of the expected weight.

Other positive controls have been added to the membrane. A total protein sample extracted from Bt11 corn leaves (Syngenta, USA) was used as a positive control for the experiment (CP3). This is possible because the polyclonal antibodies used in the Western blot assay are also capable of reacting with Cry1Ab proteins. As expected, the Cry1Ab doublet was visible in the Bt11 (CP3) maize sample, as well as other bands at weights of 40 and 30 kDa, accepted as a product of intracellular proteolytic breaks of Cry proteins in plant leaves. Positive control 4 (CP4) consisted of total proteins extracted from another Cry1Ac-expressing sugarcane event. Once again, the profile of the Cry1Ac protein appears as doublet. No other bands indicating partial Cry1Ac protein or higher molecular weight fusion protein were observed in the leaves.

Figure 15:
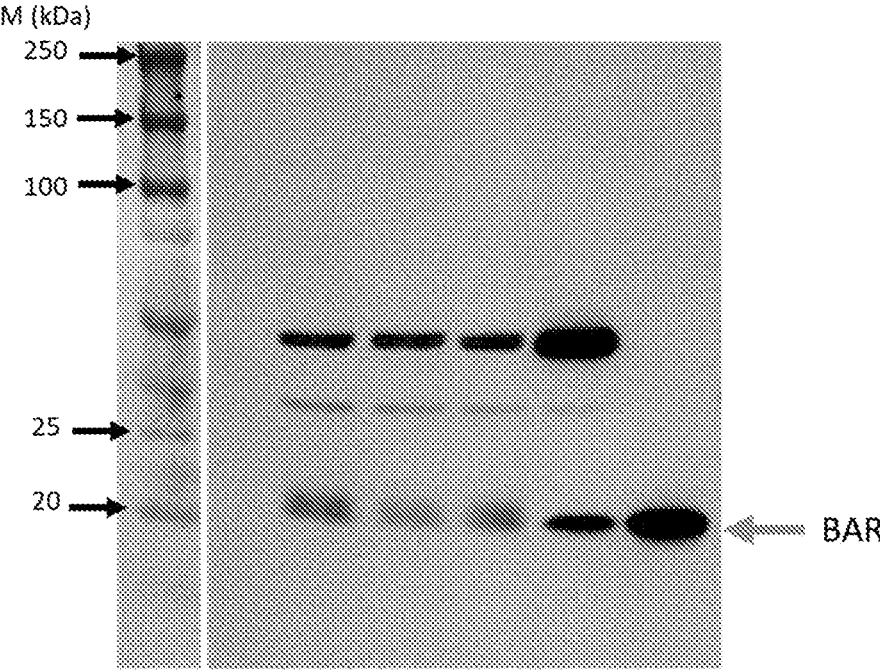
FIG. 15 is the result of the Western blot methodology for identification of Pat. M protein: molecular weight marker (kDa). R1, R2 and R3: biological repeats of the event of the invention. CP1 (positive control 1): 1 ng Bar protein diluted in total protein extracted from parental cultivar. CP2 (positive control 2): 1 ng protein Bar diluted in PBST buffer.

The protein encoded by the bar selection gene was also detected by western blot assay. Even though Pat is expressed at lower levels than the Cry1Ac protein, western blot assays demonstrated the presence of an immunoreactive band at the expected size of 22 kDa in all used biological replicates of the event of the invention (FIG. 15).

Two positive controls were added to the membrane. Positive control 1 (CP1) corresponds to 1 ng of purified bar protein (Novoprotein, China) diluted in protein extract of the parental cultivar. Positive control 2 (CP2) is the same protein diluted in PBST extraction buffer. The diagnostic band corresponding to the bar protein is present in both controls at the expected height and is identical to the band present at the event of the invention, confirming its identity.

In addition to the band corresponding to the Pat protein, it is possible to observe the presence of bands at the approximate weights of 37 kDa and 50 kDa in all samples except the purified protein diluted in the PBST extraction buffer (CP2). The presence of such bands in the positive control 1 is indicative of an artifact, probably generated by nonspecific antibody binding to endogenous sugarcane proteins.

It is therefore concluded that the identity of the Cry1Ac and Pat proteins expressed by the event of the invention was confirmed by western blot. The proteins expressed by the event of the invention are of the expected size, and no evidence of truncated/fused proteins being expressed by said event was found.

Example 5. Biological Tests: Susceptibility to the Sugarcane Borer (D. *Saccharalis*)

Biological Assays (bioassays) with target pest D. *saccharalis* (cane borer) can also be used for detection and characterization of event CTC91087-6, demonstrating the efficacy on the pest control provided by the expressed insecticidal protein Cry1Ac. Different bioassays may be contemplated within the scope of the present invention: for example, Leaf Disk Assay, Screenhouse bioassays, Tissue Dilution Assays, among others.

For leaf disc assay, leaves of event CTC91087-6 plants were collected, cut into discs of 16 mm$^2$ and distributed in bioassay plates containing gelled agar. Each well from culture plates was infested with D. *saccharalis* (0-24 h old) neonate and incubated at 27±1° C., relative humidity 60±10%, and photoperiod 12 h:12 h (light: dark) for a period of 7 days. At the end of incubation, larval mortality and inhibition of larval development of surviving individuals was evaluated, and the relative efficacy was calculated (Relative efficacy=(1-Mtc/Mev)×100). The surviving larvae were submitted to image analysis by Digimizer software (v 4.6.1) for assessment of larval stage based on width of cephalic capsule. The larvae that did not reach the first instar were considered dead. Non-transgenic sugarcane varieties that are genetically very similar to the evaluated transgenic event can be used as assay controls.

Figure 17:
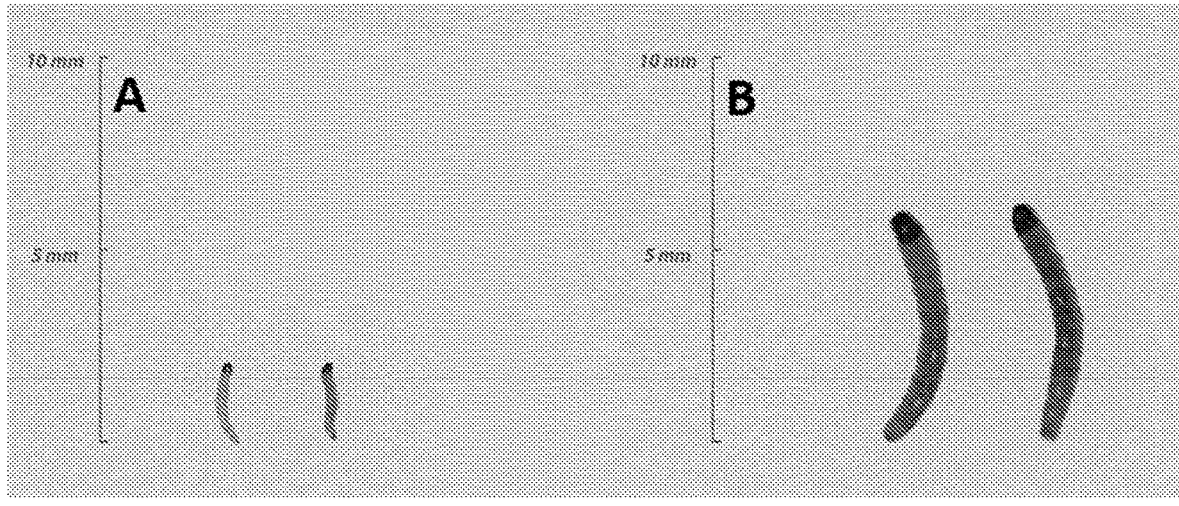
FIG. 17 shows exemplary results of larval size and development after seven days of feeding in the Leaf disc assay. On left (A) are exemplary larvae that were fed with plant material from the insect resistant CTC91087-6 event, and on right (B) are exemplary larvae that were fed with plant material from the conventional (parental—no transgenic) variety CTC9001.

To characterize event efficacy in controlling target pest D. *saccharalis* in laboratory, leaf disc assays were performed with plant tissue from CTC91087-6 event (two phenological stages, 110 and 220 DAP). Non-transgenic sugarcane CTC9001 was used as control (WT). The experimental design was completely randomized with four replicates per treatment (112 neonates per replicate). An average of 96% (df=4; P<0.0001) of mortality rate was observed when comparing the conventional variety (CTC9001) and CTC91087-6 event after 7 days feeding with leaf discs. Also, based on measurement of cephalic capsule width, it was observed that 100% of the surviving individuals did not develop beyond the first instar, evidencing high suppression in the development of D. *saccharalis* after feeding with the transgenic event (FIG. 17).

For screenhouse bioassays, seedlings of the transgenic event are planted in a screened nursery, where the plants are planted in the soil similar to natural environmental conditions, but in controlled environment to prevent the occurrence of natural infestations. At least 5 infestations are performed every 20 or 30 days, containing 20-35 *Diatraea saccharalis* eggs per tiller. The evaluation occurs when all infected stalks are harvested and cutting longitudinally to quantify the damage. Infestation Intensity is calculated dividing the number of internodes with damage by the total number of internodes, and the result was multiplied by 100 (Infestation Intensity). Percentage of Effective Damage was calculated, considering the total of internodes with damage caused by the insect divided by the total number of stalks evaluated in the plot.

Screenhouse trials were performed to characterize the efficacy of CTC91087-6 event in controlling borer attack in comparison to its parental variety CTC9001 (WT; non-transgenic) in a randomized block design, with 4 replications. Each experimental plot was composed by eight clumps of cane-plant that received 10 artificial infestations with approximately 30 eggs of *D. saccharalis* every 15 days. After eight months, the Infestation Intensity (II) and the effective Damage for both varieties were calculated. Relative efficacy in controlling infestation and damage by CTC91087-6 event was calculate by the formula [100-(event II*100)/WT II Mean].

Figure 18:
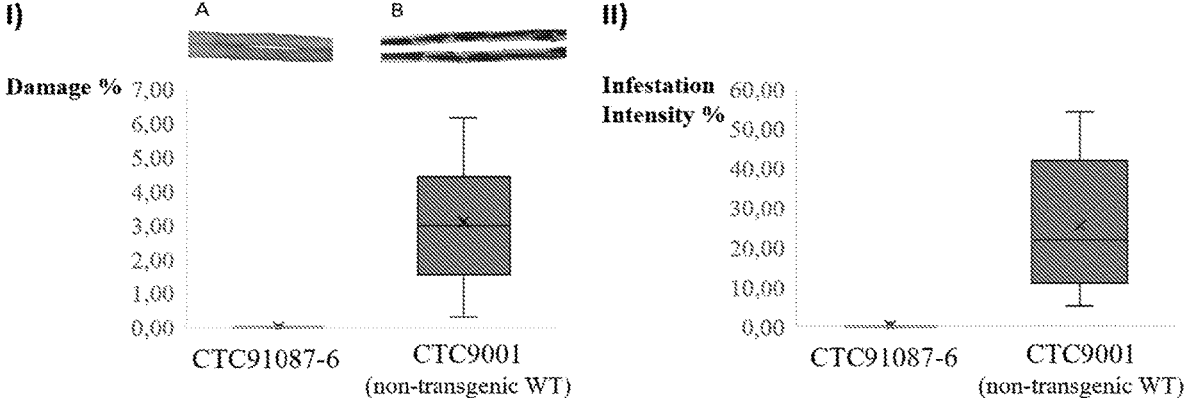
FIG. 18 shows results of screenhouse bioassays between CTC91087-6 and its conventional counterpart CTC9001 (parental variety—non transgenic). On left, I) shows exemplary images of visible damage caused by *D. saccharalis* on A: stalk from CTC91087-6 and B: stalk from CTC9001a. The graph in I) shows stalk damage (% Damage) results in the screenhouse. On right, II) shows Infestation Intensity (%) results in the screenhouse.
Figure 19:
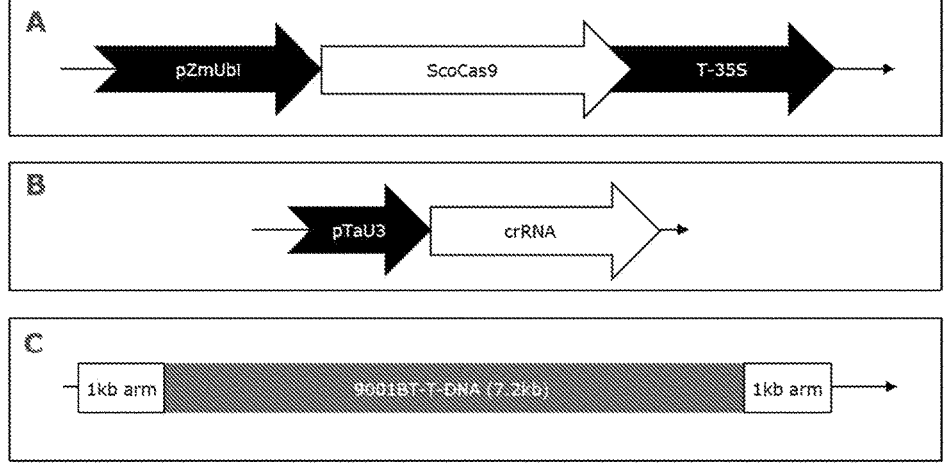
FIG. 19 demonstrates examples of cassettes for generation of event CTC91087-6 through gene editing approach. Cassette A comprises a sugarcane codon optimized Cas9 driven by pZmUbi promoter and T-35s terminator; Cassette B comprises crRNA for Cas9 driven by wheat U3 promoter and Cassette C comprises the HR template comprising 9001BT-T-DNA region with 1 kb homologous arms for site directed integration.

Under the artificial infestation the event CTC91087-6 presented relative efficacy in controlling infestation by *D. saccharalis* higher than 99.6% and in controlling stalk damage (length) superior to 99.9% in relation to its non-transgenic parental variety CTC9001 (WT). The damage caused by *D. saccharalis* in CTC91087-6 stalks was visibly lower than in the conventional sugarcane CTC9001 (FIG. 18). There were statistically differences (t-test, $P<0.05$) between CTC91087-6 and the non-transgenic variety CTC9001 in both parameters evaluated ($df=16$; $P<0.0001$), showing that under massive infestation with D. *Saccharalis* the event suppressed the damages caused by the pest.

On sugarcane conventional production *D. saccharalis* is considered controlled when the infestation intensity is lower than 3% (Gallo et al., 2002). For CTC91087-6, the intensity of infestation was lower than 0.01% reinforcing the event effectiveness to control its main target pest.

In addition to employing bioassays that use artificial infestations to observe the degree of infestation and damage caused by *D. saccharalis*, observations of infestation and damage percentage can also be made based on information collected directly from the fields where the event CTC91087-6 is grown. The II (infestation intensity), for example, can be calculated for natural infestation evaluation by defining an experimental area for stalk sampling cutting and quantification the number of internodes with and without damages) to obtain the infestation intensity (II).

Figure 16:
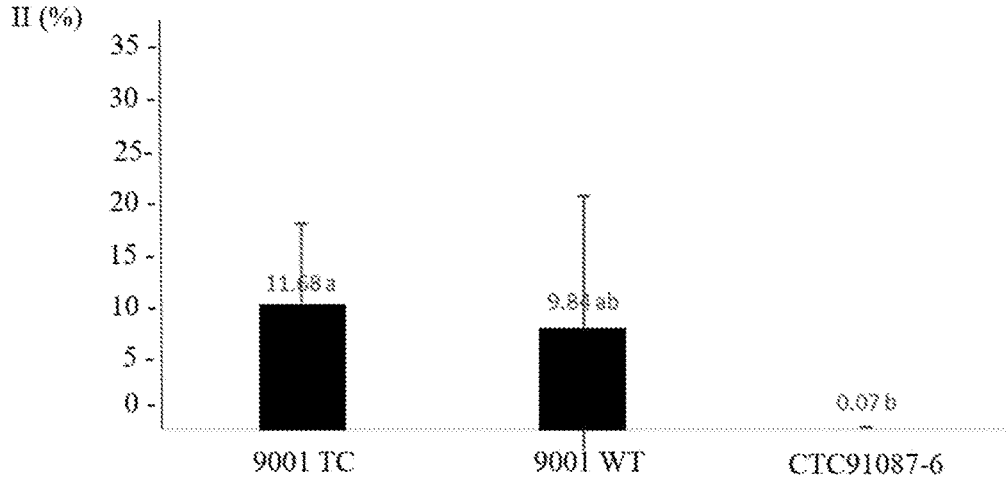
FIG. 16 represents natural Infestation Intensity (II %) of *Diatraea saccharalis* in field trials in different locations (Piracicaba (SP), Barrinha (SP), Valparaiso (SP) and Quirinópolis (GO)). CTC91087-6: event of the invention; 9001 TC: Parental cultivar with tissue culture treatment; 9001 WT: Regular Parental cultivar. x-axis represents the percentage of infestation intensity (II %; combined analysis—4 locations).

In the tests performed for the development of the event of the invention, the infestation intensity (II) was calculated in four experimental areas: Piracicaba, Barrinha, and Valparaiso (SP) and Quirinópolis (GO). The conventional variety CTC 9001 (parental; non transgenic) was used as control. This assay illustrates the resistance of the event CTC91087-6 to *D. saccharalis* infestation compared to the parental variety (CTC9001): it was observed a lower intensity of infestation for CTC91087-6 plants in comparison to the parental variety (CTC 9001=WT) in all the four experimental areas (Combined analysis; FIG. 16).

Having described examples of preferred embodiments, it should be understood that the scope of the present invention encompasses other possible variations and is limited only by the content of the appended claims, including the possible equivalents thereof.

---

The invention claimed is:

1. A recombinant nucleic acid molecule comprising the polynucleotide sequence of SEQ ID NO: 5.

2. The recombinant nucleic acid molecule of claim 1, comprising the polynucleotide sequence of SEQ ID NO: 22.

3. A genetically modified sugarcane plant comprising a recombinant nucleic acid molecule comprising the polynucleotide sequence of SEQ ID NO: 5, wherein the plant is insect-resistant.

4. A method of producing a genetically modified sugarcane plant that has improved insect resistance, comprising introducing a transfer DNA (T-DNA) fragment having the polynucleotide sequence of SEQ ID NO: 2 at a specific locus of genome positioned between sequences selected from the group consisting of SEQ ID NOs: 23 and 24, wherein a genetically modified sugarcane plant comprising a recombinant nucleic acid molecule comprising the polynucleotide sequence of SEQ ID NO: 5 is obtained.

5. The genetically modified sugarcane plant according to claim 3, comprising a recombinant nucleic acid molecule comprising the polynucleotide sequence of SEQ ID NO: 22.

6. The method according to claim 4, wherein the genetically modified sugarcane plant comprises a recombinant nucleic acid molecule comprising the polynucleotide sequence of SEQ ID NO: 22.

* * * * *

SEQUENCE LISTING

```
<160> NUMBER OF SEQ ID NOS: 70

<210> SEQ ID NO 1
<211> LENGTH: 7287
<212> TYPE: DNA
<213> ORGANISM: Artificial Sequence
<220> FEATURE:
<223> OTHER INFORMATION: Genetic construct comprising Cry1Ac and bar
      genes.

<400> SEQUENCE: 1
tggcaggata tattgtggtg taaacaaatt gacgcttaga caacttaata acacattgcg      60
gacgtcttta atgtactgaa tttagttact gatcactgat taagtactga tatcggtacc     120
gaattcgcgg ccgcaagctt cgatcgatgc ctgcagtgca gcgtgacccg gtcgtgcccc     180
tctctagaga taatgagcat tgcatgtcta agttataaaa aattaccaca tatttttttt     240
gtcacacttg tttgaagtgc agtttatcta tctttataca tatatttaaa ctttactcta     300
cgaataatat aatctatagt actacaataa tatcagtgtt ttagagaatc atataaatga     360
acagttagac atggtctaaa ggacaattga gtattttgac aacaggactc tacagtttta     420 tcttttagt gtgcatgtgt tctccttttt ttttgcaaat agcttcacct atataatact     480
tcatccattt tattagtaca tccatttagg gtttagggtt aatggttttt atagactaat     540
ttttttagta catctatttt attctatttt agcctctaaa ttaagaaaac taaaactcta     600
ttttagtttt tttatttaat aatttagata taaaatagaa taaaataaag tgactaaaaa     660
ttaaacaaat accctttaag aaattaaaaa aactaaggaa acatttttct tgtttcgagt     720
agataatgcc agcctgttaa acgccgtcga cgagtctaac ggacaccaac cagcgaacca     780
gcagcgtcgc gtcgggccaa gcgaagcaga cggcacggca tctctgtcgc tgcctctgga     840
cccctctcga gagttccgct ccaccgttgg acttgctccg ctgtcggcat ccagaaattg     900
cgtggcggag cggcagacgt gagccggcac ggcaggcggc ctcctcctcc tctcacggca     960
cggcagctac gggggattcc tttcccaccg ctccttcgct ttcccttcct cgcccgccgt    1020
```

-continued

```
aataaataga caccccctcc acaccctctt tccccaacct cgtgttgttc ggagcgcaca   1080
cacacacaac cagatctccc ccaaatccac ccgtcggcac ctccgcttca aggtacgccg   1140
ctcgtcctcc cccccccccc ctctctacct tctctagatc ggcgttccgg tccatggtta   1200
gggcccggta gttctacttc tgttcatgtt tgtgttagat ccgtgtttgt gttagatccg   1260
tgctgctagc gttcgtacac ggatgcgacc tgtacgtcag acacgttctg attgctaact   1320
tgccagtgtt tctctttggg gaatcctggg atggctctag ccgttccgca gacgggatcg   1380
atttcatgat tttttttgtt tcgttgcata gggtttggtt tgcccttttc ctttatttca   1440
atatatgccg tgcacttgtt tgtcgggtca tcttttcatg ctttttttttg tcttggttgt   1500 gatgatgtgg tctggttggg cggtcgttct agatcggagt agaattctgt ttcaaactac   1560
ctggtggatt tattaatttt ggatctgtat gtgtgtgcca tacatattca tagttacgaa   1620
ttgaagatga tggatggaaa tatcgatcta ggataggtat acatgttgat gcgggtttta   1680
ctgatgcata tacagagatg cttttttgttc gcttggttgt gatgatgtgg tgtggttggg   1740
cggtcgttca ttcgttctag atcggagtag aatactgttt caaactacct ggtgtattta   1800
ttaattttgg aactgtatgt gtgtgtcata catcttcata gttacgagtt taagatggat   1860
ggaaatatcg atctaggata ggtatacatg ttgatgtggg ttttactgat gcatatacat   1920
gatggcatat gcagcatcta ttcatatgct ctaaccttga gtacctatct attataataa   1980
acaagtatgt tttataatta ttttgatctt gatatacttg gatgatggca tatgcagcag   2040
ctatatgtgg attttttttag ccctgccttc atacgctatt tatttgcttg gtactgtttc   2100
ttttgtcgat gctcaccctg ttgtttggtg ttacttctgc aggtcgactc tagaatggac   2160
aacaacccaa acatcaacga gtgcatccca tacaactgcc tgagcaaccc agaggtggag   2220
gtgctgggtg gcgagcgcat cgagaccggt tacacccocca tcgacatctc cctgtccttg   2280
acccagttcc tgctcagcga gttcgtgcca ggtgctggct tcgtgctcgg cctggtggac   2340
atcatctggg gtatcttcgg tccatcccaa tgggacgcct tcctggtgca aatcgagcag   2400
ctgatcaacc agaggatcga agagttcgcc aggaaccagg ccatctccag gctggagggc   2460
ctgagcaacc tctaccaaat ctacgccgag agcttcaggg agtgggaggc cgacccgacc   2520
aacccagctc tccgcgagga aatgcgcatt caattcaacg acatgaacag cgccctgacc   2580
accgctatcc cactgttcgc cgtccagaac taccaagtgc cgctcctgtc cgtgtacgtg   2640
caagccgcta acctgcacct cagcgtgctg cgcgacgtga gcgtgttcgg ccaaaggtgg   2700
ggcttcgatg ctgccaccat caacagccgc tacaacgacc tgaccaggct gattggcaac   2760
tacaccgacc acgctgtgcg ctggtacaac accggcctgg agcgcgtctg gggtccggac   2820
tccagggact ggatcaggta caaccagttc aggagggagt tgaccctcac cgtgctggac   2880
attgtgtccc tcttcccgaa ctacgactcc aggacctacc cgatccgcac cgtgtcccaa   2940
ctcaccaggg agatctacac caacccagtg ctggagaact tcgacggtag cttccgcggt   3000
tccgcccagg gtatcgaggg ctccatcagg agcccacacc tgatggacat cctgaacagc   3060
atcaccatct acaccgacgc tcacaggggc gagtactact ggtccggcca ccagatcatg   3120
gcctccccag tgggcttcag cggccccgag ttcaccttcc cgctctacgg caccatgggc   3180
aacgccgctc cacagcaacg catcgtggct caactgggtc agggtgtcta caggaccctg   3240
tcctccaccc tgtacaggag gcccttcaac atcggtatca caaccagca actgtccgtg   3300 ctcgacggca ccgagttcgc ctacggcacc tcctccaacc tgccatccgc tgtctacagg   3360
aagagcggca ccgtggactc cctggacgag atcccaccac agaacaacaa cgtgccaccc   3420
```

```
aggcaaggct tctcccacag gctgagccac gtgtccatgt tccgctccgg cttcagcaac   3480
agctccgtga gcatcatcag ggctccgatg ttctcctgga tccaccgcag cgctgagttc   3540
aacaacatca tcgcctccga cagcatcacc caaatcccgg ccgtgaaggg caacttcctc   3600
ttcaacggtt ccgtcatttc cggcccaggc ttcaccggtg gcgacctcgt gaggctcaac   3660
agcagcggca acaacatcca gaacaggggc tacatcgagg tgccaatcca cttcccatcc   3720
acctccacca ggtacagggt gcgcgtgagg tacgcttccg tgaccccgat ccacctcaac   3780
gtgaactggg gtaactcctc catcttctcc aacaccgtgc cagctaccgc tacctccctg   3840
gacaacctcc aatccagcga cttcggttac ttcgagagcg ccaacgcttt cacctcctcc   3900
ctcggtaaca tcgtgggcgt gaggaacttc agcggcaccg ccggcgtgat catcgacagg   3960
ttcgagttca tcccagtgac cgccaccctc gaggctgagt gagatcgttc aaacatttgg   4020
caataaagtt tcttaagatt gaatcctgtt gccggtcttg cgatgattat catataattt   4080
ctgttgaatt acgttaagca tgtaataatt aacatgtaat gcatgacgtt atttatgaga   4140
tgggttttta tgattagagt cccgcaatta tacatttaat acgcgataga aaacaaaata   4200
tagcgcgcaa actaggataa attatcgcgc gcggtgtcat ctatgttact agatcggcgc   4260
gccaagggcg aattccagca cactggcggc cgttactagt ggatcacgcg tatgcctgca   4320
gtgcagcgtg acccggtcgt gcccctctct agagataatg agcattgcat gtctaagtta   4380
taaaaaatta ccacatattt tttttgtcac acttgtttga agtgcagttt atctatcttt   4440
atacatatat ttaaacttta ctctacgaat aatataatct atagtactac aataatatca   4500 gtgtttttaga gaatcatata aatgaacagt tagacatggt ctaaaggaca attgagtatt   4560
ttgacaacag gactctacag ttttatcttt ttagtgtgca tgtgttctcc tttttttttg   4620
caaatagctt cacctatata atacttcatc cattttatta gtacatccat ttagggttta   4680
gggttaatgg tttttataga ctaatttttt tagtacatct attttattct attttagcct   4740
ctaaattaag aaaactaaaa ctctatttta gtttttttat ttaataattt agatataaaa   4800
tagaataaaa taaagtgact aaaaattaaa caaatacccc t ttaagaaatt aaaaaaacta   4860
aggaaacatt tttcttgttt cgagtagata atgccagcct gttaaacgcc gtcgacgagt   4920
ctaacggaca ccaaccagcg aaccagcagc gtcgcgtcgg gccaagcgaa gcagacggca   4980
cggcatctct gtcgctgcct ctggacccct ctcgagagtt ccgctccacc gttggacttg   5040
ctccgctgtc ggcatccaga aattgcgtgg cggagcggca gacgtgagcc ggcacggcag   5100
gcggcctcct cctcctctca cggcacggca gctacggggg attcctttcc caccgctcct   5160
tcgctttccc ttcctcgccc gccgtaataa atagacaccc cctccacacc ctctttcccc   5220
aacctcgtgt tgttcggagc gcacacacac acaaccagat ctcccccaaa tccaccgtc   5280 ggcacctccg cttcaaggta cgccgctcgt cctcccccce cccccctctc taccttctct   5340
agatcggcgt tccggtccat ggttagggcc cggtagttct acttctgttc atgtttgtgt   5400
tagatccgtg tttgtgttag atccgtgctg ctagcgttcg tacacggatg cgacctgtac   5460
gtcagacacg ttctgattgc taacttgcca gtgtttctct ttggggaatc ctgggatggc   5520
tctagccgtt ccgcagacgg gatcgatttc atgatttttt ttgtttcgtt gcataggtt   5580 tggtttgccc ttttcctta tttcaatata tgccgtgcac ttgtttgtcg ggtcatcttt   5640
tcatgctttt ttttgtcttg gttgtgatga tgtggtctgg ttgggcggtc gttctagatc   5700
ggagtagaat tctgtttcaa actacctggt ggatttatta attttggatc tgtatgtgtg   5760
```

-continued

```
tgccatacat attcatagtt acgaattgaa gatgatggat ggaaatatcg atctaggata    5820
ggtatacatg ttgatgcggg ttttactgat gcatatacag agatgctttt tgttcgcttg    5880
gttgtgatga tgtggtgtgg ttgggcggtc gttcattcgt tctagatcgg agtagaatac    5940
tgtttcaaac tacctggtgt atttattaat tttggaactg tatgtgtgtg tcatacatct    6000
tcatagttac gagtttaaga tggatggaaa tatcgatcta ggataggtat acatgttgat    6060
gtgggtttta ctgatgcata tacatgatgg catatgcagc atctattcat atgctctaac    6120
cttgagtacc tatctattat aataaacaag tatgtttat  aattattttg atcttgatat    6180
acttggatga tggcatatgc agcagctata tgtggatttt tttagccctg ccttcatacg    6240
ctatttattt gcttggtact gtttcttttg tcgatgctca ccctgttgtt tggtgttact    6300
tctgcaggtc gactctagaa tgagcccaga acgacgcccg gccgacatcc gccgtgccac    6360
cgaggcggac atgccggcgg tctgcaccat cgtcaaccac tacatcgaga caagcacggt    6420
caacttccgt accgagccgc aggaaccgca ggagtggacg gacgacctcg tccgtctgcg    6480
ggagcgctat ccctggctcg tcgccgaggt ggacggcgag gtcgccggca tcgcctacgc    6540
gggcccctgg aaggcacgca acgcctacga ctggacggcc gagtcgaccg tgtacgtctc    6600
cccccgccac cagcggacgg gactgggctc cacgctctac acccacctgc tgaagtccct    6660
ggaggcacag ggcttcaaga gcgtggtcgc tgtcatcggg ctgcccaacg acccgagcgt    6720
gcgcatgcac gaggcgctcg gatatgcccc ccgcggcatg ctgcgggcgg ccggcttcaa    6780
gcacgggaac tggcatgacg tgggtttctg gcagctggac ttcagcctgc cggtaccgcc    6840
ccgtccggtc ctgcccgtca ccgagatctg agatcgttca aacatttggc aataaagttt    6900
cttaagattg aatcctgttg ccggtcttgc gatgattatc atataatttc tgttgaatta    6960
cgttaagcat gtaataatta acatgtaatg catgacgtta tttatgagat gggtttttat    7020
gattagagtc ccgcaattat acatttaata cgcgatagaa aacaaaatat agcgcgcaaa    7080
ctaggataaa ttatcgcgcg cggtgtcatc tatgttacta gatcggcgcg ccaagggcga    7140
attccagcac actggcggcc gttactagtg gatcgagctc gcgatcgcgg ccggccaggc    7200
cttagttact aatcagtgat cagattgtcg tttcccgcct tcagtttaaa ctatcagtgt    7260
ttgacaggat atattggcgg gtaaacc                                        7287
```

<210> SEQ ID NO 2
<211> LENGTH: 7212
<212> TYPE: DNA
<213> ORGANISM: Artificial Sequence
<220> FEATURE:
<223> OTHER INFORMATION: T-DNA fragment (event CTC91087-6)

<400> SEQUENCE: 2

```
atatcacatt gcggacgtct ttaatgtact gaatttagtt actgatcact gattaagtac      60
tgatatcggt accgaattcg cggccgcaag cttcgatcga tgcctgcagt gcagcgtgac     120
ccggtcgtgc ccctctctag agataatgag cattgcatgt ctaagttata aaaaattacc     180
acatattttt tttgtcacac ttgtttgaag tgcagtttat ctatctttat acatatattt     240
aaactttact ctacgaataa tataatctat agtactacaa taatatcagt gttttagaga     300
atcatataaa tgaacagtta gacatggtct aaaggacaat tgagtatttt gacaacagga     360
ctctacagtt ttatcttttt agtgtgcatg tgttctcctt ttttttttgca aatagcttca     420 cctatataat acttcatcca ttttattagt acatccattt agggtttagg gttaatggtt     480
tttatagact aatttttttta gtacatctat tttattctat tttagcctct aaattaagaa     540
```

-continued

```
aactaaaact ctattttagt ttttttattt aataatttag atataaaata gaataaaata    600
aagtgactaa aaattaaaca aatacccttt aagaaattaa aaaaactaag gaaacatttt    660
tcttgtttcg agtagataat gccagcctgt taaacgccgt cgacgagtct aacggacacc    720
aaccagcgaa ccagcagcgt cgcgtcgggc caagcgaagc agacggcacg gcatctctgt    780
cgctgcctct ggacccctct cgagagttcc gctccaccgt tggacttgct ccgctgtcgg    840
catccagaaa ttgcgtggcg gagcggcaga cgtgagccgg cacggcaggc ggcctcctcc    900
tcctctcacg gcacggcagc tacgggggat tcctttccca ccgctccttc gctttccctt    960
cctcgcccgc cgtaataaat agacacccc tccacaccct ctttccccaa cctcgtgttg   1020
ttcggagcgc acacacacac aaccagatct cccccaaatc cacccgtcgg cacctccgct   1080
tcaaggtacg ccgctcgtcc tccccccccc cccctctcta ccttctctag atcggcgttc   1140
cggtccatgg ttagggcccg gtagttctac ttctgttcat gtttgtgtta gatccgtgtt   1200
tgtgttagat ccgtgctgct agcgttcgta cacggatgcg acctgtacgt cagacacgtt   1260
ctgattgcta acttgccagt gtttctcttt ggggaatcct gggatggctc tagccgttcc   1320
gcagacggga tcgatttcat gatttttttt gtttcgttgc atagggtttg gtttgccctt   1380
ttcctttatt tcaatatatg ccgtgcactt gtttgtcggg tcatcttttc atgctttttt   1440
ttgtcttggt tgtgatgatg tggtctggtt gggcggtcgt tctagatcgg agtagaattc   1500
tgtttcaaac tacctggtgg atttattaat tttggatctg tatgtgtgtg ccatacatat   1560
tcatagttac gaattgaaga tgatggatgg aaatatcgat ctaggatagg tatacatgtt   1620
gatgcgggtt ttactgatgc atatacagag atgctttttg ttcgcttggt tgtgatgatg   1680
tggtgtggtt gggcggtcgt tcattcgttc tagatcggag tagaatactg tttcaaacta   1740
cctggtgtat ttattaattt tggaactgta tgtgtgtgtc atacatcttc atagttacga   1800
gtttaagatg gatggaaata tcgatctagg ataggtatac atgttgatgt gggtttttact   1860 gatgcatata catgatggca tatgcagcat ctattcatat gctctaacct tgagtaccta   1920
tctattataa taaacaagta tgtttttaaa ttattttgat cttgatatac ttggatgatg   1980
gcatatgcag cagctatatg tggattttttt tagccctgcc ttcatacgct atttatttgc   2040
ttggtactgt ttcttttgtc gatgctcacc ctgttgtttg gtgttacttc tgcaggtcga   2100
ctctagaatg gacaacaacc caaacatcaa cgagtgcatc ccatacaact gcctgagcaa   2160
cccagaggtg gaggtgctgg gtggcgagcg catcgagacc ggttacaccc ccatcgacat   2220
ctccctgtcc ttgacccagt tcctgctcag cgagttcgtg ccaggtgctg gcttcgtgct   2280
cggcctggtg gacatcatct ggggtatctt cggtccatcc caatgggacg ccttcctggt   2340
gcaaatcgag cagctgatca accagaggat cgaaagttc gccaggaacc aggccatctc   2400
caggctggag ggcctgagca acctctacca atctacgcc gagagcttca gggagtggga   2460
ggccgacccg accaacccag ctctccgcga ggaaatgcgc attcaattca cgacatgaa   2520 cagcgccctg accaccgcta tcccactgtt cgccgtccag aactaccaag tgccgctcct   2580
gtccgtgtac gtgcaagccg ctaacctgca cctcagcgtg ctgcgcgacg tgagcgtgtt   2640
cggccaaagg tggggcttcg atgctgccac catcaacagc cgctacaacg acctgaccag   2700
gctgattggc aactacaccg accacgctgt gcgctggtac aacaccggcc tggagcgcgt   2760
ctggggtccg gactccaggg actggatcag gtacaaccag ttcaggaggg agttgacct   2820 caccgtgctg gacattgtgt ccctcttccc gaactacgac tccaggacct acccgatccg   2880
```

```
caccgtgtcc caactcacca gggagatcta caccaaccca gtgctggaga acttcgacgg    2940
tagcttccgc ggttccgccc agggtatcga gggctccatc aggagcccac acctgatgga    3000
catcctgaac agcatcacca tctacaccga cgctcacagg ggcgagtact actggtccgg    3060
ccaccagatc atggcctccc cagtgggctt cagcggcccc gagttcacct tcccgctcta    3120
cggcaccatg ggcaacgccg ctccacagca acgcatcgtg gctcaactgg gtcagggtgt    3180
ctacaggacc ctgtcctcca ccctgtacag gaggcccttc aacatcggta tcaacaacca    3240
gcaactgtcc gtgctcgacg gcaccgagtt cgcctacggc acctcctcca acctgccatc    3300
cgctgtctac aggaagagcg gcaccgtgga ctccctggac gagatcccac cacagaacaa    3360
caacgtgcca cccaggcaag gcttctccca caggctgagc cacgtgtcca tgttccgctc    3420
cggcttcagc aacagctccg tgagcatcat cagggctccg atgttctcct ggatccaccg    3480
cagcgctgag ttcaacaaca tcatcgcctc cgacagcatc acccaaatcc cggccgtgaa    3540
gggcaacttc ctcttcaacg gttccgtcat ttccggccca ggcttcaccg gtggcgacct    3600
cgtgaggctc aacagcagcg gcaacaacat ccagaacagg ggctacatcg aggtgccaat    3660
ccacttccca tccacctcca ccaggtacag ggtgcgcgtg aggtacgctt ccgtgacccc    3720
gatccacctc aacgtgaact ggggtaactc ctccatcttc tccaacaccg tgccagctac    3780
cgctacctcc ctggacaacc tccaatccag cgacttcggt tacttcgaga gcgccaacgc    3840
tttcacctcc tccctcggta acatcgtggg cgtgaggaac ttcagcggca ccgccggcgt    3900
gatcatcgac aggttcgagt tcatcccagt gaccgccacc ctcgaggctg agtgagatcg    3960
ttcaaacatt tggcaataaa gtttcttaag attgaatcct gttgccggtc ttgcgatgat    4020
tatcatataa tttctgttga attacgttaa gcatgtaata attaacatgt aatgcatgac    4080
gttatttatg agatgggttt ttatgattag agtcccgcaa ttatacattt aatacgcgat    4140
agaaaacaaa atatagcgcg caaactagga taaattatcg cgcgcggtgt catctatgtt    4200
actagatcgg cgcgccaagg gcgaattcca gcacactggc ggccgttact agtggatcac    4260
gcgtatgcct gcagtgcagc gtgacccggt cgtgcccctc tctagagata atgagcattg    4320
catgtctaag ttataaaaaa ttaccacata ttttttttgt cacacttgtt tgaagtgcag    4380
tttatctatc tttatacata tatttaaact ttactctacg aataatataa tctatagtac    4440
tacaataata tcagtgtttt agagaatcat ataaatgaac agttagacat ggtctaaagg    4500
acaattgagt attttgacaa caggactcta cagtttttatc ttttttagtgt gcatgtgttc    4560 tcctttttt ttgcaaatag cttcacctat ataatacttc atccatttta ttagtacatc    4620
catttagggt ttaggggttaa tggttttttat agactaattt ttttagtaca tctattttat    4680
tctattttag cctctaaatt aagaaaacta aaactctatt ttagtttttt tatttaataa    4740
tttagatata aaatagaata aaataaagtg actaaaaatt aaacaaatac cctttaagaa    4800
attaaaaaaa ctaaggaaac attttttcttg tttcgagtag ataatgccag cctgttaaac    4860
gccgtcgacg agtctaacgg acaccaacca gcgaaccagc agcgtcgcgt cgggccaagc    4920
gaagcagacg gcacggcatc tctgtcgctg cctctggacc cctctcgaga gttccgctcc    4980
accgttggac ttgctccgct gtcggcatcc agaaattgcg tggcggagcg gcagacgtga    5040
gccggcacgg caggcggcct cctcctcctc tcacggcacg gcagctacgg gggattcctt    5100
tcccaccgct ccttcgcttt cccttcctcg cccgccgtaa taaatagaca cccctccac    5160 accctctttc cccaacctcg tgttgttcgg agcgcacaca cacacaacca gatctccccc    5220
aaatccaccc gtcggcacct ccgcttcaag gtacgccgct cgtcctcccc cccccccct    5280
```

```
ctctaccttc tctagatcgg cgttccggtc catggttagg gcccggtagt tctacttctg    5340
ttcatgtttg tgttagatcc gtgtttgtgt tagatccgtg ctgctagcgt tcgtacacgg    5400
atgcgacctg tacgtcagac acgttctgat tgctaacttg ccagtgtttc tctttgggga    5460
atcctgggat ggctctagcc gttccgcaga cgggatcgat ttcatgattt tttttgtttc    5520
gttgcatagg gtttggtttg ccctttttcct ttatttcaat atatgccgtg cacttgtttg   5580
tcgggtcatc ttttcatgct tttttttgtc ttggttgtga tgatgtggtc tggttgggcg    5640
gtcgttctag atcggagtag aattctgttt caaactacct ggtggattta ttaattttgg    5700
atctgtatgt gtgtgccata catattcata gttacgaatt gaagatgatg gatggaaata    5760
tcgatctagg ataggtatac atgttgatgc gggtttttact gatgcatata cagagatgct   5820
ttttgttcgc ttggttgtga tgatgtggtg tggttgggcg gtcgttcatt cgttctagat    5880
cggagtagaa tactgtttca aactacctgg tgtatttatt aattttggaa ctgtatgtgt    5940
gtgtcataca tcttcatagt tacgagttta agatggatgg aaatatcgat ctaggatagg    6000
tatacatgtt gatgtgggtt ttactgatgc atatacatga tggcatatgc agcatctatt    6060
catatgctct aaccttgagt acctatctat tataataaac aagtatgttt tataattatt    6120
ttgatcttga tatacttgga tgatggcata tgcagcagct atatgtggat tttttttagcc   6180 ctgccttcat acgctattta tttgcttggt actgtttctt ttgtcgatgc tcaccctgtt    6240
gtttggtgtt acttctgcag gtcgactcta gaatgagccc agaacgacgc ccggccgaca    6300
tccgccgtgc caccgaggcg gacatgccgg cggtctgcac catcgtcaac cactacatcg    6360
agacaagcac ggtcaacttc cgtaccgagc cgcaggaacc gcaggagtgg acggacgacc    6420
tcgtccgtct gcgggagcgc tatccctggc tcgtcgccga ggtggacggc gaggtcgccg    6480
gcatcgccta cgcgggcccc tggaaggcac gcaacgccta cgactggacg gccgagtcga    6540
ccgtgtacgt ctccccccgc caccagcgga cgggactggg ctccacgctc tacacccacc    6600
tgctgaagtc cctggaggca cagggcttca agagcgtggt cgctgtcatc gggctgccca    6660
acgacccgag cgtgcgcatg cacgaggcgc tcggatatgc cccccgcggc atgctgcggg    6720
cggccggctt caagcacggg aactggcatg acgtgggttt ctggcagctg gacttcagcc    6780
tgccggtacc gcccgtccg gtcctgcccg tcaccgagat ctgagatcgt tcaaacattt    6840
ggcaataaag tttcttaaga ttgaatcctg ttgccggtct tgcgatgatt atcatataat    6900
ttctgttgaa ttacgttaag catgtaataa ttaacatgta atgcatgacg ttatttatga    6960
gatgggtttt tatgattaga gtcccgcaat tatacattta atacgcgata gaaaacaaaa    7020
tatagcgcgc aaactaggat aaattatcgc gcgcggtgtc atctatgtta ctagatcggc    7080
gcgccaaggg cgaattccag cacactggcg gccgttacta gtggatcgag ctcgcgatcg    7140
cggccggcca ggccttagtt actaatcagt gatcagattg tcgtttcccg ccttcagttt    7200
aaactatcag tg                                                         7212
```

<210> SEQ ID NO 3
<211> LENGTH: 206
<212> TYPE: DNA
<213> ORGANISM: Artificial Sequence
<220> FEATURE:
<223> OTHER INFORMATION: Junction nucleotide sequence between 5' region
      of insert and sugarcane genome of event CTC91087-6.

<400> SEQUENCE: 3

```
tacgtacagg aaactggaac tggatggtgc atacagtact ctactgcgca taggatagga      60
```

-continued

```
tggaaggctg ccctgccggc cgcgttcaac aaattaagta ctgatatcac attgcggacg      120
tctttaatgt actgaattta gttactgatc actgattaag tactgatatc ggtaccgaat      180
tcgcggccgc aagcttcgat cgatgc                                          206

<210> SEQ ID NO 4
<211> LENGTH: 206
<212> TYPE: DNA
<213> ORGANISM: Artificial Sequence
<220> FEATURE:
<223> OTHER INFORMATION: Junction nucleotide sequence between 3' region
      of insert and sugarcane genome of event CTC91087-6.

<400> SEQUENCE: 4
ggccgttact agtggatcga gctcgcgatc gcggccggcc aggccttagt tactaatcag       60
tgatcagatt gtcgtttccc gccttcagtt taaactatca gtgtttgaac cgttgtacgt      120
gttcctatcg ccagcagtcg gccggccgca cacacgtacg atccctgcgc ctacttccaa      180
cataacggcc acaagttcgt tggttc                                          206

<210> SEQ ID NO 5
<211> LENGTH: 7418
<212> TYPE: DNA
<213> ORGANISM: Artificial Sequence
<220> FEATURE:
<223> OTHER INFORMATION: Event CTC91087-6: flanking sequences and T-DNA

<400> SEQUENCE: 5
tacgtacagg aaactggaac tggatggtgc atacagtact ctactgcgca taggatagga       60
tggaaggctg ccctgccggc cgcgttcaac aaattaagta ctgatatcac attgcggacg      120
tctttaatgt actgaattta gttactgatc actgattaag tactgatatc ggtaccgaat      180
tcgcggccgc aagcttcgat cgatgcctgc agtgcagcgt gacccggtcg tgccctctc       240 tagagataat gagcattgca tgtctaagtt ataaaaaatt accacatatt ttttttgtca      300
cacttgtttg aagtgcagtt tatctatctt tatacatata tttaaacttt actctacgaa      360
taatataatc tatagtacta caataatatc agtgttttag agaatcatat aaatgaacag      420
ttagacatgg tctaaaggac aattgagtat tttgacaaca ggactctaca gttttatctt      480
tttagtgtgc atgtgttctc cttttttttt gcaaatagct tcacctatat aatacttcat      540
ccattttatt agtacatcca tttagggttt agggttaatg gttttttatag actaattttt      600 ttagtacatc tattttattc tattttagcc tctaaattaa gaaaactaaa actctatttt      660
agttttttta tttaataatt tagatataaa atagaataaa ataaagtgac taaaaattaa      720
acaaataccc tttaagaaat taaaaaaact aaggaaacat ttttcttgtt tcgagtagat      780
aatgccagcc tgttaaacgc cgtcgacgag tctaacggac accaaccagc gaaccagcag      840
cgtcgcgtcg ggccaagcga agcagacggc acggcatctc tgtcgctgcc tctggacccc      900
tctcgagagt tccgctccac cgttggactt gctccgctgt cggcatccag aaattgcgtg      960
gcggagcggc agacgtgagc cggcacggca ggcggcctcc tcctcctctc acggcacggc     1020
agctacgggg gattcctttc ccaccgctcc ttcgctttcc cttcctcgcc cgccgtaata     1080
aatagacacc ccctccacac cctctttccc caacctcgtg ttgttcggag cgcacacaca     1140
cacaaccaga tctcccccaa atccacccgt cggcacctcc gcttcaaggt acgccgctcg     1200
tcctcccccc ccccccctct ctaccttctc tagatcggcg ttccggtcca tggttagggc     1260
ccggtagttc tacttctgtt catgtttgtg ttagatccgt gtttgtgtta gatccgtgct     1320
```

```
gctagcgttc gtacacggat gcgacctgta cgtcagacac gttctgattg ctaacttgcc   1380
agtgtttctc tttgggaat cctgggatgg ctctagccgt tccgcagacg ggatcgattt   1440
catgattttt tttgtttcgt tgcatagggt ttggtttgcc cttttccttt atttcaatat   1500
atgccgtgca cttgtttgtc gggtcatctt ttcatgcttt tttttgtctt ggttgtgatg   1560
atgtggtctg gttgggcggt cgttctagat cggagtagaa ttctgtttca aactacctgg   1620
tggatttatt aattttggat ctgtatgtgt gtgccataca tattcatagt tacgaattga   1680
agatgatgga tggaaatatc gatctaggat aggtatacat gttgatgcgg gttttactga   1740
tgcatataca gagatgcttt ttgttcgctt ggttgtgatg atgtggtgtg gttgggcggt   1800
cgttcattcg ttctagatcg gagtagaata ctgtttcaaa ctacctggtg tatttattaa   1860
ttttggaact gtatgtgtgt gtcatacatc ttcatagtta cgagtttaag atggatggaa   1920
atatcgatct aggataggta tacatgttga tgtgggtttt actgatgcat atacatgatg   1980
gcatatgcag catctattca tatgctctaa ccttgagtac ctatctatta taataaacaa   2040
gtatgtttta taattatttt gatcttgata tacttggatg atggcatatg cagcagctat   2100
atgtggattt ttttagccct gccttcatac gctatttatt tgcttggtac tgtttctttt   2160
gtcgatgctc accctgttgt ttggtgttac ttctgcaggt cgactctaga atggacaaca   2220
acccaaacat caacgagtgc atcccataca actgcctgag caacccagag gtggaggtgc   2280
tgggtggcga gcgcatcgag accggttaca cccccatcga catctccctg tccttgaccc   2340
agttcctgct cagcgagttc gtgccaggtg ctggcttcgt gctcggcctg gtggacatca   2400
tctggggtat cttcggtcca tcccaatggg acgccttcct ggtgcaaatc gagcagctga   2460
tcaaccagag gatcgaagag ttcgccagga accaggccat ctccaggctg gagggcctga   2520
gcaacctcta ccaaatctac gccgagagct tcagggagtg ggaggccgac ccgaccaacc   2580
cagctctccg cgaggaaatg cgcattcaat tcaacgacat gaacagcgcc ctgaccaccg   2640
ctatcccact gttcgccgtc cagaactacc aagtgccgct cctgtccgtg tacgtgcaag   2700
ccgctaacct gcacctcagc gtgctgcgcg acgtgagcgt gttcggccaa aggtggggct   2760
tcgatgctgc caccatcaac agccgctaca acgacctgac caggctgatt ggcaactaca   2820
ccgaccacgc tgtgcgctgg tacaacaccg gcctggagcg cgtctggggt ccggactcca   2880
gggactggat caggtacaac cagttcagga gggagttgac cctcaccgtg ctggacattg   2940
tgtccctctt cccgaactac gactccagga cctacccgat ccgcaccgtg tcccaactca   3000
ccagggagat ctacaccaac ccagtgctgg agaacttcga cggtagcttc cgcggttccg   3060
cccagggtat cgagggctcc atcaggagcc cacacctgat ggacatcctg aacagcatca   3120
ccatctacac cgacgctcac aggggcgagt actactggtc cggccaccag atcatggcct   3180
ccccagtggg cttcagcggc cccgagttca ccttcccgct ctacggcacc atgggcaacg   3240
ccgctccaca gcaacgcatc gtggctcaac tgggtcaggg tgtctacagg accctgtcct   3300
ccaccctgta caggaggccc ttcaacatcg gtatcaacaa ccagcaactg tccgtgctcg   3360
acggcaccga gttcgcctac ggcacctcct ccaacctgcc atccgctgtc tacaggaaga   3420
gcggcaccgt ggactccctg gacgagatcc caccacagaa caacaacgtg ccacccaggc   3480
aaggcttctc ccacaggctg agccacgtgt ccatgttccg ctccggcttc agcaacagct   3540
ccgtgagcat catcagggct ccgatgttct cctggatcca ccgcagcgct gagttcaaca   3600
acatcatcgc ctccgacagc atcacccaaa tcccggccgt gaagggcaac ttcctcttca   3660
```

-continued

```
acggttccgt catttccggc ccaggcttca ccggtggcga cctcgtgagg ctcaacagca    3720
gcggcaacaa catccagaac aggggctaca tcgaggtgcc aatccacttc ccatccacct    3780
ccaccaggta cagggtgcgc gtgaggtacg cttccgtgac cccgatccac ctcaacgtga    3840
actggggtaa ctcctccatc ttctccaaca ccgtgccagc taccgctacc tccctggaca    3900
acctccaatc cagcgacttc ggttacttcg agagcgccaa cgctttcacc tcctccctcg    3960
gtaacatcgt gggcgtgagg aacttcagcg gcaccgccgg cgtgatcatc gacaggttcg    4020
agttcatccc agtgaccgcc accctcgagg ctgagtgaga tcgttcaaac atttggcaat    4080
aaagtttctt aagattgaat cctgttgccg gtcttgcgat gattatcata taatttctgt    4140
tgaattacgt taagcatgta ataattaaca tgtaatgcat gacgttattt atgagatggg    4200 ttttttatgat tagagtcccg caattataca tttaatacgc gatagaaaac aaaatatagc    4260
gcgcaaacta ggataaatta tcgcgcgcgg tgtcatctat gttactagat cggcgcgcca    4320
agggcgaatt ccagcacact ggcggccgtt actagtggat cacgcgtatg cctgcagtgc    4380
agcgtgaccc ggtcgtgccc ctctctagag ataatgagca ttgcatgtct aagttataaa    4440
aaattaccac atattttttt tgtcacactt gtttgaagtg cagtttatct atctttatac    4500
atatatttaa actttactct acgaataata taatctatag tactacaata atatcagtgt    4560
tttagagaat catataaatg aacagttaga catggtctaa aggacaattg agtattttga    4620
caacaggact ctacagtttt atcttttttag tgtgcatgtg ttctcctttt tttttgcaaa    4680
tagcttcacc tatataatac ttcatccatt ttattagtac atccatttag ggtttagggt    4740
taatggtttt tatagactaa ttttttttagt acatctattt tattctattt tagcctctaa    4800
attaagaaaa ctaaaactct attttagttt ttttatttaa taatttagat ataaaataga    4860
ataaaataaa gtgactaaaa attaaacaaa taccctttaa gaaattaaaa aaactaagga    4920
aacatttttc ttgtttcgag tagataatgc cagcctgtta aacgccgtcg acgagtctaa    4980
cggacaccaa ccagcgaacc agcagcgtcg cgtcgggcca agcgaagcag acggcacggc    5040
atctctgtcg ctgcctctgg acccctctcg agagttccgc tccaccgttg gacttgctcc    5100
gctgtcggca tccagaaatt gcgtggcgga gcggcagacg tgagccggca cggcaggcgg    5160
cctcctcctc ctctcacggc acggcagcta cggggggattc ctttcccacc gctccttcgc    5220
tttcccttcc tcgcccgccg taataaatag acaccccctc cacaccctct ttccccaacc    5280
tcgtgttgtt cggagcgcac acacacacaa ccagatctcc cccaaatcca cccgtcggca    5340
cctccgcttc aaggtacgcc gctcgtcctc ccccccccc cctctctacc ttctctagat    5400
cggcgttccg gtccatggtt agggcccggt agttctactt ctgttcatgt ttgtgttaga    5460
tccgtgtttg tgttagatcc gtgctgctag cgttcgtaca cggatgcgac ctgtacgtca    5520
gacacgttct gattgctaac ttgccagtgt ttctctttgg ggaatcctgg gatggctcta    5580
gccgttccgc agacgggatc gatttcatga ttttttttgt ttcgttgcat agggtttggt    5640 ttgcccttttt cctttatttc aatatatgcc gtgcacttgt ttgtcgggtc atcttttcat    5700
gctttttttt gtcttggttg tgatgatgtg gtctggttgg gcggtcgttc tagatcggag    5760
tagaattctg tttcaaacta cctggtggat ttattaattt tggatctgta tgtgtgtgcc    5820
atacatattc atagttacga attgaagatg atggatggaa atatcgatct aggataggta    5880
tacatgttga tgcgggtttt actgatgcat atacagagat gctttttgtt cgcttggttg    5940
tgatgatgtg gtgtggttgg gcggtcgttc attcgttcta gatcggagta gaatactgtt    6000
tcaaactacc tggtgtattt attaattttg gaactgtatg tgtgtgtcat acatcttcat    6060
```

-continued

```
agttacgagt ttaagatgga tggaaatatc gatctaggat aggtatacat gttgatgtgg   6120
gttttactga tgcatataca tgatggcata tgcagcatct attcatatgc tctaaccttg   6180
agtacctatc tattataata aacaagtatg ttttataatt attttgatct tgatatactt   6240
ggatgatggc atatgcagca gctatatgtg gattttttta gccctgcctt catacgctat   6300
ttatttgctt ggtactgttt cttttgtcga tgctcaccct gttgtttggt gttacttctg   6360
caggtcgact ctagaatgag cccagaacga cgcccggccg acatccgccg tgccaccgag   6420
gcggacatgc cggcggtctg caccatcgtc aaccactaca tcgagacaag cacggtcaac   6480
ttccgtaccg agccgcagga accgcaggag tggacggacg acctcgtccg tctgcgggag   6540
cgctatccct ggctcgtcgc cgaggtggac ggcgaggtcg ccggcatcgc ctacgcgggc   6600
ccctggaagg cacgcaacgc ctacgactgg acggccgagt cgaccgtgta cgtctccccc   6660
cgccaccagc ggacgggact gggctccacg ctctacaccc acctgctgaa gtccctggag   6720
gcacagggct tcaagagcgt ggtcgctgtc atcgggctgc ccaacgaccc gagcgtgcgc   6780
atgcacgagg cgctcggata tgccccccgc ggcatgctgc gggcggccgg cttcaagcac   6840
gggaactggc atgacgtggg tttctggcag ctggacttca gcctgccggt accgccccgt   6900
ccggtcctgc ccgtcaccga gatctgagat cgttcaaaca tttggcaata aagtttctta   6960
agattgaatc ctgttgccgg tcttgcgatg attatcatat aatttctgtt gaattacgtt   7020
aagcatgtaa taattaacat gtaatgcatg acgttattta tgagatgggt ttttatgatt   7080
agagtcccgc aattatacat ttaatacgcg atagaaaaca aaatatagcg cgcaaactag   7140
gataaattat cgcgcgcggt gtcatctatg ttactagatc ggcgcgccaa gggcgaattc   7200
cagcacactg gcggccgtta ctagtggatc gagctcgcga tcgcggccgg ccaggcctta   7260
gttactaatc agtgatcaga ttgtcgtttc ccgccttcag tttaaactat cagtgtttga   7320
accgttgtac gtgttcctat cgccagcagt cggccggccg cacacacgta cgatccctgc   7380
gcctacttcc aacataacgg ccacaagttc gttggttc                           7418
```

```
<210> SEQ ID NO 6
<211> LENGTH: 20
<212> TYPE: DNA
<213> ORGANISM: Artificial Sequence
<220> FEATURE:
<223> OTHER INFORMATION: primer forward (Right Border)

<400> SEQUENCE: 6
cgtttcccgc cttcagttta                                                20

<210> SEQ ID NO 7
<211> LENGTH: 20
<212> TYPE: DNA
<213> ORGANISM: Artificial Sequence
<220> FEATURE:
<223> OTHER INFORMATION: primer reverse (Right border)

<400> SEQUENCE: 7
gccgttatgt tggaagtagg                                                20

<210> SEQ ID NO 8
<211> LENGTH: 19
<212> TYPE: DNA
<213> ORGANISM: Artificial Sequence
<220> FEATURE:
<223> OTHER INFORMATION: primer forward (Left border)
```

<400> SEQUENCE: 8
ggataggatg gaaggctgc                                                          19

<210> SEQ ID NO 9
<211> LENGTH: 16
<212> TYPE: DNA
<213> ORGANISM: Artificial Sequence
<220> FEATURE:
<223> OTHER INFORMATION: primer reverse (Left border)

<400> SEQUENCE: 9
gatcgaagct tgcggc                                                            16

<210> SEQ ID NO 10
<211> LENGTH: 18
<212> TYPE: DNA
<213> ORGANISM: Artificial Sequence
<220> FEATURE:
<223> OTHER INFORMATION: probe (Right border)

<400> SEQUENCE: 10
cgtgttccta tcgccagc                                                          18

<210> SEQ ID NO 11
<211> LENGTH: 17
<212> TYPE: DNA
<213> ORGANISM: Artificial Sequence
<220> FEATURE:
<223> OTHER INFORMATION: probe (Left border)

<400> SEQUENCE: 11
atatcacatt gcggacg                                                           17

<210> SEQ ID NO 12
<211> LENGTH: 117
<212> TYPE: DNA
<213> ORGANISM: Artificial Sequence
<220> FEATURE:
<223> OTHER INFORMATION: Amplicon Event CTC09187-6 (Right Border)

<400> SEQUENCE: 12
cgtttcccgc cttcagttta aactatcagt gtttgaaccg ttgtacgtgt tcctatcgcc     60
agcagtcggc cggccgcaca cacgtacgat ccctgcgcct acttccaaca taacggc      117

<210> SEQ ID NO 13
<211> LENGTH: 149
<212> TYPE: DNA
<213> ORGANISM: Artificial Sequence
<220> FEATURE:
<223> OTHER INFORMATION: Amplicon Event CTC09187-6 (Left border)

<400> SEQUENCE: 13
ggataggatg gaaggctgcc ctgccggccg cgttcaacaa attaagtact gatatcacat     60
tgcggacgtc tttaatgtac tgaatttagt tactgatcac tgattaagta ctgatatcgg    120
taccgaattc gcggccgcaa gcttcgatc                                     149

<210> SEQ ID NO 14
<211> LENGTH: 11986
<212> TYPE: DNA
<213> ORGANISM: Artificial Sequence
<220> FEATURE:
<223> OTHER INFORMATION: Binary plasmid comprising cry1Ac and bar genes

<400> SEQUENCE: 14

```
tggcaggata tattgtggtg taaacaaatt gacgcttaga caacttaata acacattgcg    60
gacgtcttta atgtactgaa tttagttact gatcactgat taagtactga tatcggtacc   120
gaattcgcgg ccgcaagctt cgatcgatgc ctgcagtgca gcgtgacccg gtcgtgcccc   180
tctctagaga taatgagcat tgcatgtcta agttataaaa aattaccaca tatttttttt   240
gtcacacttg tttgaagtgc agtttatcta tctttataca tatatttaaa ctttactcta   300
cgaataatat aatctatagt actacaataa tatcagtgtt ttagagaatc atataaatga   360
acagttagac atggtctaaa ggacaattga gtattttgac aacaggactc tacagtttta   420 tcttttagt gtgcatgtgt tctccttttt ttttgcaaat agcttcacct atataatact    480
tcatccattt tattagtaca tccatttagg gtttagggtt aatggttttt atagactaat   540
ttttttagta catctatttt attctatttt agcctctaaa ttaagaaaac taaaactcta   600
ttttagtttt tttatttaat aatttagata taaaatagaa taaaataaag tgactaaaaa   660
ttaaacaaat acccttaag aaattaaaaa aactaaggaa acatttttct tgtttcgagt     720
agataatgcc agcctgttaa acgccgtcga cgagtctaac ggacaccaac cagcgaacca   780
gcagcgtcgc gtcgggccaa gcgaagcaga cggcacggca tctctgtcgc tgcctctgga   840
cccctctcga gagttccgct ccaccgttgg acttgctccg ctgtcggcat ccagaaattg   900
cgtggcggag cggcagacgt gagccggcac ggcaggcggc ctcctcctcc tctcacggca   960
cggcagctac gggggattcc tttcccaccg ctccttcgct ttcccttcct cgcccgccgt   1020
aataaataga cacccctcc acaccctctt tccccaacct cgtgttgttc ggagcgcaca    1080
cacacacaac cagatctccc ccaaatccac ccgtcggcac ctccgcttca aggtacgccg   1140
ctcgtcctcc ccccccccc ctctctacct tctctagatc ggcgttccgg tccatggtta    1200
gggcccggta gttctacttc tgttcatgtt tgtgttagat ccgtgtttgt gttagatccg   1260
tgctgctagc gttcgtacac ggatgcgacc tgtacgtcag acacgttctg attgctaact   1320
tgccagtgtt tctctttggg gaatcctggg atggctctag ccgttccgca gacgggatcg   1380
atttcatgat ttttttgtt tcgttgcata gggtttggtt tgccctttc ctttatttca    1440 atatatgccg tgcacttgtt tgtcgggtca tcttttcatg cttttttttg tcttggttgt   1500
gatgatgtgg tctggttggg cggtcgttct agatcggagt agaattctgt ttcaaactac   1560
ctggtggatt tattaatttt ggatctgtat gtgtgtgcca tacatattca tagttacgaa   1620
ttgaagatga tggatggaaa tatcgatcta ggataggtat acatgttgat gcgggtttta   1680
ctgatgcata tacagagatg cttttttgttc gcttggttgt gatgatgtgg tgtggttggg   1740
cggtcgttca ttcgttctag atcggagtag aatactgttt caaactacct ggtgtattta   1800
ttaattttgg aactgtatgt gtgtgtcata catcttcata gttacgagtt taagatggat   1860
ggaaatatcg atctaggata ggtatacatg ttgatgtggg ttttactgat gcatatacat   1920
gatggcatat gcagcatcta ttcatatgct ctaaccttga gtacctatct attataataa   1980
acaagtatgt tttataatta ttttgatctt gatatacttg gatgatggca tatgcagcag   2040
ctatatgtgg attttttttag ccctgccttc atacgctatt tatttgcttg gtactgtttc   2100
ttttgtcgat gctcaccctg ttgtttggtg ttacttctgc aggtcgactc tagaatggac   2160
aacaacccaa acatcaacga gtgcatccca tacaactgcc tgagcaaccc agaggtggag   2220
gtgctgggtg gcgagcgcat cgagaccggt tacacccca tcgacatctc cctgtccttg    2280
acccagttcc tgctcagcga gttcgtgcca ggtgctggct tcgtgctcgg cctggtggac   2340
```

```
atcatctggg gtatcttcgg tccatcccaa tgggacgcct tcctggtgca aatcgagcag   2400
ctgatcaacc agaggatcga agagttcgcc aggaaccagg ccatctccag gctggagggc   2460
ctgagcaacc tctaccaaat ctacgccgag agcttcaggg agtgggaggc cgacccgacc   2520
aacccagctc tccgcgagga aatgcgcatt caattcaacg acatgaacag cgccctgacc   2580
accgctatcc cactgttcgc cgtccagaac taccaagtgc cgctcctgtc cgtgtacgtg   2640
caagccgcta acctgcacct cagcgtgctg cgcgacgtga gcgtgttcgg ccaaaggtgg   2700
ggcttcgatg ctgccaccat caacagccgc tacaacgacc tgaccaggct gattggcaac   2760
tacaccgacc acgctgtgcg ctggtacaac accggcctgg agcgcgtctg gggtccggac   2820
tccagggact ggatcaggta caaccagttc aggagggagt tgaccctcac cgtgctggac   2880
attgtgtccc tcttcccgaa ctacgactcc aggacctacc cgatccgcac cgtgtcccaa   2940
ctcaccaggg agatctacac caacccagtg ctggagaact tcgacggtag cttccgcggt   3000
tccgcccagg gtatcgaggg ctccatcagg agcccacacc tgatggacat cctgaacagc   3060
atcaccatct acaccgacgc tcacagggGc gagtactact ggtccggcca ccagatcatg   3120
gcctccccag tgggcttcag cggccccgag ttcaccttcc cgctctacgg caccatgggc   3180
aacgccgctc cacagcaacg catcgtggct caactgggtc agggtgtcta caggaccctg   3240
tcctccaccc tgtacaggag gcccttcaac atcggtatca acaaccagca actgtccgtg   3300
ctcgacggca ccgagttcgc ctacggcacc tcctccaacc tgccatccgc tgtctacagg   3360
aagagcggca ccgtggactc cctggacgag atcccaccac agaacaacaa cgtgccaccc   3420
aggcaaggct tctcccacag gctgagccac gtgtccatgt tccgctccgg cttcagcaac   3480
agctccgtga gcatcatcag ggctccgatg ttctcctgga tccaccgcag cgctgagttc   3540
aacaacatca tcgcctccga cagcatcacc caaatcccgg ccgtgaaggg caacttcctc   3600
ttcaacggtt ccgtcatttc cggcccaggc ttcaccggtg gcgacctcgt gaggctcaac   3660
agcagcggca acaacatcca gaacaggggc tacatcgagg tgccaatcca cttcccatcc   3720
acctccacca ggtacagggt gcgcgtgagg tacgcttccg tgaccccgat ccacctcaac   3780
gtgaactggg gtaactcctc catcttctcc aacaccgtgc cagctaccgc tacctccctg   3840
gacaacctcc aatccagcga cttcggttac ttcgagagcg ccaacgcttt cacctcctcc   3900
ctcggtaaca tcgtgggcgt gaggaacttc agcggcaccg ccggcgtgat catcgacagg   3960
ttcgagttca tcccagtgac cgccaccctc gaggctgagt gagatcgttc aaacatttgg   4020
caataaagtt tcttaagatt gaatcctgtt gccggtcttg cgatgattat catataattt   4080
ctgttgaatt acgttaagca tgtaataatt aacatgtaat gcatgacgtt atttatgaga   4140
tgggttttta tgattagagt cccgcaatta tacatttaat acgcgataga aaacaaaata   4200
tagcgcgcaa actaggataa attatcgcgc gcggtgtcat ctatgttact agatcggcgc   4260
gccaagggcg aattccagca cactggcggc cgttactagt ggatcacgcg tatgcctgca   4320
gtgcagcgtg acccggtcgt gcccctctct agagataatg agcattgcat gtctaagtta   4380
taaaaaatta ccacatattt tttttgtcac acttgtttga agtgcagttt atctatcttt   4440
atacatatat ttaaacttta ctctacgaat aatataatct atagtactac aataatatca   4500
gtgttttaga gaatcatata aatgaacagt tagacatggt ctaaaggaca attgagtatt   4560
ttgacaacag gactctacag tttttatcttt ttagtgtgca tgtgttctcc ttttttttg   4620 caaatagctt cacctatata atacttcatc cattttatta gtacatccat ttagggttta   4680
gggttaatgg ttttttataga ctaattttttt tagtacatct attttattct attttagcct   4740
```

-continued

```
ctaaattaag aaaactaaaa ctctatttta gttttttttat ttaataattt agatataaaa    4800
tagaataaaa taaagtgact aaaaattaaa caaatacccct ttaagaaatt aaaaaaacta    4860
aggaaacatt tttcttgttt cgagtagata atgccagcct gttaaacgcc gtcgacgagt    4920
ctaacggaca ccaaccagcg aaccagcagc gtcgcgtcgg gccaagcgaa gcagacggca    4980
cggcatctct gtcgctgcct ctggacccct ctcgagagtt ccgctccacc gttggacttg    5040
ctccgctgtc ggcatccaga aattgcgtgg cggagcggca gacgtgagcc ggcacggcag    5100
gcggcctcct cctcctctca cggcacggca gctacggggg attcctttcc caccgctcct    5160
tcgctttccc ttcctcgccc gccgtaataa atagacaccc cctccacacc ctctttcccc    5220
aacctcgtgt tgttcggagc gcacacacac acaaccagat ctcccccaaa tccacccgtc    5280
ggcacctccg cttcaaggta cgccgctcgt cctcccccc ccccctctc taccttctct      5340 agatcggcgt tccggtccat ggttagggcc cggtagttct acttctgttc atgtttgtgt    5400
tagatccgtg tttgtgttag atccgtgctg ctagcgttcg tacacggatg cgacctgtac    5460
gtcagacacg ttctgattgc taacttgcca gtgtttctct ttggggaatc ctgggatggc    5520
tctagccgtt ccgcagacgg gatcgatttc atgatttttt ttgtttcgtt gcatagggtt    5580
tggtttgccc ttttccttta tttcaatata tgccgtgcac ttgtttgtcg ggtcatcttt    5640
tcatgctttt ttttgtcttg gttgtgatga tgtggtctgg ttgggcggtc gttctagatc    5700
ggagtagaat tctgtttcaa actacctggt ggatttatta attttggatc tgtatgtgtg    5760
tgccatacat attcatagtt acgaattgaa gatgatggat ggaaatatcg atctaggata    5820
ggtatacatg ttgatgcggg ttttactgat gcatatacag agatgctttt tgttcgcttg    5880
gttgtgatga tgtggtgtgg ttgggcggtc gttcattcgt tctagatcgg agtagaatac    5940
tgtttcaaac tacctggtgt atttattaat tttggaactg tatgtgtgtg tcatacatct    6000
tcatagttac gagtttaaga tggatggaaa tatcgatcta ggataggtat acatgttgat    6060
gtgggtttta ctgatgcata tacatgatgg catatgcagc atctattcat atgctctaac    6120
cttgagtacc tatctattat aataaacaag tatgtttttat aattattttg atcttgatat    6180
acttggatga tggcatatgc agcagctata tgtggatttt tttagccctg ccttcatacg    6240
ctatttattt gcttggtact gtttcttttg tcgatgctca ccctgttgtt tggtgttact    6300
tctgcaggtc gactctagaa tgagcccaga acgacgcccg gccgacatcc gccgtgccac    6360
cgaggcggac atgccggcgg tctgcaccat cgtcaaccac tacatcgaga caagcacggt    6420
caacttccgt accgagccgc aggaaccgca ggagtggacg gacgacctcg tccgtctgcg    6480
ggagcgctat ccctggctcg tcgccgaggt ggacggcgag gtcgccggca tcgcctacgc    6540
gggcccctgg aaggcacgca acgcctacga ctggacggcc gagtcgaccg tgtacgtctc    6600 ccccgccac cagcggacgg gactgggctc cacgctctac acccacctgc tgaagtccct    6660
ggaggcacag ggcttcaaga gcgtggtcgc tgtcatcggg ctgcccaacg acccgagcgt    6720
gcgcatgcac gaggcgctcg gatatgcccc ccgcggcatg ctgcgggcgg ccggcttcaa    6780
gcacgggaac tggcatgacg tgggtttctg gcagctggac ttcagcctgc cggtaccgcc    6840
ccgtccggtc ctgcccgtca ccgagatctg agatcgttca aacatttggc aataaagttt    6900
cttaagattg aatcctgttg ccggtcttgc gatgattatc atataatttc tgttgaatta    6960
cgttaagcat gtaataatta acatgtaatg catgacgtta tttatgagat gggtttttat    7020
gattagagtc ccgcaattat acatttaata cgcgatagaa aacaaaatat agcgcgcaaa    7080
```

-continued

```
ctaggataaa ttatcgcgcg cggtgtcatc tatgttacta gatcggcgcg ccaagggcga    7140
attccagcac actggcggcc gttactagtg gatcgagctc gcgatcgcgg ccggccaggc    7200
cttagttact aatcagtgat cagattgtcg tttcccgcct tcagtttaaa ctatcagtgt    7260
ttgacaggat atattggcgg gtaaacctaa gagaaaagag cgtttattag aataatcgga    7320
tatttaaaag ggcgtgaaaa ggtttatccg ttcgtccatt tgtatgtcaa tatccatgat    7380
aagtcgcgct gtatgtgttt gtttgaatat tcatggaacg cagtggcggt tttcatggct    7440
tgttatgact gttttttttgg ggtacagtct atgcctcggg catccaagca gcaagcgcgt    7500
tacgccgtgg gtcgatgttt gatgttatgg agcagcaacg atgttacgca gcagggcagt    7560
cgccctaaaa caaagttaaa catcatgggt gaagcggtca tcgccgaggt gtccacccag    7620
ctgtcggaag tcgtgggtgt catcgagcgc cacctcgaac cgaccctcct cgccgtgcat    7680
ctgtatggta gcgccgttga cggcggcctt aagccccatt cggacatcga cctgcttgtc    7740
accgttaccg tccgtctcga cgagaccacg cgccgcgcgc ttatcaacga ccttctggaa    7800
acgtccgcct cccccggcga gagcgaaatc ctgcgcgcgg ttgaggtgac gattgtggtg    7860
cacgatgaca tcatcccctg gcgctatccg gccaaacgcg aactccagtt cggcgaatgg    7920
cagcgtaatg atattctggc gggtatcttt gaaccggcca ccatcgacat tgatctggcg    7980
atcctgctca ccaaggcccg ggagcatagc gtggccctcg tcggccccgc ggccgaggaa    8040
cttttcgacc cggtgccgga acaggatctg ttcgaagcac tgaacgagac gctgaccctg    8100
tggaactccc cgccggattg ggcgggcgat gagcgcaatg tggtccttac gctgagccgg    8160
atttggtact cggcggttac cggcaagatc gcgccgaagg atgtcgccgc cgactgggcg    8220
atggagcgcc ttccggcgca ataccagccc gtgatcctcg aagcgcgcca agcctatctg    8280
ggccaagaag aagaccgtct cgcgtcccgg gccgaccagc tcgaagaatt tgtccactat    8340
gtcaagggcg agatcacgaa ggtcgttggc aaataatgtc tagctagaaa ttcgttcaag    8400
ccgacgccgc ttcgcggcgc ggcttaactc aagcgttaga tgcactaagc acataattgc    8460
tcacagccaa actatcgatg agttgaagga ccccgtagaa aagatcaaag gatcttcttg    8520
agatcctttt tttctgcgcg taatctgctg cttgcaaaca aaaaaaccac cgctaccagc    8580
ggtggtttgt ttgccggatc aagagctacc aactctttttt ccgaaggtaa ctggcttcag    8640
cagagcgcag ataccaaata ctgtccttct agtgtagccg tagttaggcc accacttcaa    8700
gaactctgta gcaccgccta catacctcgc tctgctaatc ctgttaccag tggctgctgc    8760
cagtggcgat aagtcgtgtc ttaccgggtt ggactcaaga cgatagttac cggataaggc    8820
gcagcggtcg ggctgaacgg ggggttcgtg cacacagccc agcttggagc gaacgaccta    8880
caccgaactg agatacctac agcgtgagct atgagaaagc gccacgcttc cgaagggag    8940 aaaggcggac aggtatccgg taagcggcag ggtcggaaca ggagagcgca cgagggagct    9000
tccaggggga aacgcctggt atctttatag tcctgtcggg tttcgccacc tctgacttga    9060
gcgtcgattt ttgtgatgct cgtcaggggg gcggagccta tggaaaaacg ccagcaacgc    9120 ggcctttta cggttcctgg ccttttgctg gccttttgct cacatgttct ttcctgcgtt    9180
atcccctgat tctgtggata accgtattac cgcctttgag tgagctgata ccgctcgccg    9240
cagccgaacg accgagcgca gcgagtcagt gagcgaggaa gcggaagagc gcctgatgcg    9300
gtattttctc cttacgcatc tgtgcggtat ttcacaccgc ataggccgcg ataggccgac    9360
gcgaagcggc ggggcgtagg gagcgcagcg accgaagggt aggcgctttt tgcagctctt    9420
cggctgtgcg ctggccagac agttatgcac aggccaggcg ggtttttaaga gttttaataa    9480
```

```
gttttaaaga gttttaggcg gaaaaatcgc cttttttctc ttttatatca gtcacttaca    9540
tgtgtgaccg gttcccaatg tacggctttg ggttcccaat gtacgggttc cggttcccaa    9600
tgtacggctt tgggttccca atgtacgtgc tatccacagg aaagagacct tttcgacctt    9660
tttcccctgc tagggcaatt tgccctagca tctgctccgt acattaggaa ccggcggatg    9720
cttcgccctc gatcaggttg cggtagcgca tgactaggat cgggccagcc tgccccgcct    9780
cctccttcaa atcgtactcc ggcaggtcat ttgacccgat cagcttgcgc acggtgaaac    9840
agaacttctt gaactctccg gcgctgccac tgcgttcgta gatcgtcttg aacaaccatc    9900
tggcttctgc cttgcctgcg gcgcggcgtg ccaggcggta gagaaaacgg ccgatgccgg    9960
ggtcgatcaa aaagtaatcg gggtgaaccg tcagcacgtc cgggttcttg ccttctgtga    10020
tctcgcggta catccaatca gcaagctcga tctcgatgta ctccggccgc ccggtttcgc    10080
tctttacgat cttgtagcgg ctaatcaagg cttcaccctc ggataccgtc accaggcggc    10140
cgttcttggc cttcttggta cgctgcatgg caacgtgcgt ggtgtttaac cgaatgcagg    10200
tttctaccag gtcgtctttc tgctttccgc catcggctcg ccggcagaac ttgagtacgt    10260
ccgcaacgtg tggacggaac acgcggccgg gcttgtctcc cttcccttcc cggtatcggt    10320
tcatggattc ggttagatgg gaaaccgcca tcagtaccag gtcgtaatcc cacacactgg    10380
ccatgccggc ggggcctgcg gaaacctcta cgtgcccgtc tggaagctcg tagcggatca    10440
cctcgccagc tcgtcggtca cgcttcgaca gacggaaaac ggccacgtcc atgatgctgc    10500
gactatcgcg ggtgcccacg tcatagagca tcggaacgaa aaaatctggt tgctcgtcgc    10560
ccttgggcgg cttcctaatc gacggcgcac cggctgccgg cggttgccgg gattctttgc    10620
ggattcgatc agcggcccct tgccacgatt caccggggcg tgcttctgcc tcgatgcgtt    10680
gccgctgggc ggcctgcgcg gccttcaact tctccaccag gtcatcaccc agcgccgcgc    10740
cgatttgtac cgggccggat ggtttgcgac cgctcacgcc gattcctcgg gcttgggggt    10800
tccagtgcca ttgcagggcc ggcagacaac ccagccgctt acgcctggcc aaccgcccgt    10860
tcctccacac atggggcatt ccacggcgtc ggtgcctggt tgttcttgat tttccatgcc    10920
gcctccttta gccgctaaaa ttcatctact catttattca tttgctcatt tactctggta    10980
gctgcgcgat gtattcagat agcagctcgg taatggtctt gccttggcgt accgcgtaca    11040
tcttcagctt ggtgtgatcc tccgccggca actgaaagtt gacccgcttc atggctggcg    11100
tgtctgccag gctggccaac gttgcagcct tgctgctgcg tgcgctcgga cggccggcac    11160
ttagcgtgtt tgtgcttttg ctcattttct ctttacctca ttaactcaaa tgagttttga    11220
tttaatttca gcggccagcg cctggacctc gcgggcagcg tcgccctcgg gttctgattc    11280
aagaacggtt gtgccggcgg cggcagtgcc tgggtagctc acgcgctgcg tgatacggga    11340
ctcaagaatg ggcagctcgt acccggccag cgcctcggca acctcaccgc cgatgcgcgt    11400
gcctttgatc gcccgcgaca cgacaaaggc cgcttgtagc cttccatccg tgacctcaat    11460
gcgctgctta accagctcca ccaggtcggc ggtggcccaa atgtcgtaag gcttggctg     11520 caccggaatc agcacgaagt cggctgcctt gatcgcggac acagccaagt ccgccgcctg    11580
gggcgctccg tcgatcacta cgaagtcgcg ccggccgatg ccttcacgt cgcggtcaat     11640 cgtcgggcgg tcgatgccga caacggttag cggttgatct tcccgcacgg ccgcccaatc    11700
gcgggcactg ccctggggat cggaatcgac taacagaaca tcggccccgg cgagttgcag    11760
ggcgcgggct agatgggttg cgatggtcgt cttgcctgac ccgcctttct ggttaagtac    11820
```

```
agcgataacc ttcatgcgtt ccccttgcgt atttgtttat ttactcatcg catcatatac   11880
gcagcgaccg catgacgcaa gctgttttac tcaaatacac atcacctttt tagatgatca   11940
gtgattttgt gccgagctgc cggtcgggga gctgttggct ggctgg               11986
```

```
<210> SEQ ID NO 15
<211> LENGTH: 20
<212> TYPE: DNA
<213> ORGANISM: Artificial Sequence
<220> FEATURE:
<223> OTHER INFORMATION: primer forward: sugarcane poly-ubiquitin gene

<400> SEQUENCE: 15
tcgcccgccg taataaatag                                              20
```

```
<210> SEQ ID NO 16
<211> LENGTH: 21
<212> TYPE: DNA
<213> ORGANISM: Artificial Sequence
<220> FEATURE:
<223> OTHER INFORMATION: primer reverse: sugarcane poly-ubiquitin gene

<400> SEQUENCE: 16
atctggttgt gtgtgtgtgc g                                            21
```

```
<210> SEQ ID NO 17
<211> LENGTH: 15
<212> TYPE: DNA
<213> ORGANISM: Artificial Sequence
<220> FEATURE:
<223> OTHER INFORMATION: probe sugarcane poly-ubiquitin gene

<400> SEQUENCE: 17
ctccacaccc tcttt                                                   15
```

```
<210> SEQ ID NO 18
<211> LENGTH: 26
<212> TYPE: DNA
<213> ORGANISM: Artificial Sequence
<220> FEATURE:
<223> OTHER INFORMATION: Junction sequence between 5'region of insert
      and sugarcane genome of event CTC09187-6.

<400> SEQUENCE: 18
aaattaagta ctgatatcac attgcg                                       26
```

```
<210> SEQ ID NO 19
<211> LENGTH: 26
<212> TYPE: DNA
<213> ORGANISM: Artificial Sequence
<220> FEATURE:
<223> OTHER INFORMATION: Junction sequence between 3'region of insert
      and sugarcane genome of event CTC09187-6.

<400> SEQUENCE: 19
taaactatca gtgtttgaac cgttgt                                       26
```

```
<210> SEQ ID NO 20
<211> LENGTH: 1848
<212> TYPE: DNA
<213> ORGANISM: Artificial Sequence
<220> FEATURE:
<223> OTHER INFORMATION: Sugarcane optimized truncate cry1Ac gene (B.
      thurigiensis)

<400> SEQUENCE: 20
```

```
atggacaaca acccaaacat caacgagtgc atcccataca actgcctgag caacccagag        60
gtggaggtgc tgggtggcga gcgcatcgag accggttaca cccccatcga catctccctg       120
tccttgaccc agttcctgct cagcgagttc gtgccaggtg ctggcttcgt gctcggcctg       180
gtggacatca tctggggtat cttcggtcca tcccaatggg acgccttcct ggtgcaaatc       240
gagcagctga tcaaccagag gatcgaagag ttcgccagga accaggccat ctccaggctg       300
gagggcctga gcaacctcta ccaaatctac gccgagagct tcagggagtg ggaggccgac       360
ccgaccaacc cagctctccg cgaggaaatg cgcattcaat tcaacgacat gaacagcgcc       420
ctgaccaccg ctatcccact gttcgccgtc cagaactacc aagtgccgct cctgtccgtg       480
tacgtgcaag ccgctaacct gcacctcagc gtgctgcgcg acgtgagcgt gttcggccaa       540
aggtggggct tcgatgctgc caccatcaac agccgctaca acgacctgac caggctgatt       600
ggcaactaca ccgaccacgc tgtgcgctgg tacaacaccg gcctggagcg cgtctggggt       660
ccggactcca gggactggat caggtacaac cagttcagga gggagttgac cctcaccgtg       720
ctggacattg tgtccctctt cccgaactac gactccagga cctacccgat ccgcaccgtg       780
tcccaactca ccagggagat ctacaccaac ccagtgctgg agaacttcga cggtagcttc       840
cgcggttccg cccagggtat cgagggctcc atcaggagcc cacacctgat ggacatcctg       900
aacagcatca ccatctacac cgacgctcac aggggcgagt actactggtc cggccaccag       960
atcatggcct ccccagtggg cttcagcggc cccgagttca ccttcccgct ctacggcacc      1020
atgggcaacg ccgctccaca gcaacgcatc gtggctcaac tgggtcaggg tgtctacagg      1080
accctgtcct ccaccctgta caggaggccc ttcaacatcg gtatcaacaa ccagcaactg      1140
tccgtgctcg acggcaccga gttcgcctac ggcacctcct ccaacctgcc atccgctgtc      1200
tacaggaaga gcggcaccgt ggactccctg gacgagatcc caccacagaa caacaacgtg      1260
ccacccaggc aaggcttctc ccacaggctg agccacgtgt ccatgttccg ctccggcttc      1320
agcaacagct ccgtgagcat catcagggct ccgatgttct cctggatcca ccgcagcgct      1380
gagttcaaca acatcatcgc ctccgacagc atcacccaaa tcccggccgt gaagggcaac      1440
ttcctcttca acggttccgt catttccggc ccaggcttca ccggtggcga cctcgtgagg      1500
ctcaacagca gcggcaacaa catccagaac aggggctaca tcgaggtgcc aatccacttc      1560
ccatccacct ccaccaggta cagggtgcgc gtgaggtacg cttccgtgac cccgatccac      1620
ctcaacgtga actgggggtaa ctcctccatc ttctccaaca ccgtgccagc taccgctacc      1680
tccctggaca acctccaatc cagcgacttc ggttacttcg agagcgccaa cgctttcacc      1740
tcctccctcg gtaacatcgt gggcgtgagg aacttcagcg gcaccgccgg cgtgatcatc      1800
gacaggttcg agttcatccc agtgaccgcc accctcgagg ctgagtga                   1848
```

<210> SEQ ID NO 21
<211> LENGTH: 552
<212> TYPE: DNA
<213> ORGANISM: Artificial Sequence
<220> FEATURE:
<223> OTHER INFORMATION: Sugarcane optimized bar gene (B. thurigiensis)

<400> SEQUENCE: 21

```
atgagcccag aacgacgccc ggccgacatc cgccgtgcca ccgaggcgga catgccggcg        60
gtctgcacca tcgtcaacca ctacatcgag acaagcacgg tcaacttccg taccgagccg       120
caggaaccgc aggagtggac ggacgacctc gtccgtctgc gggagcgcta tccctggctc       180
gtcgccgagg tggacggcga ggtcgccggc atcgcctacg cgggcccctg gaaggcacgc       240
```

-continued

```
aacgcctacg actggacggc cgagtcgacc gtgtacgtct ccccccgcca ccagcggacg      300
ggactgggct ccacgctcta cacccacctg ctgaagtccc tggaggcaca gggcttcaag      360
agcgtggtcg ctgtcatcgg gctgcccaac gacccgagcg tgcgcatgca cgaggcgctc      420
ggatatgccc cccgcggcat gctgcgggcg gccggcttca agcacgggaa ctggcatgac      480
gtgggtttct ggcagctgga cttcagcctg ccggtaccgc cccgtccggt cctgcccgtc      540
accgagatct ga                                                          552

<210> SEQ ID NO 22
<211> LENGTH: 10712
<212> TYPE: DNA
<213> ORGANISM: Artificial Sequence
<220> FEATURE:
<223> OTHER INFORMATION: CTC91087-6 event: Flanking sequences and T DNA
      fragment

<400> SEQUENCE: 22
gcttgcattt gttcttgggt ggcggtagta gttggggatg tcacaacttg taaatctcac       60
gcagtttaac aagactcatt gtgatactct atatagtacg taaaagaaac gaacgatagt      120
aaaacaagat tcacattcac ctatctggca ttacgactca attgctcttg ttgcaaggac      180
gctgtgctca gttcctgcac tgattttttt ttcctttttt gattaccgaa ttgcatacga      240
acgcagtgtg cagagcgcag cacccagctt gtgcagctac gaagccatcg acgtgctcaa      300
tggaggcgca catactatga atctatgatt agcgagatat ttcgatacgt tcctatcgtc      360
ggggaggacg ttaaaactga cagttggaga agaggagtag gagtatcttc ttctatctcg      420
cgacacttta cgctgaatta agcatcgatg ctggcagagg tcgagccgtc gaaacaccga      480
ccatctattg tttcgtatag tatctttgct gccagtgaac gtgctgtgtg aaggatcagc      540
gtggaagctg gaaaaaggac agtgtggtga acatggaggg gcagacccag atgcatgcca      600
cgttttttgc ttaggccagt ctcaatgggg tttcattaga gttttatgga cattaattat      660
attgacgtga cactatatta ataaagagag ggatgataag agttttatgg gagtagagag      720
agttcatgtg gataaaaact cttcggtatt gttttcaaaa tctaaatatg ttgaaaacag      780
tgacatgaaa tcgtcactaa cactgcctta tgctgaaatt taacttatgc taagatattg      840
taagggaata aaaagtagct cttgctcaag cgaacagcgg ccgatggcgt ctttttccgt      900
gaattgcggc tgggctgcgg cgcggggccg gcccgtgtgg tgtctcgcca aacaggcaac      960
tcctgtcctg tgggcgcgcg cttggactct tcttcgtagc cgtggcccca cgggcagggg     1020
agatgagatc acgacggccc gtcgtcacgc cgcgctgccg tgtcatctgc tatgcgcgcg     1080
cgagcaactt gcagcctgac gctgaccctt cggggggacgt gatccatgcc cgtgtcgtcc     1140
gcgtccatcg ggacgggagg ccgaagtcgt cggacgcttg tgtaaataaa gaaaacaaac     1200
atatgttgga cgcttcctct gagtatttta ttttacctaa aataaaaaga taaacaacag     1260
aggaatcatt ggaggggagg ccccggtcgg caaggcaaag ccaagtttgg tgctcctcga     1320
atcgaatcga gtcgaatgaa taagcatcgc cgtaaaatgg acggaccgac gagcccgccc     1380
ggacgcccgg ggcctcagcc tcaggcctca gctacgcgc cgtgtcccgt gtgctccacg       1440
tagggacgaa aacggtacgg atattttccg accgtattcg agatcgaatc tgtttagagg     1500
agttttaatc tgttcatatc tgagttcaga tatttaacat ccgataccgt attcgtatcc     1560
aaatatttaa atcacatatt tatgatgttg atatccaatc gtatcctatc cgtcattttt     1620
tatactatcc gtattcgaat ccgaatctgg acataaatat gaaaacaaat acaatatcaa     1680
```

```
taatatccgt ccgtatccga tccgtttca gccctagctc cacgtgtgtg tgacgtgcgc      1740
gctgtgtgtg tgtgtctgtt gtgctgcatc gtctttcgat tcgcctgctg ttttgtgttt      1800
cctgctccgg tggttatcta gtatcggaat tattgcgctc tcatttatcg cctccggttt      1860
tctgatggcc gtcgccatcg ttctcgcgtc accaaagacg gtcggtcacg tctcttgtca      1920
aaaaaaaaaa gacggtcacg tctctctcac ctcggcttcg gtacgtacag gaaactggaa      1980
ctggatggtg catacagtac tctactgcgc ataggatagg atggaaggct gccctgccgg      2040
ccgcgttcaa caaattaagt actgatatca cattgcggac gtctttaatg tactgaattt      2100
agttactgat cactgattaa gtactgatat cggtaccgaa ttcgcggccg caagcttcga      2160
tcgatgcctg cagtgcagcg tgacccggtc gtgcccctct ctagagataa tgagcattgc      2220
atgtctaagt tataaaaaat taccacatat ttttttttgtc acacttgttt gaagtgcagt      2280
ttatctatct ttatacatat atttaaactt tactctacga ataatataat ctatagtact      2340
acaataatat cagtgtttta gagaatcata taaatgaaca gttagacatg gtctaaagga      2400
caattgagta ttttgacaac aggactctac agtttatct ttttagtgtg catgtgttct      2460 ccttttttt tgcaaatagc ttcacctata taatacttca tccattttat tagtacatcc      2520
atttagggtt tagggttaat ggttttttata gactaatttt tttagtacat ctattttatt      2580
ctattttagc ctctaaatta agaaaactaa aactctattt tagttttttt atttaataat      2640
ttagatataa aatagaataa aataaagtga ctaaaaatta aacaaatacc ctttaagaaa      2700
ttaaaaaaac taaggaaaca ttttttcttgt ttcgagtaga taatgccagc ctgttaaacg      2760
ccgtcgacga gtctaacgga caccaaccag cgaaccagca gcgtcgcgtc gggccaagcg      2820
aagcagacgg cacggcatct ctgtcgctgc ctctggaccc ctctcgagag ttccgctcca      2880
ccgttggact tgctccgctg tcggcatcca gaaattgcgt ggcggagcgg cagacgtgag      2940
ccggcacggc aggcggcctc ctcctcctct cacggcacgg cagctacggg ggattccttt      3000
cccaccgctc cttcgctttc ccttcctcgc ccgccgtaat aaatagacac ccctccaca      3060 ccctctttcc ccaacctcgt gttgttcgga gcgcacacac acacaaccag atctccccca      3120
aatccacccg tcggcacctc cgcttcaagg tacgccgctc gtcctcccccc ccccccctc      3180 tctaccttct ctagatcggc gttccggtcc atggttaggg cccggtagtt ctacttctgt      3240
tcatgtttgt gttagatccg tgtttgtgtt agatccgtgc tgctagcgtt cgtacacgga      3300
tgcgacctgt acgtcagaca cgttctgatt gctaacttgc cagtgtttct ctttggggaa      3360
tcctgggatg gctctagccg ttccgcagac gggatcgatt tcatgatttt ttttgtttcg      3420
ttgcataggg tttggtttgc cctttttcctt tatttcaata tatgccgtgc acttgtttgt      3480
cgggtcatct tttcatgctt ttttttgtct tggttgtgat gatgtggtct ggttgggcgg      3540
tcgttctaga tcggagtaga attctgtttc aaactacctg gtggatttat taattttgga      3600
tctgtatgtg tgtgccatac atattcatag ttacgaattg aagatgatgg atggaaatat      3660
cgatctagga taggtataca tgttgatgcg ggtttttactg atgcatatac agagatgctt      3720
tttgttcgct tggttgtgat gatgtggtgt ggttgggcgg tcgttcattc gttctagatc      3780
ggagtagaat actgtttcaa actacctggt gtatttatta attttggaac tgtatgtgtg      3840
tgtcatacat cttcatagtt acgagtttaa gatggatgga aatatcgatc taggataggt      3900
atacatgttg atgtgggttt tactgatgca tatacatgat ggcatatgca gcatctattc      3960
atatgctcta accttgagta cctatctatt ataataaaca agtatgtttt ataattattt      4020
```

-continued

```
tgatcttgat atacttggat gatggcatat gcagcagcta tatgtggatt tttttagccc    4080
tgccttcata cgctatttat ttgcttggta ctgtttcttt tgtcgatgct caccctgttg    4140
tttggtgtta cttctgcagg tcgactctag aatggacaac aacccaaaca tcaacgagtg    4200
catcccatac aactgcctga gcaacccaga ggtggaggtg ctgggtggcg agcgcatcga    4260
gaccggttac acccccatcg acatctccct gtccttgacc cagttcctgc tcagcgagtt    4320
cgtgccaggt gctggcttcg tgctcggcct ggtggacatc atctgggta tcttcggtcc    4380 atcccaatgg gacgccttcc tggtgcaaat cgagcagctg atcaaccaga ggatcgaaga    4440
gttcgccagg aaccaggcca tctccaggct ggagggcctg agcaacctct accaaatcta    4500
cgccgagagc ttcagggagt gggaggccga cccgaccaac ccagctctcc gcgaggaaat    4560
gcgcattcaa ttcaacgaca tgaacagcgc cctgaccacc gctatcccac tgttcgccgt    4620
ccagaactac caagtgccgc tcctgtccgt gtacgtgcaa gccgctaacc tgcacctcag    4680
cgtgctgcgc gacgtgagcg tgttcggcca aaggtggggc ttcgatgctg ccaccatcaa    4740
cagccgctac aacgacctga ccaggctgat tggcaactac accgaccacg ctgtgcgctg    4800
gtacaacacc ggcctggagc gcgtctgggg tccggactcc agggactgga tcaggtacaa    4860
ccagttcagg agggagttga ccctcaccgt gctggacatt gtgtccctct tcccgaacta    4920
cgactccagg acctacccga tccgcaccgt gtcccaactc accagggaga tctacaccaa    4980
cccagtgctg gagaacttcg acggtagctt ccgcggttcc gcccagggta tcgagggctc    5040
catcaggagc ccacacctga tggacatcct gaacagcatc accatctaca ccgacgctca    5100
caggggcgag tactactggt ccggccacca gatcatggcc tccccagtgg gcttcagcgg    5160
ccccgagttc accttcccgc tctacggcac catgggcaac gccgctccac agcaacgcat    5220
cgtggctcaa ctgggtcagg gtgtctacag gaccctgtcc tccaccctgt acaggaggcc    5280
cttcaacatc ggtatcaaca accagcaact gtccgtgctc gacggcaccg agttcgccta    5340
cggcacctcc tccaacctgc catccgctgt ctacaggaag agcggcaccg tggactccct    5400
ggacgagatc ccaccacaga acaacaacgt gccacccagg caaggcttct cccacaggct    5460
gagccacgtg tccatgttcc gctccggctt cagcaacagc tccgtgagca tcatcagggc    5520
tccgatgttc tcctggatcc accgcagcgc tgagttcaac aacatcatcg cctccgacag    5580
catcacccaa atcccggccg tgaagggcaa cttcctcttc aacggttccg tcatttccgg    5640
cccaggcttc accggtggcg acctcgtgag gctcaacagc agcggcaaca acatccagaa    5700
caggggctac atcgaggtgc caatccactt cccatccacc tccaccaggt acagggtgcg    5760
cgtgaggtac gcttccgtga ccccgatcca cctcaacgtg aactggggta actcctccat    5820
cttctccaac accgtgccag ctaccgctac ctccctggac aacctccaat ccagcgactt    5880
cggttacttc gagagcgcca acgctttcac ctcctccctc ggtaacatcg tgggcgtgag    5940
gaacttcagc ggcaccgccg gcgtgatcat cgacaggttc gagttcatcc cagtgaccgc    6000
caccctcgag gctgagtgag atcgttcaaa catttggcaa taaagtttct taagattgaa    6060
tcctgttgcc ggtcttgcga tgattatcat ataatttctg ttgaattacg ttaagcatgt    6120
aataattaac atgtaatgca tgacgttatt tatgagatgg gttttttatga ttagagtccc    6180 gcaattatac atttaatacg cgatagaaaa caaaatatag cgcgcaaact aggataaatt    6240
atcgcgcgcg gtgtcatcta tgttactaga tcggcgcgcc aagggcgaat tccagcacac    6300
tggcggccgt tactagtgga tcacgcgtat gcctgcagtg cagcgtgacc cggtcgtgcc    6360
cctctctaga gataatgagc attgcatgtc taagttataa aaaattacca catatttttt    6420
```

-continued

```
ttgtcacact tgtttgaagt gcagtttatc tatctttata catatattta aactttactc    6480
tacgaataat ataatctata gtactacaat aatatcagtg ttttagagaa tcatataaat    6540
gaacagttag acatggtcta aaggacaatt gagtattttg acaacaggac tctacagttt    6600
tatcttttta gtgtgcatgt gttctccttt tttttttgcaa atagcttcac ctatataata    6660
cttcatccat tttattagta catccattta gggtttaggg ttaatggttt ttatagacta    6720
atttttttag tacatctatt ttattctatt ttagcctcta aattaagaaa actaaaactc    6780
tattttagtt tttttatta ataatttaga tataaaatag aataaaataa agtgactaaa    6840
aattaaacaa atacccttta agaaattaaa aaaactaagg aaacattttt cttgtttcga    6900
gtagataatg ccagcctgtt aaacgccgtc gacgagtcta acggacacca accagcgaac    6960
cagcagcgtc gcgtcgggcc aagcgaagca gacggcacgg catctctgtc gctgcctctg    7020 gaccccctctc gagagttccg ctccaccgtt ggacttgctc cgctgtcggc atccagaaat    7080
tgcgtggcgg agcggcagac gtgagccggc acggcaggcg gcctcctcct cctctcacgg    7140
cacggcagct acgggggatt cctttcccac cgctccttcg ctttcccttc ctcgcccgcc    7200
gtaataaata gacacccct ccacaccctc tttccccaac ctcgtgttgt tcggagcgca    7260
cacacacaca accagatctc ccccaaatcc acccgtcggc acctccgctt caaggtacgc    7320
cgctcgtcct cccccccccc ccctctctac cttctctaga tcggcgttcc ggtccatggt    7380
tagggcccgg tagttctact tctgttcatg tttgtgttag atccgtgttt gtgttagatc    7440
cgtgctgcta gcgttcgtac acggatgcga cctgtacgtc agacacgttc tgattgctaa    7500
cttgccagtg tttctctttg gggaatcctg ggatggctct agccgttccg cagacgggat    7560
cgatttcatg attttttttg tttcgttgca tagggtttgg tttgcccttt tcctttattt    7620
caatatatgc cgtgcacttg tttgtcgggt catctttttca tgcttttttt tgtcttggtt    7680
gtgatgatgt ggtctggttg ggcggtcgtt ctagatcgga gtagaattct gtttcaaact    7740
acctggtgga tttattaatt ttggatctgt atgtgtgtgc catacatatt catagttacg    7800
aattgaagat gatggatgga aatatcgatc taggataggt atacatgttg atgcgggttt    7860
tactgatgca tatacagaga tgctttttgt tcgcttggtt gtgatgatgt ggtgtggttg    7920
ggcggtcgtt cattcgttct agatcggagt agaatactgt ttcaaactac ctggtgtatt    7980
tattaatttt ggaactgtat gtgtgtgtca tacatcttca tagttacgag tttaagatgg    8040
atggaaatat cgatctagga taggtataca tgttgatgtg ggttttactg atgcatatac    8100
atgatggcat atgcagcatc tattcatatg ctctaacctt gagtacctat ctattataat    8160
aaacaagtat gttttataat tattttgatc ttgatatact tggatgatgg catatgcagc    8220
agctatatgt ggattttttt agccctgcct tcatacgcta tttatttgct tggtactgtt    8280
tcttttgtcg atgctcaccc tgttgtttgg tgttacttct gcaggtcgac tctagaatga    8340
gcccagaacg acgcccggcc gacatccgcc gtgccaccga ggcggacatg ccggcggtct    8400
gcaccatcgt caaccactac atcgagacaa gcacggtcaa cttccgtacc gagccgcagg    8460
aaccgcagga gtggacggac gacctcgtcc gtctgcggga gcgctatccc tggctcgtcg    8520
ccgaggtgga cggcgaggtc gccggcatcg cctacgcggg cccctggaag gcacgcaacg    8580
cctacgactg gacggccgag tcgaccgtgt acgtctcccc ccgccaccag cggacgggac    8640
tgggctccac gctctacacc cacctgctga agtccctgga ggcacagggc ttcaagagcg    8700
tggtcgctgt catcgggctg cccaacgacc cgagcgtgcg catgcacgag gcgctcggat    8760
```

```
atgccccccg cggcatgctg cgggcggccg gcttcaagca cgggaactgg catgacgtgg      8820
gtttctggca gctggacttc agcctgccgg taccgccccg tccggtcctg cccgtcaccg      8880
agatctgaga tcgttcaaac atttggcaat aaagtttctt aagattgaat cctgttgccg      8940
gtcttgcgat gattatcata taatttctgt tgaattacgt taagcatgta ataattaaca      9000
tgtaatgcat gacgttattt atgagatggg tttttatgat tagagtcccg caattataca      9060
tttaatacgc gatagaaaac aaaatatagc gcgcaaacta ggataaatta tcgcgcgcgg      9120
tgtcatctat gttactagat cggcgcgcca agggcgaatt ccagcacact ggcggccgtt      9180
actagtggat cgagctcgcg atcgcggccg gccaggcctt agttactaat cagtgatcag      9240
attgtcgttt cccgccttca gtttaaacta tcagtgtttg aaccgttgta cgtgttccta      9300
tcgccagcag tcggccggcc gcacacacgt acgatccctg cgcctacttc caacataacg      9360
gccacaagtt cgttggttcc tcgacatgcc agcgtgtcat gtcgttggag cttcttggct      9420
ttcatcccga gcaccctacg ccctctgtct cacagtacta gtcgttttgg gatgtgttac      9480
ggtaaccgag gttaataaag cttaaagaca taaacaccca tacaaacgat gacagttgcg      9540
ctgtactatt gatagcttat ggtgtcagaa ccacatcttc agggagggag agcccactgg      9600
cagccggcca cccctccact ttgactttct accttatttt attcactttg gaaaccacga      9660
tgcaactatg atgcgacgga tggactggct gataggcctg tcagtgtgac tactgaggct      9720
ataacgtcaa gtaaaatgag acaaattttg aactctaaaa tgacatgtat tatgagacaa      9780
agagagtaga gaggagtttg gctagctgga tacatacaat aggtagagag ggcgtgtgtt      9840
ggctgccttg tcattctttg ttttgcctgg ctaggcaaat cggttggtag ctttgcttgc      9900
tcccctcggt ttctaaacgt tctaaggatt tttcttgcgc caaaagtggg ccgaaactac      9960
tcttccatgc tgacaacttt agcctgatca ggcaaggcaa ggttagctag atgggcaaaa     10020
caaccaaact tgccttgaga ttatttaggg caatgcttgg ttctggaaaa aaaagccgcc     10080
ctcaccttag ccgacattga gcaaccatcg ggtcagaaga gccaatttgg ctcacctacg     10140
atacgatggc ggttggtttc ctagctagtt tgtcttacct tgctatatta ggcaaggtaa     10200
tctttggcag gcttggtgag tagattttgc tctacgtcta caacaagata aatcctgcca     10260
gcatatgtgg acctcgtgat agccttacca acaatcaagt gcatgcccct cttctatatt     10320
ttgtatcagt aaggctaaat tgttcctaca cgtaataaag aatctaaggg ttagtttggc     10380
aragttgtgc tccctgattc ttcaactgtg ctccctgatt ctctgatgaa gtgattctga     10440
agctcaaaat agttttcttt gattctttag cataaactct taaaattcac tatggagaat     10500
cacttcacag aatcaggaga agctattttt tcagctctca gcctcttagt tcatttcaga     10560
gaatcacttt acagaatcac ttcactctga aaaaccgtt tggcagccgg ggagtgattc      10620
tcttcgagaa tccactccat ggaacgctcc caagcgcacc ctaaatgtta tcatagtaaa     10680
tctaaaccgt tcctagtaaa aaaaatccaa at                                   10712
```

<210> SEQ ID NO 23
<211> LENGTH: 2064
<212> TYPE: DNA
<213> ORGANISM: Artificial Sequence
<220> FEATURE:
<223> OTHER INFORMATION: CTC91087-6 event: Flanking sequence - Left
      border (5')

<400> SEQUENCE: 23

```
gcttgcattt gttcttgggt ggcggtagta gttggggatg tcacaacttg taaatctcac       60
```

-continued

```
gcagtttaac aagactcatt gtgatactct atatagtacg taaaagaaac gaacgatagt    120
aaaacaagat tcacattcac ctatctggca ttacgactca attgctcttg ttgcaaggac    180
gctgtgctca gttcctgcac tgattttttt ttcctttttt gattaccgaa ttgcatacga    240
acgcagtgtg cagagcgcag cacccagctt gtgcagctac gaagccatcg acgtgctcaa    300
tggaggcgca catactatga atctatgatt agcgagatat ttcgatacgt tcctatcgtc    360
ggggaggacg ttaaaactga cagttggaga agaggagtag gagtatcttc ttctatctcg    420
cgacacttta cgctgaatta agcatcgatg ctggcagagg tcgagccgtc gaaacaccga    480
ccatctattg tttcgtatag tatctttgct gccagtgaac gtgctgtgtg aaggatcagc    540
gtggaagctg gaaaaaggac agtgtggtga acatggaggg gcagacccag atgcatgcca    600
cgttttttgc ttaggccagt ctcaatgggg tttcattaga gtttttatgga cattaattat    660 attgacgtga cactatatta ataaagagag ggatgataag agtttatgg gagtagagag    720 agttcatgtg gataaaaact cttcggtatt gttttcaaaa tctaaatatg ttgaaaacag    780
tgacatgaaa tcgtcactaa cactgcctta tgctgaaatt taacttatgc taagatattg    840
taagggaata aaaagtagct cttgctcaag cgaacagcgg ccgatggcgt cttttttccgt    900 gaattgcggc tgggctgcgg cgcggggccg gcccgtgtgg tgtctcgcca aacaggcaac    960
tcctgtcctg tgggcgcgcg cttggactct tcttcgtagc cgtggcccca cgggcagggg   1020
agatgagatc acgacggccc gtcgtcacgc cgcgctgccg tgtcatctgc tatgcgcgcg   1080
cgagcaactt gcagcctgac gctgacccott cggggacgt gatccatgcc cgtgtcgtcc   1140
gcgtccatcg ggacgggagg ccgaagtcgt cggacgcttg tgtaaataaa gaaaacaaac   1200
atatgttgga cgcttcctct gagtatttta ttttacctaa aataaaaaga taaacaacag   1260
aggaatcatt ggaggggagg ccccggtcgg caaggcaaag ccaagtttgg tgctcctcga   1320
atcgaatcga gtcgaatgaa taagcatcgc cgtaaaatgg acggaccgac gagcccgccc   1380
ggacgcccgg ggcctcagcc tcaggcctca gctacggcgc cgtgtcccgt gtgctccacg   1440
tagggacgaa aacggtacgg atattttccg accgtattcg agatcgaatc tgtttagagg   1500
agttttaatc tgttcatatc tgagttcaga tatttaacat ccgataccgt attcgtatcc   1560
aaatatttaa atcacatatt tatgatgttg atatccaatc gtatcctatc cgtcattttt   1620
tatactatcc gtattcgaat ccgaatctgg acataaatat gaaaacaaat acaatatcaa   1680
taatatccgt ccgtatccga tccgtttttca gccctagctc cacgtgtgtg tgacgtgcgc   1740
gctgtgtgtg tgtgtctgtt gtgctgcatc gtctttcgat tcgcctgctg ttttgtgttt   1800
cctgctccgg tggttatcta gtatcggaat tattgcgctc tcatttatcg cctccggttt   1860
tctgatggcc gtcgccatcg ttctcgcgtc accaaagacg gtcggtcacg tctcttgtca   1920
aaaaaaaaaa gacggtcacg tctctctcac ctcggcttcg gtacgtacag gaaactggaa   1980
ctggatggtg catacagtac tctactgcgc ataggatagg atggaaggct gccctgccgg   2040
ccgcgttcaa caaattaagt actg                                           2064
```

<210> SEQ ID NO 24
<211> LENGTH: 1436
<212> TYPE: DNA
<213> ORGANISM: Artificial Sequence
<220> FEATURE:
<223> OTHER INFORMATION: CTC91087-6 event: Flanking sequence - Right
     border (3')

<400> SEQUENCE: 24

```
tttgaaccgt tgtacgtgtt cctatcgcca gcagtcggcc ggccgcacac acgtacgatc      60
cctgcgccta cttccaacat aacggccaca agttcgttgg ttcctcgaca tgccagcgtg     120
tcatgtcgtt ggagcttctt ggctttcatc ccgagcaccc tacgccctct gtctcacagt     180
actagtcgtt ttgggatgtg ttacggtaac cgaggttaat aaagcttaaa gacataaaca     240
cccatacaaa cgatgacagt tgcgctgtac tattgatagc ttatggtgtc agaaccacat     300
cttcagggag ggagagccca ctggcagccg gccacccctc cactttgact ttctacctta     360
ttttattcac tttggaaacc acgatgcaac tatgatgcga cggatggact ggctgatagg     420
cctgtcagtg tgactactga ggctataacg tcaagtaaaa tgagacaaat tttgaactct     480
aaaatgacat gtattatgag acaaagagag tagagaggag tttggctagc tggatacata     540
caataggtag agagggcgtg tgttggctgc cttgtcattc tttgtttttgc ctggctaggc    600 aaatcggttg gtagctttgc ttgctcccct cggtttctaa acgttctaag gattttctt      660 gcgccaaaag tgggccgaaa ctactcttcc atgctgacaa ctttagcctg atcaggcaag     720
gcaaggttag ctagatgggc aaaacaacca aacttgcctt gagattattt agggcaatgc     780
ttggttctgg aaaaaaaagc cgccctcacc ttagccgaca ttgagcaacc atcgggtcag     840
aagagccaat ttggctcacc tacgatacga tggcggttgg tttcctagct agtttgtctt     900
accttgctat attaggcaag gtaatctttg gcaggcttgg tgagtagatt ttgctctacg     960
tctacaacaa gataaatcct gccagcatat gtggacctcg tgatagcctt accaacaatc    1020
aagtgcatgc ccctcttcta tattttgtat cagtaaggct aaattgttcc tacacgtaat    1080
aaagaatcta agggttagtt tggcaragtt gtgctccctg attcttcaac tgtgctccct    1140
gattctctga tgaagtgatt ctgaagctca aaatagtttt ctttgattct ttagcataaa    1200
ctcttaaaat tcactatgga gaatcacttc acagaatcag gagaagctat tttttcagct    1260
ctcagcctct tagttcattt cagagaatca ctttacagaa tcacttcact ctgaaaaaac    1320
cgtttggcag ccggggagtg attctcttcg agaatccact ccatggaacg ctcccaagcg    1380
caccctaaat gttatcatag taaatctaaa ccgttcctag taaaaaaaat ccaaat        1436
```

```
<210> SEQ ID NO 25
<211> LENGTH: 27997
<212> TYPE: DNA
<213> ORGANISM: Artificial Sequence
<220> FEATURE:
<223> OTHER INFORMATION: Cas9/crRNA/HR template construction

<400> SEQUENCE: 25
cttagaataa cggatattta aaagggcgtg aaaaggttta tccgttcgtc catttgtatg      60
tgcatgccaa ccacagggtt cccctcggga tcaaagtact ttgatccaac ccctccgctg     120
ctatagtgca gtcggcttct gacgttcagt gcagccgtct tctgaaaacg acatgtcgca     180
caagtcctaa gttacgcgac aggctgccgc cctgcccttt tcctggcgtt ttcttgtcgc     240 gtgtttttagt cgcataaagt agaatacttg cgactagaac cggagacatt acgccatgaa     300
caagagcgcc gccgctggcc tgctgggcta tgcccgcgtc agcaccgacg accaggactt     360
gaccaaccaa cgggccgaac tgcacgcggc cggctgcacc aagctgtttt ccgagaagat     420
caccggcacc aggcgcgacc gcccggagct ggccaggatg cttgaccacc tacgccctgg     480
cgacgttgtg acagtgacca ggctagaccg cctggcccgc agcacccgcg acctactgga     540
cattgccgag cgcatccagg aggccggcgc gggcctgcgt agcctggcag agccgtgggc     600
cgacaccacc acgccggccg gccgcatggt gttgaccgtg ttcgccggca ttgccgagtt     660
```

```
cgagcgttcc ctaatcatcg accgcacccg gagcgggcgc gaggccgcca aggcccgagg    720
cgtgaagttt ggcccccgcc ctaccctcac cccggcacag atcgcgcacg cccgcgagct    780
gatcgaccag gaaggccgca ccgtgaaaga ggcggctgca ctgcttggcg tgcatcgctc    840
gaccctgtac cgcgcacttg agcgcagcga ggaagtgacg cccaccgagg ccaggcggcg    900
cggtgccttc cgtgaggacg cattgaccga ggccgacgcc ctggcggccg ccgagaatga    960
acgccaagag gaacaagcat gaaaccgcac caggacggcc aggacgaacc gtttttcatt   1020
accgaagaga tcgaggcgga gatgatcgcg gccgggtacg tgttcgagcc gcccgcgcac   1080
gtctcaaccg tgcggctgca tgaaatcctg gccggtttgt ctgatgccaa gctggcggcc   1140
tggccggcca gcttggccgc tgaagaaacc gagcgccgcc gtctaaaaag gtgatgtgta   1200
tttgagtaaa acagcttgcg tcatgcggtc gctgcgtata tgatgcgatg agtaaataaa   1260
caaatacgca aggggaacgc atgaaggtta tcgctgtact taaccagaaa ggcgggtcag   1320
gcaagacgac catcgcaacc catctagccc gcgccctgca actcgccggg gccgatgttc   1380
tgttagtcga ttccgatccc cagggcagtg cccgcgattg ggcggccgtg cgggaagatc   1440
aaccgctaac cgttgtcggc atcgaccgcc cgacgattga ccgcgacgtg aaggccatcg   1500
gccggcgcga cttcgtagtg atcgacggag cgccccaggc ggcggacttg gctgtgtccg   1560
cgatcaaggc agccgacttc gtgctgattc cggtgcagcc aagcccttac gacatatggg   1620
ccaccgccga cctggtggag ctggttaagc agcgcattga ggtcacggat ggaaggctac   1680
aagcggcctt tgtcgtgtcg cgggcgatca aaggcacgcg catcggcggt gaggttgccg   1740
aggcgctggc cgggtacgag ctgcccattc ttgagtcccg tatcacgcag cgcgtgagct   1800
acccaggcac tgccgccgcc ggcacaaccg ttcttgaatc agaacccgag ggcgacgctg   1860
cccgcgaggt ccaggcgctg gccgctgaaa ttaaatcaaa actcatttga gttaatgagg   1920
taaagagaaa atgagcaaaa gcacaaacac gctaagtgcc ggccgtccga gcgcacgcag   1980
cagcaaggct gcaacgttgg ccagcctggc agacacgcca gccatgaagc gggtcaactt   2040
tcagttgccg gcggaggatc acaccaagct gaagatgtac gcggtacgcc aaggcaagac   2100
cattaccgag ctgctatctg aatacatcgc gcagctacca gagtaaatga gcaaatgaat   2160
aaatgagtag atgaatttta gcggctaaag gaggcggcat ggaaaatcaa gaacaaccag   2220
gcaccgacgc cgtggaatgc cccatgtgtg gaggaacggg cggttggcca ggcgtaagcg   2280
gctgggttgt ctgccggccc tgcaatggca ctggaacccc caagcccgag gaatcggcgt   2340
gacggtcgca aaccatccgg cccggtacaa atcggcgcgg cgctgggtga tgacctggtg   2400
gagaagttga aggccgcgca ggccgcccag cggcaacgca tcgaggcaga agcacgcccc   2460
ggtgaatcgt ggcaagcggc cgctgatcga atccgcaaag aatcccggca accgccggca   2520
gccggtgcgc cgtcgattag gaagccgccc aagggcgacg agcaaccaga ttttttcgtt   2580
ccgatgctct atgacgtggg cacccgcgat agtcgcagca tcatggacgt ggccgttttc   2640
cgtctgtcga agcgtgaccg acgagctggc gaggtgatcc gctacgagct tccagacggg   2700
cacgtagagg tttccgcagg gccggccggc atggccagtg tgtgggatta cgacctggta   2760
ctgatggcgg tttcccatct aaccgaatcc atgaaccgat accgggaagg aagggagac    2820 aagcccggcc gcgtgttccg tccacacgtt gcggacgtac tcaagttctg ccggcgagcc   2880 gatgcggaa agcagaaaga cgacctggta gaaacctgca ttcggttaaa caccacgcac   2940
gttgccatgc agcgtacgaa gaaggccaag aacggccgcc tggtgacggt atccgagggt   3000
```

```
gaagccttga ttagccgcta caagatcgta aagagcgaaa ccgggcggcc ggagtacatc     3060
gagatcgagc tagctgattg gatgtaccgc gagatcacag aaggcaagaa cccggacgtg     3120
ctgacggttc accccgatta cttttttgatc gatcccggca tcggccgttt tctctaccgc     3180
ctggcacgcc gcgccgcagg caaggcagaa gccagatggt tgttcaagac gatctacgaa     3240
cgcagtggca gcgccggaga gttcaagaag ttctgtttca ccgtgcgcaa gctgatcggg     3300
tcaaatgacc tgccggagta cgatttgaag gaggaggcgg ggcaggctgg cccgatccta     3360
gtcatgcgct accgcaacct gatcgagggc gaagcatccg ccggttccta atgtacggag     3420
cagatgctag ggcaaattgc cctagcaggg gaaaaaggtc gaaaaggtct ctttcctgtg     3480
gatagcacgt acattgggaa cccaaagccg tacattggga accggaaccc gtacattggg     3540
aacccaaagc cgtacattgg gaaccggtca cacatgtaag tgactgatat aaaagagaaa     3600
aaaggcgatt tttccgccta aaactcttta aaacttatta aaactcttaa aacccgcctg     3660
gcctgtgcat aactgtctgg ccagcgcaca gccgaagagc tgcaaaaagc gcctaccctt     3720
cggtcgctgc gctccctacg ccccgccgct tcgcgtcggc ctatcgcggc cgctggccgc     3780
tcaaaaatgg ctggcctacg gccaggcaat ctaccagggc gcggacaagc gcgccgtcg      3840 ccactcgacc gccggcgccc acatcaaggc accctgcctc gcgcgtttcg gtgatgacgg     3900
tgaaaacctc tgacacatgc agctcccgga gacggtcaca gcttgtctgt aagcggatgc     3960
cgggagcaga caagcccgtc agggcgcgtc agcgggtgtt ggcgggtgtc ggggcgcagc     4020
catgacccag tcacgtagcg atagcggagt gtatactggc ttaactatgc ggcatcagag     4080
cagattgtac tgagagtgca ccatatgcgg tgtgaaatac cgcacagatg cgtaaggaga     4140
aaataccgca tcaggcgctc ttccgcttcc tcgctcactg actcgctgcg ctcggtcgtt     4200
cggctgcggc gagcggtatc agctcactca aaggcggtaa tacggttatc cacagaatca     4260
ggggataacg caggaaagaa catgtgagca aaaggccagc aaaaggccag gaaccgtaaa     4320
aaggccgcgt tgctggcgtt tttccatagg ctccgccccc ctgacgagca tcacaaaaat     4380
cgacgctcaa gtcagaggtg gcgaaacccg acaggactat aaagatacca ggcgtttccc     4440
cctggaagct ccctcgtgcg ctctcctgtt ccgaccctgc cgcttaccgg atacctgtcc     4500
gcctttctcc cttcgggaag cgtggcgctt tctcatagct cacgctgtag gtatctcagt     4560
tcggtgtagg tcgttcgctc caagctgggc tgtgtgcacg aacccccgt tcagcccgac      4620 cgctgcgcct tatccggtaa ctatcgtctt gagtccaacc cggtaagaca cgacttatcg     4680
ccactggcag cagccactgg taacaggatt agcagagcga ggtatgtagg cggtgctaca     4740
gagttcttga agtggtggcc taactacggc tacactagaa ggacagtatt tggtatctgc     4800
gctctgctga agccagttac cttcggaaaa agagttggta gctcttgatc cggcaaacaa     4860
accaccgctg gtagcggtgg tttttttgtt tgcaagcagc agattacgcg cagaaaaaaa     4920
ggatctcaag aagatccttt gatcttttct acggggtctg acgctcagtg gaacgaaaac     4980
tcacgttaag ggattttggt catgcattct aggtattatt tgccaacgac cttcgtgatc     5040
tcgcccttga catagtggac aaattcttcg agctggtcgg cccgggacgc gagacggtct     5100
tcttcttggc ccagataggc ttggcgcgct tcgaggatca cgggctggta ttgcgccgga     5160
aggcgctcca tcgcccagtc ggcggcgaca tccttcggcg cgatcttgcc ggtaaccgcc     5220
gagtaccaaa tccggctcag cgtaaggacc acattgcgct catcgcccgc ccaatccggc     5280
ggggagttcc acagggtcag cgtctcgttc agtgcttcga acagatcctg ttccggcacc     5340
gggtcgaaaa gttcctcggc cgcggggccg acgagggcca cgctatgctc ccgggccttg     5400
```

-continued

```
gtgagcagga tcgccagatc aatgtcgatg gtggccggtt caaagatacc cgccagaata   5460
tcattacgct gccattcgcc gaactggagt tcgcgtttgg ccggatagcg ccaggggatg   5520
atgtcatcgt gcaccacaat cgtcacctca accgcgcgca ggatttcgct ctcgccgggg   5580
gaggcggacg tttccagaag gtcgttgata agcgcgcggc gcgtggtctc gtcgagacgg   5640
acggtaacgg tgacaagcag gtcgatgtcc gaatggggct taaggccgcc gtcaacggcg   5700
ctaccataca gatgcacggc gaggagggtc ggttcgaggt ggcgctcgat gacacccacg   5760
acttccgaca gctgggtgga cacctcggcg atgaccgctt cacccattta ttatttcctt   5820
cctcttttct acagtattta aagataccc aagaagctaa ttataacaag acgaactcca   5880
attcactgtt ccttgcattc taaaaccta ataccagaa aacagctttt tcaaagttgt   5940
tttcaaagtt ggcgtataac atagtatcga cggagccgat tttgaaaccg cggtgatcac   6000
aggcagcaac gctctgtcat cgttacaatc aacatgctac cctccgcgag atcatccgtg   6060
tttcaaaccc ggcagcttag ttgccgttct tccgaatagc atcggtaaca tgagcaaagt   6120
ctgccgcctt acaacggctc tcccgctgac gccgtcccgg actgatgggc tgcctgtatc   6180
gagtggtgat tttgtgccga gctgccggtc ggggagctgt tggctggctg gtggcaggat   6240
atattgtggt gtaaacaaat tgacgcttag acaacttaat aacacattgc ggacgttttt   6300
aatgtactga attagtactg ataaatggcg cgccaagctt tggcaaacag ctattatggg   6360
tattatgggt ggtaccacgc gtcgatccac tagtaacggc cgccagtgtg ctggaattcg   6420
cccttggcgc gccgatctag taacatagat gacaccgcgc gcgataattt atcctagttt   6480
gcgcgctata ttttgttttc tatcgcgtat taaatgtata attgcgggac tctaatcata   6540
aaaacccatc tcataaataa cgtcatgcat tacatgttaa ttattacatg cttaacgtaa   6600
ttcaacagaa attatatgat aatcatcgca agaccggcaa caggattcaa tcttaagaaa   6660
ctttattgcc aaatgtttga acgatctcag aagaactcgt caagaaggcg atagaaggcg   6720
atgcgctgcg aatcgggagc ggcgataccg taaagcacga ggaagcggtc agcccattcg   6780
ccgccaagct cttcagcaat atcacgggta gccaacgcta tgtcctgata gcggtccgcc   6840
acacccagcc ggccacagtc gatgaatcca gaaaagcggc catttttccac catgatattc   6900 ggcaagcagg catcgccatg ggtcacgacg agatcctcgc cgtcgggcat gcgcgccttg   6960
agcctggcga acagttcggc tggcgcgagc ccctgatgct cttcgtccag atcatcctga   7020
tcgacaagac cggcttccat ccgagtacgt gctcgctcga tgcgatgttt cgcttggtgg   7080
tcgaatgggc aggtagccgg atcaagcgta tgcagccgcc gcattgcatc agccatgatg   7140
gatactttct cggcaggagc aaggtgagat gacaggagat cctgccccgg cacttcgccc   7200
aatagcagcc agtcccttcc cgcttcagtg acaacgtcga gcacagctgc gcaaggaacg   7260
cccgtcgtgg ccagccacga tagccgcgct gcctcgtcct gcagttcatt cagggcaccg   7320
gacaggtcgg tcttgacaaa aagaaccggg cgcccctgcg ctgacagccg gaacacggcg   7380
gcatcagagc agccgattgt ctgttgtgcc cagtcatagc cgaatagcct ctccacccaa   7440
gcggccggag aacctgcgtg caatccatct tgttcaatcc acatggtggt gtgacctgca   7500
gaagtaacac caaacaacag ggtgagcatc acaaaagaa acagtaccaa gcaaataaat   7560
agcgtatgaa ggcagggcta aaaaaatcca catatagctg ctgcatatgc catcatccaa   7620
gtatatcaag atcaaaataa ttataaaaca tacttgttta ttataataga taggtactca   7680
aggttagagc atatgaatag atgctgcata tgccatcatg tatatgcatc agtaaaaccc   7740
```

-continued

```
acatcaacat gtatacctat cctagatcga tatttccatc catcttaaac tcgtaactat   7800
gaagatgtat gacacacaca tacagttcca aaattaataa atacaccagg tagtttgaaa   7860
cagtattcta ctccgatcta gaacgaatga acgaccgccc aaccacacca catcatcaca   7920
accaagcgaa caaaaagcat ctctgtatat gcatcagtaa aacccgcatc aacatgtata   7980
cctatcctag atcgatattt ccatccatca tcttcaattc gtaactatga atatgtatgg   8040
cacacacata cagatccaaa attaataaat ccaccaggta gtttgaaaca gaattctact   8100
ccgatctaga acgaccgccc aaccagacca catcatcaca accaagacaa aaaaaagcat   8160
gaaaagatga cccgacaaac aagtgcacgg catatattga aataaaggaa aagggcaaac   8220
caaaccctat gcaacgaaac aaaaaaaatc atgaaatcga tcccgtctgc ggaacggcta   8280
gagccatccc aggattcccc aaagagaaac actggcaagt tagcaatcag aacgtgtctg   8340
acgtacaggt cgcatccgtg tacgaacgct agcagcacga atctaacaca aacacggatc   8400
taacacaaac atgaacagaa gtagaactac cgggccctaa ccatggaccg gaacgccgat   8460
ctagagaagg tagagagggg ggggggggga ggacgagcgg cgtaccttga agcggaggtg   8520
ccgacgggtg gatttggggg agatctggtt gtgtgtgtgt gcgctccgaa caacacgagg   8580
ttggggaaag agggtgtgga gggggtgtct atttattacg gcgggcgagg aagggaaagc   8640
gaaggagcgg tgggaaagga atcccccgta gctgccgtgc cgtgagagga ggaggaggcc   8700
gcctgccgtg ccggctcacg tctgccgctc cgccacgcaa tttctggatg ccgacagcgg   8760
agcaagtcca acggtggagc ggaactctcg agaggggtcc agaggcagcg acagagatgc   8820
cgtgccgtct gcttcgcttg cccgacgcg acgctgctgg ttcgctggtt ggtgtccgtt   8880
agactcgtcg acggcgttta acaggctggc attatctact cgaaacaaga aaaatgtttc   8940
cttagttttt ttaatttctt aaagggtatt tgtttaattt ttagtcactt tattttattc   9000
tattttatat ctaaattatt aaataaaaaa actaaaatag agttttagtt ttcttaattt   9060
agaggctaaa atagaataaa atagatgtac taaaaaaatt agtctataaa aaccattaac   9120
cctaaaccct aaatggatgt actaataaaa tggatgaagt attatatagg tgaagctatt   9180
tgcaaaaaaa aaggagaaca catgcacact aaaaagataa aactgtagag tcctgttgtc   9240
aaaatactca attgtccttt agaccatgtc taactgttca tttatatgat tctctaaaac   9300
actgatatta ttgtagtact atagattata ttattcgtag agtaaagttt aaatatatgt   9360
ataaagatag ataaactgca cttcaaacaa gtgtgacaaa aaaaatatgt ggtaattttt   9420
tataacttag acatgcaatg ctcattatct ctagagaggg gcacgaccgg gtcacgctgc   9480
actgcaggga tccgatctag taacatagat gacaccgcgc gcgataattt atcctagttt   9540
gcgcgctata ttttgttttc tatcgcgtat taaatgtata attgcgggac tctaatcata   9600
aaaacccatc tcataaataa cgtcatgcat tacatgttaa ttattacatg cttaacgtaa   9660
ttcaacagaa attatatgat aatcatcgca agaccggcaa caggattcaa tcttaagaaa   9720
ctttattgcc aaatgtttga acgatcccta ggacgatctc acttgtacag ctcgtccatg   9780
ccgtgggtga tgccagctgc ggtgacgaac tccagcagga ccatgtggtc gcgcttctcg   9840
ttggggtcct tgctcagagc ggactgggtg ctcaggtagt ggttgtcggg cagcagcacg   9900
ggaccgtcgc cgatgggcgt gttctgctgg tagtggtcgg cgagctggac gctgccgtcc   9960
tcgatgttgt ggcggatctt gaagttgacc ttgatgccgt tcttctgctt gtcagccatg   10020
atgtagacgt tgtggctgtt gtagttgtac tccagcttgt gccccaggat gttgccgtcc   10080
tccttgaagt cgatgccctt cagctcgatg cggttcacca gggtgtcgcc ctcgaacttc   10140
```

-continued

```
acctcggctc gggtcttgta gttgccgtcg tccttgaaga agatggtgcg ctcctggacg   10200
tagccttcgg gcatggcgga cttgaagaag tcgtgctgct tcatgtggtc ggggtagcgg   10260
ctgaagcact gcacgccgta ggtgaaggtg gtcacgaggg tgggccaggg cacgggcagc   10320
ttgccggtgg tgcagatgaa cttcagggtc agcttgccgt aggtggcgtc gccctcgccc   10380
tcgccgctga cgctgaactt gtggccgttc acgtcgccgt ccagctcgac caggatgggc   10440
accaccccag tgaacagctc ctcgcccttg ctcactacaa aaaagctccg cacgaggctg   10500
catttgtcac aaatcatgaa aagaaaaact accgatgaac aatgctgagg gattcaaatt   10560
ctacccacaa aaagaagaaa gaaagatcta gcacatctaa gcctgacgaa gcagcagaaa   10620
tatataaaaa tataaaccat agtgcccttt tcccctcttc ctgatcttgt ttagcacggc   10680
ggaaatttta aaccccccat catctccccc aacaacggcg gatcgcagat ctacatccga   10740
gagccccatt ccccgcgaga tccgggccgg atccacgccg gcgagagccc cagccgcgag   10800
atcccgcccc tcccgcgcac cgatctgggc gcgcacgaag ccgcctctcg cccacccaaa   10860
ctaccaaggc caaagatcga gaccgagacg gaaaaaaaaa cggagaaaga aagaggagag   10920
gggcggggtg gttaccggcg gcggcggagg cctcccttgg atcttatggt gtgttgtccc   10980
tgtgtgttct ccaatagtgt ggcttgagtg tgtggaagat ggttctagag gatctgctag   11040
agtcagcttg tcagcgtgtc ctctccaaat gaaatgaact tccttatata gaggaagggt   11100
cttgcgaagg atagtgggat tgtgcgtcat cccttacgtc agtggagata tcacatcaat   11160
ccacttgctt tgaagacgtg gttggaacgt cttcttttc cacgatgctc ctcgtgggtg   11220
ggggtccatc tttgggacca ctgtcggcag aggcatcttc aacgatggcc tttcctttat   11280
cgcaatgatg gcatttgtag gagccacctt cctttttccac tatcttcaca ataaagtgac   11340
agatagctgg gcaatggaat ccgaggaggt ttccggatat tacccttttgt tgaaaagtct   11400 caatcggacc atcacatcaa tccacttgct ttgaagacgt ggttggaacg tcttcttttt   11460
ccacgatgct cctcgtgggt ggggtccat ctttgggacc actgtcggca gaggcatctt   11520
caacgatggc ctttcctttta tcgcaatgat ggcatttgta ggagccacct tccttttcca   11580
ctatcttcac aataaagtga cagatagctg ggcaatggaa tccgaggagg tttccggata   11640
ttaccctttg ttgaaaagtc tcaatcggac cccctcagcc tgcagtgcag cgtgacccgg   11700
tcgtgcccct ctctagagat aatgagcatt gcatgtctaa gttataaaaa attaccacat   11760
attttttttg tcacacttgt ttgaagtgca gtttatctat ctttatacat atatttaaac   11820
tttactctac gaataatata atctatagta ctacaataat atcagtgttt tagagaatca   11880
tataaatgaa cagttagaca tggtctaaag gacaattgag tattttgaca acaggactct   11940
acagttttat cttttttagtg tgcatgtgtt ctcctttttt tttgcaaata gcttcaccta   12000
tataatactt catccatttt attagtacat ccatttaggg tttagggtta atggtttta   12060 tagactaatt ttttttagtac atctatttta ttctatttta gcctctaaat taagaaaact   12120
aaaactctat tttagttttt ttatttaata atttagatat aaaatagaat aaaataaagt   12180
gactaaaaat taaacaaata ccctttaaga aattaaaaaa actaaggaaa catttttctt   12240
gtttcgagta gataatgcca gcctgttaaa cgccgtcgac gagtctaacg acaccaacc   12300 agcgaaccag cagcgtcgcg tcgggccaag cgaagcagac ggcacggcat ctctgtcgct   12360
gcctctggac ccctctcgag agttccgctc caccgttgga cttgctccgc tgtcggcatc   12420
cagaaattgc gtggcggagc ggcagacgtg agccggcacg gcaggcggcc tcctcctcct   12480
```

-continued

```
ctcacggcac ggcagctacg ggggattcct ttcccaccgc tccttcgctt tcccttcctc   12540
gcccgccgta ataaatagac acccctcca caccctcttt ccccaacctc gtgttgttcg   12600
gagcgcacac acacacaacc agatctcccc caaatccacc cgtcggcacc tccgcttcaa   12660
ggtacgccgc tcgtcctccc ccccccccc tctctacctt ctctagatcg gcgttccggt   12720
ccatggttag ggcccggtag ttctacttct gttcatgttt gtgttagatc cgtgtttgtg   12780
ttagatccgt gctgctagcg ttcgtacacg gatgcgacct gtacgtcaga cacgttctga   12840
ttgctaactt gccagtgttt ctctttgggg aatcctggga tggctctagc cgttccgcag   12900
acgggatcga tttcatgatt ttttttgttt cgttgcatag ggtttggttt gcccttttcc   12960
tttatttcaa tatatgccgt gcacttgttt gtcgggtcat ctttttcatgc ttttttttgt   13020 cttggttgtg atgatgtggt ctggttgggc ggtcgttcta gatcggagta gaattctgtt   13080
tcaaactacc tggtggattt attaattttg gatctgtatg tgtgtgccat acatattcat   13140
agttacgaat tgaagatgat ggatggaaat atcgatctag gataggtata catgttgatg   13200
cgggttttac tgatgcatat acagagatgc ttttgttcg cttggttgtg atgatgtggt   13260
gtggttgggc ggtcgttcat tcgttctaga tcggagtaga atactgtttc aaactacctg   13320
gtgtatttat taattttgga actgtatgtg tgtgtcatac atcttcatag ttacgagttt   13380
aagatggatg gaaatatcga tctaggatag gtatacatgt tgatgtgggt tttactgatg   13440
catatacatg atggcatatg cagcatctat tcatatgctc taaccttgag tacctatcta   13500
ttataataaa caagtatgtt ttataattat tttgatcttg atatacttgg atgatggcat   13560
atgcagcagc tatatgtgga tttttttagc cctgccttca tacgctattt atttgcttgg   13620
tactgtttct tttgtcgatg ctcaccctgt tgtttggtgt tacttctgca ggcgatcgcc   13680
acaccaccat gccgaagaag aagcgcaagg tcatggacaa gaagtactcc atcggcctgg   13740
acatcggcac caacagcgtg ggctgggccg tcatcaccga cgagtacaag gtgccctcca   13800
agaagttcaa ggtcctcggc aacaccgaca ggcacagcat caagaagaac ctgatcggcg   13860
ccctgctgtt cgactccggc gagactgcgg aggctaccag gctgaagcgc actgctcgca   13920
ggcgctacac caggcgcaag aaccgcatct gctacctcca ggagattttc tccaacgaga   13980
tggccaaggt ggacgactcc ttcttccacc gcctggagga gagcttcctg gtcgaggaag   14040
acaagaagca cgagcgccac cctatcttcg gcaacatcgt ggacgaggtc gcctaccacg   14100
agaagtaccc aaccatctac cacctccgca gaagctggt ggactccacc gacaaggccg   14160
acctgaggct catctacctg gccctcgccc acatgatcaa gttccgcggc cacttcctca   14220
tcgagggcga cctgaacccg gacaacagcg acgtggacaa gctcttcatc cagctggtcc   14280
agacctacaa ccagctgttc gaggagaacc ccatcaacgc ctccggcgtg gacgctaagg   14340
ctatcctcag cgctaggctg tccaagagca ggcgcctgga gaacctcatc gcccagctcc   14400 cggggcgagaa gaagaacggc ctcttcggca acctgatcgc tctgtccctc ggcctgaccc   14460
ccaacttcaa gagcaacttc gacctggccg aggacgccaa gctccagctg tccaaggaca   14520
cctacgacga cgacctcgac aacctgctcg cccagatcgg cgaccagtac gccgacctct   14580
tcctggccgc caagaacctc tccgacgcca tcctgctcag cgacatcctg agggtgaaca   14640
ccgagatcac caaggccccg ctgtccgcca gcatgatcaa gcgctacgac gagcaccacc   14700
aggacctcac tctcctgaag gccctcgtcc gccagcagct gcccgagaag tacaaggaga   14760
ttttcttcga ccagagcaag aacggctacg cgggctacat cgatggcggc gcctcccagg   14820
aagagttcta caagttcatc aagcctatcc tggagaagat ggacggcacc gaggagctgc   14880
```

```
tcgtgaagct gaaccgcgag gacctgctcc gcaagcagag gaccttcgac aacggcagca   14940
tccctcacca gatccacctg ggcgagctgc acgctatcct ccgccgccag gaagacttct   15000
acccattcct gaaggacaac cgcgagaaga tcgagaagat cctcaccttc cgcatcccgt   15060
actacgtggg ccccctggcc cgcggcaact ccaggttcgc ctggatgacc aggaagagcg   15120
aggagaccat caccccgtgg aacttcgagg aagtggtgga caagggcgcc tccgctcaga   15180
gcttcatcga gcgcatgacc aacttcgaca agaacctccc taacgagaag gtgctgccaa   15240
agcactccct gctctacgag tacttcaccg tctacaacga gctgaccaag gtgaagtatg   15300
tgaccgaggg catgaggaag cccgccttcc tcagcggcga gcagaagaag gccatcgtgg   15360
acctgctctt caagaccaac cgcaaggtga ccgtcaagca gctgaaggaa gactacttca   15420
agaagatcga gtgcttcgac tccgtggaga tcagcggcgt ggaggaccgc ttcaacgcct   15480
ccctcggcac ctaccacgac ctgctcaaga tcatcaagga caaggacttc ctcgacaacg   15540
aggagaacga ggacatcctg gaggacatcg tgctcaccct gaccctcttc gaggaccgcg   15600
agatgatcga ggagaggctc aagacctacg cccacctgtt cgacgacaag gtcatgaagc   15660
agctgaagag gcgcaggtac actggctggg gccgcctcag caggaagctg atcaacggca   15720
tcagggacaa gcagtccggc aagaccatcc tggacttcct caagagcgac ggcttcgcca   15780
accgcaactt catgcagctc atccacgacg actccctgac cttcaaggaa gacatccaga   15840
aggctcaggt gtccggccag ggcgacagcc tccacgagca catcgctaac ctggcgggca   15900
gccctgccat caagaagggc atcctccaga ccgtgaaggt ggtggacgag ctggtgaagg   15960
tcatgggccg ccacaagcca gagaacatcg tcatcgagat ggccagggag aaccagacca   16020
cccagaaggg tcagaagaac tcccgcgaga ggatgaagag gatcgaggaa ggcatcaagg   16080
agctgggcag ccagatcctg aaggagcacc cggtggagaa cacccagctc cagaacgaga   16140
agctgtacct ctactacctg cagaacggcc gcgacatgta tgtggaccag gagctggaca   16200
tcaacaggct gtccgactac gacgtggacc acatcgtccc tcagtccttc ctcaaggacg   16260
acagcatcga caacaaggtg ctgacccgca gcgacaagaa caggggcaag tccgacaacg   16320
tcccaagcga ggaagtggtc aagaagatga agaactactg gcgccagctg ctcaacgcca   16380
agctcatcac ccagcgcaag ttcgacaacc tgactaaggc ggagaggggc ggcctgtccg   16440
agctggacaa ggctggcttc atcaagcgcc agctcgtgga gaccaggcag atcaccaagc   16500
acgtcgccca gatcctggac agcaggatga acaccaagta cgacgagaac gacaagctca   16560
tccgcgaggt gaaggtcatc accctcaagt ccaagctggt gagcgacttc cgcaaggact   16620
tccagttcta caaggtcagg gagatcaaca ctaccacca cgcccacgat gcttacctca   16680
acgcggtggt gggcaccgcc ctcatcaaga gtaccctaa gctggagagc gagttcgtgt   16740
acggcgacta caaggtgtac gacgtccgca agatgatcgc caagtccgag caggagatcg   16800
gcaaggccac cgccaagtac ttcttctaca gcaacatcat gaacttcttc aagaccgaga   16860
tcaccctcgc caacggcgag atccgcaaga ggccactgat cgagaccaac ggcgagactg   16920
gcgagatcgt gtgggacaag ggcagggact tcgccaccgt gaggaaggtc ctgtccatgc   16980
ctcaggtgaa catcgtcaag aagaccgagg tccgaccgg cggcttctcc aaggagagca   17040
tcctcccaaa gcgcaacagc gacaagctga tcgccaggaa gaaggactgg gacccgaaga   17100
agtacggtgg cttcgactcc cctactgtgg cttacagcgt cctggtggtc gccaaggtgg   17160
agaagggcaa gtccaagaag ctgaagagcg tcaaggagct gctcggcatc accatcatgg   17220
```

-continued

```
agaggtccag cttcgagaag aacccgatcg acttcctgga ggccaagggc tacaaggaag   17280
tgaagaagga cctgatcatc aagctgccca agtacagcct gttcgagctg gagaacggcc   17340
gcaagaggat gctcgcctcc gctggcgagc tgcagaaggg caacgagctg gccctcccgt   17400
ccaagtatgt gaacttcctg tacctcgcct cccactacga gaagctgaag ggcagccccg   17460
aggacaacga gcagaagcag ctcttcgtcg agcagcacaa gcactacctg gacgagatca   17520
tcgagcagat cagcgagttc agcaagcgcg tgatcctcgc cgacgccaac ctcgacaagg   17580
tcctgtccgc ctacaacaag caccgcgaca agcctatcag ggagcaggcc gagaacatca   17640
tccacctgtt caccctcacc aacctgggcg ccccagctgc cttcaagtac ttcgacacca   17700
ccatcgaccg caagaggtac accagcacca aggaagtgct ggacgccacc ctgatccacc   17760
agtccatcac cggcctgtac gagactcgca tcgacctcag ccagctgggc ggcgacccga   17820
agaagaagcg caaagtctga gggaccctcg atcgacaagc tcgagtttct ccataataat   17880
gtgtgagtag ttcccagata agggaattag ggttcctata gggtttcgct catgtgttga   17940
gcatataaga aacccttagt atgtatttgt atttgtaaaa tacttctatc aataaaattt   18000
ctaattccta aaaccaaaat ccagtactaa aatccagatc ccccgaatta acctgcaggg   18060
gcggcaggga gagttttaac attgactagc gtgctgataa tttgtgagaa ataataattg   18120
acaagtagat actgacattt gagaagagct tctgaactgt tattagtaac aaaaatggaa   18180
agctgatgca cggaaaaagg aaagaaaaag ccatactttt ttttaggtag gaaaagaaaa   18240
agccatacga gactgatgtc tctcagatgg gccgggatct gtctatctag caggcagcag   18300
ccctaccaac ctcacgggcc agcaattacg agtccttcta aaacgtcccg ccgagggcgc   18360
gtggccgtgc tgtgcagcag cacgtctaac attagtccca cctcgccagt ttacagggag   18420
cagaaccagc ttataagcgg aggcgcggca ccaagaagca ggcgatagga acacgtacaa   18480
gttttagagc tagaaatagc aagttaaaat aaggctagtc cgttatcaac ttgaaaaagt   18540
ggcaccgagt cggtgctttt ttttcctcga ggggcgatag aacacgtac aacggctgcc   18600 gtgtcatctg ctatgcgcgc gcgagcaact tgcagcctga cgctgaccct tcgggggacg   18660
tgatccatgc ccgtgtcgtc cgcgtccatc gggacgggag gccgaagtcg tcggacgctt   18720
gtgtaaataa agaaaacaaa catatgttgg acgcttcctc tgagtatttt attttaccta   18780
aaataaaaag ataaacaaca gaggaatcat tggaggggag gccccggtcg gcaaggcaaa   18840
gccaagtttg gtgctcctcg aatcgaatcg agtcgaatga ataagcatcg ccgtaaaatg   18900
gacggaccga cgagcccgcc cggacgcccg gggcctcagc ctcaggcctc agctacggcg   18960
ccgtgtcccg tgtgctccac gtagggacga aaacggtacg gatattttcc gaccgtattc   19020
gagatcgaat ctgtttagag gagttttaat ctgttcatat ctgagttcag atatttaaca   19080
tccgataccg tattcgtatc caaatattta aatcacatat ttatgatgtt gatatccaat   19140
cgtatcctat ccgtcatttt ttatactatc cgtattcgaa tccgaatctg gacataaata   19200
tgaaaacaaa tacaatatca ataatatccg tccgtatccg atccgttttc agccctagct   19260
ccacgtgtgt gtgacgtgcg cgctgtgtgt gtgtgtctgt tgtgctgcat cgtctttcga   19320
ttcgcctgct gtttttgtgtt tcctgctccg gtggttatct agtatcggaa ttattgcgct   19380
ctcatttatc gcctccggtt ttctgatggc cgtcgccatc gttctcgcgt caccaaagac   19440
ggtcggtcac gtctcttgtc aaaaaaaaaa agacggtcac gtctctctca cctcggcttc   19500
ggtacgtaca ggaaactgga actggatggt gcatacagta ctctactgcg cataggatag   19560
gatggaaggc tgccctgccg gccgcgttca acaaattaag tactgatatc acattgcgga   19620
```

-continued

```
cgtctttaat gtactgaatt tagttactga tcactgatta agtactgata tcggtaccga   19680
attcgcggcc gcaagcttcg atcgatgcct gcagtgcagc gtgacccggt cgtgcccctc   19740
tctagagata atgagcattg catgtctaag ttataaaaaa ttaccacata ttttttttgt   19800
cacacttgtt tgaagtgcag tttatctatc tttatacata tatttaaact ttactctacg   19860
aataatataa tctatagtac tacaataata tcagtgtttt agagaatcat ataaatgaac   19920
agttagacat ggtctaaagg acaattgagt attttgacaa caggactcta cagtttttatc  19980 tttttagtgt gcatgtgttc tcctttttttt ttgcaaatag cttcacctat ataatacttc  20040
atccatttta ttagtacatc catttagggt ttagggttaa tggttttttat agactaattt  20100 ttttagtaca tctattttat tctattttag cctctaaatt aagaaaacta aaactctatt   20160
ttagtttttt tatttaataa tttagatata aaatagaata aaataaagtg actaaaaatt   20220
aaacaaatac cctttaagaa attaaaaaaa ctaaggaaac atttttcttg tttcgagtag   20280
ataatgccag cctgttaaac gccgtcgacg agtctaacgg acaccaacca gcgaaccagc   20340
agcgtcgcgt cgggccaagc gaagcagacg gcacggcatc tctgtcgctg cctctggacc   20400
cctctcgaga gttccgctcc accgttggac ttgctccgct gtcggcatcc agaaattgcg   20460
tggcggagcg gcagacgtga gccggcacgg caggcggcct cctcctcctc tcacggcacg   20520
gcagctacgg gggattcctt tcccaccgct ccttcgcttt cccttcctcg cccgccgtaa   20580
taaatagaca ccccctccac accctctttc cccaacctcg tgttgttcgg agcgcacaca   20640
cacacaacca gatctccccc aaatccaccc gtcggcacct ccgcttcaag gtacgccgct   20700
cgtcctcccc cccccccct ctctaccttc tctagatcgg cgttccggtc catggttagg   20760
gcccggtagt tctacttctg ttcatgtttg tgttagatcc gtgtttgtgt tagatccgtg   20820
ctgctagcgt tcgtacacgg atgcgacctg tacgtcagac acgttctgat tgctaacttg   20880
ccagtgtttc tctttgggga atcctgggat ggctctagcc gttccgcaga cgggatcgat   20940
ttcatgattt tttttgtttc gttgcatagg gtttggtttg cccttttcct ttatttcaat   21000
atatgccgtg cacttgtttg tcgggtcatc ttttcatgct ttttttttgtc ttggttgtga  21060 tgatgtggtc tggttgggcg gtcgttctag atcggagtag aattctgttt caaactacct   21120
ggtggattta ttaattttgg atctgtatgt gtgtgccata catattcata gttacgaatt   21180
gaagatgatg gatggaaata tcgatctagg ataggtatac atgttgatgc gggtttttact  21240 gatgcatata cagagatgct ttttgttcgc ttggttgtga tgatgtggtg tggttgggcg   21300
gtcgttcatt cgttctagat cggagtagaa tactgtttca aactacctgg tgtatttatt   21360
aattttggaa ctgtatgtgt gtgtcataca tcttcatagt tacgagttta agatggatgg   21420
aaatatcgat ctaggatagg tatacatgtt gatgtgggtt ttactgatgc atatacatga   21480
tggcatatgc agcatctatt catatgctct aaccttgagt acctatctat tataataaac   21540
aagtatgttt tataattatt ttgatcttga tatacttgga tgatggcata tgcagcagct   21600
atatgtggat ttttttagcc ctgccttcat acgctattta tttgcttggt actgtttctt   21660
ttgtcgatgc tcaccctgtt gtttggtgtt acttctgcag gtcgactcta gaatggacaa   21720
caacccaaac atcaacgagt gcatcccata caactgcctg agcaacccag aggtggaggt   21780
gctgggtggc gagcgcatcg agaccggtta cacccccatc gacatctccc tgtccttgac   21840
ccagttcctg ctcagcgagt tcgtgccagg tgctggcttc gtgctcggcc tggtggacat   21900
catctggggt atcttcggtc catcccaatg ggacgccttc ctggtgcaaa tcgagcagct   21960
```

-continued

```
gatcaaccag aggatcgaag agttcgccag gaaccaggcc atctccaggc tggagggcct  22020
gagcaacctc taccaaatct acgccgagag cttcagggag tgggaggccg acccgaccaa  22080
cccagctctc cgcgaggaaa tgcgcattca attcaacgac atgaacagcg ccctgaccac  22140
cgctatccca ctgttcgccg tccagaacta ccaagtgccg ctcctgtccg tgtacgtgca  22200
agccgctaac ctgcacctca gcgtgctgcg cgacgtgagc gtgttcggcc aaaggtgggg  22260
cttcgatgct gccaccatca acagccgcta caacgacctg accaggctga ttggcaacta  22320
caccgaccac gctgtgcgct ggtacaacac cggcctggag cgcgtctggg gtccggactc  22380
cagggactgg atcaggtaca accagttcag gagggagttg accctcaccg tgctggacat  22440
tgtgtccctc ttcccgaact acgactccag gacctacccg atccgcaccg tgtcccaact  22500
caccagggag atctacacca acccagtgct ggagaacttc gacggtagct ccgcggttc  22560 cgcccagggt atcgagggct ccatcaggag cccacacctg atggacatcc tgaacagcat  22620
caccatctac accgacgctc acaggggcga gtactactgg tccggccacc agatcatggc  22680
ctccccagtg ggcttcagcg gccccgagtt caccttcccg ctctacggca ccatgggcaa  22740
cgccgctcca cagcaacgca tcgtggctca actgggtcag ggtgtctaca ggaccctgtc  22800
ctccaccctg tacaggaggc ccttcaacat cggtatcaac aaccagcaac tgtccgtgct  22860
cgacggcacc gagttcgcct acggcacctc ctccaacctg ccatccgctg tctacaggaa  22920
gagcggcacc gtggactccc tggacgagat cccaccacag aacaacaacg tgccacccag  22980
gcaaggcttc tcccacaggc tgagccacgt gtccatgttc cgctccggct tcagcaacag  23040
ctccgtgagc atcatcaggg ctccgatgtt ctcctggatc caccgcagcg ctgagttcaa  23100
caacatcatc gcctccgaca gcatcacccca aatcccggcc gtgaagggca acttcctctt  23160
caacggttcc gtcatttccg gcccaggctt caccggtggc gacctcgtga ggctcaacag  23220
cagcggcaac aacatccaga acaggggcta catcgaggtg ccaatccact tcccatccac  23280
ctccaccagg tacagggtgc gcgtgaggta cgcttccgtg accccgatcc acctcaacgt  23340
gaactggggt aactcctcca tcttctccaa caccgtgcca gctaccgcta cctccctgga  23400
caacctccaa tccagcgact tcggttactt cgagagcgcc aacgctttca cctcctccct  23460
cggtaacatc gtgggcgtga ggaacttcag cggcaccgcc ggcgtgatca tcgacaggtt  23520
cgagttcatc ccagtgaccg ccaccctcga ggctgagtga gatcgttcaa acatttggca  23580
ataaagtttc ttaagattga atcctgttgc cggtcttgcg atgattatca tataatttct  23640
gttgaattac gttaagcatg taataattaa catgtaatgc atgacgttat ttatgagatg  23700 ggttttatg attagagtcc cgcaattata catttaatac gcgatagaaa acaaaatata  23760
gcgcgcaaac taggataaat tatcgcgcgc ggtgtcatct atgttactag atcggcgcgc  23820
caagggcgaa ttccagcaca ctggcggccg ttactagtgg atcacgcgta tgcctgcagt  23880
gcagcgtgac ccggtcgtgc ccctctctag agataatgag cattgcatgt ctaagttata  23940
aaaaattacc acatattttt tttgtcacac ttgtttgaag tgcagtttat ctatctttat  24000
acatatattt aaactttact ctacgaataa tataatctat agtactacaa taatatcagt  24060
gttttagaga tcatataaa tgaacagtta gacatggtct aaaggacaat tgagtatttt  24120
gacaacagga ctctacagtt ttatcttttt agtgtgcatg tgttctcctt ttttttttgca  24180 aatagcttca cctatataat acttcatcca ttttattagt acatccattt agggtttagg  24240
gttaatggtt tttatagact aatttttttta gtacatctat tttattctat tttagcctct  24300
aaattaagaa aactaaaact ctattttagt ttttttattt aataatttag atataaaata  24360
```

```
gaataaaata aagtgactaa aaattaaaca aatacccttt aagaaattaa aaaaactaag   24420
gaaacatttt tcttgtttcg agtagataat gccagcctgt taaacgccgt cgacgagtct   24480
aacggacacc aaccagcgaa ccagcagcgt cgcgtcgggc caagcgaagc agacggcacg   24540
gcatctctgt cgctgcctct ggacccctct cgagagttcc gctccaccgt tggacttgct   24600
ccgctgtcgg catccagaaa ttgcgtggcg gagcggcaga cgtgagccgg cacggcaggc   24660
ggcctcctcc tcctctcacg gcacggcagc tacgggggat tcctttccca ccgctccttc   24720
gctttccctt cctcgcccgc cgtaataaat agacacccc tccacaccct ctttccccaa   24780
cctcgtgttg ttcggagcgc acacacacac aaccagatct cccccaaatc cacccgtcgg   24840
cacctccgct tcaaggtacg ccgctcgtcc tcccccccc cccctctcta ccttctctag   24900
atcggcgttc cggtccatgg ttagggcccg gtagttctac ttctgttcat gtttgtgtta   24960
gatccgtgtt tgtgttagat ccgtgctgct agcgttcgta cacggatgcg acctgtacgt   25020
cagacacgtt ctgattgcta acttgccagt gtttctcttt ggggaatcct gggatggctc   25080
tagccgttcc gcagacggga tcgatttcat gattttttt gtttcgttgc atagggtttg   25140
gtttgccctt ttcctttatt tcaatatatg ccgtgcactt gtttgtcggg tcatcttttc   25200
atgctttttt ttgtcttggt tgtgatgatg tggtctggtt gggcggtcgt tctagatcgg   25260
agtagaattc tgtttcaaac tacctggtgg atttattaat tttggatctg tatgtgtgtg   25320
ccatacatat tcatagttac gaattgaaga tgatggatgg aaatatcgat ctaggatagg   25380
tatacatgtt gatgcgggtt ttactgatgc atatacagag atgcttttg ttcgcttggt   25440 tgtgatgatg tggtgtggtt gggcggtcgt tcattcgttc tagatcggag tagaatactg   25500
tttcaaacta cctggtgtat ttattaattt tggaactgta tgtgtgtgtc atacatcttc   25560
atagttacga gtttaagatg gatggaaata tcgatctagg ataggtatac atgttgatgt   25620 gggtttact gatgcatata catgatggca tatgcagcat ctattcatat gctctaacct   25680
tgagtaccta tctattataa taaacaagta tgttttataa ttattttgat cttgatatac   25740
ttggatgatg gcatatgcag cagctatatg tggattttt tagccctgcc ttcatacgct   25800
atttatttgc ttggtactgt ttcttttgtc gatgctcacc ctgttgtttg gtgttacttc   25860
tgcaggtcga ctctagaatg agcccagaac gacgcccggc cgacatccgc cgtgccaccg   25920
aggcggacat gccggcggtc tgcaccatcg tcaaccacta catcgagaca agcacggtca   25980
acttccgtac cgagccgcag gaaccgcagg agtggacgga cgacctcgtc cgtctgcggg   26040
agcgctatcc ctggctcgtc gccgaggtgg acggcgaggc cgccggcatc gcctacgcgg   26100 gccctggaa ggcacgcaac gcctacgact ggacggccga gtcgaccgtg tacgtctccc   26160
cccgccacca gcggacggga ctgggctcca cgctctacac ccacctgctg aagtccctgg   26220
aggcacaggg cttcaagagc gtggtcgctg tcatcgggct gcccaacgac ccgagcgtgc   26280
gcatgcacga ggcgctcgga tatgccccc gcggcatgct gcgggcggcc ggcttcaagc   26340
acgggaactg gcatgacgtg ggtttctggc agctggactt cagcctgccg gtaccgcccc   26400
gtccggtcct gcccgtcacc gagatctgag atcgttcaaa catttggcaa taaagtttct   26460
taagattgaa tcctgttgcc ggtcttgcga tgattatcat ataatttctg ttgaattacg   26520
ttaagcatgt aataattaac atgtaatgca tgacgttatt tatgagatgg gttttatga    26580 ttagagtccc gcaattatac atttaatacg cgatagaaaa caaaatatag cgcgcaaact   26640
aggataaatt atcgcgcgcg gtgtcatcta tgttactaga tcggcgcgcc aagggcgaat   26700
```

```
tccagcacac tggcggccgt tactagtgga tcgagctcgc gatcgcggcc ggccaggcct   26760
tagttactaa tcagtgatca gattgtcgtt tcccgccttc agtttaaact atcagtgttt   26820
gaagcgttgt acgtgttcct atcgccagca gtcggccggc cgcacacacg tacgatccct   26880
gcgcctactt ccaacataac ggccacaagt tcgttggttc ctcgacatgc cagcgtgtca   26940
tgtcgttgga gcttcttggc tttcatcccg agcaccctac gccctctgtc tcacagtact   27000
agtcgttttg ggatgtgtta cggtaaccga ggttaataaa gcttaaagac ataaacaccc   27060
atacaaacga tgacagttgc gctgtactat tgatagctta tggtgtcaga accacatctt   27120
cagggaggga gagcccactg gcagccggcc acccctccac tttgactttc taccttattt   27180
tattcacttt ggaaaccacg atgcaactat gatgcgacgg atggactggc tgataggcct   27240
gtcagtgtga ctactgaggc tataacgtca agtaaaatga gacaaatttt gaactctaaa   27300
atgacatgta ttatgagaca aagagagtag agaggagttt ggctagctgg atacatacaa   27360
taggtagaga gggcgtgtgt tggctgcctt gtcattcttt gttttgcctg gctaggcaaa   27420
tcggttggta gctttgcttg ctcccctcgg tttctaaacg ttctaaggat ttttcttgcg   27480
ccaaaagtgg gccgaaacta ctcttccatg ctgacaactt tagcctgatc aggcaaggca   27540
aggttagcta gatgggcaaa acaaccaaac ttgccttgag attatttagg gcaatgcttg   27600
gttctggaaa aaaagccgc cctcacctta gccgacattg agcaaccatc gggtcagaag   27660
agccaatttg gctcacctac gatacgatgg cggttggttt cctagctagt ttgtcttacc   27720
ttgctatatt aggcaaggta atctttggca ggcttggtga gtagattttg ctctacgtct   27780
acaacaagat aaatcctgcc agcatatgtg gacctcgtga tagccttacc aacaatcacc   27840
gttgtacgtg ttcctatcgc cggtaccact agtattaatt aagtttaaac ggcgcgccaa   27900
gggcgaattc cagcacactg gcggccgtta ctagtggatc gagctcgtcg actctagact   27960
cgagggcgcg cctgacagga tatattggcg ggtaaac                             27997
```

```
<210> SEQ ID NO 26
<211> LENGTH: 18727
<212> TYPE: DNA
<213> ORGANISM: Artificial Sequence
<220> FEATURE:
<223> OTHER INFORMATION: HR template construction

<400> SEQUENCE: 26
cttagaataa cggatatta aaagggcgtg aaaaggttta tccgttcgtc catttgtatg      60
tgcatgccaa ccacagggtt cccctcggga tcaaagtact ttgatccaac ccctccgctg     120
ctatagtgca gtcggcttct gacgttcagt gcagccgtct tctgaaaacg acatgtcgca     180
caagtcctaa gttacgcgac aggctgccgc cctgcccttt tcctggcgtt ttcttgtcgc     240 gtgtttagt cgcataaagt agaatacttg cgactagaac cggagacatt acgccatgaa     300
caagagcgcc gccgctggcc tgctgggcta tgcccgcgtc agcaccgacg accaggactt     360
gaccaaccaa cgggccgaac tgcacgcggc cggctgcacc aagctgtttt ccgagaagat     420
caccggcacc aggcgcgacc gcccggagct ggccaggatg cttgaccacc tacgccctgg     480
cgacgttgtg acagtgacca ggctagaccg cctggcccgc agcacccgcg acctactgga     540
cattgccgag cgcatccagg aggccggcgc gggcctgcgt agcctggcag agccgtgggc     600
cgacaccacc acgccggccg gccgcatggt gttgaccgtg ttcgccggca ttgccgagtt     660
cgagcgttcc ctaatcatcg accgcacccg gagcgggcg gaggccgcca aggcccgagg     720
cgtgaagttt ggcccccgcc ctaccctcac cccggcacag atcgcgcacg cccgcgagct     780
```

-continued

```
gatcgaccag gaaggccgca ccgtgaaaga ggcggctgca ctgcttggcg tgcatcgctc      840
gaccctgtac cgcgcacttg agcgcagcga ggaagtgacg cccaccgagg ccaggcggcg      900
cggtgccttc cgtgaggacg cattgaccga ggccgacgcc ctggcggccg ccgagaatga      960
acgccaagag gaacaagcat gaaaccgcac caggacggcc aggacgaacc gtttttcatt     1020
accgaagaga tcgaggcgga gatgatcgcg gccgggtacg tgttcgagcc gcccgcgcac     1080
gtctcaaccg tgcggctgca tgaaatcctg gccggtttgt ctgatgccaa gctggcggcc     1140
tggccggcca gcttggccgc tgaagaaacc gagcgccgcc gtctaaaaag gtgatgtgta     1200
tttgagtaaa acagcttgcg tcatgcggtc gctgcgtata tgatgcgatg agtaaataaa     1260
caaatacgca aggggaacgc atgaaggtta tcgctgtact taaccagaaa ggcgggtcag     1320
gcaagacgac catcgcaacc catctagccc gcgccctgca actcgccggg gccgatgttc     1380
tgttagtcga ttccgatccc cagggcagtg cccgcgattg ggcggccgtg cgggaagatc     1440
aaccgctaac cgttgtcggc atcgaccgcc cgacgattga ccgcgacgtg aaggccatcg     1500
gccggcgcga cttcgtagtg atcgacggag cgccccaggc ggcggacttg gctgtgtccg     1560
cgatcaaggc agccgacttc gtgctgattc cggtgcagcc aagcccttac gacatatggg     1620
ccaccgccga cctggtggag ctggttaagc agcgcattga ggtcacggat ggaaggctac     1680
aagcggcctt tgtcgtgtcg cgggcgatca aaggcacgcg catcggcggt gaggttgccg     1740
aggcgctggc cgggtacgag ctgcccattc ttgagtcccg tatcacgcag cgcgtgagct     1800
acccaggcac tgccgccgcc ggcacaaccg ttcttgaatc agaacccgag ggcgacgctg     1860
cccgcgaggt ccaggcgctg gccgctgaaa ttaaatcaaa actcatttga gttaatgagg     1920
taaagagaaa atgagcaaaa gcacaaacac gctaagtgcc ggccgtccga gcgcacgcag     1980
cagcaaggct gcaacgttgg ccagcctggc agacacgcca gccatgaagc gggtcaactt     2040
tcagttgccg gcggaggatc acaccaagct gaagatgtac gcggtacgcc aaggcaagac     2100
cattaccgag ctgctatctg aatacatcgc gcagctacca gagtaaatga gcaaatgaat     2160
aaatgagtag atgaatttta gcggctaaag gaggcggcat ggaaaatcaa gaacaaccag     2220
gcaccgacgc cgtggaatgc cccatgtgtg gaggaacggg cggttggcca ggcgtaagcg     2280
gctgggttgt ctgccggccc tgcaatggca ctggaacccc caagcccgag gaatcggcgt     2340
gacggtcgca aaccatccgg cccggtacaa atcggcgcgg cgctgggtga tgacctggtg     2400
gagaagttga aggccgcgca ggccgcccag cggcaacgca tcgaggcaga agcacgcccc     2460
ggtgaatcgt ggcaagcggc cgctgatcga atccgcaaag aatcccggca accgccggca     2520
gccggtgcgc cgtcgattag gaagccgccc aagggcgacg agcaaccaga ttttttcgtt     2580
ccgatgctct atgacgtggg cacccgcgat agtcgcagca tcatggacgt ggccgttttc     2640
cgtctgtcga agcgtgaccg acgagctggc gaggtgatcc gctacgagct tccagacggg     2700
cacgtagagg tttccgcagg ccggccggc atggccagtg tgtgggatta cgacctggta     2760
ctgatggcgg tttcccatct aaccgaatcc atgaaccgat accgggaagg gaagggagac     2820
aagcccggcc gcgtgttccg tccacacgtt gcggacgtac tcaagttctg ccggcgagcc     2880
gatggcggaa agcagaaaga cgacctggta gaaacctgca ttcggttaaa caccacgcac     2940
gttgccatgc agcgtacgaa gaaggccaag aacggccgcc tggtgacggt atccgagggt     3000
gaagccttga ttagccgcta caagatcgta aagagcgaaa ccgggcggcc ggagtacatc     3060
gagatcgagc tagctgattg gatgtaccgc gagatcacag aaggcaagaa cccggacgtg     3120
```

-continued

```
ctgacggttc accccgatta cttttttgatc gatcccggca tcggccgttt tctctaccgc   3180
ctggcacgcc gcgccgcagg caaggcagaa gccagatggt tgttcaagac gatctacgaa   3240
cgcagtggca gcgccggaga gttcaagaag ttctgtttca ccgtgcgcaa gctgatcggg   3300
tcaaatgacc tgccggagta cgatttgaag gaggaggcgg ggcaggctgg cccgatccta   3360
gtcatgcgct accgcaacct gatcgagggc gaagcatccg ccggttccta atgtacggag   3420
cagatgctag ggcaaattgc cctagcaggg gaaaaaggtc gaaaaggtct ctttcctgtg   3480
gatagcacgt acattgggaa cccaaagccg tacattggga accggaaccc gtacattggg   3540
aacccaaagc cgtacattgg gaaccggtca cacatgtaag tgactgatat aaaagagaaa   3600
aaaggcgatt tttccgccta aaactcttta aaacttatta aaactcttaa aacccgcctg   3660
gcctgtgcat aactgtctgg ccagcgcaca gccgaagagc tgcaaaaagc gcctacccta   3720
cggtcgctgc gctccctacg ccccgccgct tcgcgtcggc ctatcgcggc cgctggccgc   3780
tcaaaaatgg ctggcctacg gccaggcaat ctaccagggc gcggacaagc cgcgccgtcg   3840
ccactcgacc gccggcgccc acatcaaggc accctgcctc gcgcgtttcg gtgatgacgg   3900
tgaaaacctc tgacacatgc agctcccgga cacggtcaca gcttgtctgt aagcggatgc   3960
cgggagcaga caagcccgtc agggcgcgtc agcgggtgtt ggcgggtgtc ggggcgcagc   4020
catgacccag tcacgtagcg atagcggagt gtatactggc ttaactatgc ggcatcagag   4080
cagattgtac tgagagtgca ccatatgcgg tgtgaaatac cgcacagatg cgtaaggaga   4140
aaataccgca tcaggcgctc ttccgcttcc tcgctcactg actcgctgcg ctcggtcgtt   4200
cggctgcggc gagcggtatc agctcactca aaggcggtaa tacggttatc cacagaatca   4260
ggggataacg caggaaagaa catgtgagca aaaggccagc aaaaggccag gaaccgtaaa   4320
aaggccgcgt tgctggcgtt tttccatagg ctccgccccc ctgacgagca tcacaaaaat   4380
cgacgctcaa gtcagaggtg gcgaaacccg acaggactat aaagatacca ggcgtttccc   4440
cctggaagct ccctcgtgcg ctctcctgtt ccgaccctgc cgcttaccgg atacctgtcc   4500
gcctttctcc cttcgggaag cgtggcgctt tctcatagct cacgctgtag gtatctcagt   4560
tcggtgtagg tcgttcgctc caagctgggc tgtgtgcacg aacccccccgt tcagcccgac   4620 cgctgcgcct tatccggtaa ctatcgtctt gagtccaacc cggtaagaca cgacttatcg   4680
ccactggcag cagccactgg taacaggatt agcagagcga ggtatgtagg cggtgctaca   4740
gagttcttga agtggtggcc taactacggc tacactagaa ggacagtatt tggtatctgc   4800
gctctgctga agccagttac cttcggaaaa agagttggta gctcttgatc cggcaaacaa   4860
accaccgctg gtagcggtgg tttttttgtt tgcaagcagc agattacgcg cagaaaaaaa   4920
ggatctcaag aagatccttt gatcttttct acggggtctg acgctcagtg gaacgaaaac   4980
tcacgttaag ggattttggt catgcattct aggtattatt tgccaacgac cttcgtgatc   5040
tcgcccttga catagtggac aaattcttcg agctggtcgg cccgggacgc gagacggtct   5100
tcttcttggc ccagataggc ttggcgcgct tcgaggatca cgggctggta ttgcgccgga   5160
aggcgctcca tcgcccagtc ggcggcgaca tccttcggcg cgatcttgcc ggtaaccgcc   5220
gagtaccaaa tccggctcag cgtaaggacc acattgcgct catcgcccgc ccaatccggc   5280
ggggagttcc acagggtcag cgtctcgttc agtgcttcga acagatcctg ttccggcacc   5340
gggtcgaaaa gttcctcggc cgcggggccg acgagggcca cgctatgctc ccgggccttg   5400
gtgagcagga tcgccagatc aatgtcgatg gtggccggtt caaagatacc cgccagaata   5460
tcattacgct gccattcgcc gaactggagt tcgcgtttgg ccggatagcg ccaggggatg   5520
```

-continued

```
atgtcatcgt gcaccacaat cgtcacctca accgcgcgca ggatttcgct ctcgccgggg    5580
gaggcggacg tttccagaag gtcgttgata agcgcgcggc gcgtggtctc gtcgagacgg    5640
acggtaacgg tgacaagcag gtcgatgtcc gaatggggct taaggccgcc gtcaacggcg    5700
ctaccataca gatgcacggc gaggagggtc ggttcgaggt ggcgctcgat gacacccacg    5760
acttccgaca gctgggtgga cacctcggcg atgaccgctt cacccattta ttatttcctt    5820
cctctttctt acagtattta aagataccccc aagaagctaa ttataacaag acgaactcca   5880
attcactgtt ccttgcattc taaaacctta ataccagaa aacagctttt tcaaagttgt     5940
tttcaaagtt ggcgtataac atagtatcga cggagccgat tttgaaaccg cggtgatcac    6000
aggcagcaac gctctgtcat cgttacaatc aacatgctac cctccgcgag atcatccgtg    6060
tttcaaaccc ggcagcttag ttgccgttct tccgaatagc atcggtaaca tgagcaaagt    6120
ctgccgcctt acaacggctc tcccgctgac gccgtcccgg actgatgggc tgcctgtatc    6180
gagtggtgat tttgtgccga gctgccggtc ggggagctgt tggctggctg gtggcaggat    6240
atattgtggt gtaaacaaat tgacgcttag acaacttaat aacacattgc ggacgttttt    6300
aatgtactga attagtactg ataaatggcg cgccaagctt tggcaaacag ctattatggg    6360
tattatgggt ggtaccacgc gtcggatccg atctagtaac atagatgaca ccgcgcgcga    6420
taatttatcc tagtttgcgc gctatatttt gttttctatc gcgtattaaa tgtataattg    6480
cgggactcta atcataaaaa cccatctcat aaataacgtc atgcattaca tgttaattat    6540
tacatgctta acgtaattca acagaaatta tatgataatc atcgcaagac cggcaacagg    6600
attcaatctt aagaaacttt attgccaaat gtttgaacga tccctaggac gatctcactt    6660
gtagagctcg tccatgccgt agaggaacag gtgatggcgg ccctcggacc tctcgtactg    6720
ctcaacaata gtgtaatcct cgttatggct agtaatatcc agcttagtat ccacgtagta    6780
gtagccaggg agctgaaccg gcttcttggc catgtagata gtcttgaact ccaccaggta    6840
atggccacca tccttcagct tgagagcctg atgaatctcg cccttcagaa cgccatccct    6900
agggtagagc ctctcagtgg aggcctccca ccccatggtc ttcttctgca tgacagggcc    6960
gtctggaggg aagttggtgc cgcgcatctt caccttgtag atgagggtgc catcttggag    7020
ggagctatcc tgagtcacag taaccaggcc accatcttca aagttcatga cgcgttccca    7080
cttgaagcct tctgggaagg agagcttctt gtaatcagga atatcagcag ggtgcttcac    7140
gtaggctttg gagccgtaca tgaactgagg ggagaggata tcccaggcga aagggagagg    7200
gccgccctta gtcactttga gcttagcagt ctgggtgcct tcataagggc ggccctcgcc    7260
ctcaccttca atctcgaact catggccgtt catggagccc tccatcctga ccttgaagcg    7320
catgaactct tgatcacggc catgttgtt gtcctcgctg gaggcggtgc cgctggagcc      7380
gctgccagtg gagccagtgc cgtggccgag aacaggtgg tgcctgccct cgctgcgctc      7440
gtactgctcc acgatggtgt agtcctcgtt gtgggaggtg atgtcgagct tggtgtcgac    7500
gtagtagtag cctggcagct gcacaggctt cttggccatg tagatggtct tgaactcgac    7560
caggtagtgg ccaccgtcct tgagcttcag ggcctggtgg atctcgccct tgagcacgcc    7620
gtccctgggg tacagcctct cagtgctagc ctcccagccc atggtcttct tctgcatgac    7680
cgggccatcg ggcgggaagt tagtgcccct catcttcacc ttgtagatga gggtgccatc    7740
ctggaggctg gagtcctgag tgacggtcac gaggccaccg tcctcgaagt tcatgacgcg    7800
ctcccacttg aagccctcgg ggaaggacag cttcttgtag tcggggatgt cggccgggtg    7860
```

-continued

```
cttcacgtag gccttgctgc cgtacatgaa ctgcggggag aggatgtccc aagcgaatgg   7920
cagcgggccg cccttagtga ccttgagctt ggcggtctgg gtgccctcgt aaggcctgcc   7980
ctcgccctcg ccctcgatct cgaactcgtg gccgttcatg ctgccctcca tcctcacctt   8040
gaagcgcatg aactccttga tcacttcctc gcccttggac accactacaa aaaagctccg   8100
cacgaggctg catttgtcac aaatcatgaa aagaaaaact accgatgaac aatgctgagg   8160
gattcaaatt ctacccacaa aaagaagaaa gaaagatcta gcacatctaa gcctgacgaa   8220
gcagcagaaa tatataaaaa tataaaccat agtgcccttt tcccctcttc ctgatcttgt   8280
ttagcacggc ggaaatttta aaccccccat catctccccc aacaacggcg gatcgcagat   8340
ctacatccga gagccccatt ccccgcgaga tccgggccgg atccacgccg gcgagagccc   8400
cagccgcgag atcccgcccc tcccgcgcac cgatctgggc gcgcacgaag ccgcctctcg   8460
cccacccaaa ctaccaaggc caaagatcga gaccgagacg gaaaaaaaa cggagaaaga   8520 aagaggagag gggcggggtg gttaccggcg cggcggagg cctcccttgg atcttatggt   8580
gtgttgtccc tgtgtgttct ccaatagtgt ggcttgagtg tgtggaagat ggttctagag   8640
gatctgctag agtcagcttg tcagcgtgtc ctctccaaat gaaatgaact tccttatata   8700
gaggaagggt cttgcgaagg atagtgggat tgtgcgtcat cccttacgtc agtggagata   8760
tcacatcaat ccacttgctt tgaagacgtg gttggaacgt cttctttttc cacgatgctc   8820
ctcgtgggtg ggggtccatc tttgggacca ctgtcggcag aggcatcttc aacgatggcc   8880
tttcctttat cgcaatgatg gcatttgtag gagccacctt ccttttccac tatcttcaca   8940
ataaagtgac agatagctgg gcaatggaat ccgaggaggt ttccggatat taccctttgt   9000
tgaaaagtct caatcggacc atcacatcaa tccacttgct ttgaagacgt ggttggaacg   9060
tcttcttttt ccacgatgct cctcgtgggt ggggtccat ctttgggacc actgtcggca   9120
gaggcatctt caacgatggc ctttccttta tcgcaatgat ggcatttgta ggagccacct   9180
tccttttcca ctatcttcac aataaagtga cagatagctg ggcaatggaa tccgaggagg   9240
tttccggata ttaccctttg ttgaaaagtc tcaatcggac cccctcagcc tgcacctcga   9300
ggggcgatag gaacacgtac aacggctgcc gtgtcatctg ctatgcgcgc gcgagcaact   9360
tgcagcctga cgctgaccct tcgggggacg tgatccatgc ccgtgtcgtc cgcgtccatc   9420
gggacgggag gccgaagtcg tcggacgctt gtgtaaataa agaaaacaaa catatgttgg   9480
acgcttcctc tgagtatttt attttaccta aaataaaaag ataaacaaca gaggaatcat   9540 tggagggggag gccccggtcg gcaaggcaaa gccaagtttg gtgctcctcg aatcgaatcg   9600
agtcgaatga ataagcatcg ccgtaaaatg gacggaccga cgagcccgcc cggacgcccg   9660
gggcctcagc ctcaggcctc agctacggcg ccgtgtcccg tgtgctccac gtagggacga   9720
aaacggtacg gatattttcc gaccgtattc gagatcgaat ctgtttagag gagtttttaat   9780 ctgttcatat ctgagttcag atatttaaca tccgataccg tattcgtatc caaatatttta   9840 aatcacatat ttatgatgtt gatatccaat cgtatcctat ccgtcatttt ttatactatc   9900
cgtattcgaa tccgaatctg gacataaata tgaaaacaaa tacaatatca ataatatccg   9960
tccgtatccg atccgttttc agccctagct ccacgtgtgt gtgacgtgcg cgctgtgtgt   10020
gtgtgtctgt tgtgctgcat cgtctttcga ttcgcctgct gttttgtgtt tcctgctccg   10080
gtggttatct agtatcggaa ttattgcgct ctcatttatc gcctccggtt ttctgatggc   10140
cgtcgccatc gttctcgcgt caccaaagac ggtcggtcac gtctcttgtc aaaaaaaaaa   10200
agacggtcac gtctctctca cctcggcttc ggtacgtaca ggaaactgga actggatggt   10260
```

-continued

```
gcatacagta ctctactgcg cataggatag gatggaaggc tgccctgccg gccgcgttca   10320
acaaattaag tactgatatc acattgcgga cgtctttaat gtactgaatt tagttactga   10380
tcactgatta agtactgata tcggtaccga attcgcggcc gcaagcttcg atcgatgcct   10440
gcagtgcagc gtgacccggt cgtgcccctc tctagagata atgagcattg catgtctaag   10500
ttataaaaaa ttaccacata ttttttttgt cacacttgtt tgaagtgcag tttatctatc   10560
tttatacata tatttaaact ttactctacg aataatataa tctatagtac tacaataata   10620
tcagtgtttt agagaatcat ataaatgaac agttagacat ggtctaaagg acaattgagt   10680
attttgacaa caggactcta cagttttatc tttttagtgt gcatgtgttc tccttttttt   10740
ttgcaaatag cttcacctat ataatacttc atccatttta ttagtacatc catttagggt   10800
ttagggttaa tggttttttat agactaattt ttttagtaca tctattttat tctattttag   10860
cctctaaatt aagaaaacta aaactctatt ttagtttttt tatttaataa tttagatata   10920
aaatagaata aaataaagtg actaaaaatt aaacaaatac cctttaagaa attaaaaaaa   10980
ctaaggaaac attttttcttg tttcgagtag ataatgccag cctgttaaac gccgtcgacg   11040
agtctaacgg acaccaacca gcgaaccagc agcgtcgcgt cgggccaagc gaagcagacg   11100
gcacggcatc tctgtcgctg cctctggacc cctctcgaga gttccgctcc accgttggac   11160
ttgctccgct gtcggcatcc agaaattgcg tggcggagcg gcagacgtga gccggcacgg   11220
caggcggcct cctcctcctc tcacggcacg gcagctacgg gggattcctt tcccaccgct   11280
ccttcgcttt cccttcctcg cccgccgtaa taaatagaca cccctccac accctctttc    11340 cccaacctcg tgttgttcgg agcgcacaca cacacaacca gatctcccc  aaatccaccc   11400 gtcggcacct ccgcttcaag gtacgccgct cgtcctcccc cccccccct  ctctaccttc   11460 tctagatcgg cgttccggtc catggttagg gcccggtagt tctacttctg ttcatgtttg   11520
tgttagatcc gtgtttgtgt tagatccgtg ctgctagcgt tcgtacacgg atgcgacctg   11580
tacgtcagac acgttctgat tgctaacttg ccagtgtttc tctttgggga atcctgggat   11640
ggctctagcc gttccgcaga cgggatcgat ttcatgattt ttttttgtttc gttgcatagg   11700 gtttggtttg cccttttcct ttatttcaat atatgccgtg cacttgtttg tcgggtcatc   11760
ttttcatgct tttttttgtc ttggttgtga tgatgtggtc tggttgggcg gtcgttctag   11820
atcggagtag aattctgttt caaactacct ggtggattta ttaattttgg atctgtatgt   11880
gtgtgccata catattcata gttacgaatt gaagatgatg gatggaaata tcgatctagg   11940
ataggtatac atgttgatgc gggtttttact gatgcatata cagagatgct ttttgttcgc   12000
ttggttgtga tgatgtggtg tggttgggcg gtcgttcatt cgttctagat cggagtagaa   12060
tactgtttca aactacctgg tgtatttatt aattttggaa ctgtatgtgt gtgtcataca   12120
tcttcatagt tacgagttta agatggatgg aaatatcgat ctaggatagg tatacatgtt   12180
gatgtgggtt ttactgatgc atatacatga tggcatatgc agcatctatt catatgctct   12240
aaccttgagt acctatctat tataataaac aagtatgttt tataattatt ttgatcttga   12300
tatacttgga tgatggcata tgcagcagct atatgtggat tttttttagcc ctgccttcat   12360 acgctattta tttgcttggt actgtttctt ttgtcgatgc tcaccctgtt gtttggtgtt   12420
acttctgcag gtcgactcta gaatggacaa caacccaaac atcaacgagt gcatcccata   12480
caactgcctg agcaacccag aggtggaggt gctgggtggc gagcgcatcg agaccggtta   12540
cacccccatc gacatctccc tgtccttgac ccagttcctg ctcagcgagt tcgtgccagg   12600
```

-continued

```
tgctggcttc gtgctcggcc tggtggacat catctggggt atcttcggtc catcccaatg   12660
ggacgccttc ctggtgcaaa tcgagcagct gatcaaccag aggatcgaag agttcgccag   12720
gaaccaggcc atctccaggc tggagggcct gagcaacctc taccaaatct acgccgagag   12780
cttcagggag tgggaggccg acccgaccaa cccagctctc cgcgaggaaa tgcgcattca   12840
attcaacgac atgaacagcg ccctgaccac cgctatccca ctgttcgccg tccagaacta   12900
ccaagtgccg ctcctgtccg tgtacgtgca agccgctaac ctgcacctca gcgtgctgcg   12960
cgacgtgagc gtgttcggcc aaaggtgggg cttcgatgct gccaccatca acagccgcta   13020
caacgacctg accaggctga ttggcaacta caccgaccac gctgtgcgct ggtacaacac   13080
cggcctggag cgcgtctggg gtccggactc cagggactgg atcaggtaca accagttcag   13140
gagggagttg accctcaccg tgctggacat tgtgtccctc ttcccgaact acgactccag   13200
gacctacccg atccgcaccg tgtcccaact caccagggag atctacacca acccagtgct   13260
ggagaacttc gacggtagct ccgcggttc cgcccagggt atcgagggct ccatcaggag   13320
cccacacctg atggacatcc tgaacagcat caccatctac accgacgctc acaggggcga   13380
gtactactgg tccggccacc agatcatggc ctccccagtg ggcttcagcg ccccgagtt   13440 caccttcccg ctctacggca ccatgggcaa cgccgctcca cagcaacgca tcgtggctca   13500
actgggtcag ggtgtctaca ggaccctgtc ctccaccctg tacaggaggc ccttcaacat   13560
cggtatcaac aaccagcaac tgtccgtgct cgacggcacc gagttcgcct acggcacctc   13620
ctccaacctg ccatccgctg tctacaggaa gagcggcacc gtggactccc tggacgagat   13680
cccaccacag aacaacaacg tgccacccag gcaaggcttc tcccacaggc tgagccacgt   13740
gtccatgttc cgctccggct tcagcaacag ctccgtgagc atcatcaggg ctccgatgtt   13800
ctcctggatc caccgcagcg ctgagttcaa caacatcatc gcctccgaca gcatcaccca   13860
aatcccggcc gtgaagggca acttcctctt caacggttcc gtcatttccg gcccaggctt   13920
caccggtggc gacctcgtga ggctcaacag cagcggcaac aacatccaga acaggggcta   13980
catcgaggtg ccaatccact tcccatccac ctccaccagg tacagggtgc gcgtgaggta   14040
cgcttccgtg accccgatcc acctcaacgt gaactggggt aactcctcca tcttctccaa   14100
caccgtgcca gctaccgcta cctccctgga caacctccaa tccagcgact tcggttactt   14160
cgagagcgcc aacgctttca cctcctccct cggtaacatc gtgggcgtga ggaacttcag   14220
cggcaccgcc ggcgtgatca tcgacaggtt cgagttcatc ccagtgaccg ccaccctcga   14280
ggctgagtga gatcgttcaa acatttggca ataaagtttc ttaagattga atcctgttgc   14340
cggtcttgcg atgattatca tataatttct gttgaattac gttaagcatg taataattaa   14400
catgtaatgc atgacgttat ttatgagatg ggtttttatg attagagtcc cgcaattata   14460
catttaatac gcgatagaaa acaaaatata gcgcgcaaac taggataaat tatcgcgcgc   14520
ggtgtcatct atgttactag atcggcgcgc caagggcgaa ttccagcaca ctggcggccg   14580
ttactagtgg atcacgcgta tgcctgcagt gcagcgtgac ccggtcgtgc ccctctctag   14640
agataatgag cattgcatgt ctaagttata aaaaattacc acatattttt tttgtcacac   14700
ttgtttgaag tgcagtttat ctatctttat acatatattt aaactttact ctacgaataa   14760
tataatctat agtactacaa taatatcagt gttttagaga atcatataaa tgaacagtta   14820
gacatggtct aaaggacaat tgagtatttt gacaacagga ctctacagtt ttatctttt   14880 agtgtgcatg tgttctcctt tttttttgca aatagcttca cctatataat acttcatcca   14940
ttttattagt acatccattt agggtttagg gttaatggtt tttatagact aattttttta   15000
```

-continued

```
gtacatctat tttattctat tttagcctct aaattaagaa aactaaaact ctattttagt    15060 tttttattt aataatttag atataaaata gaataaaata aagtgactaa aaattaaaca     15120
aatacccttt aagaaattaa aaaaactaag gaaacatttt tcttgtttcg agtagataat    15180
gccagcctgt taaacgccgt cgacgagtct aacggacacc aaccagcgaa ccagcagcgt    15240
cgcgtcgggc caagcgaagc agacggcacg gcatctctgt cgctgcctct ggacccctct    15300
cgagagttcc gctccaccgt tggacttgct ccgctgtcgg catccagaaa ttgcgtggcg    15360
gagcggcaga cgtgagccgg cacggcaggc ggcctcctcc tcctctcacg gcacggcagc    15420
tacgggggat tcctttccca ccgctccttc gctttccctt cctcgcccgc cgtaataaat    15480
agacaccccc tccacaccct ctttccccaa cctcgtgttg ttcggagcgc acacacacac    15540
aaccagatct cccccaaatc cacccgtcgg cacctccgct tcaaggtacg ccgctcgtcc    15600 tcccccccccc cccctctcta ccttctctag atcggcgttc cggtccatgg ttagggcccg    15660
gtagttctac ttctgttcat gtttgtgtta gatccgtgtt tgtgttagat ccgtgctgct    15720
agcgttcgta cacggatgcg acctgtacgt cagacacgtt ctgattgcta acttgccagt    15780
gtttctcttt ggggaatcct gggatggctc tagccgttcc gcagacggga tcgatttcat    15840 gattttttt gtttcgttgc atagggtttg gtttgccctt ttcctttatt tcaatatatg    15900
ccgtgcactt gtttgtcggg tcatcttttc atgctttttt ttgtcttggt tgtgatgatg    15960
tggtctggtt gggcggtcgt tctagatcgg agtagaattc tgtttcaaac tacctggtgg    16020
atttattaat tttggatctg tatgtgtgtg ccatacatat tcatagttac gaattgaaga    16080
tgatggatgg aaatatcgat ctaggatagg tatacatgtt gatgcgggtt ttactgatgc    16140
atatacagag atgcttttg ttcgcttggt tgtgatgatg tggtgtggtt gggcggtcgt    16200
tcattcgttc tagatcggag tagaatactg tttcaaacta cctggtgtat ttattaattt    16260
tggaactgta tgtgtgtgtc atacatcttc atagttacga gtttaagatg gatggaaata    16320
tcgatctagg ataggtatac atgttgatgt gggtttttact gatgcatata catgatggca    16380
tatgcagcat ctattcatat gctctaacct tgagtaccta tctattataa taaacaagta    16440
tgttttataa ttattttgat cttgatatac ttggatgatg gcatatgcag cagctatatg    16500
tggatttttt tagccctgcc ttcatacgct atttatttgc ttggtactgt ttcttttgtc    16560
gatgctcacc ctgttgtttg gtgttacttc tgcaggtcga ctctagaatg agcccagaac    16620
gacgcccggc cgacatccgc cgtgccaccg aggcggacat gccggcggtc tgcaccatcg    16680
tcaaccacta catcgagaca agcacggtca acttccgtac cgagccgcag gaaccgcagg    16740
agtggacgga cgacctcgtc cgtctgcggg agcgctatcc ctggctcgtc gccgaggtgg    16800
acggcgaggt cgccggcatc gcctacgcgg gccctggaa ggcacgcaac gcctacgact    16860
ggacggccga gtcgaccgtg tacgtctccc cccgccacca gcggacggga ctgggctcca    16920
cgctctacac ccacctgctg aagtccctgg aggcacaggg cttcaagagc gtggtcgctg    16980
tcatcgggct gcccaacgac ccgagcgtgc gcatgcacga ggcgctcgga tatgcccccc    17040
gcggcatgct gcgggcggcc ggcttcaagc acgggaactg gcatgacgtg ggtttctggc    17100
agctggactt cagcctgccg gtaccgcccc gtccggtcct gcccgtcacc gagatctgag    17160
atcgttcaaa catttggcaa taaagtttct taagattgaa tcctgttgcc ggtcttgcga    17220
tgattatcat ataatttctg ttgaattacg ttaagcatgt aataattaac atgtaatgca    17280
tgacgttatt tatgagatgg gttttttatga ttagagtccc gcaattatac atttaatacg    17340
```

```
cgatagaaaa caaaatatag cgcgcaaact aggataaatt atcgcgcgcg gtgtcatcta   17400
tgttactaga tcggcgcgcc aagggcgaat tccagcacac tggcggccgt tactagtgga   17460
tcgagctcgc gatcgcggcc ggccaggcct tagttactaa tcagtgatca gattgtcgtt   17520
tcccgccttc agtttaaact atcagtgttt gaagcgttgt acgtgttcct atcgccagca   17580
gtcggccggc cgcacacacg tacgatccct gcgcctactt ccaacataac ggccacaagt   17640
tcgttggttc ctcgacatgc cagcgtgtca tgtcgttgga gcttcttggc tttcatcccg   17700
agcaccctac gccctctgtc tcacagtact agtcgttttg ggatgtgtta cggtaaccga   17760
ggttaataaa gcttaaagac ataaacaccc atacaaacga tgacagttgc gctgtactat   17820
tgatagctta tggtgtcaga accacatctt cagggaggga gagcccactg gcagccggcc   17880 accccctccac tttgactttc taccttattt tattcacttt ggaaaccacg atgcaactat   17940
gatgcgacgg atggactggc tgataggcct gtcagtgtga ctactgaggc tataacgtca   18000
agtaaaatga gacaaatttt gaactctaaa atgacatgta ttatgagaca aagagagtag   18060
agaggagttt ggctagctgg atacatacaa taggtagaga gggcgtgtgt tggctgcctt   18120
gtcattcttt gttttgcctg gctaggcaaa tcggttggta gctttgcttg ctccctcgg    18180 tttctaaacg ttctaaggat ttttcttgcg ccaaaagtgg gccgaaacta ctcttccatg   18240
ctgacaactt tagcctgatc aggcaaggca aggttagcta gatgggcaaa acaaccaaac   18300
ttgccttgag attatttagg gcaatgcttg gttctgaaa aaaaagccgc cctcaccttia   18360 gccgacattg agcaaccatc gggtcagaag agccaatttg gctcacctac gatacgatgg   18420
cggttggttt cctagctagt ttgtcttacc ttgctatatt aggcaaggta atctttggca   18480
ggcttggtga gtagattttg ctctacgtct acaacaagat aaatcctgcc agcatatgtg   18540
gacctcgtga tagccttacc aacaatcacc gttgtacgtg ttcctatcgc cggtaccact   18600
agtattaatt aagtttaaac ggcgcgccaa gggcgaattc cagcacactg gcggccgtta   18660
ctagtggatc gagctcgtcg actctagact cgagggcgcg cctgacagga tatattggcg   18720
ggtaaac                                                               18727
```

<210> SEQ ID NO 27
<211> LENGTH: 18754
<212> TYPE: DNA
<213> ORGANISM: Artificial Sequence
<220> FEATURE:
<223> OTHER INFORMATION: Cas9/crRNA template construction

<400> SEQUENCE: 27

```
cttagaataa cggatatttta aaagggcgtg aaaaggttta tccgttcgtc catttgtatg     60
tgcatgccaa ccacagggtt cccctcggga tcaaagtact ttgatccaac ccctccgctg    120
ctatagtgca gtcggcttct gacgttcagt gcagccgtct tctgaaaacg acatgtcgca    180
caagtcctaa gttacgcgac aggctgccgc cctgcccttt tcctggcgtt ttcttgtcgc    240
gtgttttagt cgcataaagt agaatacttg cgactagaac cggagacatt acgccatgaa    300
caagagcgcc gccgctggcc tgctgggcta tgcccgcgtc agcaccgacg accaggactt    360
gaccaaccaa cgggccgaac tgcacgcggc cggctgcacc aagctgtttt ccgagaagat    420
caccggcacc aggcgcgacc gcccggagct ggccaggatg cttgaccacc tacgccctgg    480
cgacgttgtg acagtgacca ggctagaccg cctggcccgc agcacccgcg acctactgga    540
cattgccgag cgcatccagg aggccggcgc gggcctgcgt agcctggcag agccgtgggc    600
cgacaccacc acgccggccg gccgcatggt gttgaccgtg ttcgccggca ttgccgagtt    660
```

```
cgagcgttcc ctaatcatcg accgcacccg gagcgggcgc gaggccgcca aggcccgagg      720
cgtgaagttt ggcccccgcc ctaccctcac cccggcacag atcgcgcacg cccgcgagct      780
gatcgaccag gaaggccgca ccgtgaaaga ggcggctgca ctgcttggcg tgcatcgctc      840
gaccctgtac cgcgcacttg agcgcagcga ggaagtgacg cccaccgagg ccaggcggcg      900
cggtgccttc cgtgaggacg cattgaccga ggccgacgcc ctggcggccg ccgagaatga      960
acgccaagag gaacaagcat gaaaccgcac caggacggcc aggacgaacc gtttttcatt     1020
accgaagaga tcgaggcgga gatgatcgcg gccgggtacg tgttcgagcc gcccgcgcac     1080
gtctcaaccg tgcggctgca tgaaatcctg gccggtttgt ctgatgccaa gctggcggcc     1140
tggccggcca gcttggccgc tgaagaaacc gagcgccgcc gtctaaaaag gtgatgtgta     1200
tttgagtaaa acagcttgcg tcatgcggtc gctgcgtata tgatgcgatg agtaaataaa     1260
caaatacgca aggggaacgc atgaaggtta tcgctgtact taaccagaaa ggcgggtcag     1320
gcaagacgac catcgcaacc catctagccc gcgccctgca actcgccggg gccgatgttc     1380
tgttagtcga ttccgatccc cagggcagtg cccgcgattg ggcggccgtg cgggaagatc     1440
aaccgctaac cgttgtcggc atcgaccgcc cgacgattga ccgcgacgtg aaggccatcg     1500
gccggcgcga cttcgtagtg atcgacggag cgccccaggc ggcggacttg gctgtgtccg     1560
cgatcaaggc agccgacttc gtgctgattc cggtgcagcc aagcccttac gacatatggg     1620
ccaccgccga cctggtggag ctggttaagc agcgcattga ggtcacggat ggaaggctac     1680
aagcggcctt tgtcgtgtcg cgggcgatca aaggcacgcg catcggcggt gaggttgccg     1740
aggcgctggc cgggtacgag ctgcccattc ttgagtcccg tatcacgcag cgcgtgagct     1800
acccaggcac tgccgccgcc ggcacaaccg ttcttgaatc agaacccgag ggcgacgctg     1860
cccgcgaggt ccaggcgctg gccgctgaaa ttaaatcaaa actcatttga gttaatgagg     1920
taaagagaaa atgagcaaaa gcacaaacac gctaagtgcc ggccgtccga gcgcacgcag     1980
cagcaaggct gcaacgttgg ccagcctggc agacacgcca gccatgaagc gggtcaactt     2040
tcagttgccg gcggaggatc acaccaagct gaagatgtac gcggtacgcc aaggcaagac     2100
cattaccgag ctgctatctg aatacatcgc gcagctacca gagtaaatga gcaaatgaat     2160
aaatgagtag atgaatttta gcggctaaag gaggcggcat ggaaaatcaa gaacaaccag     2220
gcaccgacgc cgtggaatgc cccatgtgtg gaggaacggg cggttggcca ggcgtaagcg     2280
gctgggttgt ctgccggccc tgcaatggca ctggaacccc caagcccgag gaatcggcgt     2340
gacggtcgca aaccatccgg cccggtacaa atcggcgcgg cgctgggtga tgacctggtg     2400
gagaagttga aggccgcgca ggccgcccag cggcaacgca tcgaggcaga agcacgcccc     2460
ggtgaatcgt ggcaagcggc cgctgatcga atccgcaaag aatcccggca accgccggca     2520
gccggtgcgc cgtcgattag gaagccgccc aagggcgacg agcaaccaga ttttttcgtt     2580
ccgatgctct atgacgtggg cacccgcgat agtcgcagca tcatggacgt ggccgttttc     2640
cgtctgtcga agcgtgaccg acgagctggc gaggtgatcc gctacgagct tccagacggg     2700
cacgtagagg tttccgcagg gccggccggc atggccagtg tgtgggatta cgacctggta     2760
ctgatggcgg tttcccatct aaccgaatcc atgaaccgat accgggaagg gaagggagac     2820
aagcccggcc gcgtgttccg tccacacgtt gcggacgtac tcaagttctg ccggcgagcc     2880 gatgcggaa agcagaaaga cgacctggta gaaacctgca ttcggttaaa caccacgcac     2940
gttgccatgc agcgtacgaa gaaggccaag aacggccgcc tggtgacggt atccgagggt     3000
```

-continued

```
gaagccttga ttagccgcta caagatcgta aagagcgaaa ccgggcggcc ggagtacatc   3060
gagatcgagc tagctgattg gatgtaccgc gagatcacag aaggcaagaa cccggacgtg   3120
ctgacggttc accccgatta cttttttgatc gatcccggca tcggccgttt tctctaccgc   3180
ctggcacgcc gcgccgcagg caaggcagaa gccagatggt tgttcaagac gatctacgaa   3240
cgcagtggca gcgccggaga gttcaagaag ttctgtttca ccgtgcgcaa gctgatcggg   3300
tcaaatgacc tgccggagta cgatttgaag gaggaggcgg ggcaggctgg cccgatccta   3360
gtcatgcgct accgcaacct gatcgagggc gaagcatccg ccggttccta atgtacggag   3420
cagatgctag ggcaaattgc cctagcaggg gaaaaaggtc gaaaaggtct ctttcctgtg   3480
gatagcacgt acattgggaa cccaaagccg tacattggga accggaaccc gtacattggg   3540
aacccaaagc cgtacattgg gaaccggtca cacatgtaag tgactgatat aaaagagaaa   3600
aaaggcgatt tttccgccta aaactcttta aaacttatta aaactcttaa aacccgcctg   3660
gcctgtgcat aactgtctgg ccagcgcaca gccgaagagc tgcaaaaagc gcctacccttt  3720 cggtcgctgc gctccctacg ccccgccgct tcgcgtcggc ctatcgcggc cgctggccgc   3780
tcaaaaatgg ctggcctacg gccaggcaat ctaccagggc gcggacaagc gcgccgtcg    3840 ccactcgacc gccggcgccc acatcaaggc accctgcctc gcgcgtttcg gtgatgacgg   3900
tgaaaacctc tgacacatgc agctcccgga cacggtcaca gcttgtctgt aagcggatgc   3960
cgggagcaga caagcccgtc agggcgcgtc agcgggtgtt ggcgggtgtc ggggcgcagc   4020
catgacccag tcacgtagcg atagcggagt gtatactggc ttaactatgc ggcatcagag   4080
cagattgtac tgagagtgca ccatatgcgg tgtgaaatac cgcacagatg cgtaaggaga   4140
aaataccgca tcaggcgctc ttccgcttcc tcgctcactg actcgctgcg ctcggtcgtt   4200
cggctgcggc gagcggtatc agctcactca aaggcggtaa tacggttatc cacagaatca   4260
ggggataacg caggaaagaa catgtgagca aaaggccagc aaaaggccag gaaccgtaaa   4320
aaggccgcgt tgctggcgtt tttccatagg ctccgccccc ctgacgagca tcacaaaaat   4380
cgacgctcaa gtcagaggtg gcgaaacccg acaggactat aaagatacca ggcgtttccc   4440
cctggaagct ccctcgtgcg ctctcctgtt ccgaccctgc cgcttaccgg atacctgtcc   4500
gcctttctcc cttcgggaag cgtggcgctt tctcatagct cacgctgtag gtatctcagt   4560
tcggtgtagg tcgttcgctc caagctgggc tgtgtgcacg aacccccccgt tcagcccgac   4620 cgctgcgcct tatccggtaa ctatcgtctt gagtccaacc cggtaagaca cgacttatcg   4680
ccactggcag cagccactgg taacaggatt agcagagcga ggtatgtagg cggtgctaca   4740
gagttcttga agtggtggcc taactacggc tacactagaa ggacagtatt tggtatctgc   4800
gctctgctga agccagttac cttcggaaaa agagttggta gctcttgatc cggcaaacaa   4860
accaccgctg gtagcggtgg tttttttgtt tgcaagcagc agattacgcg cagaaaaaaa   4920
ggatctcaag aagatccttt gatcttttct acggggtctg acgctcagtg gaacgaaaac   4980
tcacgttaag ggattttggt catgcattct aggtattatt tgccaacgac cttcgtgatc   5040
tcgcccttga catagtggac aaattcttcg agctggtcgg cccgggacgc gagacggtct   5100
tcttcttggc ccagataggc ttggcgcgct tcgaggatca cgggctggta ttgcgccgga   5160
aggcgctcca tcgcccagtc ggcggcgaca tccttcggcg cgatcttgcc ggtaaccgcc   5220
gagtaccaaa tccggctcag cgtaaggacc acattgcgct catcgcccgc ccaatccggc   5280
ggggagttcc acagggtcag cgtctcgttc agtgcttcga acagatcctg ttccggcacc   5340
gggtcgaaaa gttcctcggc cgcggggccg acgagggcca cgctatgctc ccgggccttg   5400
```

-continued

```
gtgagcagga tcgccagatc aatgtcgatg gtggccggtt caaagatacc cgccagaata      5460
tcattacgct gccattcgcc gaactggagt tcgcgtttgg ccggatagcg ccaggggatg      5520
atgtcatcgt gcaccacaat cgtcacctca accgcgcgca ggatttcgct ctcgccgggg      5580
gaggcggacg tttccagaag gtcgttgata agcgcgcggc gcgtggtctc gtcgagacgg      5640
acggtaacgg tgacaagcag gtcgatgtcc gaatggggct taaggccgcc gtcaacggcg      5700
ctaccataca gatgcacggc gaggagggtc ggttcgaggt ggcgctcgat gacacccacg      5760
acttccgaca gctgggtgga cacctcggcg atgaccgctt cacccattta ttatttcctt      5820 cctctttct acagtattta aagataccc aagaagctaa ttataacaag acgaactcca      5880
attcactgtt ccttgcattc taaaaccta aataccagaa aacagctttt tcaaagttgt      5940
tttcaaagtt ggcgtataac atagtatcga cggagccgat tttgaaaccg cggtgatcac      6000
aggcagcaac gctctgtcat cgttacaatc aacatgctac cctccgcgag atcatccgtg      6060
tttcaaaccc ggcagcttag ttgccgttct tccgaatagc atcggtaaca tgagcaaagt      6120
ctgccgcctt acaacggctc tcccgctgac gccgtcccgg actgatgggc tgcctgtatc      6180
gagtggtgat tttgtgccga gctgccggtc ggggagctgt tggctggctg gtggcaggat      6240
atattgtggt gtaaacaaat tgacgcttag acaacttaat aacacattgc ggacgttttt      6300
aatgtactga attagtactg ataaatggcg cgccaagctt tggcaaacag ctattatggg      6360
tattatgggt ggtaccacgc gtcgatccac tagtaacggc cgccagtgtg ctggaattcg      6420
cccttggcgc gccgatctag taacatagat gacaccgcgc gcgataattt atcctagttt      6480
gcgcgctata ttttgttttc tatcgcgtat aaatgtata attgcgggac tctaatcata      6540
aaaacccatc tcataaataa cgtcatgcat tacatgttaa ttattacatg cttaacgtaa      6600
ttcaacagaa attatatgat aatcatcgca agaccggcaa caggattcaa tcttaagaaa      6660
ctttattgcc aaatgtttga acgatctcag aagaactcgt caagaaggcg atagaaggcg      6720
atgcgctgcg aatcgggagc ggcgataccg taaagcacga ggaagcggtc agcccattcg      6780
ccgccaagct cttcagcaat atcacgggta gccaacgcta tgtcctgata gcggtccgcc      6840
acacccagcc ggccacagtc gatgaatcca gaaaagcggc cattttccac catgatattc      6900
ggcaagcagg catcgccatg ggtcacgacg agatcctcgc cgtcgggcat gcgcgccttg      6960
agcctggcga acagttcggc tggcgcgagc ccctgatgct cttcgtccag atcatcctga      7020
tcgacaagac cggcttccat ccgagtacgt gctcgctcga tgcgatgttt cgcttggtgg      7080
tcgaatgggc aggtagccgg atcaagcgta tgcagccgcc gcattgcatc agccatgatg      7140
gatactttct cggcaggagc aaggtgagat gacaggagat cctgccccgg cacttcgccc      7200
aatagcagcc agtcccttcc cgcttcagtg acaacgtcga gcacagctgc gcaaggaacg      7260
cccgtcgtgg ccagccacga tagccgcgct gcctcgtcct gcagttcatt cagggcaccg      7320
gacaggtcgg tcttgacaaa aagaaccggg cgcccctgcg ctgacagccg gaacacggcg      7380
gcatcagagc agccgattgt ctgttgtgcc cagtcatagc cgaatagcct ctccacccaa      7440
gcggccggag aacctgcgtg caatccatct tgttcaatcc acatggtggt gtgacctgca      7500
gaagtaacac caaacaacag ggtgagcatc acaaaagaa acagtaccaa gcaaataaat      7560
agcgtatgaa ggcagggcta aaaaaatcca catatagctg ctgcatatgc catcatccaa      7620
gtatatcaag atcaaaataa ttataaaaca tacttgttta ttataataga taggtactca      7680
aggttagagc atatgaatag atgctgcata tgccatcatg tatatgcatc agtaaaaccc      7740
```

-continued

```
acatcaacat gtatacctat cctagatcga tatttccatc catcttaaac tcgtaactat   7800
gaagatgtat gacacacaca tacagttcca aaattaataa atacaccagg tagtttgaaa   7860
cagtattcta ctccgatcta gaacgaatga acgaccgccc aaccacacca catcatcaca   7920
accaagcgaa caaaaagcat ctctgtatat gcatcagtaa aacccgcatc aacatgtata   7980
cctatcctag atcgatattt ccatccatca tcttcaattc gtaactatga atatgtatgg   8040
cacacacata cagatccaaa attaataaat ccaccaggta gtttgaaaca gaattctact   8100
ccgatctaga acgaccgccc aaccagacca catcatcaca accaagacaa aaaaaagcat   8160
gaaaagatga cccgacaaac aagtgcacgg catatattga aataaaggaa aagggcaaac   8220
caaaccctat gcaacgaaac aaaaaaaatc atgaaatcga tcccgtctgc ggaacggcta   8280
gagccatccc aggattcccc aaagagaaac actggcaagt tagcaatcag aacgtgtctg   8340
acgtacaggt cgcatccgtg tacgaacgct agcagcacga atctaacaca aacacggatc   8400
taacacaaac atgaacagaa gtagaactac cgggccctaa ccatggaccg gaacgccgat   8460
ctagagaagg tagagagggg gggggggggga ggacgagcgg cgtaccttga agcggaggtg   8520
ccgacgggtg gatttggggg agatctggtt gtgtgtgtgt gcgctccgaa caacacgagg   8580
ttggggaaag agggtgtgga gggggtgtct atttattacg gcgggcgagg aagggaaagc   8640
gaaggagcgg tgggaaagga atcccccgta gctgccgtgc cgtgagagga ggaggaggcc   8700
gcctgccgtg ccggctcacg tctgccgctc cgccacgcaa tttctggatg ccgacagcgg   8760
agcaagtcca acggtggagc ggaactctcg agaggggtcc agaggcagcg acagagatgc   8820
cgtgccgtct gcttcgcttg ccccgacgcg acgctgctgg ttcgctggtt ggtgtccgtt   8880
agactcgtcg acggcgttta acaggctggc attatctact cgaaacaaga aaaatgtttc   8940
cttagttttt ttaatttctt aaagggtatt tgtttaattt ttagtcactt tattttattc   9000
tattttatat ctaaattatt aaataaaaaa actaaaatag agttttagtt ttcttaattt   9060
agaggctaaa atagaataaa atagatgtac taaaaaaatt agtctataaa aaccattaac   9120 cctaaacct aaatggatgt actaataaaa tggatgaagt attatatagg tgaagctatt   9180
tgcaaaaaaa aaggagaaca catgcacact aaaaagataa aactgtagag tcctgttgtc   9240
aaaatactca attgtccttt agaccatgtc taactgttca tttatatgat tctctaaaac   9300
actgatatta ttgtagtact atagattata ttattcgtag agtaaagttt aaatatatgt   9360
ataaagatag ataaactgca cttcaaacaa gtgtgacaaa aaaaatatgt ggtaattttt   9420
tataacttag acatgcaatg ctcattatct ctagagaggg gcacgaccgg gtcacgctgc   9480
actgcaggga tccgatctag taacatagat gacaccgcgc gcgataattt atcctagttt   9540
gcgcgctata ttttgttttc tatcgcgtat taaatgtata attgcgggac tctaatcata   9600
aaaacccatc tcataaataa cgtcatgcat tacatgttaa ttattacatg cttaacgtaa   9660
ttcaacagaa attatatgat aatcatcgca agaccggcaa caggattcaa tcttaagaaa   9720
ctttattgcc aaatgtttga acgatcccta ggacgatctc acttgtacag ctcgtccatg   9780
ccgtgggtga tgccagctgc ggtgacgaac tccagcagga ccatgtggtc gcgcttctcg   9840
ttggggtcct tgctcagagc ggactgggtg ctcaggtagt ggttgtcggg cagcagcacg   9900
ggaccgtcgc cgatgggcgt gttctgctgg tagtggtcgg cgagctggac gctgccgtcc   9960
tcgatgttgt ggcggatctt gaagttgacc ttgatgccgt tcttctgctt gtcagccatg   10020
atgtagacgt tgtggctgtt gtagttgtac tccagcttgt gccccaggat gttgccgtcc   10080
tccttgaagt cgatgccctt cagctcgatg cggttcacca gggtgtcgcc ctcgaacttc   10140
```

-continued

```
acctcggctc gggtcttgta gttgccgtcg tccttgaaga agatggtgcg ctcctggacg   10200
tagccttcgg gcatggcgga cttgaagaag tcgtgctgct tcatgtggtc ggggtagcgg   10260
ctgaagcact gcacgccgta ggtgaaggtg gtcacgaggg tgggccaggg cacgggcagc   10320
ttgccggtgg tgcagatgaa cttcagggtc agcttgccgt aggtggcgtc gccctcgccc   10380
tcgccgctga cgctgaactt gtggccgttc acgtcgccgt ccagctcgac caggatgggc   10440
accaccccag tgaacagctc ctcgcccttg ctcactacaa aaaagctccg cacgaggctg   10500
catttgtcac aaatcatgaa aagaaaaact accgatgaac aatgctgagg gattcaaatt   10560
ctacccacaa aaagaagaaa gaaagatcta gcacatctaa gcctgacgaa gcagcagaaa   10620
tatataaaaa tataaaccat agtgcccttt tccctcttc ctgatcttgt ttagcacggc   10680
ggaaatttta aaccccccat catctccccc aacaacggcg gatcgcagat ctacatccga   10740
gagccccatt ccccgcgaga tccgggccgg atccacgccg gcgagagccc cagccgcgag   10800
atcccgcccc tcccgcgcac cgatctgggc gcgcacgaag ccgcctctcg cccacccaaa   10860
ctaccaaggc caaagatcga gaccgagacg gaaaaaaaaa cggagaaaga aagaggagag   10920 gggcgggggtg gttaccggcg gcggcggagg cctcccttgg atcttatggt gtgttgtccc   10980
tgtgtgttct ccaatagtgt ggcttgagtg tgtggaagat ggttctagag gatctgctag   11040
agtcagcttg tcagcgtgtc ctctccaaat gaaatgaact tccttatata gaggaagggt   11100
cttgcgaagg atagtgggat tgtgcgtcat cccttacgtc agtggagata tcacatcaat   11160
ccacttgctt tgaagacgtg gttggaacgt cttcttttc cacgatgctc ctcgtgggtg   11220
ggggtccatc tttgggacca ctgtcggcag aggcatcttc aacgatggcc tttcctttat   11280
cgcaatgatg gcatttgtag gagccacctt ccttttccac tatcttcaca ataaagtgac   11340
agatagctgg gcaatggaat ccgaggaggt ttccggatat tacccttgt tgaaaagtct   11400 caatcggacc atcacatcaa tccacttgct ttgaagacgt ggttggaacg tcttcttttt   11460
ccacgatgct cctcgtgggt ggggggtccat ctttgggacc actgtcggca gaggcatctt   11520
caacgatggc ctttccttta tcgcaatgat ggcatttgta ggagccacct tccttttcca   11580
ctatcttcac aataaagtga cagatagctg ggcaatggaa tccgaggagg tttccggata   11640 ttacccttg ttgaaaagtc tcaatcggac ccctcagcc tgcagtgcag cgtgacccgg   11700
tcgtgcccct ctctagagat aatgagcatt gcatgtctaa gttataaaaa attaccacat   11760 atttttttg tcacacttgt ttgaagtgca gtttatctat ctttatacat atatttaaac   11820
tttactctac gaataatata atctatagta ctacaataat atcagtgttt tagagaatca   11880
tataaatgaa cagttagaca tggtctaaag gacaattgag tattttgaca acaggactct   11940
acagttttat cttttagtg tgcatgtgtt ctccttttt tttgcaaata gcttcaccta   12000
tataatactt catccatttt attagtacat ccatttaggg tttagggtta atggttttta   12060
tagactaatt tttttagtac atctatttta ttctatttta gcctctaaat taagaaaact   12120
aaaactctat tttagttttt ttatttaata atttagatat aaaatagaat aaaataaagt   12180
gactaaaaat taaacaaata ccctttaaga aattaaaaaa actaaggaaa cattttctt   12240 gtttcgagta gataatgcca gcctgttaaa cgccgtcgac gagtctaacg gacaccaacc   12300
agcgaaccag cagcgtcgcg tcgggccaag cgaagcagac ggcacggcat ctctgtcgct   12360
gcctctggac ccctctcgag agttccgctc caccgttgga cttgctccgc tgtcggcatc   12420
cagaaattgc gtggcggagc ggcagacgtg agccggcacg gcaggcggcc tcctcctcct   12480
```

-continued

```
ctcacggcac ggcagctacg ggggattcct ttcccaccgc tccttcgctt tcccttcctc   12540
gcccgccgta ataaatagac accccctcca caccctcttt ccccaacctc gtgttgttcg   12600
gagcgcacac acacacaacc agatctcccc caaatccacc cgtcggcacc tccgcttcaa   12660
ggtacgccgc tcgtcctccc cccccccccc tctctacctt ctctagatcg gcgttccggt   12720
ccatggttag ggcccggtag ttctacttct gttcatgttt gtgttagatc cgtgtttgtg   12780
ttagatccgt gctgctagcg ttcgtacacg gatgcgacct gtacgtcaga cacgttctga   12840
ttgctaactt gccagtgttt ctctttgggg aatcctggga tggctctagc cgttccgcag   12900
acgggatcga tttcatgatt tttttgtttt cgttgcatag ggtttggttt gccctttcc    12960 tttatttcaa tatatgccgt gcacttgttt gtcgggtcat cttttcatgc ttttttttgt   13020
cttggttgtg atgatgtggt ctggttgggc ggtcgttcta gatcggagta gaattctgtt   13080
tcaaactacc tggtggattt attaattttg gatctgtatg tgtgtgccat acatattcat   13140
agttacgaat tgaagatgat ggatggaaat atcgatctag gataggtata catgttgatg   13200 cgggtttttac tgatgcatat acagagatgc ttttgttcg cttggttgtg atgatgtggt   13260
gtggttgggc ggtcgttcat tcgttctaga tcggagtaga atactgtttc aaactacctg   13320
gtgtatttat taattttgga actgtatgtg tgtgtcatac atcttcatag ttacgagttt   13380
aagatggatg gaaatatcga tctaggatag gtatacatgt tgatgtgggt tttactgatg   13440
catatacatg atggcatatg cagcatctat tcatatgctc taaccttgag tacctatcta   13500
ttataataaa caagtatgtt ttataattat tttgatcttg atatacttgg atgatggcat   13560
atgcagcagc tatatgtgga tttttttagc cctgccttca tacgctattt atttgcttgg   13620
tactgtttct tttgtcgatg ctcaccctgt tgtttggtgt tacttctgca ggcgatcgcc   13680
acaccaccat gccgaagaag aagcgcaagg tcatggacaa gaagtactcc atcggcctgg   13740
acatcggcac caacagcgtg ggctgggccg tcatcaccga cgagtacaag gtgccctcca   13800
agaagttcaa ggtcctcggc aacaccgaca ggcacagcat caagaagaac ctgatcggcg   13860
ccctgctgtt cgactccggc gagactgcgg aggctaccag gctgaagcgc actgctcgca   13920
ggcgctacac caggcgcaag aaccgcatct gctacctcca ggagatttc tccaacgaga   13980 tggccaaggt ggacgactcc ttcttccacc gcctggagga gagcttcctg gtcgaggaag   14040
acaagaagca cgagcgccac cctatcttcg gcaacatcgt ggacgaggtc gcctaccacg   14100
agaagtaccc aaccatctac cacctccgca agaagctggt ggactccacc gacaaggccg   14160
acctgaggct catctacctg gccctcgccc acatgatcaa gttccgcggc cacttcctca   14220
tcgagggcga cctgaacccg gacaacagcg acgtggacaa gctcttcatc cagctggtcc   14280
agacctacaa ccagctgttc gaggagaacc ccatcaacgc ctccggcgtg gacgctaagg   14340
ctatcctcag cgctaggctg tccaagagca ggcgcctgga gaacctcatc gcccagctcc   14400
cgggcgagaa gaagaacggc ctcttcggca acctgatcgc tctgtccctc ggcctgaccc   14460
ccaacttcaa gagcaacttc gacctggccg aggacgccaa gctccagctg tccaaggaca   14520
cctacgacga cgacctcgac aacctgctcg cccagatcgg cgaccagtac gccgacctct   14580
tcctggccgc caagaacctc tccgacgcca tcctgctcag cgacatcctg agggtgaaca   14640
ccgagatcac caaggccccg ctgtccgcca gcatgatcaa gcgctacgac gagcaccacc   14700
aggacctcac tctcctgaag gccctcgtcc gccagcagct gcccgagaag tacaaggaga   14760
ttttcttcga ccagagcaag aacggctacg cgggctacat cgatggcggc gcctcccagg   14820
aagagttcta caagttcatc aagcctatcc tggagaagat ggacggcacc gaggagctgc   14880
```

-continued

```
tcgtgaagct gaaccgcgag gacctgctcc gcaagcagag gaccttcgac aacggcagca   14940
tccctcacca gatccacctg ggcgagctgc acgctatcct ccgccgccag gaagacttct   15000
acccattcct gaaggacaac cgcgagaaga tcgagaagat cctcaccttc cgcatcccgt   15060
actacgtggg ccccctggcc cgcggcaact ccaggttcgc ctggatgacc aggaagagcg   15120
aggagaccat cacccgtggg aacttcgagg aagtggtgga caagggcgcc tccgctcaga   15180
gcttcatcga gcgcatgacc aacttcgaca agaacctccc taacgagaag gtgctgccaa   15240
agcactccct gctctacgag tacttcaccg tctacaacga gctgaccaag gtgaagtatg   15300
tgaccgaggg catgaggaag cccgccttcc tcagcggcga gcagaagaag gccatcgtgg   15360
acctgctctt caagaccaac cgcaaggtga ccgtcaagca gctgaaggaa gactacttca   15420
agaagatcga gtgcttcgac tccgtggaga tcagcggcgt ggaggaccgc ttcaacgcct   15480
ccctcggcac ctaccacgac ctgctcaaga tcatcaagga caaggacttc ctcgacaacg   15540
aggagaacga ggacatcctg gaggacatcg tgctcaccct gaccctcttc gaggaccgcg   15600
agatgatcga ggagaggctc aagacctacg cccacctgtt cgacgacaag gtcatgaagc   15660
agctgaagag gcgcaggtac actggctggg gccgcctcag caggaagctg atcaacggca   15720
tcagggacaa gcagtccggc aagaccatcc tggacttcct caagagcgac ggcttcgcca   15780
accgcaactt catgcagctc atccacgacg actccctgac cttcaaggaa gacatccaga   15840
aggctcaggt gtccggccag ggcgacagcc tccacgagca catcgctaac ctggcgggca   15900
gccctgccat caagaagggc atcctccaga ccgtgaaggt ggtggacgag ctggtgaagg   15960
tcatgggccg ccacaagcca gagaacatcg tcatcgagat ggccagggag aaccagacca   16020
cccagaaggg tcagaagaac tcccgcgaga ggatgaagag gatcgaggaa ggcatcaagg   16080
agctgggcag ccagatcctg aaggagcacc cggtggagaa cacccagctc cagaacgaga   16140
agctgtacct ctactacctg cagaacggcc gcgacatgta tgtggaccag gagctggaca   16200
tcaacaggct gtccgactac gacgtggacc acatcgtccc tcagtccttc ctcaaggacg   16260
acagcatcga caacaaggtg ctgacccgca gcgacaagaa caggggcaag tccgacaacg   16320
tcccaagcga ggaagtggtc aagaagatga gaactactg gcgccagctg ctcaacgcca   16380
agctcatcac ccagcgcaag ttcgacaacc tgactaaggc ggagaggggc ggcctgtccg   16440
agctggacaa ggctggcttc atcaagcgcc agctcgtgga gaccaggcag atcaccaagc   16500
acgtcgccca gatcctggac agcaggatga acaccaagta cgacgagaac gacaagctca   16560
tccgcgaggt gaaggtcatc accctcaagt ccaagctggt gagcgacttc cgcaaggact   16620
tccagttcta caaggtcagg gagatcaaca ctaccacca cgcccacgat gcttacctca   16680
acgcggtggt gggcaccgcc ctcatcaaga gtaccctaa gctggagagc gagttcgtgt   16740
acggcgacta caaggtgtac gacgtccgca agatgatcgc caagtccgag caggagatcg   16800
gcaaggccac cgccaagtac ttcttctaca gcaacatcat gaacttcttc aagaccgaga   16860
tcaccctcgc caacggcgag atccgcaaga ggccactgat cgagaccaac ggcgagactg   16920
gcgagatcgt gtgggacaag ggcagggact tcgccaccgt gaggaaggtc ctgtccatgc   16980
ctcaggtgaa catcgtcaag aagaccgagg tccgaccgg cggcttctcc aaggagagca   17040
tcctcccaaa gcgcaacagc gacaagctga tcgccaggaa gaaggactgg gacccgaaga   17100
agtacggtgg cttcgactcc cctactgtgg cttacagcgt cctggtggtc gccaaggtgg   17160
agaagggcaa gtccaagaag ctgaagagcg tcaaggagct gctcggcatc accatcatgg   17220
```

```
agaggtccag cttcgagaag aacccgatcg acttcctgga ggccaagggc tacaaggaag   17280
tgaagaagga cctgatcatc aagctgccca agtacagcct gttcgagctg gagaacggcc   17340
gcaagaggat gctcgcctcc gctggcgagc tgcagaaggg caacgagctg gccctcccgt   17400
ccaagtatgt gaacttcctg tacctcgcct cccactacga gaagctgaag ggcagccccg   17460
aggacaacga gcagaagcag ctcttcgtcg agcagcacaa gcactacctg gacgagatca   17520
tcgagcagat cagcgagttc agcaagcgcg tgatcctcgc cgacgccaac ctcgacaagg   17580
tcctgtccgc ctacaacaag caccgcgaca agcctatcag ggagcaggcc gagaacatca   17640
tccacctgtt caccctcacc aacctgggcg ccccagctgc cttcaagtac ttcgacacca   17700
ccatcgaccg caagaggtac accagcacca aggaagtgct ggacgccacc ctgatccacc   17760
agtccatcac cggcctgtac gagactcgca tcgacctcag ccagctgggc ggcgacccga   17820
agaagaagcg caaagtctga gggaccctcg atcgacaagc tcgagtttct ccataataat   17880
gtgtgagtag ttcccagata agggaattag ggttcctata gggtttcgct catgtgttga   17940
gcatataaga aacccttagt atgtatttgt atttgtaaaa tacttctatc aataaaattt   18000
ctaattccta aaaccaaaat ccagtactaa aatccagatc ccccgaatta acctgcaggg   18060
gcggcaggga gagtttaac attgactagc gtgctgataa tttgtgagaa ataataattg   18120
acaagtagat actgacattt gagaagagct tctgaactgt tattagtaac aaaaatggaa   18180
agctgatgca cggaaaaagg aaagaaaaag ccatactttt ttttaggtag gaaaagaaaa   18240
agccatacga gactgatgtc tctcagatgg gccgggatct gtctatctag caggcagcag   18300
ccctaccaac ctcacgggcc agcaattacg agtccttcta aaacgtcccg ccgagggcgc   18360
gtggccgtgc tgtgcagcag cacgtctaac attagtccca cctcgccagt ttacagggag   18420
cagaaccagc ttataagcgg aggcgcggca ccaagaagca ggcgatagga acacgtacaa   18480
gttttagagc tagaaatagc aagttaaaat aaggctagtc cgttatcaac ttgaaaaagt   18540
ggcaccgagt cggtgctttt ttttcctcga ggggcgatag gaacacgtac aacgccgtt   18600 gtacgtgttc ctatcgccgg taccactagt attaattaag tttaaacggc gcgccaaggg   18660
cgaattccag cacactggcg gccgttacta gtggatcgag ctcgtcgact ctagactcga   18720
gggcgcgcct gacaggatat attggcgggt aaac                                18754
```

<210> SEQ ID NO 28
<211> LENGTH: 20
<212> TYPE: DNA
<213> ORGANISM: Artificial Sequence
<220> FEATURE:
<223> OTHER INFORMATION: Cas9 - crRNA

<400> SEQUENCE: 28

```
ggcgatagga acacgtacaa                                                  20
```

<210> SEQ ID NO 29
<211> LENGTH: 10712
<212> TYPE: DNA
<213> ORGANISM: Artificial Sequence
<220> FEATURE:
<223> OTHER INFORMATION: Complementary sequence of SEQ ID NO 22
      (reverse-complement)

<400> SEQUENCE: 29

```
atttggattt tttttactag gaacggttta gatttactat gataacattt agggtgcgct   60
tgggagcgtt ccatggagtg gattctcgaa gagaatcact ccccggctgc caaacggttt   120
```

-continued

```
tttcagagtg aagtgattct gtaaagtgat tctctgaaat gaactaagag gctgagagct     180
gaaaaaatag cttctcctga ttctgtgaag tgattctcca tagtgaattt taagagttta     240
tgctaaagaa tcaaagaaaa ctattttgag cttcagaatc acttcatcag agaatcaggg     300
agcacagttg aagaatcagg gagcacaact rtgccaaact aacccttaga ttctttatta     360
cgtgtaggaa caatttagcc ttactgatac aaaatataga agaggggcat gcacttgatt     420
gttggtaagg ctatcacgag gtccacatat gctggcagga tttatcttgt tgtagacgta     480
gagcaaaatc tactcaccaa gcctgccaaa gattaccttg cctaatatag caaggtaaga     540
caaactagct aggaaaccaa ccgccatcgt atcgtaggtg agccaaattg gctcttctga     600
cccgatggtt gctcaatgtc ggctaaggtg agggcggctt ttttttccag aaccaagcat     660
tgccctaaat aatctcaagg caagtttggt tgttttgccc atctagctaa ccttgccttg     720
cctgatcagg ctaaagttgt cagcatggaa gagtagtttc ggcccacttt tggcgcaaga     780
aaaatcctta gaacgtttag aaaccgaggg gagcaagcaa agctaccaac cgatttgcct     840
agccaggcaa aacaaagaat gacaaggcag ccaacacacg ccctctctac ctattgtatg     900
tatccagcta gccaaactcc tctctactct ctttgtctca taatacatgt cattttagag     960
ttcaaaattt gtctcatttt acttgacgtt atagcctcag tagtcacact gacaggccta    1020
tcagccagtc catccgtcgc atcatagttg catcgtggtt tccaaagtga ataaaataag    1080
gtagaaagtc aaagtggagg ggtggccggc tgccagtggg ctctccctcc ctgaagatgt    1140
ggttctgaca ccataagcta tcaatagtac agcgcaactg tcatcgtttg tatgggtgtt    1200
tatgtcttta agctttatta acctcggtta ccgtaacaca tcccaaaacg actagtactg    1260
tgagacagag ggcgtagggt gctcgggatg aaagccaaga agctccaacg acatgacacg    1320
ctggcatgtc gaggaaccaa cgaacttgtg gccgttatgt tggaagtagg cgcagggatc    1380
gtacgtgtgt gcggccggcc gactgctggc gataggaaca cgtacaacgg ttcaaacact    1440
gatagtttaa actgaaggcg ggaaacgaca atctgatcac tgattagtaa ctaaggcctg    1500
gccggccgcg atcgcgagct cgatccacta gtaacggccg ccagtgtgct ggaattcgcc    1560
cttggcgcgc cgatctagta acatagatga caccgcgcgc gataatttat cctagtttgc    1620
gcgctatatt ttgttttcta tcgcgtatta aatgtataat tgcgggactc taatcataaa    1680
aacccatctc ataaataacg tcatgcatta catgttaatt attacatgct taacgtaatt    1740
caacagaaat tatatgataa tcatcgcaag accggcaaca ggattcaatc ttaagaaact    1800
ttattgccaa atgtttgaac gatctcagat ctcggtgacg ggcaggaccg gacggggcgg    1860
taccggcagg ctgaagtcca gctgccagaa acccacgtca tgccagttcc cgtgcttgaa    1920
gccggccgcc cgcagcatgc cgcgggggggc atatccgagc gcctcgtgca tgcgcacgct    1980
cgggtcgttg ggcagcccga tgacagcgac cacgctcttg aagccctgtg cctccaggga    2040
cttcagcagg tgggtgtaga gcgtggagcc cagtcccgtc cgctggtggc gggggggagac    2100 gtacacggtc gactcggccg tccagtcgta ggcgttgcgt gccttccagg ggcccgcgta    2160
ggcgatgccg gcgacctcgc cgtccacctc ggcgacgagc cagggatagc gctcccgcag    2220
acggacgagg tcgtccgtcc actcctgcgg ttcctgcggc tcggtacgga agttgaccgt    2280
gcttgtctcg atgtagtggt tgacgatggt gcagaccgcc ggcatgtccg cctcggtggc    2340
acggcggatg tcggccgggc gtcgttctgg gctcattcta gagtcgacct gcagaagtaa    2400
caccaaacaa cagggtgagc atcgacaaaa gaaacagtac caagcaaata aatagcgtat    2460
gaaggcaggg ctaaaaaaat ccacatatag ctgctgcata tgccatcatc caagtatatc    2520
```

```
aagatcaaaa taattataaa acatacttgt ttattataat agataggtac tcaaggttag    2580
agcatatgaa tagatgctgc atatgccatc atgtatatgc atcagtaaaa cccacatcaa    2640
catgtatacc tatcctagat cgatatttcc atccatctta aactcgtaac tatgaagatg    2700
tatgacacac acatacagtt ccaaaattaa taaatacacc aggtagtttg aaacagtatt    2760
ctactccgat ctagaacgaa tgaacgaccg cccaaccaca ccacatcatc acaaccaagc    2820
gaacaaaaag catctctgta tatgcatcag taaaacccgc atcaacatgt atacctatcc    2880
tagatcgata tttccatcca tcatcttcaa ttcgtaacta tgaatatgta tggcacacac    2940
atacagatcc aaaattaata aatccaccag gtagtttgaa acagaattct actccgatct    3000
agaacgaccg cccaaccaga ccacatcatc acaaccaaga caaaaaaaag catgaaaaga    3060
tgacccgaca aacaagtgca cggcatatat tgaaataaag gaaaagggca aaccaaaccc    3120
tatgcaacga aacaaaaaaa atcatgaaat cgatcccgtc tgcggaacgg ctagagccat    3180
cccaggattc cccaaagaga aacactggca agttagcaat cagaacgtgt ctgacgtaca    3240
ggtcgcatcc gtgtacgaac gctagcagca cggatctaac acaaacacgg atctaacaca    3300
aacatgaaca gaagtagaac taccgggccc taaccatgga ccggaacgcc gatctagaga    3360
aggtagagag ggggggggg ggaggacgag cggcgtacct tgaagcggag gtgccgacgg    3420
gtggatttgg gggagatctg gttgtgtgtg tgtgcgctcc gaacaacacg aggttgggga    3480
aagagggtgt ggagggggtg tctatttatt acggcgggcg aggaagggaa agcgaaggag    3540
cggtgggaaa ggaatccccc gtagctgccg tgccgtgaga ggaggaggag gccgcctgcc    3600
gtgccggctc acgtctgccg ctccgccacg caatttctgg atgccgacag cggagcaagt    3660
ccaacggtgg agcggaactc tcgagagggg tccagaggca gcgacagaga tgccgtgccg    3720
tctgcttcgc ttggcccgac gcgacgctgc tggttcgctg gttggtgtcc gttagactcg    3780
tcgacggcgt ttaacaggct ggcattatct actcgaaaca agaaaaatgt ttccttagtt    3840
tttttaattt cttaaagggt atttgtttaa tttttagtca ctttattttta ttctatttta    3900 tatctaaatt attaaataaa aaaactaaaa tagagtttta gttttcttaa tttagaggct    3960
aaaatagaat aaaatagatg tactaaaaaa attagtctat aaaaaccatt aaccctaaac    4020
cctaaatgga tgtactaata aaatggatga agtattatat aggtgaagct atttgcaaaa    4080 aaaaggaga acacatgcac actaaaaaga taaaactgta gagtcctgtt gtcaaaatac    4140
tcaattgtcc tttagaccat gtctaactgt tcatttatat gattctctaa aacactgata    4200
ttattgtagt actatagatt atattattcg tagagtaaag tttaaatata tgtataaaga    4260
tagataaact gcacttcaaa caagtgtgac aaaaaaaata tgtggtaatt ttttataact    4320
tagacatgca atgctcatta tctctagaga ggggcacgac cgggtcacgc tgcactgcag    4380
gcatacgcgt gatccactag taacggccgc cagtgtgctg gaattcgccc ttggcgcgcc    4440
gatctagtaa catagatgac accgcgcgcg ataatttatc ctagtttgcg cgctatattt    4500
tgttttctat cgcgtattaa atgtataatt gcgggactct aatcataaaa acccatctca    4560
taaataacgt catgcattac atgttaatta ttacatgctt aacgtaattc aacagaaatt    4620
atatgataat catcgcaaga ccggcaacag gattcaatct taagaaactt tattgccaaa    4680
tgtttgaacg atctcactca gcctcgaggg tggcggtcac tgggatgaac tcgaacctgt    4740
cgatgatcac gccggcggtg ccgctgaagt tcctcacgcc cacgatgtta ccgagggagg    4800
aggtgaaagc gttggcgctc tcgaagtaac cgaagtcgct ggattggagg ttgtccaggg    4860
```

-continued

```
aggtagcggt agctggcacg gtgttggaga agatggagga gttaccccag ttcacgttga      4920
ggtggatcgg ggtcacggaa gcgtacctca cgcgcaccct gtacctggtg gaggtggatg      4980
ggaagtggat tggcacctcg atgtagcccc tgttctggat gttgttgccg ctgctgttga      5040
gcctcacgag gtcgccaccg gtgaagcctg ggccggaaat gacggaaccg ttgaagagga      5100
agttgccctt cacggccggg atttgggtga tgctgtcgga ggcgatgatg ttgttgaact      5160
cagcgctgcg gtggatccag gagaacatcg gagccctgat gatgctcacg gagctgttgc      5220
tgaagccgga gcggaacatg gacacgtggc tcagcctgtg ggagaagcct tgcctgggtg      5280
gcacgttgtt gttctgtggt gggatctcgt ccagggagtc cacggtgccg ctcttcctgt      5340
agacagcgga tggcaggttg gaggaggtgc cgtaggcgaa ctcggtgccg tcgagcacgg      5400
acagttgctg gttgttgata ccgatgttga agggcctcct gtacagggtg gaggacaggg      5460
tcctgtagac accctgaccc agttgagcca cgatgcgttg ctgtggagcg gcgttgccca      5520
tggtgccgta gagcgggaag gtgaactcgg ggccgctgaa gcccactggg gaggccatga      5580
tctggtggcc ggaccagtag tactcgcccc tgtgagcgtc ggtgtagatg gtgatgctgt      5640
tcaggatgtc catcaggtgt gggctcctga tggagccctc gataccctgg gcggaaccgc      5700
ggaagctacc gtcgaagttc tccagcactg ggttggtgta gatctccctg gtgagttggg      5760
acacggtgcg gatcgggtag gtcctggagt cgtagttcgg gaagagggac acaatgtcca      5820
gcacggtgag ggtcaactcc ctcctgaact ggttgtacct gatccagtcc ctggagtccg      5880
gaccccagac gcgctccagg ccggtgttgt accagcgcac agcgtggtcg gtgtagttgc      5940
caatcagcct ggtcaggtcg ttgtagcggc tgttgatggt ggcagcatcg aagccccacc      6000
tttggccgaa cacgctcacg tcgcgcagca cgctgaggtg caggttagcg gcttgcacgt      6060
acacggacag gagcggcact tggtagttct ggacggcgaa cagtgggata gcggtggtca      6120
gggcgctgtt catgtcgttg aattgaatgc gcatttcctc gcggagagct gggttggtcg      6180
ggtcggcctc ccactccctg aagctctcgg cgtagatttg gtagaggttg ctcaggccct      6240
ccagcctgga gatggcctgg ttcctggcga actcttcgat cctctggttg atcagctgct      6300
cgatttgcac caggaaggcg tcccattggg atggaccgaa gatacccag atgatgtcca       6360 ccaggccgag cacgaagcca gcacctggca cgaactcgct gagcaggaac tgggtcaagg      6420
acagggagat gtcgatgggg gtgtaaccgg tctcgatgcg ctcgccaccc agcacctcca      6480
cctctgggtt gctcaggcag ttgtatggga tgcactcgtt gatgtttggg ttgttgtcca      6540
ttctagagtc gacctgcaga agtaacacca aacaacaggg tgagcatcga caaaagaaac      6600
agtaccaagc aaataaatag cgtatgaagg cagggctaaa aaaatccaca tatagctgct      6660
gcatatgcca tcatccaagt atatcaagat caaaataatt ataaaacata cttgtttatt      6720
ataatagata ggtactcaag gttagagcat atgaatagat gctgcatatg ccatcatgta      6780
tatgcatcag taaaacccac atcaacatgt atacctatcc tagatcgata tttccatcca      6840
tcttaaactc gtaactatga agatgtatga cacacacata cagttccaaa attaataaat      6900
acaccaggta gtttgaaaca gtattctact ccgatctaga acgaatgaac gaccgcccaa      6960
ccacaccaca tcatcacaac caagcgaaca aaaagcatct ctgtatatgc atcagtaaaa      7020
cccgcatcaa catgtatacc tatcctagat cgatatttcc atccatcatc ttcaattcgt      7080
aactatgaat atgtatggca cacacataca gatccaaaat taataaatcc accaggtagt      7140
ttgaaacaga attctactcc gatctagaac gaccgcccaa ccagaccaca tcatcacaac      7200
caagacaaaa aaaagcatga aaagatgacc cgacaaacaa gtgcacggca tatattgaaa      7260
```

-continued

```
taaaggaaaa gggcaaacca aaccctatgc aacgaaacaa aaaaaatcat gaaatcgatc    7320
ccgtctgcgg aacggctaga gccatcccag gattccccaa agagaaacac tggcaagtta    7380
gcaatcagaa cgtgtctgac gtacaggtcg catccgtgta cgaacgctag cagcacggat    7440
ctaacacaaa cacggatcta acacaaacat gaacagaagt agaactaccg ggccctaacc    7500
atggaccgga acgccgatct agagaaggta gagagggggg gggggggagg acgagcggcg    7560
taccttgaag cggaggtgcc gacgggtgga tttgggggag atctggttgt gtgtgtgtgc    7620
gctccgaaca acacgaggtt ggggaaagag ggtgtggagg gggtgtctat ttattacggc    7680
gggcgaggaa gggaaagcga aggagcggtg ggaaaggaat cccccgtagc tgccgtgccg    7740
tgagaggagg aggaggccgc ctgccgtgcc ggctcacgtc tgccgctccg ccacgcaatt    7800
tctggatgcc gacagcggag caagtccaac ggtggagcgg aactctcgag aggggtccag    7860
aggcagcgac agagatgccg tgccgtctgc ttcgcttggc ccgacgcgac gctgctggtt    7920
cgctggttgg tgtccgttag actcgtcgac ggcgtttaac aggctggcat tatctactcg    7980
aaacaagaaa aatgtttcct tagttttttt aatttcttaa agggtatttg tttaattttt    8040
agtcacttta ttttattcta ttttatatct aaattattaa ataaaaaaac taaaatagag    8100
ttttagtttt cttaatttag aggctaaaat agaataaaat agatgtacta aaaaaattag    8160
tctataaaaa ccattaaccc taaaccctaa atggatgtac taataaaatg gatgaagtat    8220
tatataggtg aagctatttg caaaaaaaaa ggagaacaca tgcacactaa aaagataaaa    8280
ctgtagagtc ctgttgtcaa aatactcaat tgtcctttag accatgtcta actgttcatt    8340
tatatgattc tctaaaacac tgatattatt gtagtactat agattatatt attcgtagag    8400
taaagtttaa atatatgtat aaagatagat aaactgcact tcaaacaagt gtgacaaaaa    8460
aaatatgtgg taattttta taacttagac atgcaatgct cattatctct agagaggggc    8520
acgaccgggt cacgctgcac tgcaggcatc gatcgaagct tgcggccgcg aattcggtac    8580
cgatatcagt acttaatcag tgatcagtaa ctaaattcag tacattaaag acgtccgcaa    8640
tgtgatatca gtacttaatt tgttgaacgc ggccggcagg gcagccttcc atcctatcct    8700
atgcgcagta gagtactgta tgcaccatcc agttccagtt tcctgtacgt accgaagccg    8760
aggtgagaga gacgtgaccg tcttttttt tttgacaaga gacgtgaccg accgtctttg    8820
gtgacgcgag aacgatggcg acggccatca gaaaaccgga ggcgataaat gagagcgcaa    8880
taattccgat actagataac caccggagca ggaaacacaa aacagcaggc gaatcgaaag    8940
acgatgcagc acaacagaca cacacacaca gcgcgcacgt cacacacacg tggagctagg    9000
gctgaaaacg gatcggatac ggacggatat tattgatatt gtatttgttt tcatatttat    9060
gtccagattc ggattcgaat acggatagta taaaaaatga cggataggat acgattggat    9120
atcaacatca taaatatgtg atttaaatat ttggatacga atacggtatc ggatgttaaa    9180
tatctgaact cagatatgaa cagattaaaa ctcctctaaa cagattcgat ctcgaatacg    9240
gtcggaaaat atccgtaccg ttttcgtccc tacgtggagc acacgggaca cggcgccgta    9300
gctgaggcct gaggctgagg ccccgggcgt ccgggcgggc tcgtcggtcc gtccatttta    9360
cggcgatgct tattcattcg actcgattcg attcgaggag caccaaactt ggctttgcct    9420
tgccgaccgg ggcctcccct ccaatgattc ctctgttgtt tatctttta tttttaggtaa   9480 aataaaatac tcagaggaag cgtccaacat atgtttgttt tctttattta cacaagcgtc    9540
cgacgacttc ggcctcccgt cccgatggac gcggacgaca cgggcatgga tcacgtcccc    9600
```

-continued

```
cgaagggtca gcgtcaggct gcaagttgct cgcgcgcgca tagcagatga cacggcagcg     9660
cggcgtgacg acgggccgtc gtgatctcat ctcccctgcc cgtggggcca cggctacgaa     9720
gaagagtcca agcgcgcgcc cacaggacag gagttgcctg tttggcgaga caccacacgg     9780
gccggccccg cgccgcagcc cagccgcaat tcacggaaaa agacgccatc ggccgctgtt     9840
cgcttgagca agagctactt tttattccct tacaatatct tagcataagt taaatttcag     9900
cataaggcag tgttagtgac gatttcatgt cactgttttc aacatattta gattttgaaa     9960
acaataccga agagttttta tccacatgaa ctctctctac tcccataaaa ctcttatcat     10020
ccctctcttt attaatatag tgtcacgtca atataattaa tgtccataaa actctaatga     10080
aaccccattg agactggcct aagcaaaaaa cgtggcatgc atctgggtct gccctccat     10140 gttcaccaca ctgtcctttt tccagcttcc acgctgatcc ttcacacagc acgttcactg     10200
gcagcaaaga tactatacga aacaatagat ggtcggtgtt tcgacggctc gacctctgcc     10260
agcatcgatg cttaattcag cgtaaagtgt cgcgagatag aagaagatac tcctactcct     10320
cttctccaac tgtcagtttt aacgtcctcc ccgacgatag gaacgtatcg aaatatctcg     10380
ctaatcatag attcatagta tgtgcgcctc cattgagcac gtcgatggct tcgtagctgc     10440
acaagctggg tgctgcgctc tgcacactgc gttcgtatgc aattcggtaa tcaaaaaagg     10500
aaaaaaaaat cagtgcagga actgagcaca gcgtccttgc aacaagagca attgagtcgt     10560
aatgccagat aggtgaatgt gaatcttgtt ttactatcgt tcgtttcttt tacgtactat     10620
atagagtatc acaatgagtc ttgttaaact gcgtgagatt tacaagttgt gacatcccca     10680
actactaccg ccacccaaga acaaatgcaa gc                                   10712
```

<210> SEQ ID NO 30
<211> LENGTH: 2064
<212> TYPE: DNA
<213> ORGANISM: Artificial Sequence
<220> FEATURE:
<223> OTHER INFORMATION: Complementary sequence of SEQ ID NO 23
      (reverse-complement)

<400> SEQUENCE: 30

```
cagtacttaa tttgttgaac gcggccggca gggcagcctt ccatcctatc ctatgcgcag       60
tagagtactg tatgcaccat ccagttccag tttcctgtac gtaccgaagc cgaggtgaga      120
gagacgtgac cgtctttttt tttttgacaa gagacgtgac cgaccgtctt tggtgacgcg      180
agaacgatgg cgacggccat cagaaaaccg gaggcgataa atgagagcgc aataattccg      240
atactagata accaccggag caggaaacac aaaacagcag gcgaatcgaa agacgatgca      300
gcacaacaga cacacacaca cagcgcgcac gtcacacaca cgtggagcta gggctgaaaa      360
cggatcggat acgacggat attattgata ttgtatttgt tttcatattt atgtccagat      420
tcggattcga atacggatag tataaaaaat gacggatagg atacgattgg atatcaacat      480
cataaatatg tgatttaaat atttggatac gaatacggta tcggatgtta aatatctgaa      540
ctcagatatg aacagattaa aactcctcta aacagattcg atctcgaata cggtcggaaa      600
atatccgtac cgttttcgtc cctacgtgga gcacacggga cacggcgccg tagctgaggc      660
ctgaggctga ggccccgggc gtccgggcgg gctcgtcggt ccgtccattt tacggcgatg      720
cttattcatt cgactcgatt cgattcgagg agcaccaaac ttggctttgc cttgccgacc      780
ggggcctccc ctccaatgat tcctctgttg tttatctttt tattttaggt aaaataaaat      840
actcagagga agcgtccaac atatgtttgt tttctttatt tacacaagcg tccgacgact      900
```

```
tcggcctccc gtcccgatgg acgcggacga cacgggcatg gatcacgtcc cccgaagggt    960
cagcgtcagg ctgcaagttg ctcgcgcgcg catagcagat gacacggcag cgcggcgtga   1020
cgacgggccg tcgtgatctc atctcccctg cccgtggggc cacggctacg aagaagagtc   1080
caagcgcgcg cccacaggac aggagttgcc tgtttggcga gacaccacac gggccggccc   1140
cgcgccgcag cccagccgca attcacggaa aaagacgcca tcggccgctg ttcgcttgag   1200
caagagctac tttttattcc cttacaatat cttagcataa gttaaatttc agcataaggc   1260
agtgttagtg acgatttcat gtcactgttt tcaacatatt tagattttga aaacaatacc   1320
gaagagtttt tatccacatg aactctctct actcccataa aactcttatc atccctctct   1380
ttattaatat agtgtcacgt caatataatt aatgtccata aaactctaat gaaaccccat   1440
tgagactggc ctaagcaaaa aacgtggcat gcatctgggt ctgcccctcc atgttcacca   1500
cactgtcctt tttccagctt ccacgctgat ccttcacaca gcacgttcac tggcagcaaa   1560
gatactatac gaaacaatag atggtcggtg tttcgacggc tcgacctctg ccagcatcga   1620
tgcttaattc agcgtaaagt gtcgcgagat agaagaagat actcctactc ctcttctcca   1680
actgtcagtt ttaacgtcct ccccgacgat aggaacgtat cgaaatatct cgctaatcat   1740
agattcatag tatgtgcgcc tccattgagc acgtcgatgg cttcgtagct gcacaagctg   1800
ggtgctgcgc tctgcacact gcgttcgtat gcaattcggt aatcaaaaaa ggaaaaaaaa   1860
atcagtgcag gaactgagca cagcgtcctt gcaacaagag caattgagtc gtaatgccag   1920
ataggtgaat gtgaatcttg ttttactatc gttcgtttct tttacgtact atatagagta   1980
tcacaatgag tcttgttaaa ctgcgtgaga tttacaagtt gtgacatccc caactactac   2040
cgccacccaa gaacaaatgc aagc                                          2064
```

<210> SEQ ID NO 31
<211> LENGTH: 1436
<212> TYPE: DNA
<213> ORGANISM: Artificial Sequence
<220> FEATURE:
<223> OTHER INFORMATION: Complementary sequence of SEQ ID NO 24
      (reverse-complement)

<400> SEQUENCE: 31

```
atttggattt tttttactag gaacggttta gatttactat gataacattt agggtgcgct     60
tgggagcgtt ccatggagtg gattctcgaa gagaatcact ccccggctgc caaacggttt    120
tttcagagtg aagtgattct gtaaagtgat tctctgaaat gaactaagag gctgagagct    180
gaaaaaatag cttctcctga ttctgtgaag tgattctcca tagtgaattt taagagttta    240
tgctaaagaa tcaaagaaaa ctattttgag cttcagaatc acttcatcag agaatcaggg    300
agcacagttg aagaatcagg gagcacaact rtgccaaact aacccttaga ttctttatta    360
cgtgtaggaa caatttagcc ttactgatac aaaatataga agaggggcat gcacttgatt    420
gttggtaagg ctatcacgag gtccacatat gctggcagga tttatcttgt tgtagacgta    480
gagcaaaatc tactcaccaa gcctgccaaa gattaccttg cctaatatag caaggtaaga    540
caaactagct aggaaaccaa ccgccatcgt atcgtaggtg agccaaattg gctcttctga    600 cccgatggt gctcaatgtc ggctaaggtg agggcggctt ttttttccag aaccaagcat     660
tgccctaaat aatctcaagg caagtttggt tgttttgccc atctagctaa ccttgccttg    720
cctgatcagg ctaaagttgt cagcatggaa gagtagtttc ggcccacttt tggcgcaaga    780
aaaatcctta gaacgtttag aaaccgaggg gagcaagcaa agctaccaac cgatttgcct    840
```

```
agccaggcaa aacaaagaat gacaaggcag ccaacacacg ccctctctac ctattgtatg    900
tatccagcta gccaaactcc tctctactct ctttgtctca taatacatgt cattttagag    960
ttcaaaattt gtctcatttt acttgacgtt atagcctcag tagtcacact gacaggccta   1020
tcagccagtc catccgtcgc atcatagttg catcgtggtt tccaaagtga ataaaataag   1080
gtagaaagtc aaagtggagg ggtggccggc tgccagtggg ctctccctcc ctgaagatgt   1140
ggttctgaca ccataagcta tcaatagtac agcgcaactg tcatcgtttg tatgggtgtt   1200
tatgtcttta agctttatta acctcggtta ccgtaacaca tcccaaaacg actagtactg   1260
tgagacagag ggcgtagggt gctcgggatg aaagccaaga agctccaacg acatgacacg   1320
ctggcatgtc gaggaaccaa cgaacttgtg gccgttatgt tggaagtagg cgcagggatc   1380
gtacgtgtgt gcggccggcc gactgctggc gataggaaca cgtacaacgg ttcaaa       1436
```

```
<210> SEQ ID NO 32
<211> LENGTH: 26
<212> TYPE: DNA
<213> ORGANISM: Artificial Sequence
<220> FEATURE:
<223> OTHER INFORMATION: Complemmentary sequence of SEQ ID NO 18
      (reverse-complement)

<400> SEQUENCE: 32
cgcaatgtga tatcagtact taattt                                            26
```

```
<210> SEQ ID NO 33
<211> LENGTH: 26
<212> TYPE: DNA
<213> ORGANISM: Artificial Sequence
<220> FEATURE:
<223> OTHER INFORMATION: Complementary sequence of SEQ ID NO 19
      (reverse-complement)

<400> SEQUENCE: 33
acaacggttc aaacactgat agttta                                            26
```

```
<210> SEQ ID NO 34
<211> LENGTH: 615
<212> TYPE: PRT
<213> ORGANISM: Artificial Sequence
<220> FEATURE:
<223> OTHER INFORMATION: Truncate cry1Ac protein (B. thurigiensis)

<400> SEQUENCE: 34

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
            115                 120                 125
```

-continued

```
Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
                180                 185                 190

Tyr Asn Asp Leu Thr Arg Leu Ile Gly Asn Tyr Thr Asp His Ala Val
                195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
                260                 265                 270

Leu Glu Asn Phe Asp Gly Ser Phe Arg Gly Ser Ala Gln Gly Ile Glu
                275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
                340                 345                 350

Gln Leu Gly Gln Gly Val Tyr Arg Thr Leu Ser Ser Thr Leu Tyr Arg
                355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
                420                 425                 430

Val Ser Met Phe Arg Ser Gly Phe Ser Asn Ser Ser Val Ser Ile Ile
    435                 440                 445

Arg Ala Pro Met Phe Ser Trp Ile His Arg Ser Ala Glu Phe Asn Asn
    450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
                500                 505                 510

Tyr Ile Glu Val Pro Ile His Phe Pro Ser Thr Ser Thr Arg Tyr Arg
                515                 520                 525

Val Arg Val Arg Tyr Ala Ser Val Thr Pro Ile His Leu Asn Val Asn
    530                 535                 540
```

-continued

```
Trp Gly Asn Ser Ser Ile Phe Ser Asn Thr Val Pro Ala Thr Ala Thr
545             550             555             560

Ser Leu Asp Asn Leu Gln Ser Ser Asp Phe Gly Tyr Phe Glu Ser Ala
            565             570             575

Asn Ala Phe Thr Ser Ser Leu Gly Asn Ile Val Gly Val Arg Asn Phe
                580             585             590

Ser Gly Thr Ala Gly Val Ile Ile Asp Arg Phe Glu Phe Ile Pro Val
        595             600             605

Thr Ala Thr Leu Glu Ala Glu
    610             615

<210> SEQ ID NO 35
<211> LENGTH: 183
<212> TYPE: PRT
<213> ORGANISM: Artificial Sequence
<220> FEATURE:
<223> OTHER INFORMATION: Pat protein (Streptomyces hygroscopicus)

<400> SEQUENCE: 35

Met Ser Pro Glu Arg Arg Pro Ala Asp Ile Arg Arg Ala Thr Glu Ala
1               5               10              15

Asp Met Pro Ala Val Cys Thr Ile Val Asn His Tyr Ile Glu Thr Ser
            20              25              30

Thr Val Asn Phe Arg Thr Glu Pro Gln Glu Pro Gln Glu Trp Thr Asp
        35              40              45

Asp Leu Val Arg Leu Arg Glu Arg Tyr Pro Trp Leu Val Ala Glu Val
    50              55              60

Asp Gly Glu Val Ala Gly Ile Ala Tyr Ala Gly Pro Trp Lys Ala Arg
65              70              75              80

Asn Ala Tyr Asp Trp Thr Ala Glu Ser Thr Val Tyr Val Ser Pro Arg
            85              90              95

His Gln Arg Thr Gly Leu Gly Ser Thr Leu Tyr Thr His Leu Leu Lys
            100             105             110

Ser Leu Glu Ala Gln Gly Phe Lys Ser Val Val Ala Val Ile Gly Leu
        115             120             125

Pro Asn Asp Pro Ser Val Arg Met His Glu Ala Leu Gly Tyr Ala Pro
    130             135             140

Arg Gly Met Leu Arg Ala Ala Gly Phe Lys His Gly Asn Trp His Asp
145             150             155             160

Val Gly Phe Trp Gln Leu Asp Phe Ser Leu Pro Val Pro Pro Arg Pro
            165             170             175

Val Leu Pro Val Thr Glu Ile
            180

<210> SEQ ID NO 36
<211> LENGTH: 7212
<212> TYPE: DNA
<213> ORGANISM: Artificial Sequence
<220> FEATURE:
<223> OTHER INFORMATION: Complementary sequence of SEQ ID NO 02
      (reverse-complement)

<400> SEQUENCE: 36
cactgatagt ttaaactgaa ggcgggaaac gacaatctga tcactgatta gtaactaagg      60
cctggccggc cgcgatcgcg agctcgatcc actagtaacg gccgccagtg tgctggaatt     120
cgcccttggc gcgccgatct agtaacatag atgacaccgc gcgcgataat ttatcctagt     180
ttgcgcgcta tattttgttt tctatcgcgt attaaatgta taattgcggg actctaatca     240
```

```
taaaaaccca tctcataaat aacgtcatgc attacatgtt aattattaca tgcttaacgt     300
aattcaacag aaattatatg ataatcatcg caagaccggc aacaggattc aatcttaaga     360
aactttattg ccaaatgttt gaacgatctc agatctcggt gacgggcagg accggacggg     420
gcggtaccgg caggctgaag tccagctgcc agaaacccac gtcatgccag ttcccgtgct     480
tgaagccggc cgcccgcagc atgccgcggg gggcatatcc gagcgcctcg tgcatgcgca     540
cgctcgggtc gttgggcagc ccgatgacag cgaccacgct cttgaagccc tgtgcctcca     600
gggacttcag caggtgggtg tagagcgtgg agcccagtcc cgtccgctgg tggcgggggg     660
agacgtacac ggtcgactcg gccgtccagt cgtaggcgtt gcgtgccttc caggggcccg     720
cgtaggcgat gccggcgacc tcgccgtcca cctcggcgac gagccaggga tagcgctccc     780
gcagacggac gaggtcgtcc gtccactcct gcggttcctg cggctcggta cggaagttga     840
ccgtgcttgt ctcgatgtag tggttgacga tggtgcagac cgccggcatg tccgcctcgg     900
tggcacggcg gatgtcggcc gggcgtcgtt ctgggctcat tctagagtcg acctgcagaa     960
gtaacaccaa acaacagggt gagcatcgac aaaagaaaca gtaccaagca aataaatagc    1020
gtatgaaggc agggctaaaa aaatccacat atagctgctg catatgccat catccaagta    1080
tatcaagatc aaaataatta taaaacatac ttgtttatta taatagatag gtactcaagg    1140
ttagagcata tgaatagatg ctgcatatgc catcatgtat atgcatcagt aaaacccaca    1200
tcaacatgta tacctatcct agatcgatat ttccatccat cttaaactcg taactatgaa    1260
gatgtatgac acacacatac agttccaaaa ttaataaata caccaggtag tttgaaacag    1320
tattctactc cgatctagaa cgaatgaacg accgcccaac cacaccacat catcacaacc    1380
aagcgaacaa aaagcatctc tgtatatgca tcagtaaaac ccgcatcaac atgtatacct    1440
atcctagatc gatatttcca tccatcatct tcaattcgta actatgaata tgtatggcac    1500
acacatacag atccaaaatt aataaatcca ccaggtagtt tgaaacagaa ttctactccg    1560
atctagaacg accgcccaac cagaccacat catcacaacc aagacaaaaa aaagcatgaa    1620
aagatgaccc gacaaacaag tgcacggcat atattgaaat aaaggaaaag ggcaaaccaa    1680
accctatgca acgaaacaaa aaaaatcatg aaatcgatcc cgtctgcgga acggctagag    1740
ccatcccagg attccccaaa gagaaacact ggcaagttag caatcagaac gtgtctgacg    1800
tacaggtcgc atccgtgtac gaacgctagc agcacggatc taacacaaac acggatctaa    1860
cacaaacatg aacagaagta gaactaccgg gccctaacca tggaccggaa cgccgatcta    1920
gagaaggtag agagggggg ggggggagga cgagcggcgt accttgaagc ggaggtgccg    1980
acgggtggat ttgggggaga tctggttgtg tgtgtgtgcg ctccgaacaa cacgaggttg    2040
gggaaagagg gtgtggaggg ggtgtctatt tattacggcg ggcgaggaag ggaaagcgaa    2100
ggagcggtgg gaaaggaatc ccccgtagct gccgtgccgt gagaggagga ggaggccgcc    2160
tgccgtgccg gctcacgtct gccgctccgc cacgcaattt ctggatgccg acagcggagc    2220
aagtccaacg gtggagcgga actctcgaga ggggtccaga ggcagcgaca gagatgccgt    2280
gccgtctgct tcgcttggcc cgacgcgacg ctgctggttc gctggttggt gtccgttaga    2340
ctcgtcgacg gcgtttaaca ggctggcatt atctactcga aacaagaaaa atgtttcctt    2400
agttttttta atttcttaaa gggtatttgt ttaattttta gtcactttat tttattctat    2460
tttatatcta aattattaaa taaaaaaact aaaatagagt tttagttttc ttaatttaga    2520
ggctaaaata gaataaaata gatgtactaa aaaaattagt ctataaaaac cattaaccct    2580
```

-continued

```
aaaccctaaa tggatgtact aataaaatgg atgaagtatt atataggtga agctatttgc      2640
aaaaaaaaag gagaacacat gcacactaaa aagataaaac tgtagagtcc tgttgtcaaa      2700
atactcaatt gtcctttaga ccatgtctaa ctgttcattt atatgattct ctaaaacact      2760
gatattattg tagtactata gattatatta ttcgtagagt aaagtttaaa tatatgtata      2820
aagatagata aactgcactt caaacaagtg tgacaaaaaa aatatgtggt aattttttat      2880
aacttagaca tgcaatgctc attatctcta gagaggggca cgaccgggtc acgctgcact      2940
gcaggcatac gcgtgatcca ctagtaacgg ccgccagtgt gctggaattc gcccttggcg      3000
cgccgatcta gtaacataga tgacaccgcg cgcgataatt tatcctagtt tgcgcgctat      3060
attttgtttt ctatcgcgta ttaaatgtat aattgcggga ctctaatcat aaaaacccat      3120
ctcataaata acgtcatgca ttacatgtta attattacat gcttaacgta attcaacaga      3180
aattatatga taatcatcgc aagaccggca acaggattca atcttaagaa actttattgc      3240
caaatgtttg aacgatctca ctcagcctcg agggtggcgg tcactgggat gaactcgaac      3300
ctgtcgatga tcacgccggc ggtgccgctg aagttcctca cgcccacgat gttaccgagg      3360
gaggaggtga aagcgttggc gctctcgaag taaccgaagt cgctggattg gaggttgtcc      3420
agggaggtag cggtagctgg cacggtgttg gagaagatag aggagttacc ccagttcacg      3480
ttgaggtgga tcggggtcac ggaagcgtac ctcacgcgca ccctgtacct ggtggaggtg      3540
gatgggaagt ggattggcac ctcgatgtag cccctgttct ggatgttgtt gccgctgctg      3600
ttgagcctca cgaggtcgcc accggtgaag cctgggccgg aaatgacgga accgttgaag      3660
aggaagttgc ccttcacggc cgggatttgg gtgatgctgt cggaggcgat gatgttgttg      3720
aactcagcgc tgcggtggat ccaggagaac atcggagccc tgatgatgct cacggagctg      3780
ttgctgaagc cggagcggaa catggacacg tggctcagcc tgtgggagaa gccttgcctg      3840
ggtggcacgt tgttgttctg tggtgggatc tcgtccaggg agtccacggt gccgctcttc      3900
ctgtagacag cggatggcag gttggaggag gtgccgtagg cgaactcggt gccgtcgagc      3960
acggacagtt gctggttgtt gataccgatg ttgaagggcc tcctgtacag ggtggaggac      4020
agggtcctgt agacaccctg acccagttga gccacgatgc gttgctgtgg agcggcgttg      4080
cccatggtgc cgtagagcgg gaaggtgaac tcggggccgc tgaagcccac tggggaggcc      4140
atgatctggt ggccggacca gtagtactcg cccctgtgag cgtcggtgta gatggtgatg      4200
ctgttcagga tgtccatcag gtgtgggctc ctgatggagc cctcgatacc ctgggcggaa      4260
ccgcggaagc taccgtcgaa gttctccagc actgggttgg tgtagatctc cctggtgagt      4320
tgggacacgg tgcggatcgg gtaggtcctg gagtcgtagt tcgggaagag ggacacaatg      4380
tccagcacgg tgagggtcaa ctccctcctg aactggttgt acctgatcca gtccctggag      4440
tccggacccc agacgcgctc caggccggtg ttgtaccagc gcacagcgtg gtcggtgtag      4500
ttgccaatca gcctggtcag gtcgttgtag cggctgttga tggtggcagc atcgaagccc      4560
cacctttggc cgaacacgct cacgtcgcgc agcacgctga ggtgcaggtt agcggcttgc      4620
acgtacacgg acaggagcgg cacttggtag ttctggacgg cgaacagtgg gatagcggtg      4680
gtcagggcgc tgttcatgtc gttgaattga atgcgcattt cctcgcggag agctgggttg      4740
gtcgggtcgg cctcccactc cctgaagctc tcggcgtaga tttggtagag gttgctcagg      4800
ccctccagcc tggagatggc ctggttcctg gcgaactctt cgatcctctg gttgatcagc      4860
tgctcgattt gcaccaggaa ggcgtcccat tgggatggac cgaagatacc ccagatgatg      4920
tccaccaggc cgagcacgaa gccagcacct ggcacgaact cgctgagcag gaactgggtc      4980
```

-continued

```
aaggacaggg agatgtcgat gggggtgtaa ccggtctcga tgcgctcgcc acccagcacc      5040
tccacctctg ggttgctcag gcagttgtat gggatgcact cgttgatgtt tgggttgttg      5100
tccattctag agtcgacctg cagaagtaac accaaacaac agggtgagca tcgacaaaag      5160
aaacagtacc aagcaaataa atagcgtatg aaggcagggc taaaaaaatc cacatatagc      5220
tgctgcatat gccatcatcc aagtatatca agatcaaaat aattataaaa catacttgtt      5280
tattataata gataggtact caaggttaga gcatatgaat agatgctgca tatgccatca      5340
tgtatatgca tcagtaaaac ccacatcaac atgtatacct atcctagatc gatatttcca      5400
tccatcttaa actcgtaact atgaagatgt atgacacaca catacagttc caaaattaat      5460
aaatacacca ggtagtttga aacagtattc tactccgatc tagaacgaat gaacgaccgc      5520
ccaaccacac cacatcatca caaccaagcg aacaaaaagc atctctgtat atgcatcagt      5580
aaaacccgca tcaacatgta tacctatcct agatcgatat ttccatccat catcttcaat      5640
tcgtaactat gaatatgtat ggcacacaca tacagatcca aaattaataa atccaccagg      5700
tagtttgaaa cagaattcta ctccgatcta gaacgaccgc ccaaccagac cacatcatca      5760
caaccaagac aaaaaaaagc atgaaaagat gacccgacaa acaagtgcac ggcatatatt      5820
gaaataaagg aaaagggcaa accaaaccct atgcaacgaa acaaaaaaaa tcatgaaatc      5880
gatcccgtct gcggaacggc tagagccatc ccaggattcc ccaaagagaa acactggcaa      5940
gttagcaatc agaacgtgtc tgacgtacag gtcgcatccg tgtacgaacg ctagcagcac      6000
ggatctaaca caaacacgga tctaacacaa acatgaacag aagtagaact accgggccct      6060
aaccatggac cggaacgccg atctagagaa ggtagagagg ggggggggg gaggacgagc      6120 ggcgtacctt gaagcggagg tgccgacggg tggatttggg ggagatctgg ttgtgtgtgt      6180
gtgcgctccg aacaacacga ggttggggaa agagggtgtg gaggggggtgt ctatttatta      6240 cggcgggcga ggaagggaaa gcgaaggagc ggtgggaaag gaatcccccg tagctgccgt      6300
gccgtgagag gaggaggagg ccgcctgccg tgccggctca cgtctgccgc tccgccacgc      6360
aatttctgga tgccgacagc ggagcaagtc caacggtgga gcggaactct cgagaggggt      6420
ccagaggcag cgacagagat gccgtgccgt ctgcttcgct tggcccgacg cgacgctgct      6480
ggttcgctgg ttggtgtccg ttagactcgt cgacggcgtt taacaggctg gcattatcta      6540
ctcgaaacaa gaaaaatgtt tccttagttt ttttaatttc ttaaagggta tttgtttaat      6600
ttttagtcac tttattttat tctattttat atctaaatta ttaaataaaa aaactaaaat      6660 agagtttttag ttttcttaat ttagaggcta aaatagaata aaatagatgt actaaaaaaa      6720
ttagtctata aaaaccatta accctaaacc ctaaatggat gtactaataa aatggatgaa      6780
gtattatata ggtgaagcta tttgcaaaaa aaaggagaa cacatgcaca ctaaaaagat      6840
aaaactgtag agtcctgttg tcaaaatact caattgtcct ttagaccatg tctaactgtt      6900
catttatatg attctctaaa acactgatat tattgtagta ctatagatta tattattcgt      6960
agagtaaagt ttaaatatat gtataaagat agataaactg cacttcaaac aagtgtgaca      7020
aaaaaaatat gtggtaattt tttataactt agacatgcaa tgctcattat ctctagagag      7080
gggcacgacc gggtcacgct gcactgcagg catcgatcga agcttgcggc cgcgaattcg      7140
gtaccgatat cagtacttaa tcagtgatca gtaactaaat tcagtacatt aaagacgtcc      7200
gcaatgtgat at                                                          7212
```

<210> SEQ ID NO 37

```
<211> LENGTH: 7418
<212> TYPE: DNA
<213> ORGANISM: Artificial Sequence
<220> FEATURE:
<223> OTHER INFORMATION: Complementary sequence of SEQ ID NO 05
      (reverse-complement)

<400> SEQUENCE: 37
gaaccaacga acttgtggcc gttatgttgg aagtaggcgc agggatcgta cgtgtgtgcg        60
gccggccgac tgctggcgat aggaacacgt acaacggttc aaacactgat agtttaaact       120
gaaggcggga aacgacaatc tgatcactga ttagtaacta aggcctggcc ggccgcgatc       180
gcgagctcga tccactagta acggccgcca gtgtgctgga attcgccctt ggcgcgccga       240
tctagtaaca tagatgacac cgcgcgcgat aatttatcct agtttgcgcg ctatattttg       300
ttttctatcg cgtattaaat gtataattgc gggactctaa tcataaaaac ccatctcata       360
aataacgtca tgcattacat gttaattatt acatgcttaa cgtaattcaa cagaaattat       420
atgataatca tcgcaagacc ggcaacagga ttcaatctta agaaacttta ttgccaaatg       480
tttgaacgat ctcagatctc ggtgacgggc aggaccggac ggggcggtac cggcaggctg       540
aagtccagct gccagaaacc cacgtcatgc cagttcccgt gcttgaagcc ggccgccgc        600 agcatgccgc gggggcata tccgagcgcc tcgtgcatgc gcacgctcgg gtcgttgggc        660
agcccgatga cagcgaccac gctcttgaag ccctgtgcct ccaggactt cagcaggtgg        720 gtgtagagcg tggagcccag tcccgtccgc tggtggcggg gggagacgta cacggtcgac       780
tcggccgtcc agtcgtaggc gttgcgtgcc ttccaggggc ccgcgtaggc gatgccggcg       840
acctcgccgt ccacctcggc gacgagccag ggatagcgct cccgcagacg gacgaggtcg       900
tccgtccact cctgcggttc ctgcggctcg gtacggaagt tgaccgtgct tgtctcgatg       960
tagtggttga cgatggtgca gaccgccggc atgtccgcct cggtggcacg gcggatgtcg      1020
gccgggcgtc gttctgggct cattctagag tcgacctgca gaagtaacac caaacaacag      1080
ggtgagcatc gacaaaagaa acagtaccaa gcaaataaat agcgtatgaa ggcagggcta      1140
aaaaaatcca catatagctg ctgcatatgc catcatccaa gtatatcaag atcaaaataa      1200
ttataaaaca tacttgttta ttataataga taggtactca aggttagagc atatgaatag      1260
atgctgcata tgccatcatg tatatgcatc agtaaaaccc acatcaacat gtatacctat      1320
cctagatcga tatttccatc catcttaaac tcgtaactat gaagatgtat gacacacaca      1380
tacagttcca aaattaataa atacaccagg tagtttgaaa cagtattcta ctccgatcta      1440
gaacgaatga acgaccgccc aaccacacca catcatcaca accaagcgaa caaaaagcat      1500
ctctgtatat gcatcagtaa aacccgcatc aacatgtata cctatcctag atcgatattt      1560
ccatccatca tcttcaattc gtaactatga atatgtatgg cacacacata cagatccaaa      1620
attaataaat ccaccaggta gtttgaaaca gaattctact ccgatctaga acgaccgccc      1680
aaccagacca catcatcaca accaagacaa aaaaaagcat gaaaagatga cccgacaaac      1740
aagtgcacgg catatattga aataaaggaa aagggcaaac caaaccctat gcaacgaaac      1800
aaaaaaaatc atgaaatcga tcccgtctgc ggaacggcta gagccatccc aggattcccc      1860
aaagagaaac actggcaagt tagcaatcag aacgtgtctg acgtacaggt cgcatccgtg      1920
tacgaacgct agcagcacgg atctaacaca aacacggatc taacacaaac atgaacagaa      1980
gtagaactac cggccctaa ccatggaccg gaacgccgat ctagagaagg tagagagggg      2040 gggggggggga ggacgagcgg cgtaccttga agcggaggtg ccgacgggtg gatttggggg      2100
```

-continued

```
agatctggtt gtgtgtgtgt gcgctccgaa caacacgagg ttggggaaag agggtgtgga    2160 ggggggtgtct atttattacg gcgggcgagg aagggaaagc gaaggagcgg tgggaaagga    2220 atccccgta gctgccgtgc cgtgagagga ggaggaggcc gcctgccgtg ccggctcacg    2280
tctgccgctc cgccacgcaa tttctggatg ccgacagcgg agcaagtcca acggtggagc    2340
ggaactctcg agaggggtcc agaggcagcg acagagatgc cgtgccgtct gcttcgcttg    2400
gcccgacgcg acgctgctgg ttcgctggtt ggtgtccgtt agactcgtcg acggcgttta    2460
acaggctggc attatctact cgaaacaaga aaaatgtttc cttagttttt ttaatttctt    2520
aaagggtatt tgtttaattt ttagtcactt tattttattc tatttttatat ctaaattatt    2580 aaataaaaaa actaaaatag agttttagtt ttcttaattt agaggctaaa atagaataaa    2640
atagatgtac taaaaaaatt agtctataaa aaccattaac cctaaacccct aaatggatgt    2700 actaataaaa tggatgaagt attatatagg tgaagctatt tgcaaaaaaa aaggagaaca    2760
catgcacact aaaaagataa aactgtagag tcctgttgtc aaaatactca attgtccttt    2820
agaccatgtc taactgttca tttatatgat tctctaaaac actgatatta ttgtagtact    2880
atagattata ttattcgtag agtaaagttt aaatatatgt ataaagatag ataaactgca    2940
cttcaaacaa gtgtgacaaa aaaaatatgt ggtaattttt tataacttag acatgcaatg    3000
ctcattatct ctagagaggg gcacgaccgg gtcacgctgc actgcaggca tacgcgtgat    3060
ccactagtaa cggccgccag tgtgctggaa ttcgcccttg gcgcgccgat ctagtaacat    3120
agatgacacc gcgcgcgata atttatccta gtttgcgcgc tatattttgt tttctatcgc    3180
gtattaaatg tataattgcg ggactctaat cataaaaacc catctcataa ataacgtcat    3240
gcattacatg ttaattatta catgcttaac gtaattcaac agaaattata tgataatcat    3300
cgcaagaccg gcaacaggat tcaatcttaa gaaactttat tgccaaatgt ttgaacgatc    3360
tcactcagcc tcgagggtgg cggtcactgg gatgaactcg aacctgtcga tgatcacgcc    3420
ggcggtgccg ctgaagttcc tcacgcccac gatgttaccg agggaggagg tgaaagcgtt    3480
ggcgctctcg aagtaaccga agtcgctgga ttggaggttg tccagggagg tagcggtagc    3540
tggcacggtt ttggagaaga tggaggagtt accccagttc acgttgaggt ggatcggggt    3600
cacggaagcg tacctcacgc gcaccctgta cctggtggag gtggatggga agtggattgg    3660
cacctcgatg tagcccctgt tctggatgtt gttgccgctg ctgttgagcc tcacgaggtc    3720
gccaccggtg aagcctgggc cggaaatgac ggaaccgttg aagaggaagt gcccttcac    3780 ggccgggatt tgggtgatgc tgtcggaggc gatgatgttg ttgaactcag cgctgcggtg    3840
gatccaggag aacatcggag ccctgatgat gctcacggag ctgttgctga agccggagcg    3900
gaacatggac acgtggctca gcctgtggga gaagccttgc ctgggtggca cgttgttgtt    3960
ctgtggtggg atctcgtcca gggagtccac ggtgccgctc ttcctgtaga cagcggatgg    4020
caggttggag gaggtgccgt aggcgaactc ggtgccgtcg agcacggaca gttgctggtt    4080
gttgataccg atgttgaagg gcctcctgta caggtggag gacagggtcc tgtagacacc    4140
ctgacccagt tgagccacga tgcgttgctg tggagcggcg ttgcccatgg tgccgtagag    4200
cgggaaggtg aactcgggc cgctgaagcc cactggggag gccatgatct ggtggccgga    4260
ccagtagtac tcgcccctgt gagcgtcggt gtagatggtg atgctgttca ggatgtccat    4320
caggtgtggg ctcctgatgg agccctcgat accctgggcg gaaccgcgga agctaccgtc    4380
gaagttctcc agcactgggt tggtgtagat ctccctggtg agttgggaca cggtgcggat    4440
cgggtaggtc ctggagtcgt agttcgggaa gagggacaca atgtccagca cggtgagggt    4500
```

-continued

```
caactccctc ctgaactggt tgtacctgat ccagtccctg gagtccggac cccagacgcg    4560
ctccaggccg gtgttgtacc agcgcacagc gtggtcggtg tagttgccaa tcagcctggt    4620
caggtcgttg tagcggctgt tgatggtggc agcatcgaag ccccaccttt ggccgaacac    4680
gctcacgtcg cgcagcacgc tgaggtgcag gttagcggct tgcacgtaca cggacaggag    4740
cggcacttgg tagttctgga cggcgaacag tgggatagcg gtggtcaggg cgctgttcat    4800
gtcgttgaat tgaatgcgca tttcctcgcg gagagctggg ttggtcgggt cggcctccca    4860
ctccctgaag ctctcggcgt agatttggta gaggttgctc aggccctcca gcctggagat    4920
ggcctggttc ctggcgaact cttcgatcct ctggttgatc agctgctcga tttgcaccag    4980
gaaggcgtcc cattgggatg gaccgaagat accccagatg atgtccacca ggccgagcac    5040
gaagccagca cctggcacga actcgctgag caggaactgg gtcaaggaca gggagatgtc    5100
gatgggggtg taaccggtct cgatgcgctc gccacccagc acctccacct ctgggttgct    5160
caggcagttg tatgggatgc actcgttgat gtttgggttg ttgtccattc tagagtcgac    5220
ctgcagaagt aacaccaaac aacagggtga gcatcgacaa aagaaacagt accaagcaaa    5280
taaatagcgt atgaaggcag ggctaaaaaa atccacatat agctgctgca tatgccatca    5340
tccaagtata tcaagatcaa aataattata aaacatactt gtttattata atagataggt    5400
actcaaggtt agagcatatg aatagatgct gcatatgcca tcatgtatat gcatcagtaa    5460
aacccacatc aacatgtata cctatcctag atcgatattt ccatccatct taaactcgta    5520
actatgaaga tgtatgacac acacatacag ttccaaaatt aataaataca ccaggtagtt    5580
tgaaacagta ttctactccg atctagaacg aatgaacgac cgcccaacca caccacatca    5640
tcacaaccaa gcgaacaaaa agcatctctg tatatgcatc agtaaaaccc gcatcaacat    5700
gtatacctat cctagatcga tatttccatc catcatcttc aattcgtaac tatgaatatg    5760
tatggcacac acatacagat ccaaaattaa taaatccacc aggtagtttg aaacagaatt    5820
ctactccgat ctagaacgac cgcccaacca gaccacatca tcacaaccaa gacaaaaaaa    5880
agcatgaaaa gatgacccga caaacaagtg cacggcatat attgaaataa aggaaaaggg    5940
caaaccaaac cctatgcaac gaaacaaaaa aaatcatgaa atcgatcccg tctgcggaac    6000
ggctagagcc atcccaggat tccccaaaga gaaacactgg caagttagca atcagaacgt    6060
gtctgacgta caggtcgcat ccgtgtacga acgctagcag cacggatcta acacaaacac    6120
ggatctaaca caaacatgaa cagaagtaga actaccgggc cctaaccatg gaccggaacg    6180
ccgatctaga gaaggtagag aggggggggg ggggaggacg agcggcgtac cttgaagcgg    6240
aggtgccgac gggtggattt gggggagatc tggttgtgtg tgtgtgcgct ccgaacaaca    6300
cgaggttggg gaaagagggt gtggaggggg tgtctattta ttacggcggg cgaggaaggg    6360
aaagcgaagg agcggtggga aaggaatccc ccgtagctgc cgtgccgtga gaggaggagg    6420
aggccgcctg ccgtgccggc tcacgtctgc cgctccgcca cgcaatttct ggatgccgac    6480
agcggagcaa gtccaacggt ggagcggaac tctcgagagg ggtccagagg cagcgacaga    6540
gatgccgtgc cgtctgcttc gcttggcccg acgcgacgct gctggttcgc tggttggtgt    6600
ccgttagact cgtcgacggc gtttaacagg ctggcattat ctactcgaaa caagaaaaat    6660
gtttccttag ttttttttaat ttcttaaagg gtatttgttt aatttttagt cactttattt    6720
tattctattt tatatctaaa ttattaaata aaaaaactaa aatagagttt tagttttctt    6780
aatttagagg ctaaaataga ataaaataga tgtactaaaa aaattagtct ataaaaacca    6840
```

-continued

```
ttaaccctaa accctaaatg gatgtactaa taaaatggat gaagtattat ataggtgaag      6900
ctatttgcaa aaaaaaagga gaacacatgc acactaaaaa gataaaactg tagagtcctg      6960
ttgtcaaaat actcaattgt cctttagacc atgtctaact gttcatttat atgattctct      7020
aaaacactga tattattgta gtactataga ttatattatt cgtagagtaa agtttaaata      7080
tatgtataaa gatagataaa ctgcacttca aacaagtgtg acaaaaaaaa tatgtggtaa      7140 tttttttataa cttagacatg caatgctcat tatctctaga gaggggcacg accgggtcac     7200
gctgcactgc aggcatcgat cgaagcttgc ggccgcgaat tcggtaccga tatcagtact     7260
taatcagtga tcagtaacta aattcagtac attaaagacg tccgcaatgt gatatcagta     7320
cttaatttgt tgaacgcggc cggcagggca gccttccatc ctatcctatg cgcagtagag     7380
tactgtatgc accatccagt tccagtttcc tgtacgta                             7418
```

```
<210> SEQ ID NO 38
<211> LENGTH: 206
<212> TYPE: DNA
<213> ORGANISM: Artificial Sequence
<220> FEATURE:
<223> OTHER INFORMATION: Complementary sequence of SEQ ID NO 03
      (reverse-complement)

<400> SEQUENCE: 38
gcatcgatcg aagcttgcgg ccgcgaattc ggtaccgata tcagtactta atcagtgatc       60
agtaactaaa ttcagtacat taaagacgtc cgcaatgtga tatcagtact taatttgttg      120
aacgcggccg gcagggcagc cttccatcct atcctatgcg cagtagagta ctgtatgcac      180
catccagttc cagtttcctg tacgta                                          206
```

```
<210> SEQ ID NO 39
<211> LENGTH: 206
<212> TYPE: DNA
<213> ORGANISM: Artificial Sequence
<220> FEATURE:
<223> OTHER INFORMATION: Complementary sequence of SEQ ID NO 04
      (reverse-complement)

<400> SEQUENCE: 39
gaaccaacga acttgtggcc gttatgttgg aagtaggcgc agggatcgta cgtgtgtgcg       60
gccggccgac tgctggcgat aggaacacgt acaacggttc aaacactgat agtttaaact      120
gaaggcggga aacgacaatc tgatcactga ttagtaacta aggcctggcc ggccgcgatc      180
gcgagctcga tccactagta acggcc                                          206
```

```
<210> SEQ ID NO 40
<211> LENGTH: 22
<212> TYPE: DNA
<213> ORGANISM: Artificial Sequence
<220> FEATURE:
<223> OTHER INFORMATION: Ubi.BAR.CN.Fw

<400> SEQUENCE: 40
gctcaccctg ttgtttggtg tt                                               22
```

```
<210> SEQ ID NO 41
<211> LENGTH: 22
<212> TYPE: DNA
<213> ORGANISM: Artificial Sequence
<220> FEATURE:
<223> OTHER INFORMATION: CRY.4-ubi.CN.Rv

<400> SEQUENCE: 41
```
tcgttgatgt ttgggttgtt gt                                                 22

<210> SEQ ID NO 42
<211> LENGTH: 17
<212> TYPE: DNA
<213> ORGANISM: Artificial Sequence
<220> FEATURE:
<223> OTHER INFORMATION: Ubi.BAR_probe

<400> SEQUENCE: 42
cttctgcagg tcgactc                                                       17

<210> SEQ ID NO 43
<211> LENGTH: 19
<212> TYPE: DNA
<213> ORGANISM: Artificial Sequence
<220> FEATURE:
<223> OTHER INFORMATION: CRY.571.CN.Fw

<400> SEQUENCE: 43
agccgctaca acgacctga                                                     19

<210> SEQ ID NO 44
<211> LENGTH: 17
<212> TYPE: DNA
<213> ORGANISM: Artificial Sequence
<220> FEATURE:
<223> OTHER INFORMATION: CRY.649.CN.Rv

<400> SEQUENCE: 44
gctccaggcc ggtgttg                                                       17

<210> SEQ ID NO 45
<211> LENGTH: 20
<212> TYPE: DNA
<213> ORGANISM: Artificial Sequence
<220> FEATURE:
<223> OTHER INFORMATION: CRY.probe

<400> SEQUENCE: 45
ggcaactaca ccgaccacgc                                                    20

<210> SEQ ID NO 46
<211> LENGTH: 22
<212> TYPE: DNA
<213> ORGANISM: Artificial Sequence
<220> FEATURE:
<223> OTHER INFORMATION: Ubi.BAR.CN.Fw

<400> SEQUENCE: 46
gctcaccctg ttgtttggtg tt                                                 22

<210> SEQ ID NO 47
<211> LENGTH: 20
<212> TYPE: DNA
<213> ORGANISM: Artificial Sequence
<220> FEATURE:
<223> OTHER INFORMATION: Ubi.BAR.CN.Rv

<400> SEQUENCE: 47
cgtcgttctg ggctcattct                                                    20

<210> SEQ ID NO 48
<211> LENGTH: 17
<212> TYPE: DNA

-continued

<213> ORGANISM: Artificial Sequence
<220> FEATURE:
<223> OTHER INFORMATION: Ubi.BAR_probe

<400> SEQUENCE: 48
cttctgcagg tcgactc                                                17

<210> SEQ ID NO 49
<211> LENGTH: 21
<212> TYPE: DNA
<213> ORGANISM: Artificial Sequence
<220> FEATURE:
<223> OTHER INFORMATION: Nested PCR 1 (BsrGl)

<400> SEQUENCE: 49
tgcaatgctc attatctcta g                                           21

<210> SEQ ID NO 50
<211> LENGTH: 21
<212> TYPE: DNA
<213> ORGANISM: Artificial Sequence
<220> FEATURE:
<223> OTHER INFORMATION: Nested PCR 1(BsrGl)

<400> SEQUENCE: 50
agcatcacca tctacaccga c                                           21

<210> SEQ ID NO 51
<211> LENGTH: 19
<212> TYPE: DNA
<213> ORGANISM: Artificial Sequence
<220> FEATURE:
<223> OTHER INFORMATION: Nested PCR 2(BsrGl)

<400> SEQUENCE: 51
tgcactgcag gcatcgatc                                              19

<210> SEQ ID NO 52
<211> LENGTH: 22
<212> TYPE: DNA
<213> ORGANISM: Artificial Sequence
<220> FEATURE:
<223> OTHER INFORMATION: Nested PCR 3(BsrGl)

<400> SEQUENCE: 52
gatatcagta ctaattcagt ac                                          22

<210> SEQ ID NO 53
<211> LENGTH: 19
<212> TYPE: DNA
<213> ORGANISM: Artificial Sequence
<220> FEATURE:
<223> OTHER INFORMATION: Nested PCR 1 (Ndel)

<400> SEQUENCE: 53
tgcactgcag gcatcgatc                                              19

<210> SEQ ID NO 54
<211> LENGTH: 18
<212> TYPE: DNA
<213> ORGANISM: Artificial Sequence
<220> FEATURE:
<223> OTHER INFORMATION: Nested PCR 1 (Ndel)

<400> SEQUENCE: 54
acggatgcga cctgtacg                                               18

-continued

```
<210> SEQ ID NO 55
<211> LENGTH: 19
<212> TYPE: DNA
<213> ORGANISM: Artificial Sequence
<220> FEATURE:
<223> OTHER INFORMATION: Nested PCR 2 (Ndel)

<400> SEQUENCE: 55
tgcactgcag gcatcgatc                                                                    19

<210> SEQ ID NO 56
<211> LENGTH: 22
<212> TYPE: DNA
<213> ORGANISM: Artificial Sequence
<220> FEATURE:
<223> OTHER INFORMATION: Nested PCR 3 (Ndel)

<400> SEQUENCE: 56
gatatcagta ctaattcagt ac                                                                22

<210> SEQ ID NO 57
<211> LENGTH: 20
<212> TYPE: DNA
<213> ORGANISM: Artificial Sequence
<220> FEATURE:
<223> OTHER INFORMATION: Nested PCR 1 (Kpn1)

<400> SEQUENCE: 57
aattatacat ttaatacgcg                                                                   20

<210> SEQ ID NO 58
<211> LENGTH: 21
<212> TYPE: DNA
<213> ORGANISM: Artificial Sequence
<220> FEATURE:
<223> OTHER INFORMATION: Nested PCR 1 (Kpn1)

<400> SEQUENCE: 58
aataacgtca tgcattacat g                                                                 21

<210> SEQ ID NO 59
<211> LENGTH: 20
<212> TYPE: DNA
<213> ORGANISM: Artificial Sequence
<220> FEATURE:
<223> OTHER INFORMATION: Nested PCR 2 (Kpn1)

<400> SEQUENCE: 59
cgcggtgtca tctatgttac                                                                   20

<210> SEQ ID NO 60
<211> LENGTH: 20
<212> TYPE: DNA
<213> ORGANISM: Artificial Sequence
<220> FEATURE:
<223> OTHER INFORMATION: Nested PCR 2 (Kpn1)

<400> SEQUENCE: 60
gataatcatc gcaagaccgg                                                                   20

<210> SEQ ID NO 61
<211> LENGTH: 20
<212> TYPE: DNA
<213> ORGANISM: Artificial Sequence
<220> FEATURE:
```

-continued

<223> OTHER INFORMATION: Nested PCR 3 (Kpn1)

<400> SEQUENCE: 61
tcgtcgactc tagactcgag                                        20

<210> SEQ ID NO 62
<211> LENGTH: 20
<212> TYPE: DNA
<213> ORGANISM: Artificial Sequence
<220> FEATURE:
<223> OTHER INFORMATION: Nested PCR 3 (Kpn1)

<400> SEQUENCE: 62
cgatctcaga tctcggtgac                                        20

<210> SEQ ID NO 63
<211> LENGTH: 20
<212> TYPE: DNA
<213> ORGANISM: Artificial Sequence
<220> FEATURE:
<223> OTHER INFORMATION: FS_C91-087_RB_1,4k.a

<400> SEQUENCE: 63
caacaaccca aacatcaacg                                        20

<210> SEQ ID NO 64
<211> LENGTH: 20
<212> TYPE: DNA
<213> ORGANISM: Artificial Sequence
<220> FEATURE:
<223> OTHER INFORMATION: FS_C91-087_RB_1,4k.a

<400> SEQUENCE: 64
taacatttag ggtgcgcttg                                        20

<210> SEQ ID NO 65
<211> LENGTH: 20
<212> TYPE: DNA
<213> ORGANISM: Artificial Sequence
<220> FEATURE:
<223> OTHER INFORMATION: FS_C91-087_LB_2k.a

<400> SEQUENCE: 65
gttcttgggt ggcggtagta                                        20

<210> SEQ ID NO 66
<211> LENGTH: 20
<212> TYPE: DNA
<213> ORGANISM: Artificial Sequence
<220> FEATURE:
<223> OTHER INFORMATION: FS_C91-087_LB_2k.a/b

<400> SEQUENCE: 66
cgtcggtgta gatggtgatg                                        20

<210> SEQ ID NO 67
<211> LENGTH: 20
<212> TYPE: DNA
<213> ORGANISM: Artificial Sequence
<220> FEATURE:
<223> OTHER INFORMATION: FS_C91-087_LB_2k.b

<400> SEQUENCE: 67
ttgggtggcg gtagtagttg                                        20

-continued

```
<210> SEQ ID NO 68
<211> LENGTH: 22
<212> TYPE: DNA
<213> ORGANISM: Artificial Sequence
<220> FEATURE:
<223> OTHER INFORMATION: sugargane polyubiquitine gene forward primer

<400> SEQUENCE: 68
accattaccc tggaggttga ga                                               22

<210> SEQ ID NO 69
<211> LENGTH: 20
<212> TYPE: DNA
<213> ORGANISM: Artificial Sequence
<220> FEATURE:
<223> OTHER INFORMATION: sugarcane polyubiquitine gene antisense
      initiator

<400> SEQUENCE: 69
gtcctggatc ttcgccttca                                                  20

<210> SEQ ID NO 70
<211> LENGTH: 16
<212> TYPE: DNA
<213> ORGANISM: Artificial Sequence
<220> FEATURE:
<223> OTHER INFORMATION: sugarcane polyubiquitin gene probe

<400> SEQUENCE: 70
ctctgacacc atcgac                                                      16
```